United States Patent
Darwish et al.

(10) Patent No.: US 10,851,093 B2
(45) Date of Patent: Dec. 1, 2020

(54) TYROSINE KINASE INHIBITORS

(71) Applicant: Rigel Pharmaceuticals, Inc., South San Francisco, CA (US)

(72) Inventors: Ihab Darwish, San Carlos, CA (US); Jiaxin Yu, San Carlos, CA (US); Rao Kolluri, Foster City, CA (US); Sacha Holland, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 16/424,619

(22) Filed: May 29, 2019

(65) Prior Publication Data

US 2019/0382395 A1 Dec. 19, 2019

Related U.S. Application Data

(60) Provisional application No. 62/679,095, filed on Jun. 1, 2018.

(51) Int. Cl.
| | | |
|---|---|---|
| *C07D 215/00* | (2006.01) | |
| *C07D 413/14* | (2006.01) | |
| *C07D 417/14* | (2006.01) | |
| *C07D 491/107* | (2006.01) | |
| *C07D 453/00* | (2006.01) | |

(52) U.S. Cl.
CPC ......... *C07D 413/14* (2013.01); *C07D 417/14* (2013.01); *C07D 453/00* (2013.01); *C07D 491/107* (2013.01)

(58) Field of Classification Search
CPC .. C07D 215/00; C07D 413/14; C07D 417/14; C07D 491/107
USPC .................................................. 546/152, 153
See application file for complete search history.

(56) References Cited

U.S. PATENT DOCUMENTS

| | | | | |
|---|---|---|---|---|
| 8,999,982 B2* | 4/2015 | Schultz-Fademrecht | ................ C07D 215/233 | 514/235.2 |
| 9,029,538 B2* | 5/2015 | Dandu | ................. C07D 401/12 | 544/310 |
| 9,133,162 B2* | 9/2015 | Xi | .......................... A61K 45/06 | |
| 2008/0004273 A1* | 1/2008 | Raeppel | ............... C07D 401/12 | 514/235.2 |

FOREIGN PATENT DOCUMENTS

| | | |
|---|---|---|
| CN | 103965107 | 8/2014 |
| CN | 104072480 | 10/2014 |
| WO | WO 2007/146824 | 12/2007 |
| WO | WO 2012/028332 | 3/2012 |
| WO | 2016104617 | * 6/2016 |

OTHER PUBLICATIONS

Kung et al., European Journal of Medicinal Chemistry (2008), 43(6), 1321-1329.*
Mannion et al. Bioorganic & Medicinal Chemistry Letters (2009), 19(23), 6552-6556.*
Lovering et al. Chemical Biology & Drug Design (2012), 80(5), 657-664.*
Bhattacharya et al. Bioorganic & Medicinal Chemistry Letters (2012), 22(24), 7523-7529.*
Smith et al., Journal of medicinal Chemistry (2015), 58(3), 1426-1441.*
Kumar et al., Journal of Chemical Information and Modeling (2016), 56(6), 965-973.*
Huang et al., Bioorganic & Medicinal Chemistry Letters (2017), 27(8), 1776-1779.*
Tang et al., "Design, synthesis, and structure-activity relationships of novel 6,7-disubstituted-4-phenoxyquinoline derivatives as potential antitumor agents", European Journal of Medicinal Chemistry, Editions Scientifique Elsevier, Paris, FR, vol. 69, Nov. 1, 2013, pp. 77-89.
International Search Report and Written Opinion of International Application No. PCT/US2019/034239 dated Jul. 24, 2019, 17 pages.

* cited by examiner

*Primary Examiner* — Niloofar Rahmani
(74) *Attorney, Agent, or Firm* — James J. Diehl

(57) ABSTRACT

Disclosed are imidazole compounds, as well as pharmaceutical compositions and methods of use thereof. One embodiment is a compound having the structure

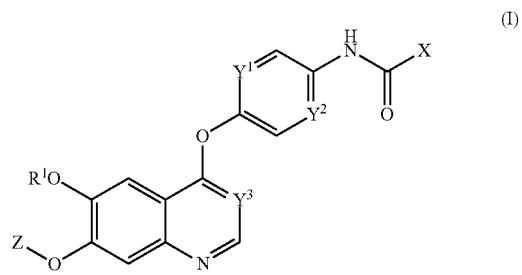

(I)

and pharmaceutically acceptable salts, prodrugs and N-oxides thereof (and solvates and hydrates thereof), wherein $R^1$, X, $Y^1$, $Y^2$, $Y^3$ and Z are as described herein. In certain embodiments, a compound disclosed herein inhibits a cellular TAM receptor, and can be used to treat disease mediated by or involving the TAM receptor family.

17 Claims, No Drawings

TYROSINE KINASE INHIBITORS

CROSS-REFERENCE TO RELATED APPLICATION

This application is a nonprovisional application which claims priority to U.S. Provisional Application Ser. No. 62/679,095 filed on Jun. 1, 2018, the disclosure of which is incorporated herein by reference in its entirety.

BACKGROUND

Field of Invention

This invention relates to the field of compounds, pharmaceutical compositions, and methods of using the compounds and compositions containing them. This invention relates more particularly to the field of pyrimidoisoquinolone compounds and pharmaceutical compositions thereof, methods of inhibiting one or more kinases, such as one or more of the TAM (Tyro 3, Axl and Mer) receptor family with the compounds, and methods of treating and/or preventing disease with the compounds.

TECHNICAL BACKGROUND

In recent years, inhibition of specific cancer-associated tyrosine kinases has emerged as an important approach for cancer therapy. Tyrosine kinases as mediators of cell signaling, play a role in many diverse physiological pathways including cell growth and differentiation. Deregulation of tyrosine kinases activity can result in cellular transformation leading to the development of cancer.

Tyro 3 has been implicated in several malignant diseases, and its expression is upregulated in AML, CML, multiple myeloma, endometrial cancer and melanoma. Tyro 3 has also been shown to have transforming abilities, and may function as a prosurvival factor in tumorigenesis. In melanoma cells, Tyro 3 knockdown inhibits proliferation and leads to increased sensitivity to chemotherapeutic agents in vitro.

The Axl receptor tyrosine kinase (Axl) is overexpressed in a number of different tumor cell types. Axl signaling has been shown to favor tumor growth through activation of proliferative and anti-apoptotic signaling pathways, as well as through promotion of angiogenesis and tumor invasiveness. Axl is associated with the development and maintenance of various cancers including lung cancer, mycloid leukemia, uterine cancer, ovarian cancer, gliomas, melanoma, prostate cancer, breast cancer, gastric cancer, osteosarcoma, renal cell carcinoma, and thyroid cancer. In some type of cancers, particularly non-small cell lung cancer (NSCLC), myeloid leukemia, and gastric cancers, the overexpression of this cell signaling molecule indicates a poor prognosis for the patient.

Mer is a transmembrane receptor tyrosine kinase composed of two immunoglobulin domains and two fibronectin III domains in the extracellular portion, and a tyrosine kinase domain in the intracellular portion. Mer overexpression has been linked to a number of different cancers including subsets of B and T cell leukemia, lymphoma, pituitary adenoma, gastric cancer, and rhabdomyosarcoma.

SUMMARY

In view of the foregoing, we recognized that new therapeutic agents that inhibit one or more kinases, in particular tyrosine receptor kinases of the TAM (Tyro 3, Axl and Mer) receptor family may be useful and therefore desirable for the treatment of proliferative disorders, in particular hematological neoplasms, such as acute myeloid leukemia (AML).

Accordingly, the present invention comprises compounds, pharmaceutical compositions, and methods of using them to treat and/or prevent disease by inhibiting one or more of the TAM (Tyro 3, Axl and Mer) receptor family.

Disclosed herein are compounds having structural formula (I)

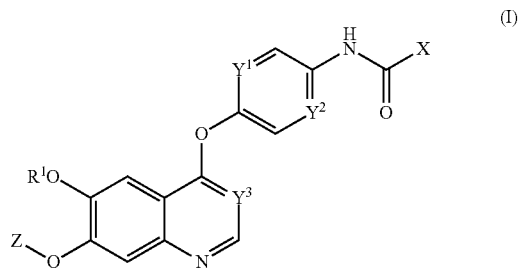

(I)

and pharmaceutically acceptable salts, prodrugs, and N-oxides thereof (and solvates and hydrates thereof), wherein $R^1$, X, $Y^1$, $Y^2$, $Y^3$ and Z are as described herein.

Also disclosed herein are pharmaceutical compositions. Examples of such compositions include those having at least one pharmaceutically acceptable carrier, diluent, or excipient; and a compound, pharmaceutically acceptable salt, prodrug, or N-oxide (or solvate or hydrate) as described herein.

Another aspect of the present invention comprises methods for treating and/or preventing disease by inhibiting a cellular TAM receptor. Accordingly, the invention also comprises methods for treating disease using the presently disclosed compounds and pharmaceutical compositions.

All publications referenced herein are incorporated by reference in their entirety to the extent they are not inconsistent with the teachings presented herein.

DETAILED DESCRIPTION

In one aspect, the invention comprises compounds that inhibit one or more of the TAM (Tyro 3, Axl and Mer) receptor family.

In embodiment $I_1$ of this first aspect, the compounds have structural formula (I):

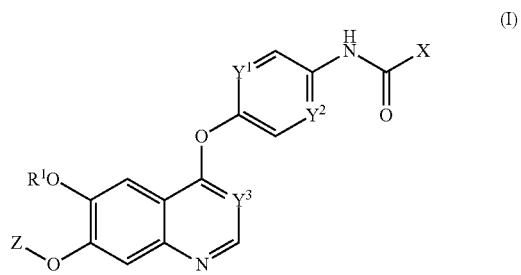

(I)

or a pharmaceutically acceptable salt, prodrug, or N-oxide thereof, or a solvate or hydrate thereof, wherein X is Het or Hca, wherein Het and Hca are substituted by 1, 2, 3, or 4 —$R^{X1}$ groups, wherein each —$R^{X1}$ is independently halogen, cyano, $C_1$-$C_6$alkyl, $C_1$-$C_6$haloalkyl, —$C_1$-$C_6$alkoxy, —$C_1$-$C_6$haloalkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$, —CH$_2$—OP(O)(OR), Cak($C_0$-$C_6$alkyl), Ar($C_0$-$C_6$alkyl) or Hca($C_0$-$C_6$alkyl), wherein Cak, Ar and Hca are optionally substituted with one or two —$R^{X2}$ groups, wherein each —$R^{X2}$ is independently halogen, cyano, nitro, oxo, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$alkyl, $C_1$-$C_6$haloalkyl or Ar;

$Y^1$ is CH or CF:
$Y^2$ is N or CH;
$Y^3$ is N or CH;
Z is $C_1$-$C_6$alkyl, Ar($C_0$-$C_6$alkyl) or Hca($C_0$-$C_6$alkyl), each optionally substituted by 1, 2 or 3 —$R^{Z1}$ groups;

wherein each —$R^{Z1}$ is independently halogen, cyano, $C_1$-$C_6$alkyl, $C_1$-$C_6$haloalkyl, —$C_1$-$C_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR), or —CH$_2$—OP(O)(OR);

each R is independently hydrogen or $C_1$-$C_6$alkyl; and
$R^1$ is hydrogen or $C_1$-$C_6$alkyl;
wherein
Hca is a 3-15 membered non-aromatic ring or non-aromatic ring system comprising 1, 2, 3, or 4 O, S, or N atoms, provided no O or S is adjacent to another O or S;
Het is a 5-15 membered aromatic ring or aromatic ring system comprising 1, 2, 3, or 4 O, S, or N atoms, provided no O or S is adjacent to another O or S;
Cak is a 3-15 membered non-aromatic carbocyclic ring or non-aromatic carbocyclic ring system, which may be saturated or partially unsaturated, and optionally including one or more other aromatic and non-aromatic rings, which form fused, spiro or bridged ring systems; and
Ar is a 6-16 membered aromatic ring or aromatic ring system having at least one carbocyclic aromatic ring optionally fused one or more aromatic or non-aromatic rings;
provided that
(a) when $Y^3$ is N or Z is $C_1$-$C_6$alkyl, X is

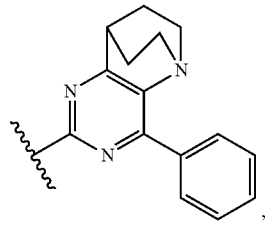 [SMILES: *c1nc(-c2ccccc2)c2c(n1)C1CCN2CC1 ; ","]

and
(b) when Z is Hca($C_0$-$C_6$alkyl), $Y_1$ is CH and $Y_2$ is N, X is not

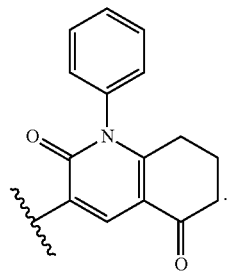 [SMILES: *c1cc2c(n(-c3ccccc3)c1=O)CCCC2=O ; "."]

In some embodiments, the invention comprises compounds of embodiment $I_1$ provided that the compound is not any compound disclosed in U.S. Patent Application No. US2017/0088542.

In embodiment $I_2$, the compounds are of embodiment $I_1$, wherein $Y^1$ is CH; and $Y^2$ is N.

In embodiment $I_3$, the compounds are of embodiment $I_1$, wherein $Y^1$ is CH; and $Y^2$ is CH.

In embodiment $I_4$, the compounds are of embodiment $I_1$, wherein $Y^1$ is CF; and $Y^2$ is N.

In embodiment $I_5$, the compounds are of embodiment $I_1$, wherein $Y^1$ is CF; and $Y^2$ is CH.

In embodiment $I_6$, the compounds are of any of embodiments $I_1$-$I_5$, wherein X is N.

In embodiment $I_7$, the compounds are of any of embodiments $I_1$-$I_5$, wherein X is CH.

In embodiment $I_8$, the compounds are any of embodiments $I_1$-$I_7$, wherein $R^1$ is $C_1$-$C_6$alkyl.

In embodiment $I_9$, the compounds are any of embodiments $I_1$-$I_7$, wherein $R^1$ is methyl.

In embodiment $I_{10}$, the compounds are of any of embodiments $I_1$-$I_7$, wherein $R^1$ is hydrogen.

In embodiment $I_{11}$, the compounds are of any of embodiments $I_1$-$I_{10}$, wherein Z is 3-morpholinopropoxyl.

In embodiment $I_{12}$, the invention further comprises subgenera of formula (I) in which structural formula (I), X, $Y^1$, $Y^2$, $Y^3$, Z, $R^1$ and R are any group or combinations of groups as defined sections $I^a$-$I^d$ immediately below (e.g., wherein the compound is of structural formula (I) as defined in any of the above embodiments and X is pyridinyl optionally substituted with one $R^{X1}$ group, wherein $R^{X1}$ is methyl; or the compound is of formula (Ib), X is group (1jj), Y is group (2r), and Z is group (3h)):

$I^a$—Structural Formula (I) is One of Formulae (Ia)-(Io):

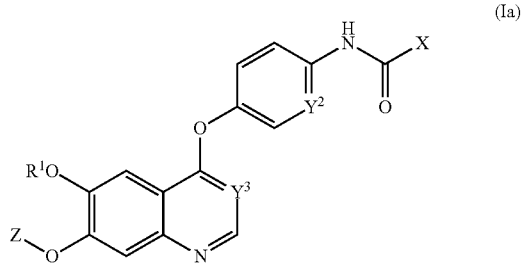

(Ia)

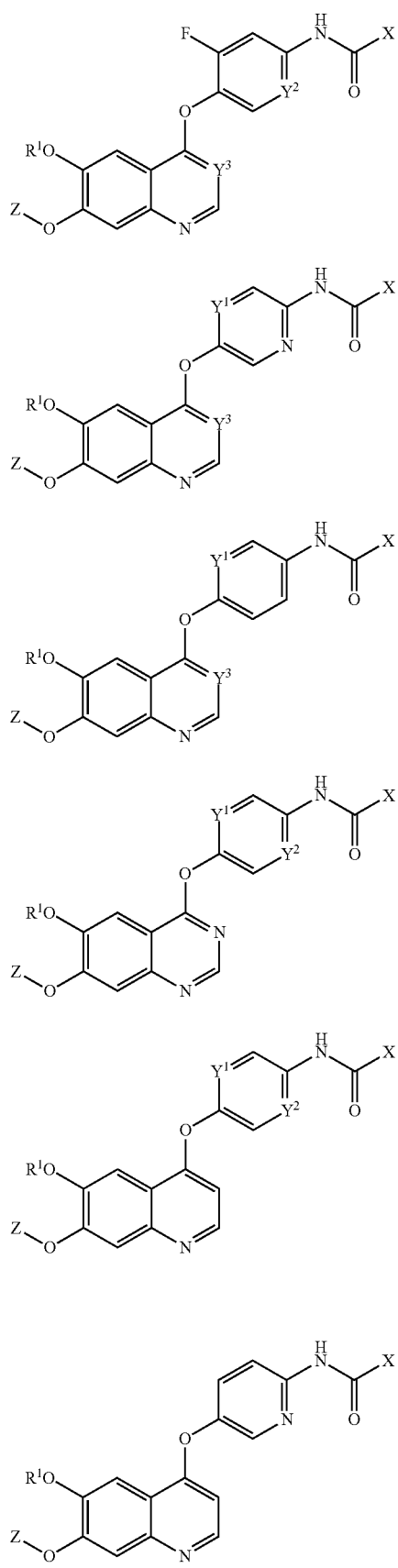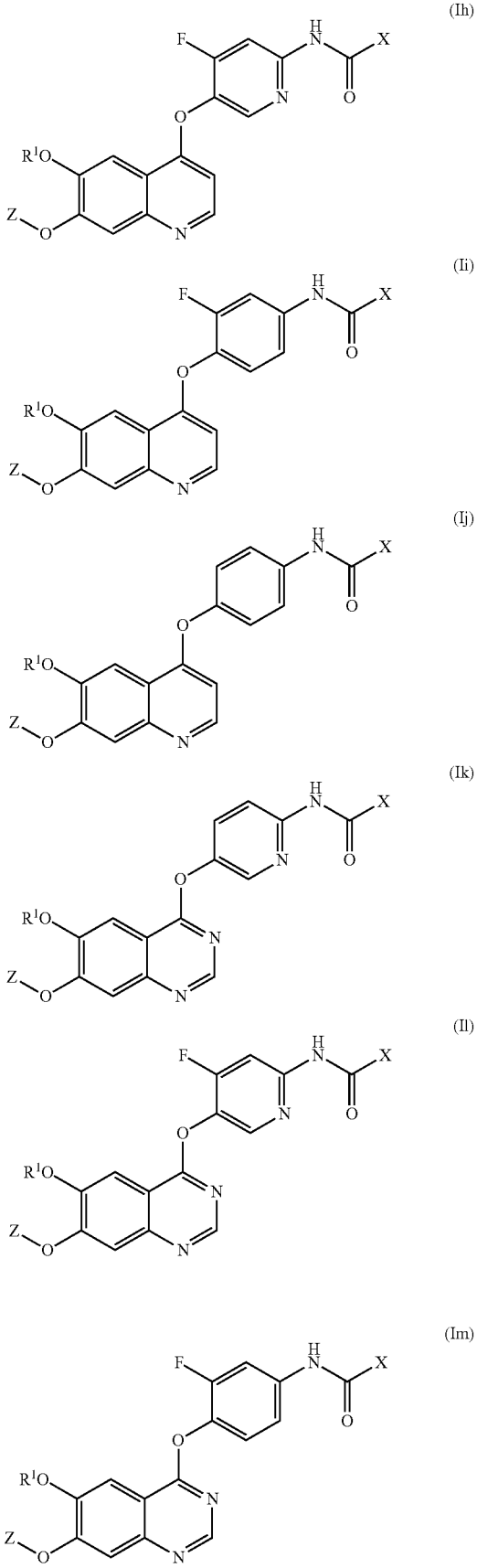

(In)

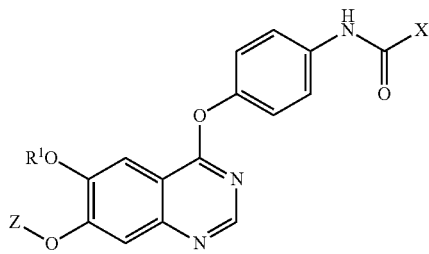

(Io)

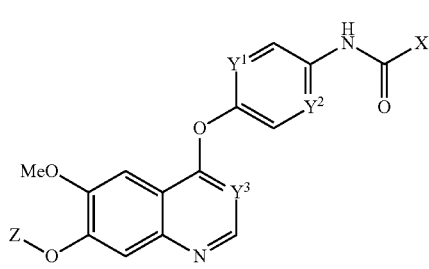

I$^b$—X is Selected from One of the Following Groups (1a)-(1ffff):

(1a) X is Het or Hca, wherein Het and Hca are substituted by 1, 2, 3, or 4 —R$^{X1}$ groups, wherein
each —R$^{X1}$ is independently halogen, cyano, C$_1$-C$_6$alkyl, C$_1$-C$_6$haloalkyl, —C$_1$-C$_6$alkoxy, —C$_1$-C$_6$haloalkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$, —CH$_2$—OP(O)(OR), Cak(C$_0$-C$_6$alkyl), Ar(C$_0$-C$_6$alkyl) or Hca(C$_0$-C$_6$alkyl), wherein Cak, Ar and Hca are optionally substituted with one or two —R$^{X2}$ groups,
wherein each —R$^{X2}$ is independently halogen, cyano, nitro, oxo, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR, —N(R)C(O)R, —N(R)C(O)OR, —N(R)C(O)NR$_2$, —N(R)S(O)R, —N(R)S(O)$_2$R, C$_1$-C$_6$alkyl, C$_1$-C$_6$haloalkyl or Ar.

(1b) X is according to group (1a), wherein Het and Hca are optionally substituted by 1, 2 or 3 —R$^{X1}$ groups.

(1c) X is according to group (1a), wherein Het and Hca are optionally substituted by 1 or 2 —R$^{X1}$ groups.

(1d) X is according to group (1a), wherein Het and Hca are optionally substituted by 1 —R$^{X1}$ groups.

(1e) X is according to group (1a), wherein Het and Hca are optionally substituted by 2 —R$^{X1}$ groups.

(1f) X is according to group (1a), wherein Het and Hca are optionally substituted by 3 —R$^{X1}$ groups.

(1g) X is according to group (1a), wherein Het and Hca are optionally substituted by 4 —R$^{X1}$ groups.

(1h) X is any of groups (1a)-(1g), wherein X is Het.

(1i) X is any of groups (1a)-(1g), wherein X is Hca.

(1j) Group (1a), wherein X is

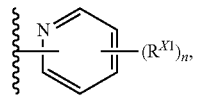 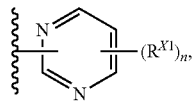

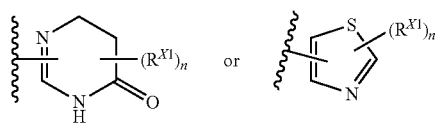

wherein n is 0, 1, 2, 3 or 4.

(1k) Group (1a), wherein X is

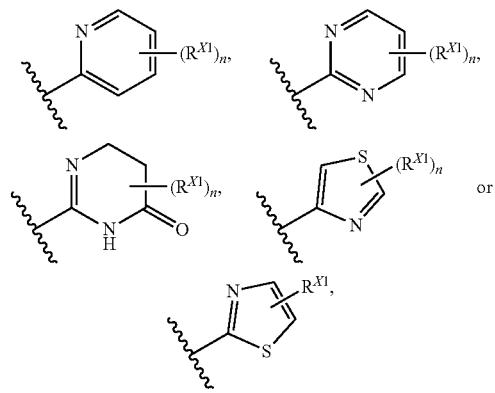

wherein n is 0, 1, 2, 3 or 4.

(1l) Group (1a), wherein X is

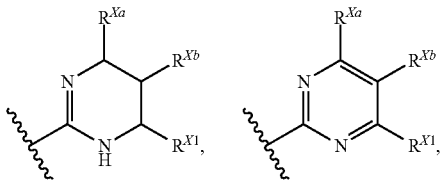

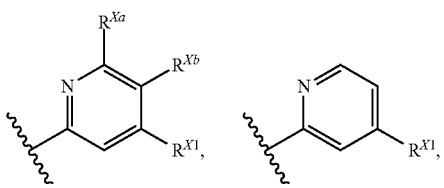

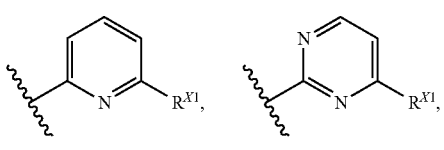

wherein R$^{Xa}$ and R$^{Xb}$ are each hydrogen, or R$^{Xa}$ and R$^{Xb}$ combine with the atoms to which they are attached to form an Ar or Hca;

(1m) Group (1a), wherein X is

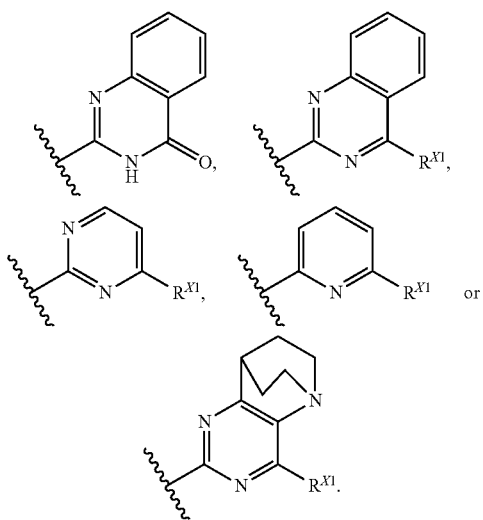

(1n) Group (1a), wherein X is

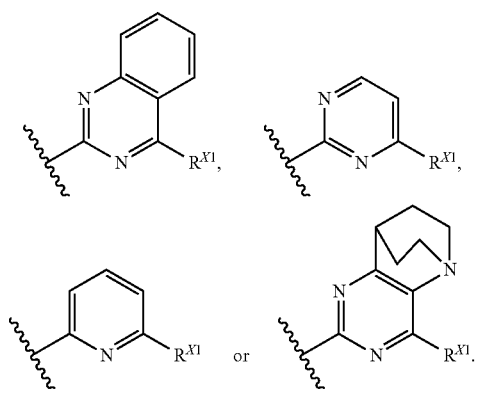

(1o) Group (1a), wherein X is

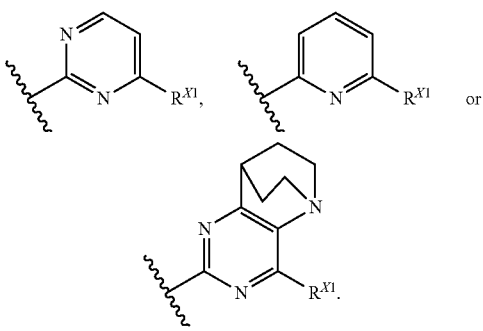

(1p) X is any of groups (1a)-(1o), wherein —$R^{X1}$ is independently halogen, cyano, $C_1$-$C_6$alkyl, $C_1$-$C_6$haloalkyl, —$C_1$-$C_6$alkoxy, —$C_1$-$C_6$haloalkoxy, oxo, —OR, —SR, —$NR_2$, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), Ar($C_0$-$C_6$alkyl) or Hca($C_0$-$C_6$alkyl), wherein Ar and Hca are optionally substituted with one or two —$R^{X2}$ groups.

(1q) X is any of groups (1a)-(1o), wherein —$R^{X1}$ is independently halogen, $C_1$-$C_6$alkyl, $C_1$-$C_6$haloalkyl, —$C_1$-$C_6$alkoxy, —$C_1$-$C_6$haloalkoxy, oxo, —OR, —SR, —$NR_2$, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), Ar($C_0$-$C_6$alkyl) or Hca($C_0$-$C_6$alkyl), wherein Ar and Hca are optionally substituted with one or two —$R^{X2}$ groups.

(1r) X is any of groups (1a)-(1o), wherein —$R^{X1}$ is independently halogen, cyano, $C_1$-$C_6$alkyl, $C_1$-$C_6$haloalkyl, —$C_1$-$C_6$alkoxy, —$C_1$-$C_6$haloalkoxy, oxo, —OR, —C(O)R, —C(O)OR, —C(O)$NR_2$, —S(O)$_2$NR, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), Ar($C_0$-$C_6$alkyl) or Hca($C_0$-$C_6$alkyl), wherein Ar and Hca are optionally substituted with one or two —$R^{X2}$ groups.

(1s) X is any of groups (1a)-(1o), wherein —$R^{X1}$ is independently halogen, cyano, $C_1$-$C_6$alkyl, $C_1$-$C_6$haloalkyl, —$C_1$-$C_6$alkoxy, —$C_1$-$C_6$haloalkoxy, oxo, —OR, —SR, —$NR_2$, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, Ar($C_0$-$C_6$alkyl) or Hca($C_0$-$C_6$alkyl), wherein Ar and Hca are optionally substituted with one or two —$R^{X1}$ groups.

(1t) X is any of groups (1a)-(1o), wherein —$R^{X1}$ is independently halogen, cyano, $C_1$-$C_6$alkyl, $C_1$-$C_6$haloalkyl, —$C_1$-$C_6$alkoxy, —$C_1$-$C_6$haloalkoxy, oxo, —OR, —SR, —$NR_2$. —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, Ar($C_0$-$C_6$alkyl) or Hca($C_0$-$C_6$alkyl), wherein Ar and Hca are optionally substituted with one or two —$R^{X2}$ groups.

(1u) X is any of groups (1a)-(1o), wherein —$R^{X1}$ is independently halogen, $C_1$-$C_6$alkyl, $C_1$-$C_6$haloalkyl, —$C_1$-$C_6$alkoxy, —$C_1$-$C_6$haloalkoxy, oxo, —OR, —C(O)R, —C(O)OR, —C(O)$NR_2$, —S(O)$_2$NR, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, Ar($C_0$-$C_6$alkyl) or Hca($C_0$-$C_6$alkyl), wherein Ar and Hca are optionally substituted with one or two —$R^{X2}$ groups.

(1v) X is any of groups (1a)-(1o), wherein —$R^{X1}$ is independently halogen, $C_1$-$C_6$alkyl, $C_1$-$C_6$haloalkyl, —$C_1$-$C_6$alkoxy, —$C_1$-$C_6$haloalkoxy, oxo, —OR, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, Ar($C_0$-$C_6$alkyl) or Hca($C_0$-$C_6$alkyl), wherein Ar and Hca are optionally substituted with one or two —$R^{X2}$ groups.

(1w) X is any of groups (1a)-(1o), wherein —$R^{X1}$ is independently halogen, $C_1$-$C_6$alkyl, $C_1$-$C_6$haloalkyl, —$C_1$-$C_6$alkoxy, —$C_1$-$C_6$haloalkoxy, oxo, —OR, —C(O)R, —C(O)OR, —C(O)$NR_2$, —OC(O)R, —N(R)C(O)R, —OC(O)OR, —OC(O)$NR_2$, —N(R)C(O)OR, —N(R)C(O)$NR_2$, —N(R)S(O)$_2$R, Ar($C_0$-$C_6$alkyl) or Hca($C_0$-$C_6$alkyl), wherein Ar and Hca are optionally substituted with one or two —$R^{X2}$ groups.

(1x) X is any of groups (1a)-(1o), wherein —R$^{X1}$ is independently halogen, C$_1$-C$_6$alkyl, C$_1$-C$_6$haloalkyl, —C$_1$-C$_6$alkoxy, —C$_1$-C$_6$haloalkoxy, oxo, —OR, —C(O)R, —C(O)OR. —C(O)NR$_2$, —OC(O)R, —N(R)C(O)R, —N(R)C(O)OR, —N(R)C(O)NR$_2$, —N(R)S(O)$_2$R, Ar(C$_0$-C$_6$alkyl) or Hca(C$_0$-C$_6$alkyl), wherein Ar and Hca are optionally substituted with one or two —R$^{X2}$ groups.

(1y) X is any of groups (1a)-(1o), wherein —R$^{X1}$ is independently halogen, C$_1$-C$_6$alkyl, C$_1$-C$_6$haloalkyl, —C$_1$-C$_6$alkoxy, —C$_1$-C$_6$haloalkoxy, oxo, —OR, —C(O)R, —C(O)OR, —C(O)NR$_2$, —N(R)C(O)R, —N(R)C(O)OR, —N(R)C(O)NR$_2$, —N(R)S(O)$_2$R, Ar(C$_0$-C$_6$alkyl) or Hca(C$_0$-C$_6$alkyl), wherein Ar and Hca are optionally substituted with one or two —R$^{X2}$ groups.

(1z) X is any of groups (1a)-(1o), wherein —R$^{X1}$ is independently halogen, C$_1$-C$_6$alkyl, C$_1$-C$_6$haloalkyl, —C$_1$-C$_6$alkoxy, —C$_1$-C$_6$haloalkoxy, oxo, —OR, —C(O)R, —C(O)OR, —C(O)NR$_2$, Ar(C$_0$-C$_6$alkyl) or Hca(C$_0$-C$_6$alkyl), wherein Ar and Hca are optionally substituted with one or two —R$^{X2}$ groups.

(1aa) X is any of groups (1a)-(1o), wherein —R$^{X1}$ is independently halogen, C$_1$-C$_6$alkyl, C$_1$-C$_6$haloalkyl, —C$_1$-C$_6$haloalkoxy, oxo, —OR, —C(O)R, —C(O)OR, —C(O)NR$_2$, Ar(C$_0$-C$_6$alkyl) or Hca(C$_0$-C$_6$alkyl), wherein Ar and Hca are optionally substituted with one or two —R$^{X2}$ groups.

(1bb) X is any of groups (1a)-(1o), wherein —R$^{X1}$ is independently halogen, C$_1$-C$_6$alkyl, C$_1$-C$_6$haloalkyl, —C$_1$-C$_6$haloalkoxy, oxo, —OR, Ar(C$_0$-C$_6$alkyl) or Hca(C$_0$-C$_6$alkyl), wherein Ar and Hca are optionally substituted with one or two —R$^{X2}$ groups.

(1cc) X is any of groups (1a)-(1o), wherein —R$^{X1}$ is independently halogen, C$_1$-C$_6$alkyl. C$_1$-C$_6$haloalkyl, oxo, —OR, Ar(C$_0$-C$_6$alkyl) or Hca(C$_0$-C$_6$alkyl), wherein Ar and Hca are optionally substituted with one or two —R$^{X2}$ groups.

(1dd) X is any of groups (1a)-(1o), wherein —R$^{X1}$ is independently halogen, C$_1$-C$_6$alkyl, oxo, —OR, Ar(C$_0$-C$_6$alkyl) or Hca(C$_0$-C$_6$alkyl), wherein Ar and Hca are optionally substituted with one or two —R$^{X2}$ groups.

(1ee) X is any of groups (1a)-(1o), wherein —R$^{X1}$ is independently halogen, C$_1$-C$_6$alkyl, oxo, Ar(C$_0$-C$_6$alkyl) or Hca(C$_0$-C$_6$alkyl), wherein Ar and Hca are optionally substituted with one or two —R$^{X2}$ groups.

(1ff) X is any of groups (1a)-(1o), wherein —R$^{X1}$ is independently halogen, C$_1$-C$_6$alkyl, Ar(C$_0$-C$_6$alkyl) or Hca(C$_0$-C$_6$alkyl), wherein Ar and Hca are optionally substituted with one or two —R$^{X2}$ groups.

(1gg) X is any of groups (1a)-(1o), wherein —R$^{X1}$ is independently halogen, Ar(C$_0$-C$_6$alkyl) or Hca(C$_0$-C$_6$alkyl), wherein Ar and Hca are optionally substituted with one or two —R$^{X2}$ groups.

(1hh) X is any of groups (1a)-(1o), wherein —R$^{X1}$ is independently Ar(C$_0$-C$_6$alkyl) or Hca(C$_0$-C$_6$alkyl), wherein Ar and Hca are optionally substituted with one or two —R$^{X2}$ groups.

(1ii) X is any of groups (1a)-(1o), wherein —R$^{X1}$ is independently Ar(C$_0$-C$_6$alkyl) or Hca(C$_0$-C$_6$alkyl), wherein Ar and Hca are optionally substituted with one or two —R$^{X2}$ groups.

(1jj) X is any of groups (1a)-(1o), wherein —R$^{X1}$ is independently Ar or Hca, wherein Ar and Hca are optionally substituted with one or two —R$^{X2}$ groups.

(1kk) X is any of groups (1a)-(1o), wherein —R$^{X1}$ is Ar(C$_0$-C$_6$alkyl), wherein Ar is optionally substituted with one or two —R$^{X2}$ groups.

(1ll) X is any of groups (1a)-(1o), wherein —R$^{X1}$ is Ar(C$_0$-C$_6$alkyl), wherein Ar is optionally substituted with one —R$^{X2}$ group.

(1mm) X is any of groups (1a)-(1o), wherein —R$^{X1}$ is Ar(C$_0$-C$_6$alkyl), wherein Ar is substituted with one —R$^{X2}$ group. (1nn) X is any of groups (1a)-(1o), wherein —R$^{X1}$ is Hca(C$_0$-C$_6$alkyl), wherein Hca is optionally substituted with one or two —R$^{X2}$ groups.

(1oo) X is any of groups (1a)-(1o), wherein —R$^{X1}$ is Hca(C$_0$-C$_6$alkyl), wherein Hca is optionally substituted with one —R$^{X2}$ groups.

(1pp) X is any of groups (1a)-(1o), wherein —R$^{X1}$ is Hca(C$_0$-C$_6$alkyl), wherein Hca is substituted with one —R$^{X2}$ groups.

(1qq) X is any of groups (1a)-(1o), wherein —R$^{X1}$ is Hca(C$_0$-C$_6$alkyl), wherein Hca is substituted with one —R$^{X2}$ groups.

(1rr) X is any of groups (1a)-(1o), wherein —R$^{X1}$ is phenyl, piperidinyl, morpholinyl, piperazinyl, pyrrolidinyl, 7-oxa-2-azaspiro[3.5]nonan-2-yl, 2-oxa-6-azaspiro[3.3]heptan-6-yl, azetidinyl, halogen, C$_1$-C$_6$alkyl, —C$_1$-C$_6$haloalkyl, oxo or —OR.

(1ss) X is any of groups (1a)-(1o), wherein —R$^{X1}$ is phenyl, piperidinyl, morpholinyl, piperazinyl, pyrrolidinyl, 7-oxa-2-azaspiro[3.5]nonan-2-yl, 2-oxa-6-azaspiro[3.3]heptan-6-yl, azetidinyl, fluoro, bromo, methoxy, trifluoromethyl or oxo.

(1tt) X is any of groups (1a)-(1o), wherein —R$^{X1}$ is halogen, C$_1$-C$_6$alkyl, —C$_1$-C$_6$haloalkyl, oxo or —OR.

(1uu) X is any of groups (1a)-(1o), wherein —R$^{X1}$ is is fluoro, bromo, methyl, trifluoromethyl, oxo or methoxy.

(1vv) X is any of groups (1a)-(1o), wherein —R$^{X1}$ is halogen, C$_1$-C$_6$alkyl, oxo or —OR. (1ww) X is any of groups (1a)-(1o), wherein —R$^{X1}$ is fluoro, bromo, methyl, oxo or methoxy.

(1xx) X is any of groups (1a)-(1o), wherein —R$^{X1}$ is halogen, C$_1$-C$_6$alkyl or —OR.

(1yy) X is any of groups (1a)-(1o), wherein —R$^{X1}$ is fluoro, bromo methyl or methoxy.

(1zz) X is any of groups (1a)-(1mm), wherein Ar(C$_0$-C$_6$alkyl) is phenyl or fluorophenyl.

(1aaa) X is any of groups (1a)-(1 mm), wherein Ar(C$_0$-C$_6$alkyl) is 4-fluorophenyl.

(1bbb) X is any of groups (1a)-(1 mm), wherein Ar(C$_0$-C$_6$alkyl) is phenyl.

(1ccc) X is any of groups (1a)-(1jj) and (1nn)-(1qq), wherein —R$^{X1}$ is piperidinyl, morpholinyl, piperazinyl, pyrrolidinyl, 7-oxa-2-azaspiro[3.5]nonan-2-yl, 2-oxa-6-azaspiro[3.3]heptan-6-yl or azetidinyl.

(1ddd) X is any of groups (1a)-(1jj) and (1nn)-(1qq), wherein —R$^{X1}$ is 4-methylpiperazin-1-yl, 4-hydroxypiperidin-1-yl, piperidinyl, morpholinyl, 4-ethoxypiperidin-1-yl, pyrrolidinyl, 4-phenylpiperidin-1-yl, 7-oxa-2-azaspiro[3.5]nonan-2-yl, 2-oxa-6-azaspiro[3.3]heptan-6-yl, 3,3-difluoroazetidin-1-yl, 4,4-difluoropiperidin-1-yl or 4,4-dimethylpiperidin-1-yl.

(1eee) X is any of groups (1a)-(1o), wherein —R$^{X1}$ is

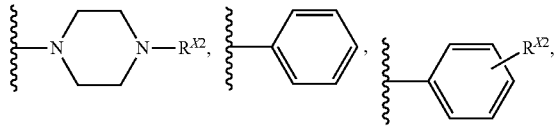

-continued

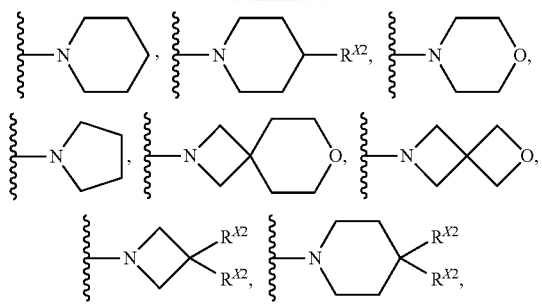

halogen, $C_1$-$C_6$alkyl, —$C_1$-$C_6$alkoxy or $C_1$-$C_6$haloalkyl.

(1fff) X is any of groups (1a)-(1o), wherein —$R^{X1}$ is

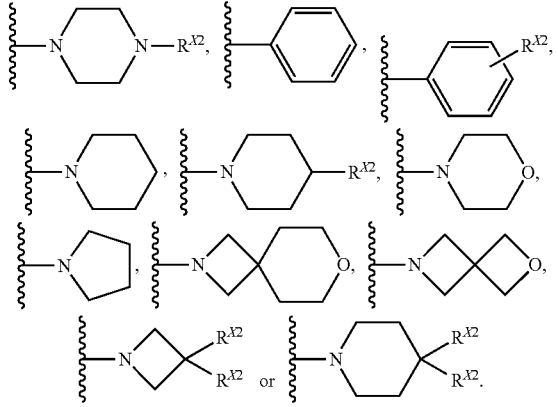

(1ggg) X is any of groups (1a)-(1o), wherein —$R^{X1}$ is

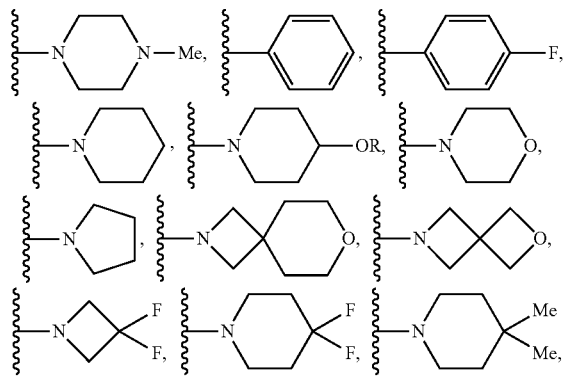

fluoro, bromo, methyl, —OR or —$CF_3$.

(1hhh) X is any of groups (1a)-(1o), wherein —$R^{X1}$ is

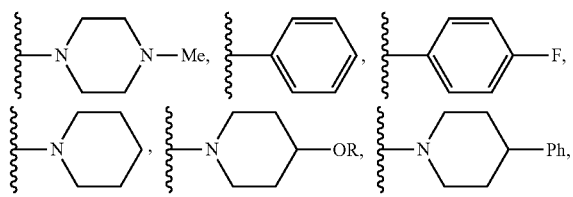

-continued

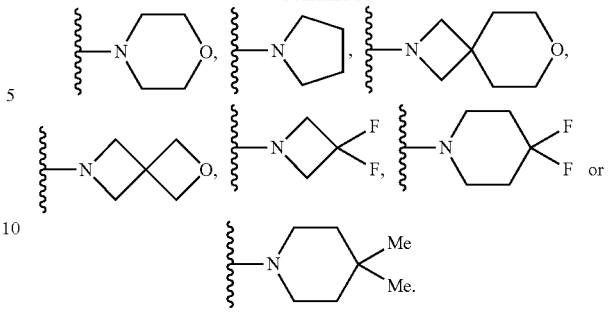

(1iii) X is any of groups (1a)-(1o), wherein —$R^{X1}$ is

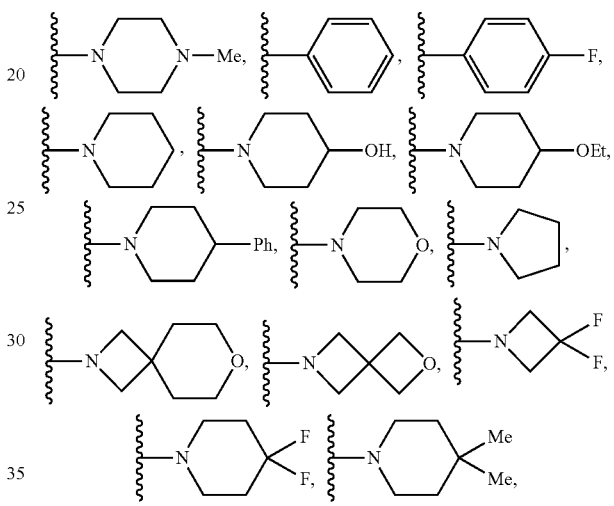

fluoro, bromo, methyl, —OMe or —$CF_3$.

(1jjj) X is any of groups (1a)-(1o), wherein —$R^{X1}$ is

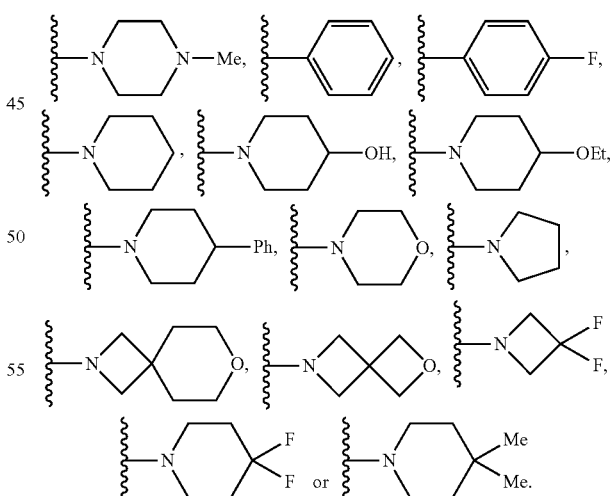

(1kkk) X is any of groups (1a)-(1o), wherein —$R^{X1}$ is independently halogen, cyano, $C_1$-$C_6$alkyl, $C_1$-$C_6$haloalkyl, —$C_1$-$C_6$alkoxy, —$C_1$-$C_6$haloalkoxy, oxo, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C (O)OR, —N(R)C(O)NR$_2$, —N(R)S(O)$_2$R, —OP(O)(OR)$_2$ or —CH$_2$—OP(O)(OR).
(1lll) X is any of groups (1a)-(1o), wherein —R$^{X1}$ is independently halogen, cyano, C$_1$-C$_6$alkyl, C$_1$-C$_6$haloalkyl, —C$_1$-C$_6$alkoxy, —C$_1$-C$_6$haloalkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR, —N(R)C(O)OR, —N(R)C(O)NR$_2$ or —N(R)S(O)$_2$R
(1mmm) X is any of groups (1a)-(1o), wherein —R$^{X1}$ is independently halogen, C$_1$-C$_6$alkyl, C$_1$-C$_6$haloalkyl, —C$_1$-C$_6$alkoxy, —C$_1$-C$_6$haloalkoxy, oxo, —OR, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$ or —N(R)S(O)$_2$R.
(1nnn) X is any of groups (1a)-(1o), wherein —R$^{X1}$ is independently halogen, C$_1$-C$_6$alkyl, C$_1$-C$_6$haloalkyl, —C$_1$-C$_6$alkoxy, —C$_1$-C$_6$haloalkoxy, oxo, —OR, —C(O)R, —C(O)OR, —C(O)NR$_2$, —OC(O)R, —N(R)C(O)R, —N(R)C(O)OR, —N(R)C(O)NR$_2$ or —N(R)S(O)$_2$R.
(1ooo) X is any of groups (1a)-(1o), wherein —R$^{X1}$ is independently halogen, C$_1$-C$_6$alkyl, C$_1$-C$_6$haloalkyl, —C$_1$-C$_6$alkoxy, —C$_1$-C$_6$haloalkoxy, oxo, —OR, —C(O)R, —C(O)OR, —C(O)NR$_2$, —N(R)C(O)R, —N(R)C(O)OR, —N(R)C(O)NR$_2$ or —N(R)S(O)$_2$R.
(1ppp) X is any of groups (1a)-(1o), wherein —R$^{X1}$ is independently halogen, C$_1$-C$_6$alkyl, C$_1$-C$_6$haloalkyl, —C$_1$-C$_6$haloalkoxy, oxo, —OR, —C(O)R, —C(O)OR or —C(O)NR$_2$.
(1qqq) X is any of groups (1a)-(1o), wherein —R$^{X1}$ is independently halogen, C$_1$-C$_6$alkyl, C$_1$-C$_6$haloalkyl, —C$_1$-C$_6$haloalkoxy, oxo or —OR.
(1rrr) X is any of groups (1a)-(1o), wherein —R$^{X1}$ is independently halogen, C$_1$-C$_6$alkyl, C$_1$-C$_6$haloalkyl, oxo or —OR.
(1sss) X is any of groups (1a)-(1o), wherein —R$^{X1}$ is independently halogen, C$_1$-C$_6$alkyl, oxo or —OR.
(1ttt) X is any of groups (1a)-(1o), wherein —R$^{X1}$ is independently halogen, C$_1$-C$_6$alkyl or oxo.
(1uuu) X is any of groups (1a)-(1o), wherein —R$^{X1}$ is independently halogen or C$_1$-C$_6$alkyl.
(1vvv) X is any of groups (1a)-(1o), wherein —R$^{X1}$ is halogen.
(1www) X is any of groups (1a)-(1fff) and (1kkk)-(1vvv), wherein —R$^{X1}$ is independently halogen, cyano, nitro, oxo, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, C$_1$-C$_6$haloalkyl or Ar
(1xxx) X is any of groups (1a)-(1fff) and (1kkk)-(1vvv), wherein —R$^{X2}$ is independently halogen, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, C$_1$-C$_6$alkyl, C$_1$-C$_6$haloalkyl or Ar.
(1yyy) X is any of groups (1a)-(1fff) and (1kkk)-(1vvv), wherein —R$^{X2}$ is independently halogen, —OR, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, C$_1$-C$_6$alkyl, C$_1$-C$_6$haloalkyl or Ar.
(1zzz) X is any of groups (1a)-(1fff) and (1kkk)-(1vvv), wherein —R$^{X2}$ is independently fluoro, —OR, —C$_1$-C$_6$alkyl, C$_1$-C$_6$haloalkyl or Ar.
(1aaaa) X is any of groups (1a)-(1fff) and (1kkk)-(1vvv), wherein —R$^x$ is independently halogen, —OR, —C$_1$-C$_6$alkyl or Ar.
(1bbbb) X is any of groups (1a)-(1fff) and (1kkk)-(1vvv), wherein —R$^{X2}$ is independently fluoro, —OR, methyl or phenyl,
(1cccc) X is any of groups (1a)-(1fff) and (1kkk)-(1vvv), wherein —R$^{X2}$ is independently fluoro, —OH, —OMe, methyl or phenyl.
(1dddd) X is any of groups (1a)-(1fff) and (1kkk)-(1vvv), wherein —R$^{X2}$ is independently halogen, —OR or C$_1$-C$_6$alkyl.
(1eeee) X is any of groups (1a)-(1fff) and (1kkk)-(1vvv), wherein —R$^{X2}$ is independently fluoro, —OR or methyl.
(1ffff) X is any of groups (1a)-(1fff) and (1kkk)-(1vvv), wherein —R$^{X2}$ is independently fluoro, —OH, —OMe or methyl.

I$^c$—Z is selected from one of the following groups (2a)-(2bbb):
(2a) Z is C$_1$-C$_6$alkyl, Ar(C$_0$-C$_6$alkyl) or Hca(C$_0$-C$_6$alkyl), each optionally substituted by 1, 2 or 3 —R$^{Z1}$ groups: wherein each —R$^{1'}$ is independently halogen, cyano, C$_1$-C$_6$alkyl, C$_1$-C$_6$haloalkyl, —C$_1$-C$_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).
(2b) Z is Ar(C$_0$-C$_6$alkyl) or Hca(C$_0$-C$_6$alkyl), each optionally substituted by 1, 2 or 3 —R$^{Z1}$ groups; wherein each —R$^{Z1}$ is independently halogen, cyano, C$_1$-C$_6$alkyl, C$_1$-C$_6$haloalkyl, —C$_1$-C$_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR. —N(R)C(O)NR$_2$, —N(R)S(O)$_2$R, —OP(O)(OR)$_2$ or —CH$_2$—OP(O)OR).
(2c) Z is according to group (2a), wherein C$_1$-C$_6$alkyl, Ar(C$_0$-C$_6$alkyl) or Hca(C$_0$-C$_6$alkyl) is optionally substituted by 1 or 2 —R$^{Z1}$ groups.
(2d) Z is according to group (2a), wherein C$_1$-C$_6$alkyl, Ar(C$_0$-C$_6$alkyl) or Hca(C$_0$-C$_6$alkyl) is optionally substituted by 1 —R$^{Z1}$ group.
(2e) Z is according to group (2a), wherein C$_1$-C$_6$alkyl, Ar(C$_0$-C$_6$alkyl) or Hca(C$_0$-C$_6$alkyl) is optionally substituted by 2 —R$^{Z1}$ groups.
(2f) Z is according to group (2a), wherein C$_1$-C$_6$alkyl, Ar(C$_0$-C$_6$alkyl) or Hca(C$_0$-C$_6$alkyl) is optionally substituted by 3 —R$^{Z1}$ groups.
(2g) Z is according to group (2a), wherein C$_1$-C$_6$alkyl, Ar(C$_0$-C$_6$alkyl) or Hca(C$_0$-C$_6$alkyl) is substituted by 1 or 2 —R$^{Z1}$ groups.
(2h) Z is according to group (2a), wherein C$_1$-C$_6$alkyl, Ar(C$_0$-C$_6$alkyl) or Hca(C$_0$-C$_6$alkyl) is substituted by 1 —R$^{Z1}$ group.
(2i) Z is according to group (2a), wherein C$_1$-C$_6$alkyl, Ar(C$_0$-C$_6$alkyl) or Hca(C$_0$-C$_6$alkyl) is substituted by 2 —R$^{Z1}$ groups.
(2j) Z is according to group (2b), wherein Ar(C$_0$-C$_6$alkyl) or Hca(C$_0$-C$_6$alkyl) is optionally substituted by 1 or 2 —R$^{Z1}$ groups.
(2k) Z is according to group (2b), wherein Ar(C$_0$-C$_6$alkyl) or Hca(C$_0$-C$_6$alkyl) is optionally substituted by 1 —R$^{Z1}$ group.

(2l) Z is according to group (2b), wherein Ar($C_0$-$C_6$alkyl) or Hca($C_0$-$C_6$alkyl) is optionally substituted by 2 —$R^{Z1}$ groups.
(2m) Z is according to group (2b), wherein Ar($C_0$-$C_6$alkyl) or Hca($C_0$-$C_6$alkyl) is optionally substituted by 3 —$R^{Z1}$ groups.
(2n) Z is according to group (2b), wherein Ar($C_0$-$C_6$alkyl) or Hca($C_0$-$C_6$alkyl) is substituted by 1 or 2 —$R^{Z1}$ groups.
(2o) Z is according to group (2b), wherein Ar($C_0$-$C_6$alkyl) or Hca($C_0$-$C_6$alkyl) is substituted by 1 —$R^{Z1}$ group.
(2p) Z is according to group (2b), wherein Ar($C_0$-$C_6$alkyl) or Hca($C_0$-$C_6$alkyl) is substituted by 2 —$R^{z1}$ groups.
(2q) Z is any of groups (2a)-(2p), wherein Z is Ar($C_0$-$C_6$alkyl) or Hca($C_0$-$C_6$alkyl).
(2r) Z is any of groups (2a)-(2p), wherein Z is $C_1$-$C_6$alkyl or Ar($C_0$-$C_6$alkyl).
(2s) Z is any of groups (2a)-(2p), wherein Z is $C_1$-$C_6$alkyl or Hca($C_1$-$C_6$alkyl).
(2t) Z is any of groups (2a)-(2p), wherein Z is Ar($C_0$-$C_6$alkyl) or Hca($C_0$-$C_6$alkyl).
(2u) Z is any of groups (2a)-(2p), wherein Z is $C_1$-$C_6$alkyl.
(2v) Z is any of groups (2a)-(2p), wherein Z is Ar($C_0$-$C_6$alkyl).
(2w) Z is any of groups (2a)-(2p), wherein Z is Hca($C_0$-$C_6$alkyl).
(2x) Z is any of groups (2a)-(2p), wherein Z is $C_1$-$C_{36}$alkyl, Ar($C_3$-$C_6$alkyl) or Hca($C_3$-$C_6$alkyl).
(2y) Z is any of groups (2a)-(2p), wherein Z is $C_1$-$C_3$alkyl or Ar($C_3$-$C_6$alkyl).
(2z) Z is any of groups (2a)-(2p), wherein Z is $C_1$-$C_3$alkyl or Hca($C_3$-$C_6$alkyl).
(2aa) Z is any of groups (2a)-(2p), wherein Z is Ar($C_3$-$C_6$alkyl) or Hca($C_3$-$C_6$alkyl).
(2bb) Z is any of groups (2a)-(2p), wherein Z is $C_1$-$C_3$alkyl.
(2cc) Z is any of groups (2a)-(2p), wherein Z is Ar($C_3$-$C_6$alkyl).
(2dd) Z is any of groups (2a)-(2p), wherein Z is Hca($C_3$-$C_6$alkyl).
(2ee) Z is any of groups (2a)-(2p), wherein Z is methyl, Ar($C_1$alkyl) or Hca($C_3$alkyl).
(2ff) Z is any of groups (2a)-(2p), wherein Z is methyl or Ar($C_1$alkyl).
(2gg) Z is any of groups (2a)-(2p), wherein Z is methyl or Hca($C_3$alkyl).
(2hh) Z is any of groups (2a)-(2p), wherein Z is Ar($C_1$alkyl) or Hca($C_3$alkyl).
(2ii) Z is any of groups (2a)-(2p), wherein Z is methyl.
(2jj) Z is any of groups (2a)-(2p), wherein Z is Ar($C_1$alkyl).
(2kk) Z is any of groups (2a)-(2p), wherein Z is Hca($C_3$alkyl).
(2ll) Z is any of groups (2a)-(2p), wherein Z is methyl, —$CH_2$-phenyl, —$(CH_2)_3$-morpholinyl or —$(CH_2)_3$-piperidinyl.
(2 mm) Z is any of groups (2a)-(2p), wherein Z is —$CH_2$-phenyl, —$(CH_2)_3$-morpholinyl or —$(CH_2)_3$-piperidinyl.
(2nn) Z is any of groups (2a)-(2p), wherein Z is methyl or —$CH_2$-phenyl.
(2oo) Z is any of groups (2a)-(2p), wherein Z is methyl.
(2pp) Z is any of groups (2a)-(2p), wherein Z is —$CH_2$-phenyl.
(2qq) Z is any of groups (2a)-(2p), wherein Z is —$(CH_2)_3$-morpholinyl or —$(CH_2)_3$— piperidinyl.
(2rr) Z is any of groups (2a)-(2p), wherein Z is —$(CH_2)_3$-morpholinyl.
(2ss) Z is any of groups (2a)-(2p), wherein Z is —$(CH_2)_3$-piperidinyl.
(2tt) Z is any of groups (2a)-(2ss), wherein —$R^{Z1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, —C(O)$NR_2$, —S(O)$_2NR_2$, —S(O)$_2$R, —OC(O)R, —N(R)C(O)R. —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR).
(2uu) Z is any of groups (2a)-(2ss), wherein —$R^{Z1}$ is independently halogen, $C_1$-$C_6$alkyl, $C_1$-$C_6$haloalkyl, —$C_1$-$C_6$alkoxy, oxo, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$ or —N(R)S(O)$_2$R.
(2vv) Z is any of groups (2a)-(2ss), wherein —$R^{Z1}$ is independently halogen, $C_1$-$C_6$alkyl, $C_1$-$C_6$haloalkyl, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$ or —N(R)S(O)$_2$R.
(2ww) Z is any of groups (2a)-(2ss), wherein —$R^{Z1}$ is independently halogen, $C_1$-$C_6$alkyl, $C_1$-$C_6$haloalkyl, —OR, $NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$ or —N(R)S(O)$_2$R.
(2xx) Z is any of groups (2a)-(2ss), wherein —$R^{Z1}$ is independently halogen, $C_1$-$C_6$alkyl, $C_1$-$C_6$haloalkyl, —OR, —$NR_2$, —S(O)$_2NR_2$ or —S(O)$_2$R.
(2yy) Z is any of groups (2a)-(2ss), wherein —$R^{Z1}$ is independently halogen, $C_1$-$C_6$alkyl, $C_1$-$C_6$haloalkyl or —OR.
(2zz) Z is any of groups (2a)-(2ss), wherein —$R^{Z1}$ is independently halogen, $C_1$-$C_6$alkyl or —OR.
(2aaa) Z is any of groups (2a)-(2ss), wherein —$R^{Z1}$ is independently halogen or $C_1$-$C_6$alkyl.
(2bbb) Z is any of groups (2a)-(2ss), wherein —$R^{Z1}$ is independently $C_1$-$C_6$alkyl or —OR.

$I^d$—$R^1$ is selected from one of the following groups (3a)-(3h):
(3a) $R^1$ is hydrogen or $C_1$-$C_6$alkyl.
(3b) $R^1$ is hydrogen, methyl, ethyl, propyl, isopropyl, or butyl.
(3c) $R^1$ is methyl, ethyl, propyl, isopropyl, or butyl.
(3d) $R^1$ is hydrogen, methyl, ethyl, propyl or isopropyl.
(3e) $R^1$ is hydrogen, methyl or ethyl.
(3f) $R^1$ is hydrogen or methyl.
(3g) $R^1$ is methyl.
(3h) $R^1$ is hydrogen.

Particular embodiments of this aspect of the invention comprise compounds of any one of the formulae (I) and (1a)-(1o), each as defined in each of the following rows (or a pharmaceutically acceptable salt, prodrug, or N-oxide thereof, or a solvate or hydrate thereof), wherein each entry is a group number as defined above (e.g., (2aa) refers to Z is methyl, and a dash "-" indicates that the variable is as defined in embodiment $I_1$ or defined according to any one of the applicable variable definitions (1a)-(3h) [e.g., when Z is a dash, it can be either as defined in any of embodiments $I_1$-$I_{10}$ or any one of definitions (2a)-(2tt)]):

|         | (I)   | X       | Z      | R¹   |
|---------|-------|---------|--------|------|
| (1)-1   | (Ia)  | (1a)    | (2a)   | (3a) |
| (1)-2   | (Ia)  | (1c)    | (2b)   | (3b) |
| (1)-3   | (Ia)  | (1d)    | (2x)   | (3c) |
| (1)-4   | (Ia)  | (1h)    | (2aa)  | (3d) |
| (1)-5   | (Ia)  | (1i)    | (2bb)  | (3e) |
| (1)-6   | (Ia)  | (1j)    | (2cc)  | (3f) |
| (1)-7   | (Ia)  | (1k)    | (2dd)  | (3g) |
| (1)-8   | (Ia)  | (1l)    | (2kk)  | (3h) |
| (1)-9   | (Ia)  | (1m)    | (2ll)  | (3e) |
| (1)-10  | (Ia)  | (1n)    | (2mm)  | (3a) |
| (1)-11  | (Ia)  | (1o)    | (2rr)  | (3b) |
| (1)-12  | (Ia)  | (1p)    | (2ss)  | (3c) |
| (1)-13  | (Ia)  | (1x)    | (2tt)  | (3d) |
| (1)-14  | (Ia)  | (1ee)   | (2a)   | (3e) |
| (1)-15  | (Ia)  | (1jj)   | (2b)   | (3f) |
| (1)-16  | (Ia)  | (1kk)   | (2x)   | (3g) |
| (1)-17  | (Ia)  | (1nn)   | (2rr)  | (3h) |
| (1)-18  | (Ia)  | (1rr)   | (2ss)  | (3a) |
| (1)-19  | (Ia)  | (1eee)  | (2tt)  | (3b) |
| (1)-20  | (Ia)  | (1ggg)  | (2b)   | (3c) |
| (1)-21  | (Ia)  | (1hhh)  | (2x)   | (3d) |
| (1)-22  | (Ia)  | (1www)  | (2rr)  | (3e) |
| (1)-23  | (Ia)  | (1aaaa) | (2rr)  | (3f) |
| (1)-24  | (Ia)  | (1bbbb) | (2ss)  | (3g) |
| (1)-25  | (Ia)  | (1j)    | (2cc)  | (3f) |
| (1)-26  | (Ia)  | (1k)    | (2aa)  | (3d) |
| (1)-27  | (Ia)  | (1x)    | (2bb)  | (3e) |
| (1)-28  | (Ia)  | (1ee)   | (2ss)  | (3e) |
| (1)-29  | (Ia)  | (1d)    | (2x)   | (3d) |
| (1)-30  | (Ia)  | (1h)    | (2aa)  | (3e) |
| (1)-31  | (Ia)  | (1i)    | (2bb)  | (3f) |
| (1)-32  | (Ia)  | (1l)    | (2bb)  | (3g) |
| (1)-33  | (Ia)  | (1m)    | (2cc)  | (3a) |
| (1)-34  | (Ia)  | (1n)    | (2dd)  | (3b) |
| (1)-35  | (Ia)  | (1o)    | (2kk)  | (3d) |
| (1)-36  | (Ia)  | (1p)    | (2rr)  | (3e) |
| (1)-37  | (Ia)  | (1x)    | (2ss)  | (3e) |
| (1)-38  | (Ia)  | (1ee)   | (2mm)  | (3f) |
| (1)-39  | (Ia)  | (1jj)   | (2rr)  | (3g) |
| (1)-40  | (Ia)  | (1kk)   | (2a)   | (3h) |
| (1)-41  | (Ia)  | (1nn)   | (2b)   | (3f) |
| (1)-42  | (Ia)  | (1ggg)  | (2x)   | (3d) |
| (1)-43  | (Ia)  | (1hhh)  | (2ss)  | (3e) |
| (1)-44  | (Ib)  | (1a)    | (2a)   | (3a) |
| (1)-45  | (Ib)  | (1c)    | (2b)   | (3b) |
| (1)-46  | (Ib)  | (1d)    | (2x)   | (3c) |
| (1)-47  | (Ib)  | (1h)    | (2aa)  | (3d) |
| (1)-48  | (Ib)  | (1i)    | (2bb)  | (3e) |
| (1)-49  | (Ib)  | (1j)    | (2cc)  | (3f) |
| (1)-50  | (Ib)  | (1k)    | (2dd)  | (3g) |
| (1)-51  | (Ib)  | (1l)    | (2kk)  | (3h) |
| (1)-52  | (Ib)  | (1m)    | (2ll)  | (3e) |
| (1)-53  | (Ib)  | (1n)    | (2mm)  | (3a) |
| (1)-54  | (Ib)  | (1o)    | (2rr)  | (3b) |
| (1)-55  | (Ib)  | (1p)    | (2ss)  | (3c) |
| (1)-56  | (Ib)  | (1x)    | (2tt)  | (3d) |
| (1)-57  | (Ib)  | (1ee)   | (2a)   | (3e) |
| (1)-58  | (Ib)  | (1jj)   | (2b)   | (3f) |
| (1)-59  | (Ib)  | (1kk)   | (2x)   | (3g) |
| (1)-60  | (Ib)  | (1nn)   | (2rr)  | (3h) |
| (1)-61  | (Ib)  | (1rr)   | (2ss)  | (3a) |
| (1)-62  | (Ib)  | (1eee)  | (2tt)  | (3b) |
| (1)-63  | (Ib)  | (1ggg)  | (2b)   | (3c) |
| (1)-64  | (Ib)  | (1hhh)  | (2x)   | (3d) |
| (1)-65  | (Ib)  | (1www)  | (2rr)  | (3e) |
| (1)-66  | (Ib)  | (1aaaa) | (2rr)  | (3f) |
| (1)-67  | (Ib)  | (1bbbb) | (2ss)  | (3g) |
| (1)-68  | (Ib)  | (1j)    | (2cc)  | (3f) |
| (1)-69  | (Ib)  | (1k)    | (2aa)  | (3d) |
| (1)-70  | (Ib)  | (1x)    | (2bb)  | (3e) |
| (1)-71  | (Ib)  | (1ee)   | (2ss)  | (3e) |
| (1)-72  | (Ib)  | (1d)    | (2x)   | (3d) |
| (1)-73  | (Ib)  | (1h)    | (2aa)  | (3e) |
| (1)-74  | (Ib)  | (1i)    | (2bb)  | (3f) |
| (1)-75  | (Ib)  | (1l)    | (2bb)  | (3g) |
| (1)-76  | (Ib)  | (1m)    | (2cc)  | (3a) |
| (1)-77  | (Ib)  | (1n)    | (2dd)  | (3b) |
| (1)-78  | (Ib)  | (1o)    | (2kk)  | (3d) |
| (1)-79  | (Ib)  | (1p)    | (2rr)  | (3e) |
| (1)-80  | (Ib)  | (1x)    | (2ss)  | (3e) |
| (1)-81  | (Ib)  | (1ee)   | (2mm)  | (3f) |
| (1)-82  | (Ib)  | (1jj)   | (2rr)  | (3g) |
| (1)-83  | (Ib)  | (1kk)   | (2a)   | (3h) |
| (1)-84  | (Ib)  | (1nn)   | (2b)   | (3f) |
| (1)-85  | (Ib)  | (1ggg)  | (2x)   | (3d) |
| (1)-86  | (Ib)  | (1hhh)  | (2ss)  | (3e) |
| (1)-87  | (Ic)  | (1a)    | (2a)   | (3a) |
| (1)-88  | (Ic)  | (1c)    | (2b)   | (3b) |
| (1)-89  | (Ic)  | (1d)    | (2x)   | (3c) |
| (1)-90  | (Ic)  | (1h)    | (2aa)  | (3d) |
| (1)-91  | (Ic)  | (1i)    | (2bb)  | (3e) |
| (1)-92  | (Ic)  | (1j)    | (2cc)  | (3f) |
| (1)-93  | (Ic)  | (1k)    | (2dd)  | (3g) |
| (1)-94  | (Ic)  | (1l)    | (2kk)  | (3h) |
| (1)-95  | (Ic)  | (1m)    | (2ll)  | (3e) |
| (1)-96  | (Ic)  | (1n)    | (2mm)  | (3a) |
| (1)-97  | (Ic)  | (1o)    | (2rr)  | (3b) |
| (1)-98  | (Ic)  | (1p)    | (2ss)  | (3c) |
| (1)-99  | (Ic)  | (1x)    | (2tt)  | (3d) |
| (1)-100 | (Ic)  | (1ee)   | (2a)   | (3e) |
| (1)-101 | (Ic)  | (1jj)   | (2b)   | (3f) |
| (1)-102 | (Ic)  | (1kk)   | (2x)   | (3g) |
| (1)-103 | (Ic)  | (1nn)   | (2rr)  | (3h) |
| (1)-104 | (Ic)  | (1rr)   | (2ss)  | (3a) |
| (1)-105 | (Ic)  | (1eee)  | (2tt)  | (3b) |
| (1)-106 | (Ic)  | (1ggg)  | (2b)   | (3c) |
| (1)-107 | (Ic)  | (1hhh)  | (2x)   | (3d) |
| (1)-108 | (Ic)  | (1www)  | (2rr)  | (3e) |
| (1)-109 | (Ic)  | (1aaaa) | (2rr)  | (3f) |
| (1)-110 | (Ic)  | (1bbbb) | (2ss)  | (3g) |
| (1)-111 | (Ic)  | (1j)    | (2cc)  | (3f) |
| (1)-112 | (Ic)  | (1k)    | (2aa)  | (3d) |
| (1)-113 | (Ic)  | (1x)    | (2bb)  | (3e) |
| (1)-114 | (Ic)  | (1ee)   | (2ss)  | (3e) |
| (1)-115 | (Ic)  | (1d)    | (2x)   | (3d) |
| (1)-116 | (Ic)  | (1h)    | (2aa)  | (3e) |
| (1)-117 | (Ic)  | (1i)    | (2bb)  | (3f) |
| (1)-118 | (Ic)  | (1l)    | (2bb)  | (3g) |
| (1)-119 | (Ic)  | (1m)    | (2cc)  | (3a) |
| (1)-120 | (Ic)  | (1n)    | (2dd)  | (3b) |
| (1)-121 | (Ic)  | (1o)    | (2kk)  | (3d) |
| (1)-122 | (Ic)  | (1p)    | (2rr)  | (3e) |
| (1)-123 | (Ic)  | (1x)    | (2ss)  | (3e) |
| (1)-124 | (Ic)  | (1ee)   | (2mm)  | (3f) |
| (1)-125 | (Ic)  | (1jj)   | (2rr)  | (3g) |
| (1)-126 | (Ic)  | (1kk)   | (2a)   | (3h) |
| (1)-127 | (Ic)  | (1nn)   | (2b)   | (3f) |
| (1)-128 | (Ic)  | (1ggg)  | (2x)   | (3d) |
| (1)-129 | (Ic)  | (1hhh)  | (2ss)  | (3e) |
| (1)-130 | (Id)  | (1a)    | (2a)   | (3a) |
| (1)-131 | (Id)  | (1c)    | (2b)   | (3b) |
| (1)-132 | (Id)  | (1d)    | (2x)   | (3c) |
| (1)-133 | (Id)  | (1h)    | (2aa)  | (3d) |
| (1)-134 | (Id)  | (1i)    | (2bb)  | (3e) |
| (1)-135 | (Id)  | (1j)    | (2cc)  | (3f) |
| (1)-136 | (Id)  | (1k)    | (2dd)  | (3g) |
| (1)-137 | (Id)  | (1l)    | (2kk)  | (3h) |
| (1)-138 | (Id)  | (1m)    | (2ll)  | (3e) |
| (1)-139 | (Id)  | (1n)    | (2mm)  | (3a) |
| (1)-140 | (Id)  | (1o)    | (2rr)  | (3b) |
| (1)-141 | (Id)  | (1p)    | (2ss)  | (3c) |
| (1)-142 | (Id)  | (1x)    | (2tt)  | (3d) |
| (1)-143 | (Id)  | (1ee)   | (2a)   | (3e) |
| (1)-144 | (Id)  | (1jj)   | (2b)   | (3f) |
| (1)-145 | (Id)  | (1kk)   | (2x)   | (3g) |
| (1)-146 | (Id)  | (1nn)   | (2rr)  | (3h) |
| (1)-147 | (Id)  | (1rr)   | (2ss)  | (3a) |
| (1)-148 | (Id)  | (1eee)  | (2tt)  | (3b) |
| (1)-149 | (Id)  | (1ggg)  | (2b)   | (3c) |
| (1)-150 | (Id)  | (1hhh)  | (2x)   | (3d) |
| (1)-151 | (Id)  | (1www)  | (2rr)  | (3e) |
| (1)-152 | (Id)  | (1aaaa) | (2rr)  | (3f) |
| (1)-153 | (Id)  | (1bbbb) | (2ss)  | (3g) |
| (1)-154 | (Id)  | (1j)    | (2cc)  | (3f) |
| (1)-155 | (Id)  | (1k)    | (2aa)  | (3d) |
| (1)-156 | (Id)  | (1x)    | (2bb)  | (3e) |

|  | (I) | X | Z | R¹ |
|---|---|---|---|---|
| (1)-157 | (Id) | (1ee) | (2ss) | (3e) |
| (1)-158 | (Id) | (1d) | (2x) | (3d) |
| (1)-159 | (Id) | (1h) | (2aa) | (3e) |
| (1)-160 | (Id) | (1i) | (2bb) | (3f) |
| (1)-161 | (Id) | (1l) | (2bb) | (3g) |
| (1)-162 | (Id) | (1m) | (2cc) | (3a) |
| (1)-163 | (Id) | (1n) | (2dd) | (3b) |
| (1)-164 | (Id) | (1o) | (2kk) | (3d) |
| (1)-165 | (Id) | (1p) | (2rr) | (3e) |
| (1)-166 | (Id) | (1x) | (2ss) | (3e) |
| (1)-167 | (Id) | (1ee) | (2mm) | (3f) |
| (1)-168 | (Id) | (1jj) | (2rr) | (3g) |
| (1)-169 | (Id) | (1kk) | (2a) | (3h) |
| (1)-170 | (Id) | (1nn) | (2b) | (3f) |
| (1)-171 | (Id) | (1ggg) | (2x) | (3d) |
| (1)-172 | (Id) | (1hhh) | (2ss) | (3e) |
| (1)-173 | (Ig) | (1a) | (2a) | (3a) |
| (1)-174 | (Ig) | (1c) | (2b) | (3b) |
| (1)-175 | (Ig) | (1d) | (2x) | (3c) |
| (1)-176 | (Ig) | (1h) | (2aa) | (3d) |
| (1)-177 | (Ig) | (1i) | (2bb) | (3e) |
| (1)-178 | (Ig) | (1j) | (2cc) | (3f) |
| (1)-179 | (Ig) | (1k) | (2dd) | (3g) |
| (1)-180 | (Ig) | (1l) | (2kk) | (3h) |
| (1)-181 | (Ig) | (1m) | (2ll) | (3e) |
| (1)-182 | (Ig) | (1n) | (2mm) | (3a) |
| (1)-183 | (Ig) | (1o) | (2rr) | (3b) |
| (1)-184 | (Ig) | (1p) | (2ss) | (3c) |
| (1)-185 | (Ig) | (1x) | (2tt) | (3d) |
| (1)-186 | (Ig) | (1ee) | (2a) | (3e) |
| (1)-187 | (Ig) | (1jj) | (2b) | (3f) |
| (1)-188 | (Ig) | (1kk) | (2x) | (3g) |
| (1)-189 | (Ig) | (1nn) | (2rr) | (3h) |
| (1)-190 | (Ig) | (1rr) | (2ss) | (3a) |
| (1)-191 | (Ig) | (1eee) | (2tt) | (3b) |
| (1)-192 | (Ig) | (1ggg) | (2b) | (3c) |
| (1)-193 | (Ig) | (1hhh) | (2x) | (3d) |
| (1)-194 | (Ig) | (1www) | (2rr) | (3e) |
| (1)-195 | (Ig) | (1aaaa) | (2rr) | (3f) |
| (1)-196 | (Ig) | (1bbbb) | (2ss) | (3g) |
| (1)-197 | (Ig) | (1j) | (2cc) | (3f) |
| (1)-198 | (Ig) | (1k) | (2aa) | (3d) |
| (1)-199 | (Ig) | (1x) | (2bb) | (3e) |
| (1)-200 | (Ig) | (1ee) | (2ss) | (3e) |
| (1)-201 | (Ig) | (1d) | (2x) | (3d) |
| (1)-202 | (Ig) | (1h) | (2aa) | (3e) |
| (1)-203 | (Ig) | (1i) | (2bb) | (3f) |
| (1)-204 | (Ig) | (1l) | (2bb) | (3g) |
| (1)-205 | (Ig) | (1m) | (2cc) | (3a) |
| (1)-206 | (Ig) | (1n) | (2dd) | (3b) |
| (1)-207 | (Ig) | (1o) | (2kk) | (3d) |
| (1)-208 | (Ig) | (1p) | (2rr) | (3e) |
| (1)-209 | (Ig) | (1x) | (2ss) | (3e) |
| (1)-210 | (Ig) | (1ee) | (2mm) | (3f) |
| (1)-211 | (Ig) | (1jj) | (2rr) | (3g) |
| (1)-212 | (Ig) | (1kk) | (2a) | (3h) |
| (1)-213 | (Ig) | (1nn) | (2b) | (3f) |
| (1)-214 | (Ig) | (1ggg) | (2x) | (3d) |
| (1)-215 | (Ig) | (1hhh) | (2ss) | (3e) |
| (1)-216 | (Ih) | (1a) | (2a) | (3a) |
| (1)-217 | (Ih) | (1c) | (2b) | (3b) |
| (1)-218 | (Ih) | (1d) | (2x) | (3c) |
| (1)-219 | (Ih) | (1h) | (2aa) | (3d) |
| (1)-220 | (Ih) | (1i) | (2bb) | (3e) |
| (1)-221 | (Ih) | (1j) | (2cc) | (3f) |
| (1)-222 | (Ih) | (1k) | (2dd) | (3g) |
| (1)-223 | (Ih) | (1l) | (2kk) | (3h) |
| (1)-224 | (Ih) | (1m) | (2ll) | (3e) |
| (1)-225 | (Ih) | (1n) | (2mm) | (3a) |
| (1)-226 | (Ih) | (1o) | (2rr) | (3b) |
| (1)-227 | (Ih) | (1p) | (2ss) | (3c) |
| (1)-228 | (Ih) | (1x) | (2tt) | (3d) |
| (1)-229 | (Ih) | (1ee) | (2a) | (3e) |
| (1)-230 | (Ih) | (1jj) | (2b) | (3f) |
| (1)-231 | (Ih) | (1kk) | (2x) | (3g) |
| (1)-232 | (Ih) | (1nn) | (2rr) | (3h) |
| (1)-233 | (Ih) | (1rr) | (2ss) | (3a) |
| (1)-234 | (Ih) | (1eee) | (2tt) | (3b) |
| (1)-235 | (Ih) | (1ggg) | (2b) | (3c) |
| (1)-236 | (Ih) | (1hhh) | (2x) | (3d) |
| (1)-237 | (Ih) | (1www) | (2rr) | (3e) |
| (1)-238 | (Ih) | (1aaaa) | (2rr) | (3f) |
| (1)-239 | (Ih) | (1bbbb) | (2ss) | (3g) |
| (1)-240 | (Ih) | (1j) | (2cc) | (3f) |
| (1)-241 | (Ih) | (1k) | (2aa) | (3d) |
| (1)-242 | (Ih) | (1x) | (2bb) | (3e) |
| (1)-243 | (Ih) | (1ee) | (2ss) | (3e) |
| (1)-244 | (Ih) | (1d) | (2x) | (3d) |
| (1)-245 | (Ih) | (1h) | (2aa) | (3e) |
| (1)-246 | (Ih) | (1i) | (2bb) | (3f) |
| (1)-247 | (Ih) | (1l) | (2bb) | (3g) |
| (1)-248 | (Ih) | (1m) | (2cc) | (3a) |
| (1)-249 | (Ih) | (1n) | (2dd) | (3b) |
| (1)-250 | (Ih) | (1o) | (2kk) | (3d) |
| (1)-251 | (Ih) | (1p) | (2rr) | (3e) |
| (1)-252 | (Ih) | (1x) | (2ss) | (3e) |
| (1)-253 | (Ih) | (1ee) | (2mm) | (3f) |
| (1)-254 | (Ih) | (1jj) | (2rr) | (3g) |
| (1)-255 | (Ih) | (1kk) | (2a) | (3h) |
| (1)-256 | (Ih) | (1nn) | (2b) | (3f) |
| (1)-257 | (Ih) | (1ggg) | (2x) | (3d) |
| (1)-258 | (Ih) | (1hhh) | (2ss) | (3e) |
| (1)-259 | (Io) | (1a) | (2a) | (3a) |
| (1)-260 | (Io) | (1c) | (2b) | (3b) |
| (1)-261 | (Io) | (1d) | (2x) | (3c) |
| (1)-262 | (Io) | (1h) | (2aa) | (3d) |
| (1)-263 | (Io) | (1i) | (2bb) | (3e) |
| (1)-264 | (Io) | (1j) | (2cc) | (3f) |
| (1)-265 | (Io) | (1k) | (2dd) | (3g) |
| (1)-266 | (Io) | (1l) | (2kk) | (3h) |
| (1)-267 | (Io) | (1m) | (2ll) | (3e) |
| (1)-268 | (Io) | (1n) | (2mm) | (3a) |
| (1)-269 | (Io) | (1o) | (2rr) | (3b) |
| (1)-270 | (Io) | (1p) | (2ss) | (3c) |
| (1)-271 | (Io) | (1x) | (2tt) | (3d) |
| (1)-272 | (Io) | (1ee) | (2a) | (3e) |
| (1)-273 | (Io) | (1jj) | (2b) | (3f) |
| (1)-274 | (Io) | (1kk) | (2x) | (3g) |
| (1)-275 | (Io) | (1nn) | (2rr) | (3h) |
| (1)-276 | (Io) | (1rr) | (2ss) | (3a) |
| (1)-277 | (Io) | (1eee) | (2tt) | (3b) |
| (1)-278 | (Io) | (1ggg) | (2b) | (3c) |
| (1)-279 | (Io) | (1hhh) | (2x) | (3d) |
| (1)-280 | (Io) | (1www) | (2rr) | (3e) |
| (1)-281 | (Io) | (1aaaa) | (2rr) | (3f) |
| (1)-282 | (Io) | (1bbbb) | (2ss) | (3g) |
| (1)-283 | (Io) | (1j) | (2cc) | (3f) |
| (1)-284 | (Io) | (1k) | (2aa) | (3d) |
| (1)-285 | (Io) | (1x) | (2bb) | (3e) |
| (1)-286 | (Io) | (1ee) | (2ss) | (3e) |
| (1)-287 | (Io) | (1d) | (2x) | (3d) |
| (1)-288 | (Io) | (1h) | (2aa) | (3e) |
| (1)-289 | (Io) | (1i) | (2bb) | (3f) |
| (1)-290 | (Io) | (1l) | (2bb) | (3g) |
| (1)-291 | (Io) | (1m) | (2cc) | (3a) |
| (1)-292 | (Io) | (1n) | (2dd) | (3b) |
| (1)-293 | (Io) | (1o) | (2kk) | (3d) |
| (1)-294 | (Io) | (1p) | (2rr) | (3e) |
| (1)-295 | (Io) | (1x) | (2ss) | (3e) |
| (1)-296 | (Io) | (1ee) | (2mm) | (3f) |
| (1)-297 | (Io) | (1jj) | (2rr) | (3g) |
| (1)-298 | (Io) | (1kk) | (2a) | (3h) |
| (1)-299 | (Io) | (1nn) | (2b) | (3f) |
| (1)-300 | (Io) | (1ggg) | (2x) | (3d) |

In some embodiments, the compound of formulae (I) or (Ia)-(Io) is one of the following compounds (or a pharmaceutically acceptable salt, prodrug, or N-oxide thereof, or a solvate or hydrate thereof):

| No. | Structure | Name |
|---|---|---|
| 1 | 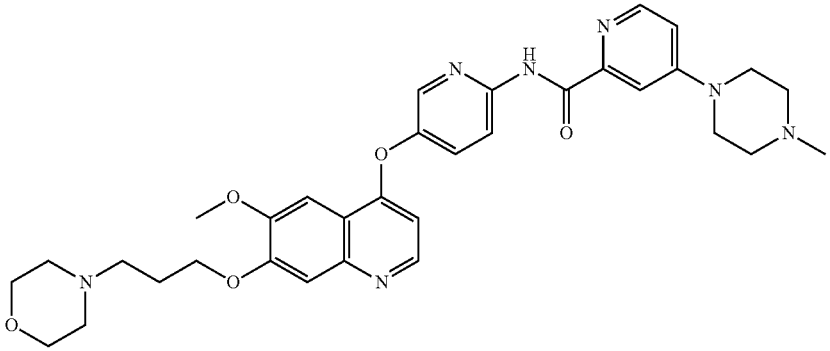 [SMILES: COc1cc2c(Oc3ccc(NC(=O)c4cc(N5CCN(C)CC5)ccn4)nc3)ccnc2cc1OCCCN1CCOCC1] | N-(5-((6-Methoxy-7-(3-morpholinopropoxy)quinolin-4-yl)oxy)pyridin-2-yl)-4-(4-methylpiperazin-1-yl)picolinamide |
| 2 | 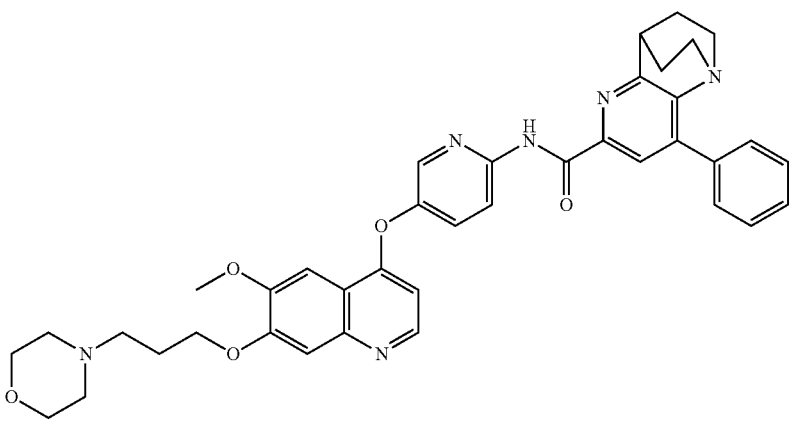 [SMILES: COc1cc2c(Oc3ccc(NC(=O)c4cc(-c5ccccc5)c5c(n4)C4CCN5CC4)nc3)ccnc2cc1OCCCN1CCOCC1] | N-(5-((6-Methoxy-7-(3-morpholinopropoxy)quinolin-4-yl)oxy)pyridin-2-yl)-8-phenyl-3,4-dihydro-2H-1,4-ethano-1,5-naphthyridine-6-carboxamide |
| 3 | 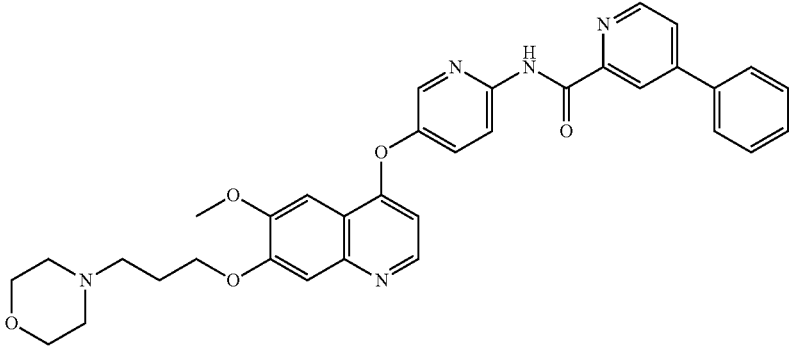 [SMILES: COc1cc2c(Oc3ccc(NC(=O)c4cc(-c5ccccc5)ccn4)nc3)ccnc2cc1OCCCN1CCOCC1] | N-(5-((6-Methoxy-7-(3-morpholinopropoxy)quinolin-4-yl)oxy)pyridin-2-yl)-4-phenylpicolinamide |
| 4 | 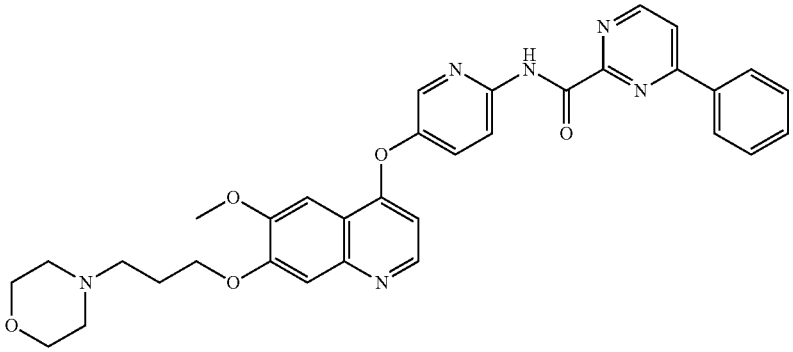 [SMILES: COc1cc2c(Oc3ccc(NC(=O)c4nccc(-c5ccccc5)n4)nc3)ccnc2cc1OCCCN1CCOCC1] | N-(5-((6-Methoxy-7-(3-morpholinopropoxy)quinolin-4-yl)oxy)pyridin-2-yl)-4-phenylpyrimidine-2-carboxamide |

-continued

| No. | Structure | Name |
|-----|-----------|------|
| 5 | 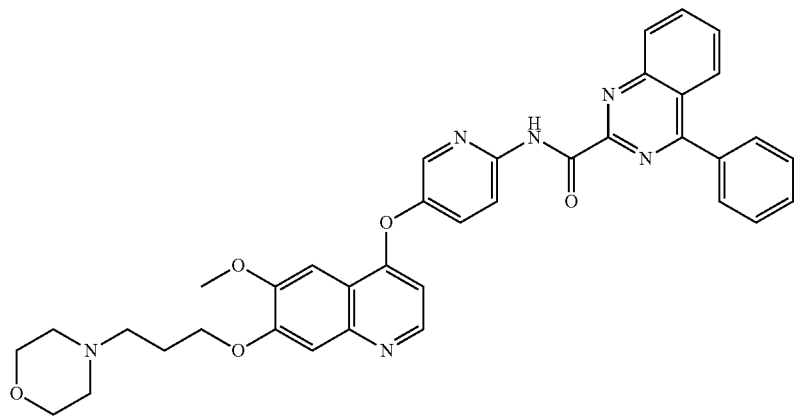 [SMILES: COc1cc2c(Oc3ccc(NC(=O)c4nc(-c5ccccc5)c5ccccc5n4)nc3)ccnc2cc1OCCCN1CCOCC1] | N-(5-((6-Methoxy-7-(3-morpholinopropoxy)quinolin-4-yl)oxy)pyridin-2-yl)-4-phenylquinazoline-2-carboxamide |
| 6 | 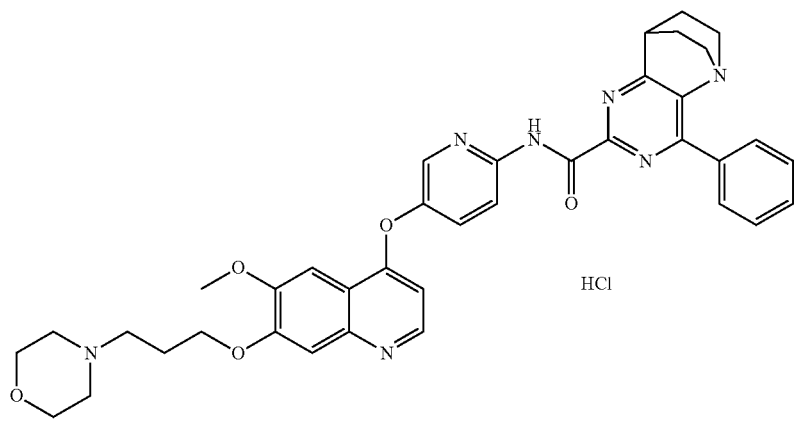 [SMILES: COc1cc2c(Oc3ccc(NC(=O)c4nc(-c5ccccc5)c5c(n4)C4CCN5CC4)nc3)ccnc2cc1OCCCN1CCOCC1 ; Cl] HCl | N-(5-((6-methoxy-7-(3-morpholinopropoxy)quinolin-4-yl)oxy)pyridin-2-yl)-4-phenyl-7,8-dihydro-6H-5,8-ethanopyrido[3,2-d]pyrimidine-2-carboxamide, hydrochloric acid |
| 7 | 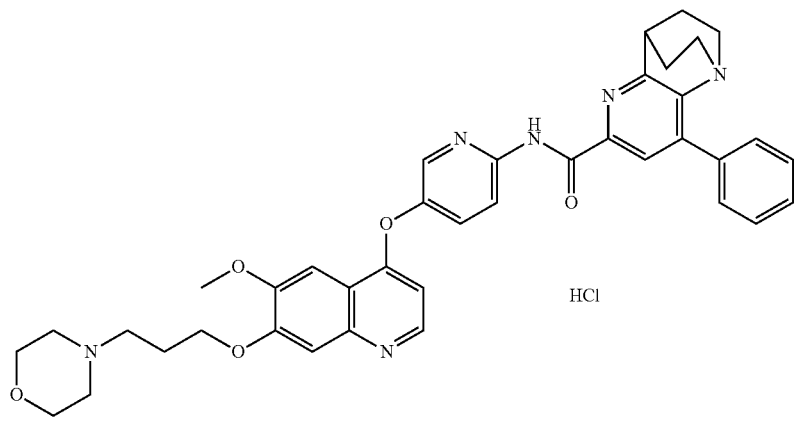 [SMILES: COc1cc2c(Oc3ccc(NC(=O)c4cc(-c5ccccc5)c5c(n4)C4CCN5CC4)nc3)ccnc2cc1OCCCN1CCOCC1 ; Cl] HCl | N-(5-((6-Methoxy-7-(3-morpholinopropoxy)quinolin-4-yl)oxy)pyridin-2-yl)-8-phenyl-3,4-dihydro-2H-1,4-ethano-1,5-naphthyridine-6-carboxamide, hydrochloric acid |
| 8 | 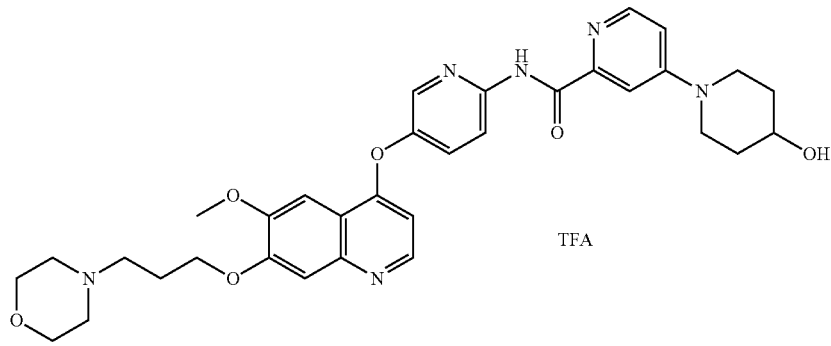 [SMILES: COc1cc2c(Oc3ccc(NC(=O)c4cc(N5CCC(O)CC5)ccn4)nc3)ccnc2cc1OCCCN1CCOCC1 ; "TFA"] TFA | 4-(4-Hydroxypiperidin-1-yl)-N-(5-((6-methoxy-7-(3-morpholinopropoxy)quinolin-4-yl)oxy)pyridin-2-yl)picolinamide, trifluoroacetic acid |

| No. | Structure | Name |
|---|---|---|
| 9 | 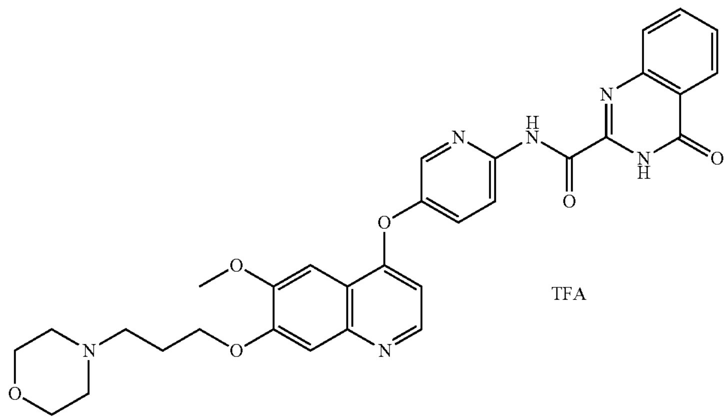 [SMILES: COc1cc2c(Oc3ccc(NC(=O)c4nc5ccccc5c(=O)[nH]4)nc3)ccnc2cc1OCCCN1CCOCC1 ; "TFA"] | N-(5-(((6-Methoxy-7-(3-morpholinopropoxy)quinolin-4-yl)oxy)pyridin-2-yl)-4-oxo-3,4-dihydroquinazoline-2-carboxamide, trifluoroacetic acid |
| 10 | 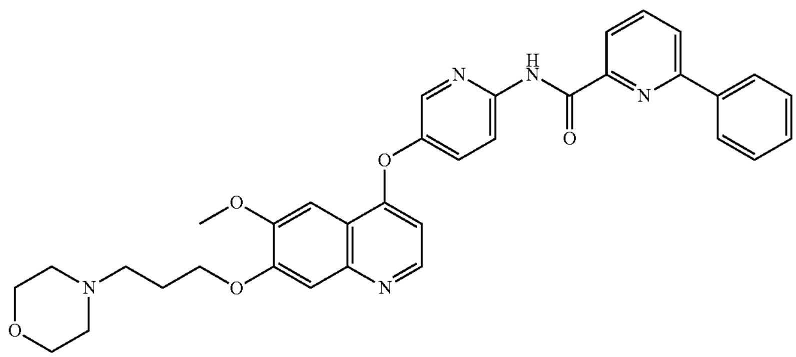 [SMILES: COc1cc2c(Oc3ccc(NC(=O)c4cccc(-c5ccccc5)n4)nc3)ccnc2cc1OCCCN1CCOCC1] | N-(5-(((6-Methoxy-7-(3-morpholinopropoxy)quinolin-4-yl)oxy)pyridin-2-yl)-6-phenylpicolinamide |
| 11 | 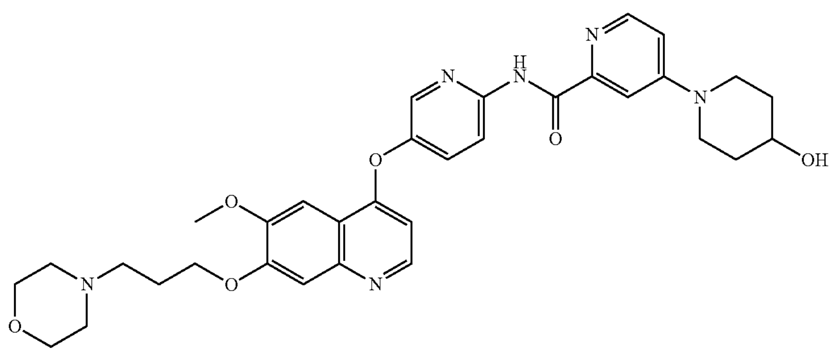 [SMILES: COc1cc2c(Oc3ccc(NC(=O)c4cc(N5CCC(O)CC5)ccn4)nc3)ccnc2cc1OCCCN1CCOCC1] | 4-(4-Hydroxypiperidin-1-yl)-N-(5-(((6-methoxy-7-(3-morpholinopropoxy)quinolin-4-yl)oxy)pyridin-2-yl)picolinamide |
| 12 | 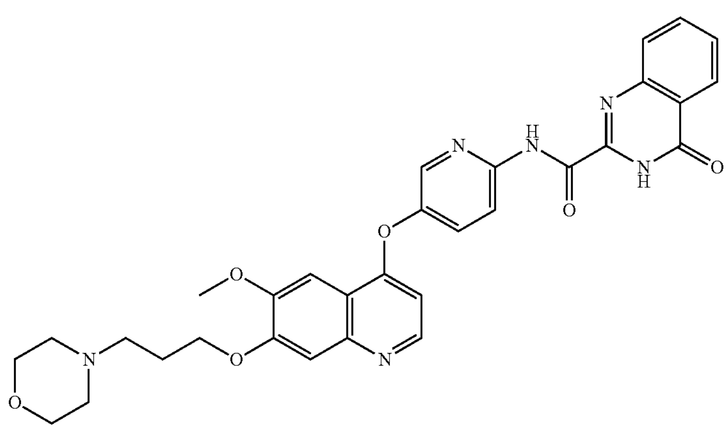 [SMILES: COc1cc2c(Oc3ccc(NC(=O)c4nc5ccccc5c(=O)[nH]4)nc3)ccnc2cc1OCCCN1CCOCC1] | N-(5-(((6-Methoxy-7-(3-morpholinopropoxy)quinolin-4-yl)oxy)pyridin-2-yl)-4-oxo-3,4-dihydroquinazoline-2-carboxamide |

-continued

| No. | Structure | Name |
|---|---|---|
| 13 | 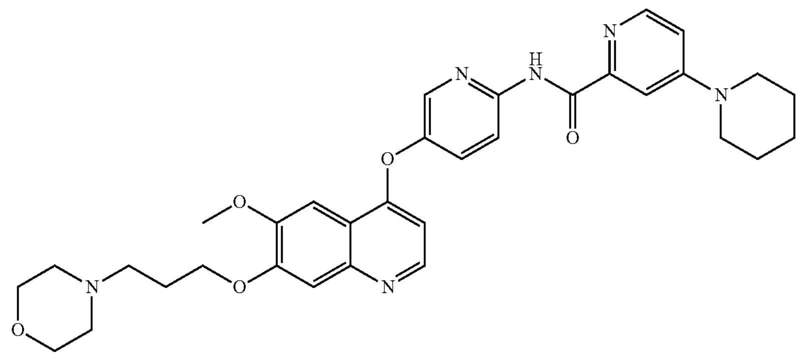 [SMILES: COc1cc2c(Oc3ccc(NC(=O)c4cc(N5CCCCC5)ccn4)nc3)ccnc2cc1OCCCN1CCOCC1] | N-(5-(((6-methoxy-7-(3-morpholinopropoxy)quinolin-4-yl)oxy)pyridin-2-yl)-4-(piperidin-1-yl)picolinamide |
| 14 | 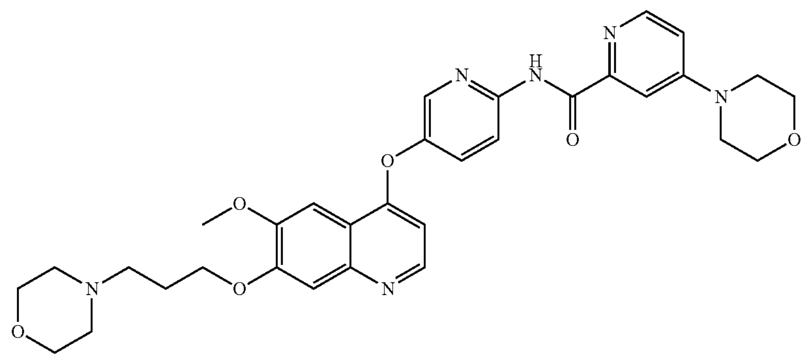 [SMILES: COc1cc2c(Oc3ccc(NC(=O)c4cc(N5CCOCC5)ccn4)nc3)ccnc2cc1OCCCN1CCOCC1] | N-(5-(((6-methoxy-7-(3-morpholinopropoxy)quinolin-4-yl)oxy)pyridin-2-yl)-4-morpholinopicolinamide |
| 15 | 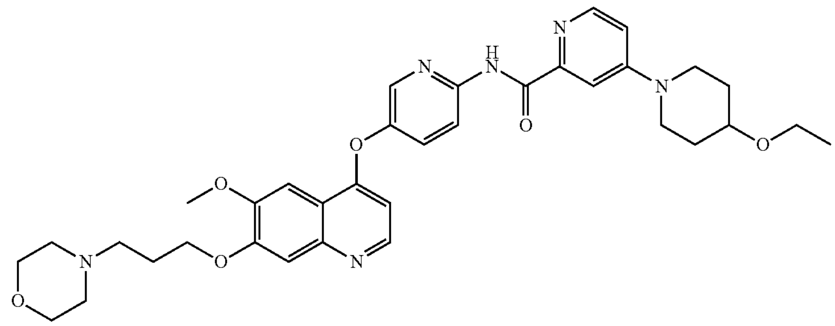 [SMILES: CCOC1CCN(c2ccnc(C(=O)Nc3ccc(Oc4ccnc5cc(OCCCN6CCOCC6)c(OC)cc45)cn3)c2)CC1] | 4-(4-ethoxypiperidin-1-yl)-N-(5-(((6-methoxy-7-(3-morpholinopropoxy)quinolin-4-yl)oxy)pyridin-2-yl)picolinamide |
| 16 | 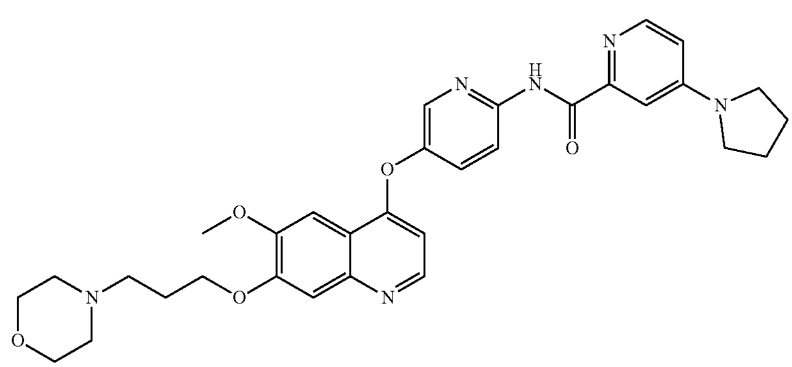 [SMILES: COc1cc2c(Oc3ccc(NC(=O)c4cc(N5CCCC5)ccn4)nc3)ccnc2cc1OCCCN1CCOCC1] | N-(5-(((6-methoxy-7-(3-morpholinopropoxy)quinolin-4-yl)oxy)pyridin-2-yl)-4-(pyrrolidin-1-yl)picolinamide |

-continued

| No. | Structure | Name |
|---|---|---|
| 17 | 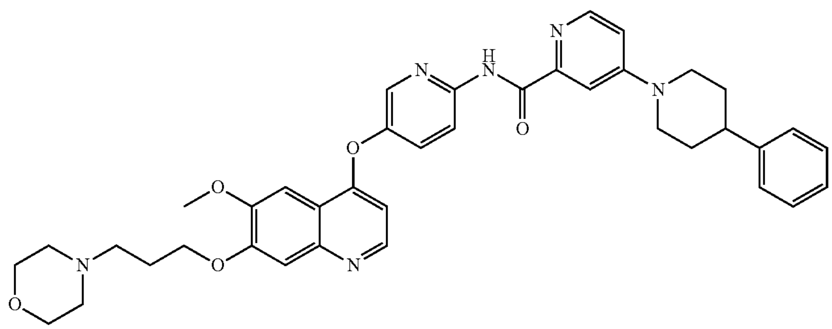 [SMILES: COc1cc2c(Oc3ccc(NC(=O)c4cc(N5CCC(c6ccccc6)CC5)ccn4)nc3)ccnc2cc1OCCCN1CCOCC1] | N-(5-((6-methoxy-7-(3-morpholinopropoxy)quinolin-4-yl)oxy)pyridin-2-yl)-4-(4-phenylpiperidin-1-yl)picolinamide |
| 18 | 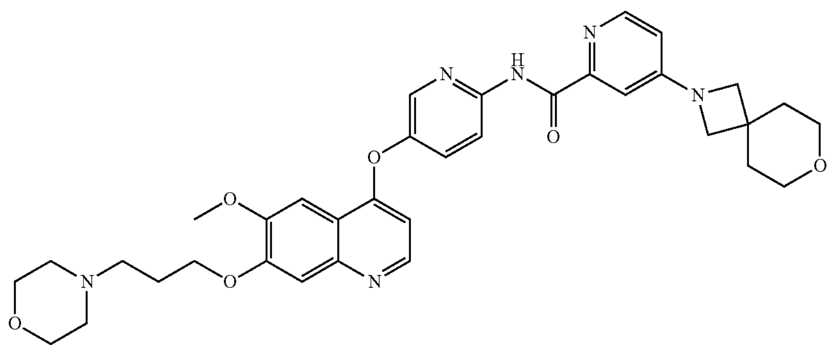 [SMILES: COc1cc2c(Oc3ccc(NC(=O)c4cc(N5CC6(CCOCC6)C5)ccn4)nc3)ccnc2cc1OCCCN1CCOCC1] | N-(5-((6-methoxy-7-(3-morpholinopropoxy)quinolin-4-yl)oxy)pyridin-2-yl)-4-(7-oxa-2-azaspiro[3.5]nonan-2-yl)picolinamide |
| 19 | 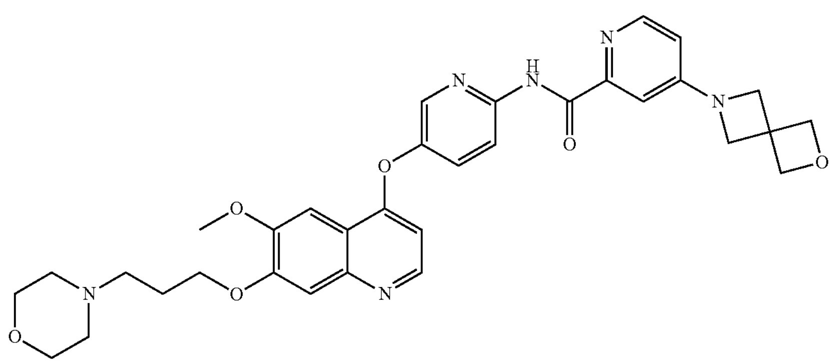 [SMILES: COc1cc2c(Oc3ccc(NC(=O)c4cc(N5CC6(COC6)C5)ccn4)nc3)ccnc2cc1OCCCN1CCOCC1] | N-(5-((6-methoxy-7-(3-morpholinopropoxy)quinolin-4-yl)oxy)pyridin-2-yl)-4-(2-oxa-6-azaspiro[3.3]heptan-6-yl)picolinamide |
| 20 | 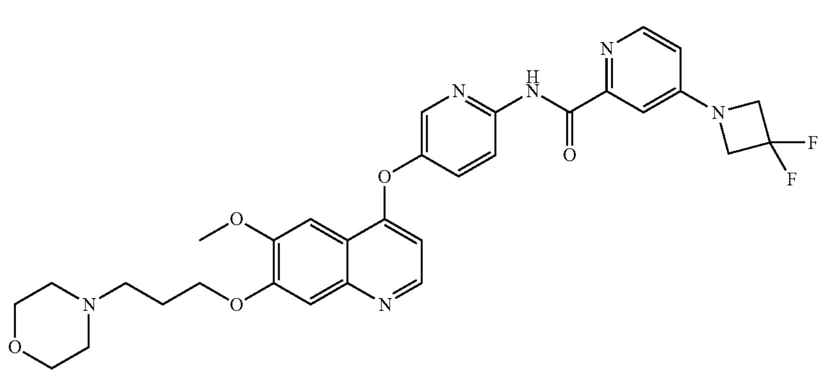 [SMILES: COc1cc2c(Oc3ccc(NC(=O)c4cc(N5CC(F)(F)C5)ccn4)nc3)ccnc2cc1OCCCN1CCOCC1] | 4-(3,3-difluoroazetidin-1-yl)-N-(5-((6-methoxy-7-(3-morpholinopropoxy)quinolin-4-yl)oxy)pyridin-2-yl)picolinamide |

-continued

| No. | Structure | Name |
|---|---|---|
| 21 | 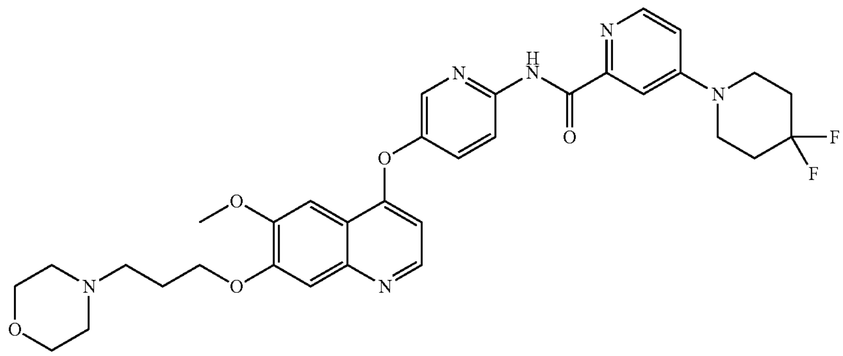 [SMILES: COc1cc2c(Oc3ccc(NC(=O)c4cc(N5CCC(F)(F)CC5)ccn4)nc3)ccnc2cc1OCCCN1CCOCC1] | 4-(4,4-difluoropiperidin-1-yl)-N-(5-((6-methoxy-7-(3-morpholinopropoxy)quinolin-4-yl)oxy)pyridin-2-yl)picolinamide |
| 22 | 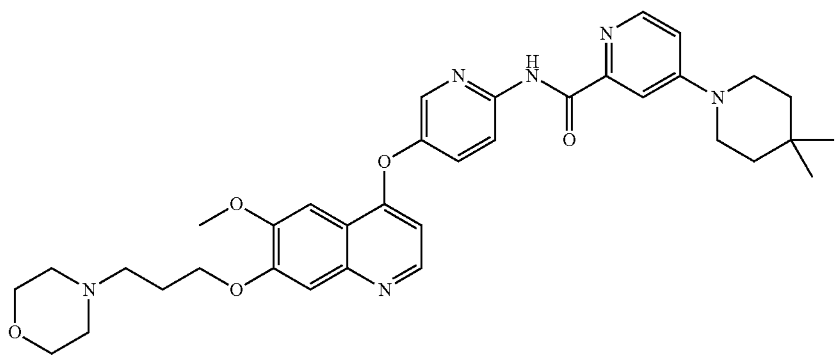 [SMILES: COc1cc2c(Oc3ccc(NC(=O)c4cc(N5CCC(C)(C)CC5)ccn4)nc3)ccnc2cc1OCCCN1CCOCC1] | 4-(4,4-dimethylpiperidin-1-yl)-N-(5-((6-methoxy-7-(3-morpholinopropoxy)quinolin-4-yl)oxy)pyridin-2-yl)picolinamide |
| 23 | 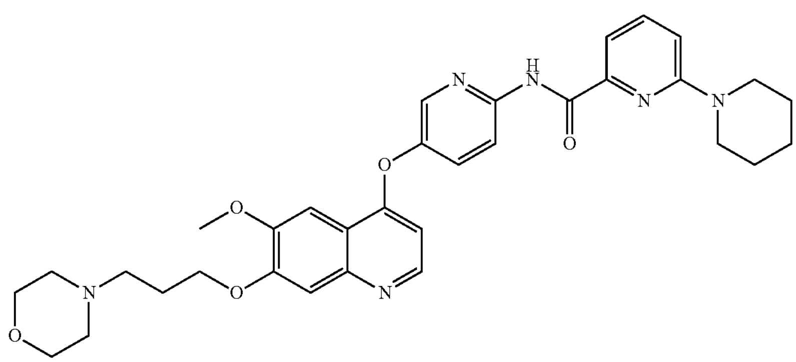 [SMILES: COc1cc2c(Oc3ccc(NC(=O)c4cccc(N5CCCCC5)n4)nc3)ccnc2cc1OCCCN1CCOCC1] | N-(5-((6-methoxy-7-(3-morpholinopropoxy)quinolin-4-yl)oxy)pyridin-2-yl)-6-(piperidin-1-yl)picolinamide |
| 24 | 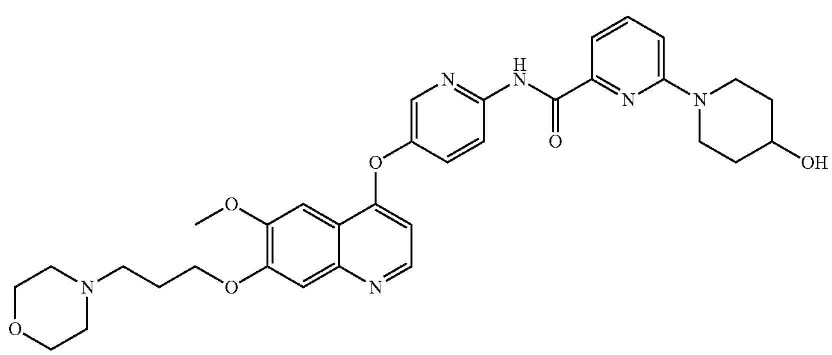 [SMILES: COc1cc2c(Oc3ccc(NC(=O)c4cccc(N5CCC(O)CC5)n4)nc3)ccnc2cc1OCCCN1CCOCC1] | 6-(4-hydroxypiperidin-1-yl)-N-(5-((6-methoxy-7-(3-morpholinopropoxy)quinolin-4-yl)oxy)pyridin-2-yl)picolinamide |

| No. | Structure | Name |
|---|---|---|
| 25 | 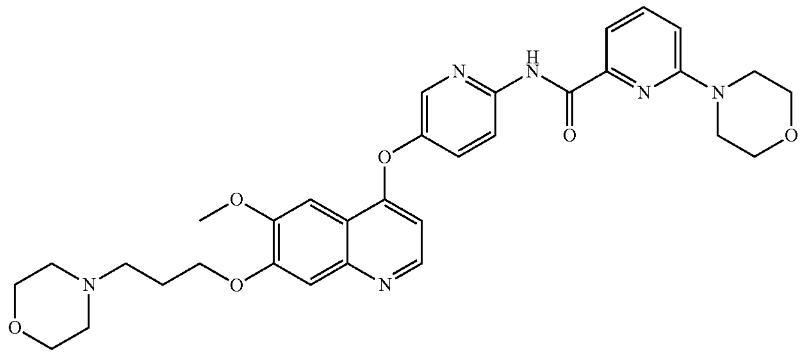 [SMILES: COc1cc2c(Oc3ccc(NC(=O)c4cccc(N5CCOCC5)n4)nc3)ccnc2cc1OCCCN1CCOCC1] | N-(5-((6-methoxy-7-(3-morpholinopropoxy)quinolin-4-yl)oxy)pyridin-2-yl)-6-morpholinopicolinamide |
| 26 | 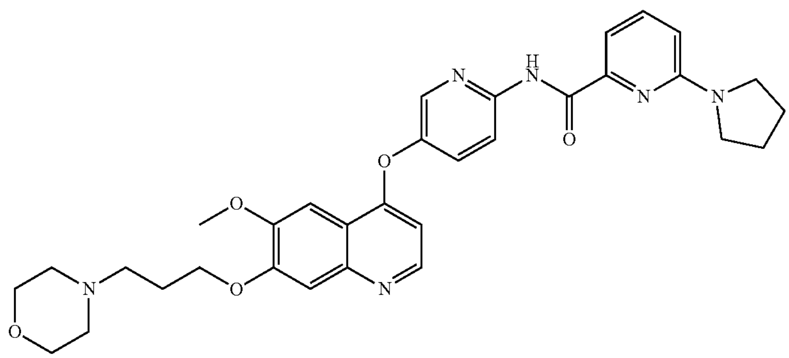 [SMILES: COc1cc2c(Oc3ccc(NC(=O)c4cccc(N5CCCC5)n4)nc3)ccnc2cc1OCCCN1CCOCC1] | N-(5-((6-methoxy-7-(3-morpholinopropoxy)quinolin-4-yl)oxy)pyridin-2-yl)-6-(pyrrolidin-1-yl)picolinamide |
| 27 | 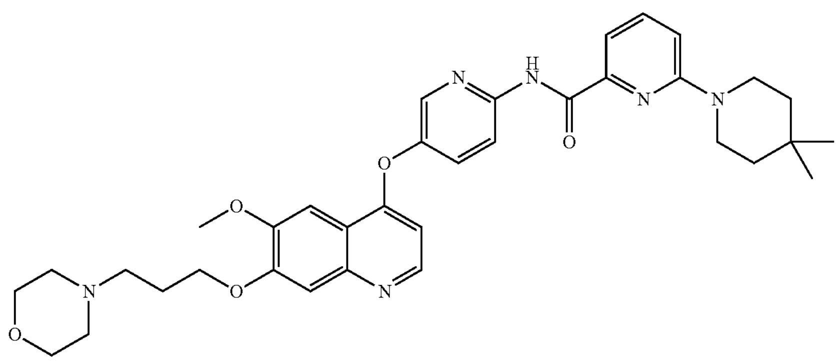 [SMILES: COc1cc2c(Oc3ccc(NC(=O)c4cccc(N5CCC(C)(C)CC5)n4)nc3)ccnc2cc1OCCCN1CCOCC1] | 6-(4,4-dimethylpiperidin-1-yl)-N-(5-((6-methoxy-7-(3-morpholinopropoxy)quinolin-4-yl)oxy)pyridin-2-yl)picolinamide |
| 28 | 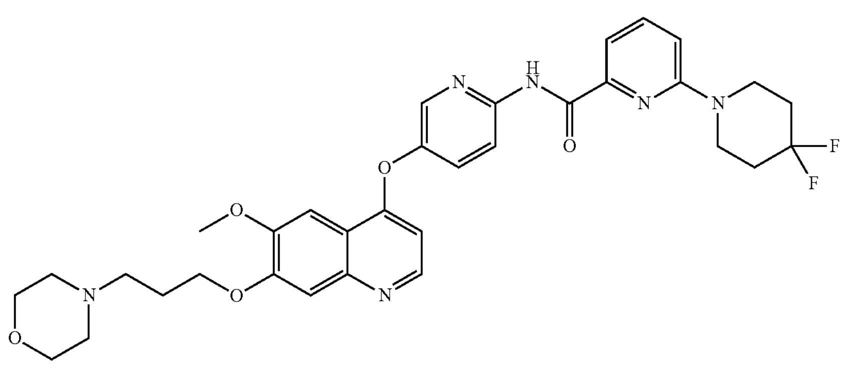 [SMILES: COc1cc2c(Oc3ccc(NC(=O)c4cccc(N5CCC(F)(F)CC5)n4)nc3)ccnc2cc1OCCCN1CCOCC1] | 6-(4,4-difluoropiperidin-1-yl)-N-(5-((6-methoxy-7-(3-morpholinopropoxy)quinolin-4-yl)oxy)pyridin-2-yl)picolinamide |

| No. | Structure | Name |
|---|---|---|
| 29 | 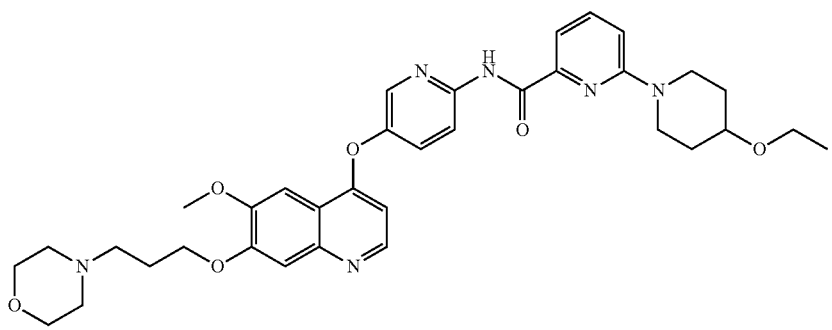 [SMILES: CCOC1CCN(c2cccc(C(=O)Nc3ccc(Oc4ccnc5cc(OCCCN6CCOCC6)c(OC)cc45)cn3)n2)CC1] | 6-(4-ethoxypiperidin-1-yl)-N-(5-(((6-methoxy-7-(3-morpholinopropoxy)quinolin-4-yl)oxy)pyridin-2-yl)picolinamide |
| 30 | 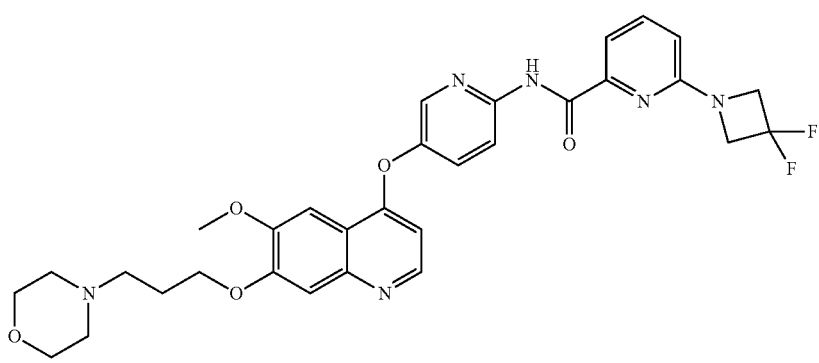 [SMILES: COc1cc2c(Oc3ccc(NC(=O)c4cccc(N5CC(F)(F)C5)n4)nc3)ccnc2cc1OCCCN1CCOCC1] | 6-(3,3-difluoroazetidin-1-yl)-N-(5-(((6-methoxy-7-(3-morpholinopropoxy)quinolin-4-yl)oxy)pyridin-2-yl)picolinamide |
| 31 | 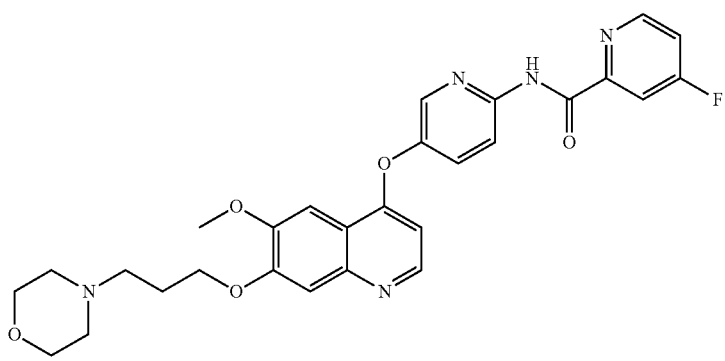 [SMILES: COc1cc2c(Oc3ccc(NC(=O)c4cc(F)ccn4)nc3)ccnc2cc1OCCCN1CCOCC1] | 4-Fluoro-N-(5-(((6-methoxy-7-(3-morpholinopropoxy)quinolin-4-yl)oxy)pyridin-2-yl)picolinamide |
| 32 | 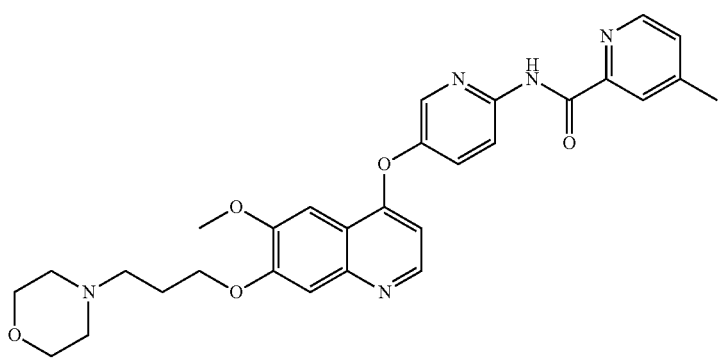 [SMILES: COc1cc2c(Oc3ccc(NC(=O)c4cc(C)ccn4)nc3)ccnc2cc1OCCCN1CCOCC1] | N-(5-(((6-Methoxy-7-(3-morpholinopropoxy)quinolin-4-yl)oxy)pyridin-2-yl)-4-methylpicolinamide |

| No. | Structure | Name |
|---|---|---|
| 33 | 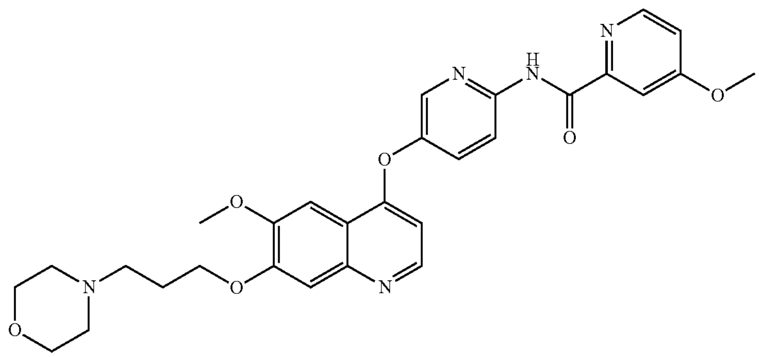 [SMILES: COc1ccnc(C(=O)Nc2ccc(Oc3ccnc4cc(OCCCN5CCOCC5)c(OC)cc34)cn2)c1] | 4-Methoxy-N-(5-((6-methoxy-7-(3-morpholinopropoxy)quinolin-4-yl)oxy)pyridin-2-yl)picolinamide |
| 34 | 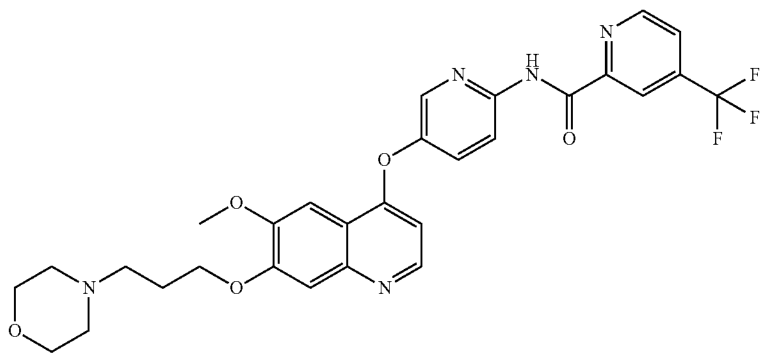 [SMILES: COc1cc2c(Oc3ccc(NC(=O)c4cc(C(F)(F)F)ccn4)nc3)ccnc2cc1OCCCN1CCOCC1] | N-(5-((6-Methoxy-7-(3-morpholinopropoxy)quinolin-4-yl)oxy)pyridin-2-yl)-4-(trifluoromethyl)picolinamide |
| 35 | 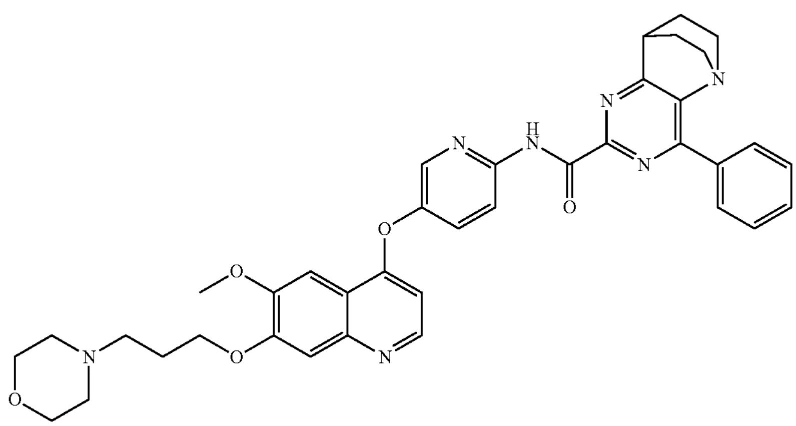 [SMILES: COc1cc2c(Oc3ccc(NC(=O)c4nc(-c5ccccc5)c5c(n4)C4CCN5CC4)nc3)ccnc2cc1OCCCN1CCOCC1] | N-(5-((6-methoxy-7-(3-morpholinopropoxy)quinolin-4-yl)oxy)pyridin-2-yl)-4-phenyl-7,8-dihydro-6H-5,8-ethanopyrido[3,2-d]pyrimidine-2-carboxamide |
| 36 | 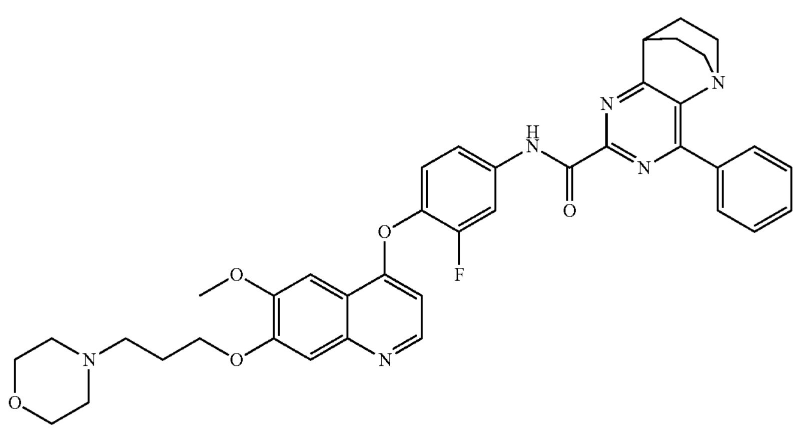 [SMILES: COc1cc2c(Oc3ccc(NC(=O)c4nc(-c5ccccc5)c5c(n4)C4CCN5CC4)cc3F)ccnc2cc1OCCCN1CCOCC1] | N-(3-fluoro-4-((6-methoxy-7-(3-morpholinopropoxy)quinolin-4-yl)oxy)phenyl)-4-phenyl-7,8-dihydro-6H-5,8-ethanopyrido[3,2-d]pyrimidine-2-carboxamide |

-continued

| No. | Structure | Name |
|---|---|---|
| 37 | 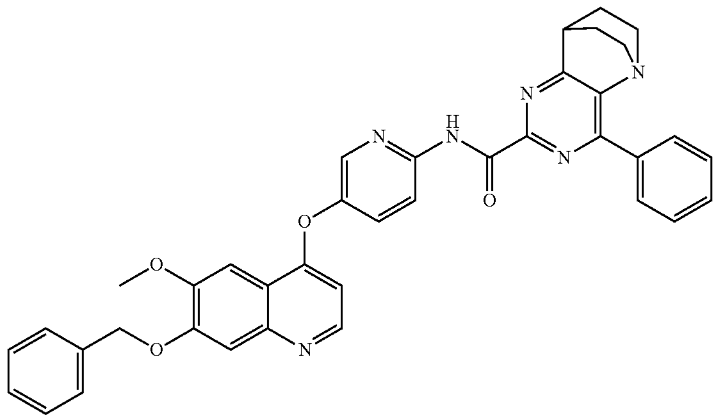 [SMILES: COc1cc2c(Oc3ccc(NC(=O)c4nc(-c5ccccc5)c5c(n4)C4CCN5CC4)nc3)ccnc2cc1OCc1ccccc1] | N-(5-((7-(benzyloxy)-6-methoxyquinolin-4-yl)oxy)pyridin-2-yl)-4-phenyl-7,8-dihydro-6H-5,8-ethanopyrido[3,2-d]pyrimidine-2-carboxamide |
| 38 | 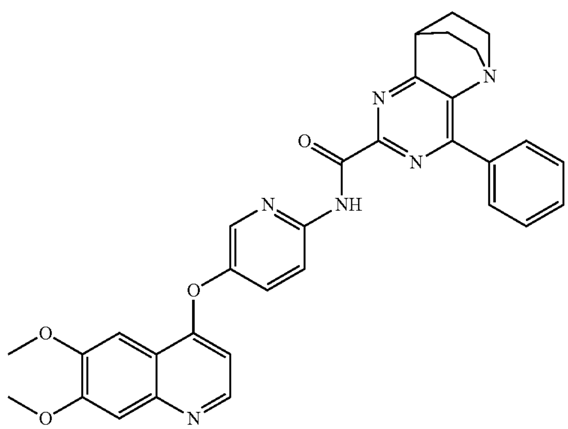 [SMILES: COc1cc2nccc(Oc3ccc(NC(=O)c4nc(-c5ccccc5)c5c(n4)C4CCN5CC4)nc3)c2cc1OC] | N-(5-((6,7-dimethoxyquinolin-4-yl)oxy)pyridin-2-yl)-4-phenyl-7,8-dihydro-6H-5,8-ethanopyrido[3,2-d]pyrimidine-2-carboxamide |
| 39 | 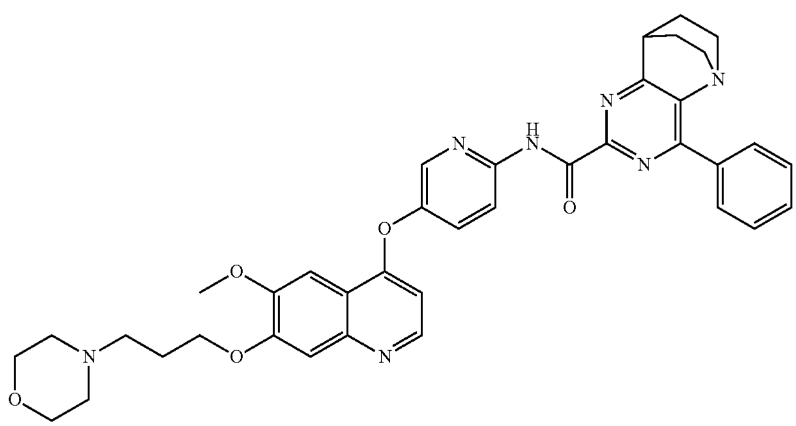 [SMILES: COc1cc2c(Oc3ccc(NC(=O)c4nc(-c5ccccc5)c5c(n4)C4CCN5CC4)nc3)ccnc2cc1OCCCN1CCOCC1] | N-(5-((6-methoxy-7-(3-(piperidin-1-yl)propoxy)quinolin-4-yl)oxy)pyridin-2-yl)-4-phenyl-7,8-dihydro-6H-5,8-ethanopyrido[3,2-d]pyrimidine-2-carboxamide |
| 40 | 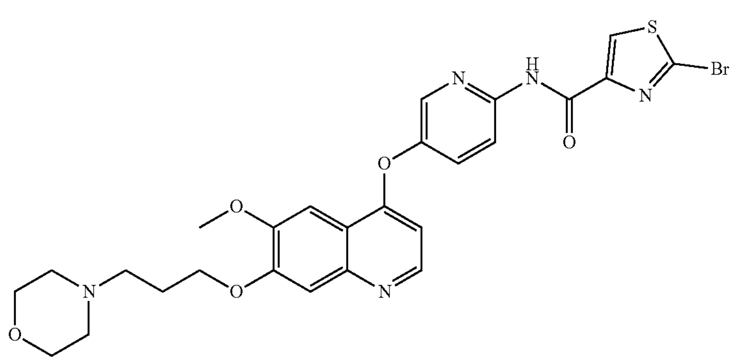 [SMILES: COc1cc2c(Oc3ccc(NC(=O)c4csc(Br)n4)nc3)ccnc2cc1OCCCN1CCOCC1] | 2-bromo-N-(5-((6-methoxy-7-(3-morpholinopropoxy)quinolin-4-yl)oxy)pyridin-2-yl)thiazole-4-carboxamide |

-continued

| No. | Structure | Name |
|---|---|---|
| 41 | 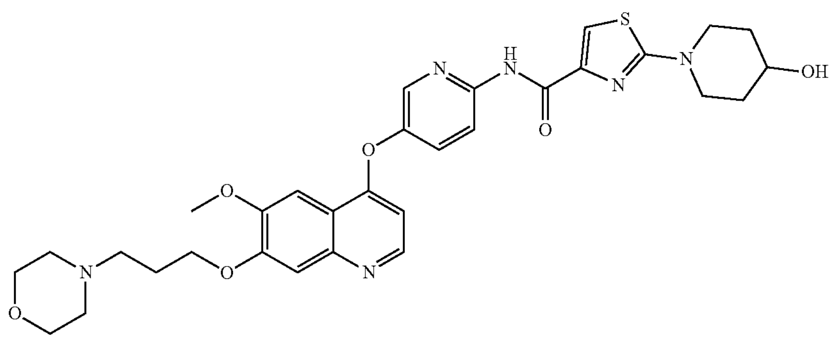 [SMILES: COc1cc2c(Oc3ccc(NC(=O)c4csc(N5CCC(O)CC5)n4)nc3)ccnc2cc1OCCCN1CCOCC1] | 2-(4-hydroxypiperidin-1-yl)-N-(5-((6-methoxy-7-(3-morpholinopropoxy)quinolin-4-yl)oxy)pyridin-2-yl)thiazole-4-carboxamide |
| 42 | 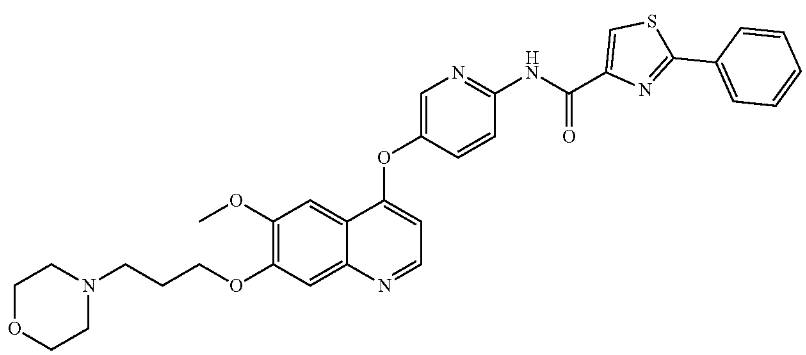 [SMILES: COc1cc2c(Oc3ccc(NC(=O)c4csc(-c5ccccc5)n4)nc3)ccnc2cc1OCCCN1CCOCC1] | N-(5-((6-methoxy-7-(3-morpholinopropoxy)quinolin-4-yl)oxy)pyridin-2-yl)-2-phenylthiazole-4-carboxamide |
| 43 | 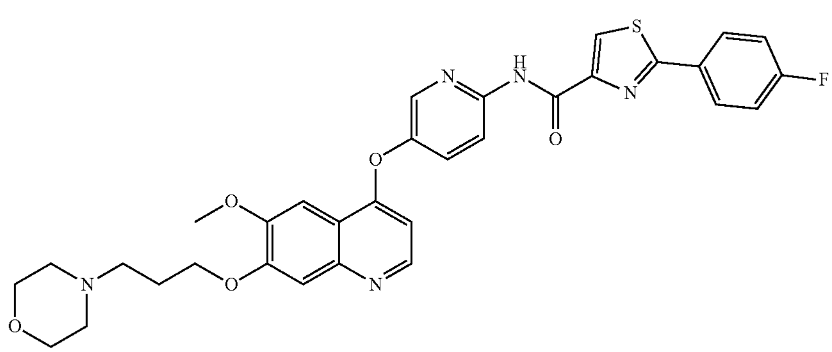 [SMILES: COc1cc2c(Oc3ccc(NC(=O)c4csc(-c5ccc(F)cc5)n4)nc3)ccnc2cc1OCCCN1CCOCC1] | 2-(4-fluorophenyl)-N-(5-((6-methoxy-7-(3-morpholinopropoxy)quinolin-4-yl)oxy)pyridin-2-yl)thiazole-4-carboxamide |
| 44 | 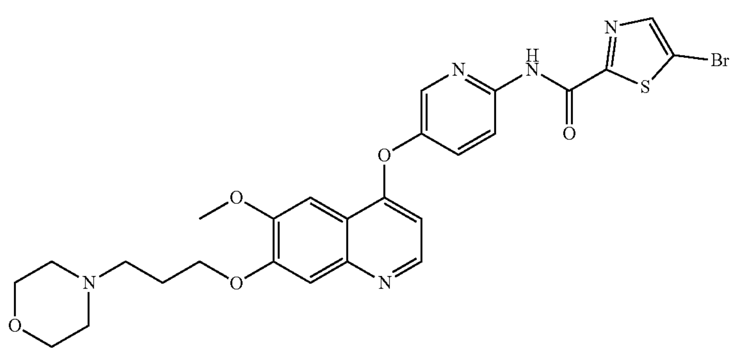 [SMILES: COc1cc2c(Oc3ccc(NC(=O)c4ncc(Br)s4)nc3)ccnc2cc1OCCCN1CCOCC1] | 5-bromo-N-(5-((6-methoxy-7-(3-morpholinopropoxy)quinolin-4-yl)oxy)pyridin-2-yl)thiazole-2-carboxamide |

-continued

| No. | Structure | Name |
|---|---|---|
| 45 | 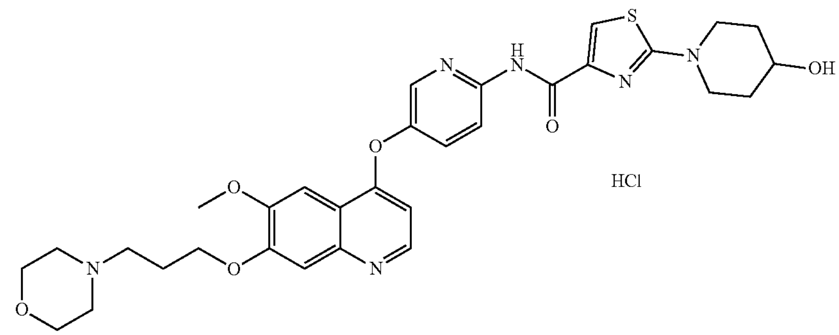 [SMILES: COc1cc2c(Oc3ccc(NC(=O)c4csc(N5CCC(O)CC5)n4)nc3)ccnc2cc1OCCCN1CCOCC1 ; Cl] | 2-(4-hydroxypiperidin-1-yl)-N-(5-((6-methoxy-7-(3-morpholinopropoxy)quinolin-4-yl)oxy)pyridin-2-yl)thiazole-4-carboxamide, hydrochloric acid |
| 46 | 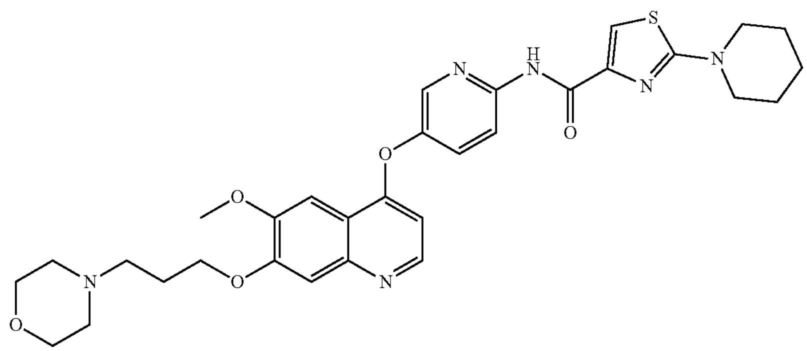 [SMILES: COc1cc2c(Oc3ccc(NC(=O)c4csc(N5CCCCC5)n4)nc3)ccnc2cc1OCCCN1CCOCC1] | N-(5-((6-methoxy-7-(3-morpholinopropoxy)quinolin-4-yl)oxy)pyridin-2-yl)-2-(piperidin-1-yl)thiazole-4-carboxamide |
| 47 | 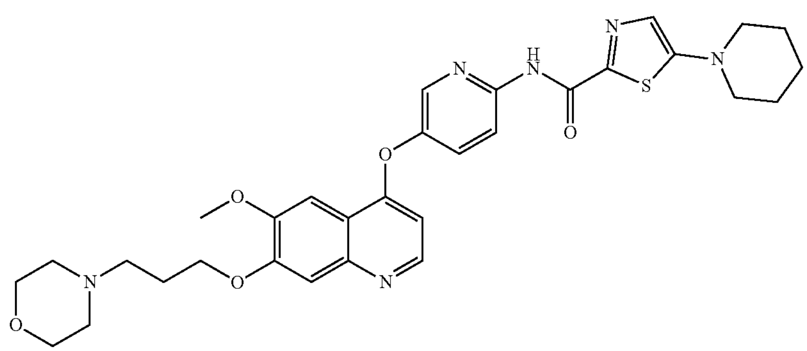 [SMILES: COc1cc2c(Oc3ccc(NC(=O)c4ncc(N5CCCCC5)s4)nc3)ccnc2cc1OCCCN1CCOCC1] | N-(5-((6-methoxy-7-(3-morpholinopropoxy)quinolin-4-yl)oxy)pyridin-2-yl)-5-(piperidin-1-yl)thiazole-2-carboxamide |
| 48 | 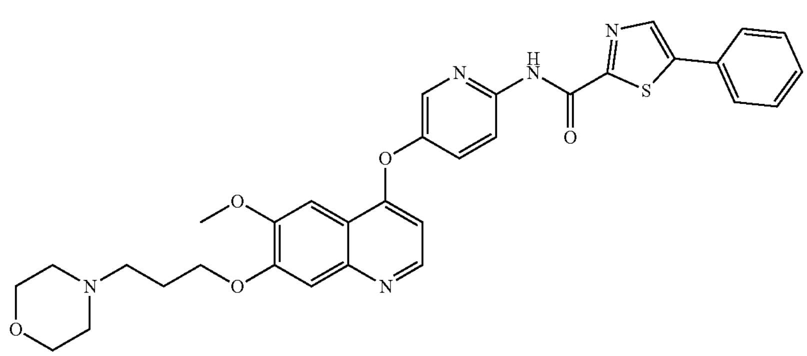 [SMILES: COc1cc2c(Oc3ccc(NC(=O)c4ncc(-c5ccccc5)s4)nc3)ccnc2cc1OCCCN1CCOCC1] | N-(5-((6-methoxy-7-(3-morpholinopropoxy)quinolin-4-yl)oxy)pyridin-2-yl)-5-phenylthiazole-2-carboxamide |

| No. | Structure | Name |
|---|---|---|
| 49 | 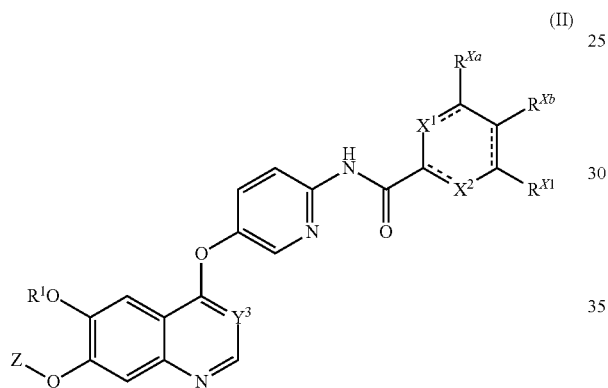 | N-(5-((6,7-dimethoxyquinazolin-4-yl)oxy)pyridin-2-yl)-4-phenyl-7,8-dihydro-6H-5,8-ethanopyrido[3,2-d]pyrimidine-2-carboxamide |

In embodiment $II_1$ of this aspect, the invention comprises compounds having the structure of formula (II):

(II)

or a pharmaceutically acceptable salt, prodrug or N-oxide thereof, or solvate or hydrate thereof, $Y^3$ is N or CH;
$X^1$ is —N=, —C(H)=;
$X^2$ is =C(H)—, =N—, —N(H)—;
$R^{X1}$ is independently halogen, cyano, $C_1$-$C_6$alkyl, $C_1$-$C_6$haloalkyl, —$C_1$-$C_6$alkoxy, —$C_1$-$C_6$haloalkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$, —CH$_2$—OP(OX)(OR), Ar($C_0$-$C_6$alkyl) or Hca ($C_0$-$C_6$alkyl), wherein Ar and Hca are optionally substituted with one or two —$R^{X2}$ groups,
wherein each —$R^{X2}$ is independently halogen, cyano, nitro, oxo, —OR, —SR, —NR$_2$, —C(O)OR, —C(O)NR$_2$, —C(O)R, —S(O)R, —S(O)R$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$alkyl, $C_1$-$C_6$haloalkyl or Ar;
$R^{Xa}$ and $R^{Xb}$ are each hydrogen, or $R^{Xa}$ and $R^{Xb}$ combine with the atoms to which they are attached to form an Ar or Hca;
Z is $C_1$-$C_6$alkyl, Ar($C_0$-$C_6$alkyl) or Hca($C_0$-$C_6$alkyl), each optionally substituted by 1, 2 or 3 —$R^{Z1}$ groups;
wherein each —$R^{Z1}$ is independently halogen, cyano, $C_1$-$C_6$alkyl, $C_1$-$C_6$haloalkyl, —$C_1$-$C_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR); and
$R^1$ is hydrogen or $C_1$-$C_6$alkyl;
each R is independently hydrogen or $C_1$-$C_6$alkyl;
wherein
Hca is a 3-15 membered non-aromatic ring or non-aromatic ring system comprising 1, 2, 3, or 4 O, S, or N atoms, provided no O or S is adjacent to another O or S;
Het is a 5-15 membered aromatic ring or aromatic ring system comprising 1, 2, 3, or 4 O, S, or N atoms, provided no O or S is adjacent to another O or S;
Cak is a 3-15 membered non-aromatic carbocyclic ring or non-aromatic carbocyclic ring system, which may be saturated or partially unsaturated, and optionally including one or more other aromatic and non-aromatic rings, which form fused, spiro or bridged ring systems; and
Ar is a 6-16 membered aromatic ring or aromatic ring system having at least one carbocyclic aromatic ring optionally fused one or more aromatic or non-aromatic rings;
provided that when Z is $C_1$-$C_6$alkyl, $X^1$ is —N=; $X^2$ is =N—; $R^{X1}$ is phenyl; and $R^{Xa}$ and $R^{Xb}$ combine with the atoms to which they are attached to form a 1-azabicyclo[2.2.2]oct-2-enyl ring system.

In embodiment $II_2$, the compounds are of embodiment $I_1$, wherein $X^1$ is —N=.
In embodiment $II_3$, the compounds are of embodiment $I_1$ or $II_2$, wherein $X^2$ is =C(H)—.
In embodiment $II_4$, the compounds are of any of embodiments $I_1$-$II_3$, wherein $R^{Xa}$ and $R^{Xb}$) are each hydrogen.
In embodiment $II_5$, the compounds are of any of embodiments $I_1$-$II_3$, wherein $R^{Xa}$ and $R^{Xb}$ combine with the atoms to which they are attached to form an Ar.
In embodiment $II_6$, the compounds are of any of embodiments $I_1$-$II_3$, wherein $R^{Xa}$ and $R^{Xb}$ combine with the atoms to which they are attached to form an Hca.
In embodiment $II_7$, the compounds are of any of embodiments $I_1$-$II_6$, wherein $R^1$ is $C_1$-$C_6$alkyl.
In embodiment $II_8$, the compounds are of any of embodiments $I_1$-$II_6$, wherein $R^1$ is methyl.
In embodiment $II_9$, the compounds are of any of embodiments $I_1$-$II_8$, wherein Z is 3-morpholinopropoxyl.

In embodiment II₁₀, the compounds of the invention are one of formulae (Ia)-(IIf), wherein $X^1$, $X^2$, $R^{X1}$, $R^{Xa}$, $R^{Xb}$, Z, —$R^{Z1}$ and $R^1$ are as defined in embodiments II₁-II₉ above:
Structural Formula (II) is One of Formulae (IIa)-(III):
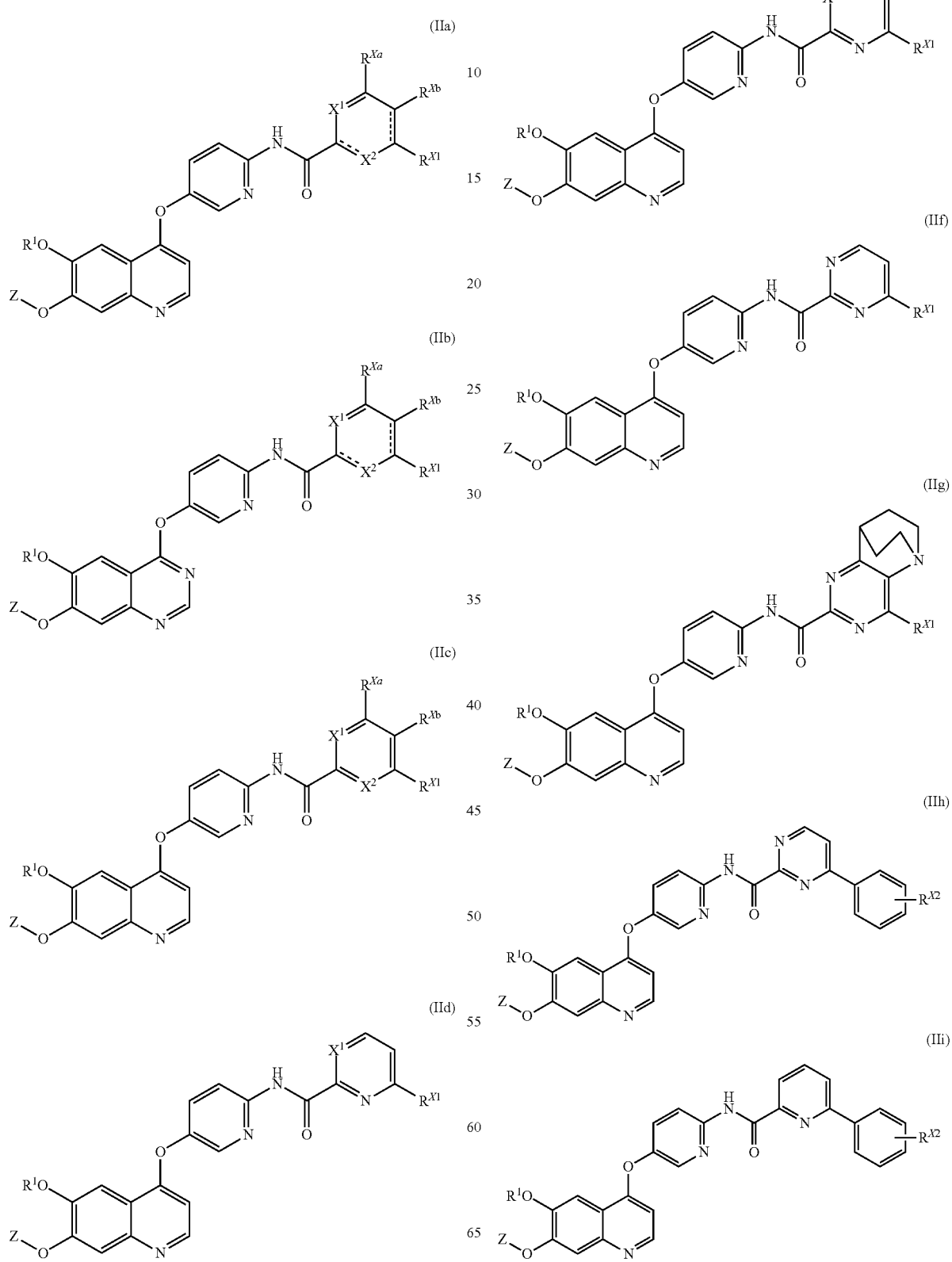

-continued

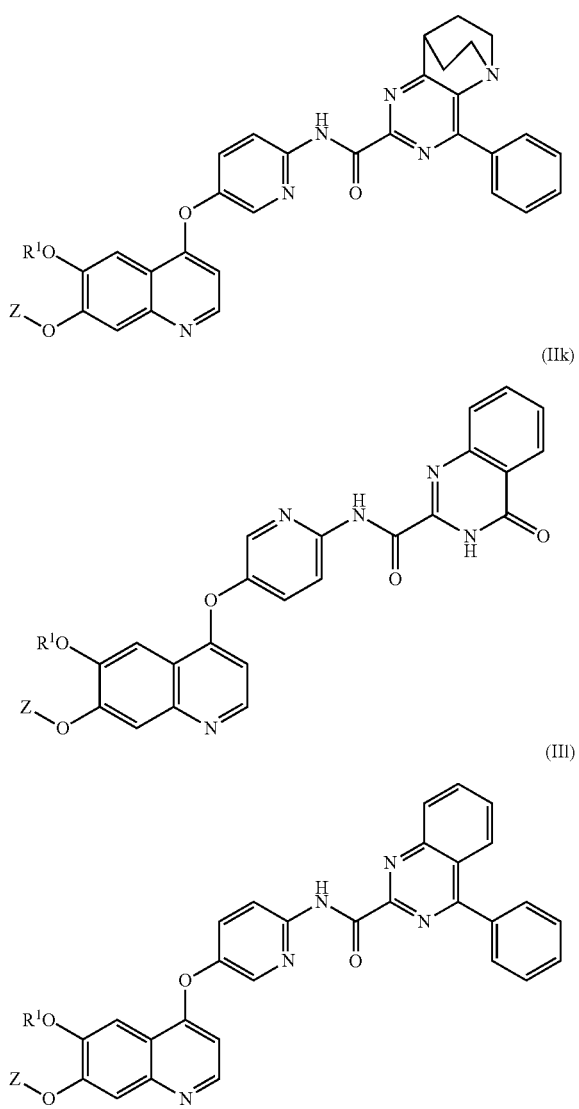

(IIj)

(IIk)

(III)

In embodiment III₁ of this aspect, the invention comprises compounds having the structure of formula (m):

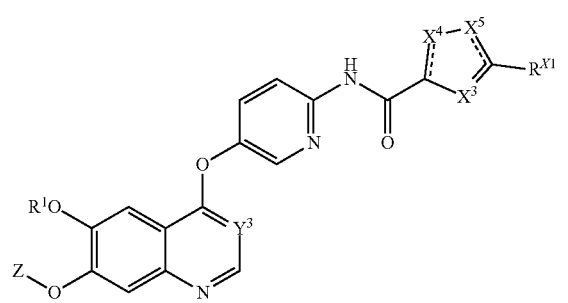

(III)

or a pharmaceutically acceptable salt, prodrug or N-oxide thereof, or solvate or hydrate thereof, $Y^3$ is N or CH;

$X^3$ is —N= or —S—;

$X^4$ is =N—, =C(H)—;

$X^5$ is —S—, =C(H)—;

$R^{X1}$ is independently halogen, cyano, $C_1$-$C_6$alkyl, $C_1$-$C_6$haloalkyl, —$C_1$-$C_6$alkoxy, —$C_1$-$C_6$haloalkoxy, oxo, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂, —CH₂—OP(O)(OR), Ar($C_0$-$C_6$alkyl) or Hca($C_0$-$C_6$alkyl), wherein Ar and Hca are optionally substituted with one or two —$R^{X2}$ groups, wherein each —$R^{X2}$ is independently halogen, cyano, nitro, oxo, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, $C_1$-$C_6$alkyl, $C_1$-$C_6$haloalkyl or Ar;

Z is $C_1$-$C_6$alkyl, Ar($C_0$-$C_6$alkyl) or Hca($C_0$-$C_6$alkyl), each optionally substituted by 1, 2 or 3 —$R^{Z1}$ groups;

wherein each —$R^{Z1}$ is independently halogen, cyano, $C_1$-$C_6$alkyl, $C_1$-$C_6$haloalkyl, —$C_1$-$C_6$alkoxy, oxo, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR); and $R^1$ is hydrogen or $C_1$-$C_6$alkyl;

each R is independently hydrogen or $C_1$-$C_6$alkyl;

wherein

Hca is a 3-15 membered non-aromatic ring or non-aromatic ring system comprising 1, 2, 3, or 4 O, S, or N atoms, provided no O or S is adjacent to another O or S;

Het is a 5-15 membered aromatic ring or aromatic ring system comprising 1, 2, 3, or 4 O, S, or N atoms, provided no O or S is adjacent to another O or S;

Cak is a 3-15 membered non-aromatic carbocyclic ring or non-aromatic carbocyclic ring system, which may be saturated or partially unsaturated, and optionally including one or more other aromatic and non-aromatic rings, which form fused, spiro or bridged ring systems, and Ar is a 6-16 membered aromatic ring or aromatic ring system having at least one carbocyclic aromatic ring optionally fused one or more aromatic or non-aromatic rings.

In embodiment III₂, the compounds of the invention are one of formulae (IIIa)-(II), wherein $X^3$, $X^4$, $X^5$, $R^{X1}$, Z, —$R^{Z1}$ and $R^1$ are as defined in embodiment III₁ above:

Structural Formula (II) is one of formulae (IIIa)-(IIIn):

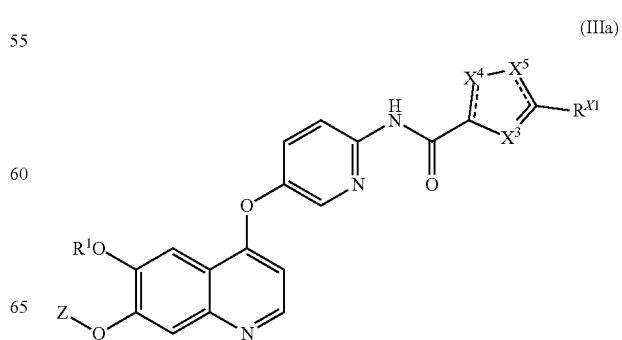

(IIIa)

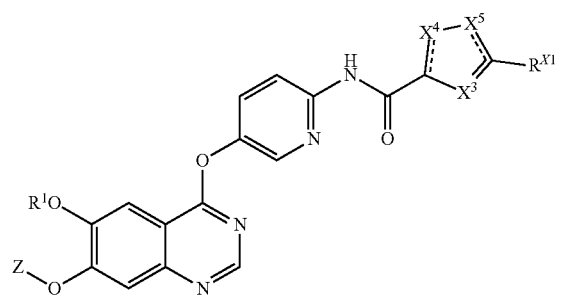
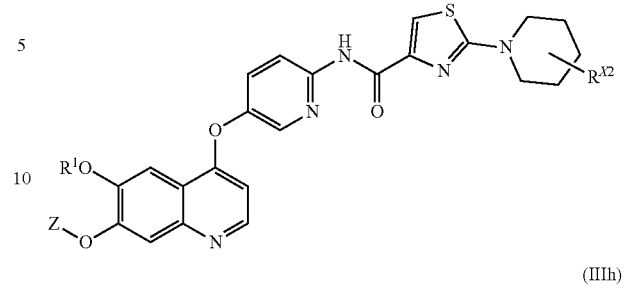
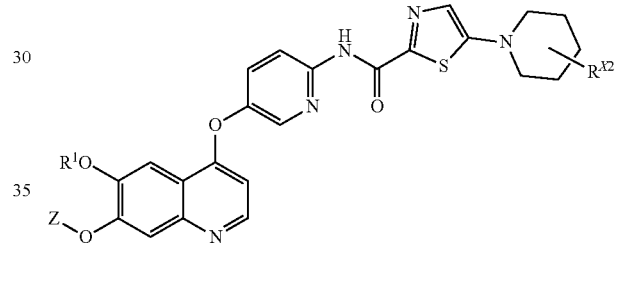
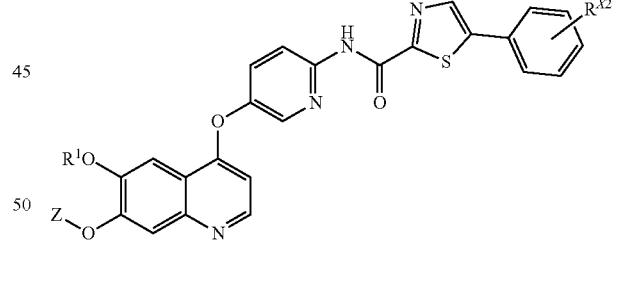
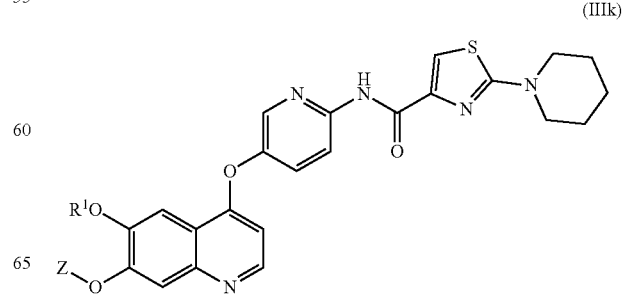

-continued

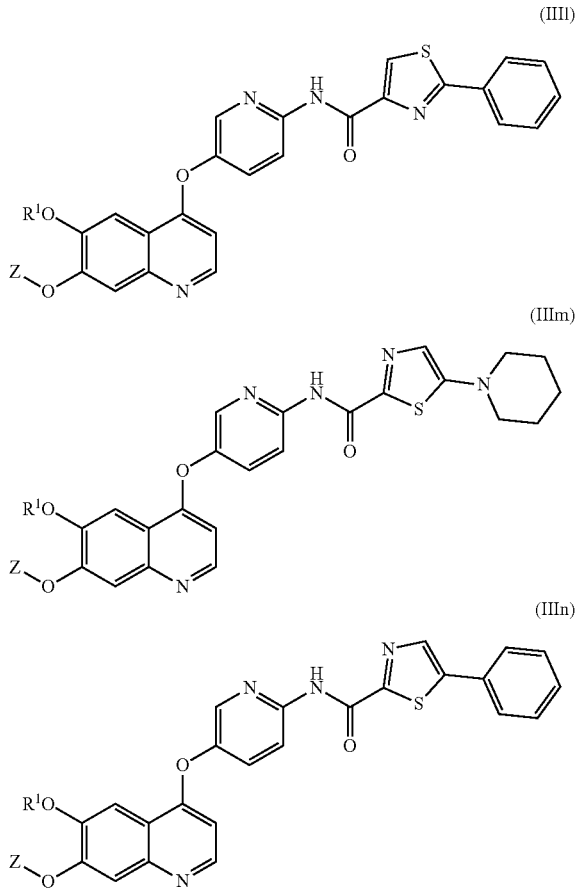

In embodiment III₃, the compounds are of embodiment II₁ or III₂, wherein X³ is —N═; X⁴ is ═C(H)—; and X⁵ is —S—.

In embodiment III₄, the compounds are of embodiment III₁ or III₂, wherein X³ is —S—; X⁴ is ═N—; and X⁵ is ═C(H)—.

In embodiment III₅, the compounds are of any of embodiments $R^{X1}$ is halogen or hydroxyl.

$R^{X1}$ is selected from one of the following groups (4a) (4ttt):

(4a) $R^{X1}$ is halogen, cyano, $C_1$-$C_6$alkyl, $C_1$-$C_6$haloalkyl, —$C_1$-$C_6$alkoxy, —$C_1$-$C_6$haloalkoxy, oxo, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂, —CH₂—OP(O)(OR), Ar($C_0$-$C_6$alkyl) or Hca($C_0$-$C_6$alkyl), wherein Ar and Hca are optionally substituted with one or two —$R^{X2}$ groups.

(4b) $R^{X1}$ is halogen, $C_1$-$C_6$alkyl, $C_1$-$C_6$haloalkyl, —$C_1$-$C_6$alkoxy, —$C_1$-$C_6$haloalkoxy, oxo, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂, —CH₂—OP(O)(OR), Ar($C_0$-$C_6$alkyl) or Hca($C_0$-$C_6$alkyl), wherein Ar and Hca are optionally substituted with one or two —$R^{X2}$ groups.

(4c) $R^{X1}$ is halogen, cyano, $C_1$-$C_6$haloalkyl, —$C_1$-$C_6$alkoxy, —$C_1$-$C_6$haloalkoxy, oxo, —OR, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂, —CH₂—OP(O)(OR), Ar($C_0$-$C_6$alkyl) or Hca($C_0$-$C_6$alkyl), wherein Ar and Hca are optionally substituted with one or two —$R^{X2}$ groups.

(4d) $R^{X1}$ is halogen, cyano, $C_1$-$C_6$haloalkyl, —$C_1$-$C_6$alkoxy, —$C_1$-$C_6$haloalkoxy, oxo, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, Ar($C_0$-$C_6$alkyl) or Hca($C_0$-$C_6$alkyl), wherein Ar and Hca are optionally substituted with one or two —$R^{X2}$ groups.

(4e) $R^{X1}$ is halogen, cyano, $C_1$-$C_6$haloalkyl, —$C_1$-$C_6$alkoxy, —$C_1$-$C_6$haloalkoxy, oxo, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, Ar($C_0$-$C_6$alkyl) or Hca($C_0$-$C_6$alkyl), wherein Ar and Hca are optionally substituted with one or two —$R^{X2}$ groups.

(4f) $R^{X1}$ is halogen, $C_1$-$C_6$alkyl, $C_1$-$C_6$haloalkyl, —$C_1$-$C_6$alkoxy, —$C_1$-$C_6$haloalkoxy, oxo, —OR, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, Ar($C_0$-$C_6$alkyl) or Hca($C_0$-$C_6$alkyl), wherein Ar and Hca are optionally substituted with one or two —$R^{X2}$ groups.

(4g) $R^{X1}$ is halogen, $C_1$-$C_6$alkyl, $C_1$-$C_6$haloalkyl, —$C_1$-$C_6$alkoxy, —$C_1$-$C_6$haloalkoxy, oxo, —OR, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, Ar($C_0$-$C_6$alkyl) or Hca($C_0$-$C_6$alkyl), wherein Ar and Hca are optionally substituted with one or two —$R^{X2}$ groups.

(4h) $R^{X1}$ is halogen, $C_1$-$C_6$alkyl, $C_1$-$C_6$haloalkyl, —$C_1$-$C_6$alkoxy, —$C_1$-$C_6$haloalkoxy, oxo, —OR, —C(O)R, —C(O)OR, —C(O)NR₂, —OC(O)R, —N(R)C(O)R, —OC(O)OR, —OC(O)NR₂, —N(R)C(O)OR, —N(R)C(O)NR₂, —N(R)S(O)₂R, Ar($C_0$-$C_6$alkyl) or Hca($C_0$-$C_6$alkyl), wherein Ar and Hca are optionally substituted with one or two —R" groups.

(4i) $R^{X1}$ is halogen, $C_1$-$C_6$alkyl, $C_1$-$C_6$haloalkyl, —$C_1$-$C_6$alkoxy, —$C_1$-$C_6$haloalkoxy, oxo, —OR, —C(O)R, —C(O)OR, —C(O)NR₂, —OC(O)R, —N(R)C(O)R, —N(R)C(O)OR, —N(R)C(O)NR₂, —N(R)S(O)₂K, Ar($C_0$-$C_6$alkyl) or Hca($C_0$-$C_6$alkyl), wherein Ar and Hca are optionally substituted with one or two —$R^{X2}$ groups.

(4j) $R^{X1}$ is halogen, $C_1$-$C_6$alkyl, $C_1$-$C_6$haloalkyl, —$C_1$-$C_6$alkoxy, —$C_1$-$C_6$haloalkoxy, oxo, —OR, —C(O)R, —C(O)OR, —C(O)NR₂, —N(R)C(O)R, —N(R)C(O)OR, —N(R)C(O)NR₂, —N(R)S(O)₂R, Ar($C_0$-$C_6$alkyl) or Hca($C_0$-$C_6$alkyl), wherein Ar and Hca are optionally substituted with one or two —$R^{X2}$ groups, (4k) $R^{X1}$ is halogen, $C_1$-$C_6$alkyl, $C_1$-$C_6$haloalkyl, —$C_1$-$C_6$alkoxy, —$C_1$-$C_6$haloalkoxy, oxo, —C(O)R, —C(O)OR, —C(O)NR₂, Ar($C_0$-$C_6$alkyl) or Hca($C_0$-$C_6$alkyl), wherein Ar and Hca are optionally substituted with one or two —$R^{X2}$ groups.

(4l) $R^{X1}$ is halogen, $C_1$-$C_6$alkyl, $C_1$-$C_6$haloalkyl, —$C_1$-$C_6$haloalkoxy, oxo, —OR, —C(O)R, —C(O)OR, —C(O)NR₂, Ar($C_0$-$C_6$alkyl) or Hca($C_0$-$C_6$alkyl), wherein Ar and Hca are optionally substituted with one or two —$R^{X2}$ groups.

(4m) $R^{X1}$ is halogen, $C_1$-$C_6$alkyl, $C_1$-$C_6$haloalkyl, —$C_1$-$C_6$haloalkoxy, oxo, —OR, Ar($C_0$-$C_6$alkyl) or Hca($C_0$-

C₆alkyl), wherein Ar and Hca are optionally substituted with one or two —R^{X2} groups.

(4n) R^{X1} is halogen, C₁-C₆alkyl, C₁-C₆haloalkyl, oxo, —OR, Ar(C₀-C₆alkyl) or Hca(C₀-C₆alkyl), wherein Ar and Hca are optionally substituted with one or two —R^{X2} groups.

(4o) R^{X1} is halogen, C₁-C₆alkyl, oxo, —OR, Ar(C₀-C₆alkyl) or Hca(C₀-C₆alkyl), wherein Ar and Hca are optionally substituted with one or two —R^{X2} groups.

(4p) R^{X1} is halogen, C₁-C₆alkyl, oxo, Ar(C₀-C₆alkyl) or Hca(C₀-C₆alkyl), wherein Ar and Hca are optionally substituted with one or two —R^{X1} groups.

(4q) R^{X1} is halogen, C₁-C₆alkyl, Ar(C₀-C₆alkyl) or Hca(C₀-C₆alkyl), wherein Ar and Hca are optionally substituted with one or two —R^{X2} groups.

(4r) R^{X1} is halogen, Ar(C₀-C₆alkyl) or Hca(C₀-C₆alkyl), wherein Ar and Hca are optionally substituted with one or two —R^{X2} groups.

(4s) R^{X1} is Ar(C₀-C₆alkyl) or Hca(C₀-C₆alkyl), wherein Ar and Hca are optionally substituted with one or two —R^{X2} groups.

(4t) R^{X1} is halogen or Hca(C₀-C₆alkyl), wherein Hca is optionally substituted with one or two —R^{X2} groups.

(4u) R^{X1} is Ar or Hca, wherein Ar and Hca are optionally substituted with one or two —R^{X2} groups.

(4v) R^{X1} is Ar(C₀-C₆alkyl), wherein Ar is optionally substituted with one or two —R^{X2} groups.

(4w) R^{X1} is Ar(C₀-C₆alkyl), wherein Ar is optionally substituted with one —R^{X2} group.

(4x) R^{X1} is Ar(C₀-C₆alkyl), wherein Ar is substituted with one —R^{X2} group.

(4y) R^{X1} is Hca(C₀-C₆alkyl), wherein Hca is optionally substituted with one or two —R^{X2} groups.

(4z) R^{X1} is Hca(C₀-C₆alkyl), wherein Hca is optionally substituted with one —R^{X2} groups.

(4aa) R^{X1} is Hca(C₀-C₆alkyl), wherein Hca is substituted with one —R^{X2} groups.

(4bb) R^{X1} is Hca(C₀-C₆alkyl), wherein Hca is substituted with one —R^{X2} groups.

(4cc) R^{X1} is phenyl, piperidinyl, morpholinyl, piperazinyl, pyrrolidinyl, 7-oxa-2-azaspiro[3.5]nonan-2-yl, 2-oxa-6-azaspiro[3.3]heptan-6-yl, azetidinyl, halogen, C₁-C₆alkyl, —C₁-C₆haloalkyl, oxo or —OR (4dd) R^{X1} is phenyl, piperidinyl, morpholinyl, piperazinyl, pyrrolidinyl, 7-oxa-2-azaspiro[3.5]nonan-2-yl, 2-oxa-6-azaspiro[3.3]heptan-6-yl, azetidinyl, fluoro, bromo, methoxy, trifluoromethyl or oxo.

(4ee) R^{X1} is halogen, C₁-C₆alkyl, —C₁-C₆haloalkyl, oxo or —OR.

(4ff) R^{X1} is is fluoro, bromo, methyl, trifluoromethyl, oxo or methoxy.

(4gg) R^{X1} is halogen, C₁-C₆alkyl, oxo or —OR.

(4hh) R^{X1} is fluoro, bromo, methyl, oxo or methoxy.

(4ii) R^{X1} is halogen, C₁-C₆alkyl or —OR.

(4jj) R^{X1} is fluoro, bromo methyl or methoxy.

(4kk) R^{X1} is any of groups (4a)-(4x), wherein Ar(C₀-C₆alkyl) is phenyl or fluorophenyl.

(4ll) R^{X1} is any of groups (4a)-(4x), wherein Ar(C₀-C₆alkyl) is 4-fluorophenyl.

(4mm) R^{X1} is any of groups (4a)-(4x), wherein Ar(C₀-C₆alkyl) is phenyl.

(4nn) R^{X1} is piperidinyl, morpholinyl, piperazinyl, pyrrolidinyl, 7-oxa-2-azaspiro[3.5]nonan-2-yl, 2-oxa-6-azaspiro[3.3]heptan-6-yl or azetidinyl.

(4oo) R^{X1} is 4-methylpiperazin-1-yl, 4-hydroxypiperidin-1-yl, piperidinyl, morpholinyl, 4-ethoxypiperidin-1-yl, pyrrolidinyl, 4-phenylpiperidin-1-yl, 7-oxa-2-azaspiro[3.5]nonan-2-yl, 2-oxa-6-azaspiro[3.3]heptan-6-yl, 3,3-difluoroazetidin-1-yl, 4,4-difluoropiperidin-1-yl or 4,4-dimethylpiperidin-1-yl.

(4pp) R^{X1} is

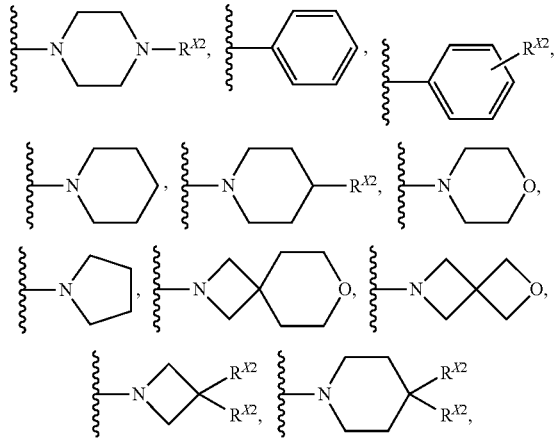

halogen, C₁-C₆alkyl, —C₁-C₆alkoxy or C₁-C₆haloalkyl.

(4qq) R^{X1} is

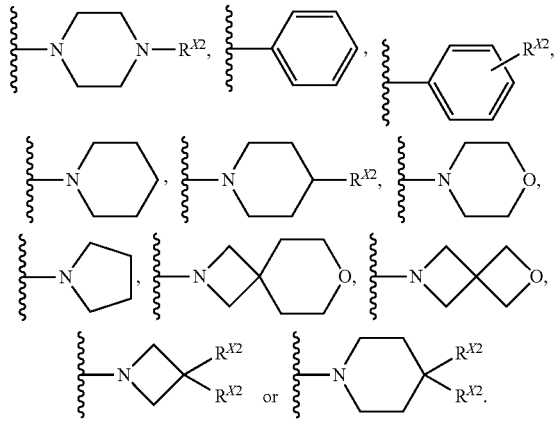

(4rr) R^{X1} is

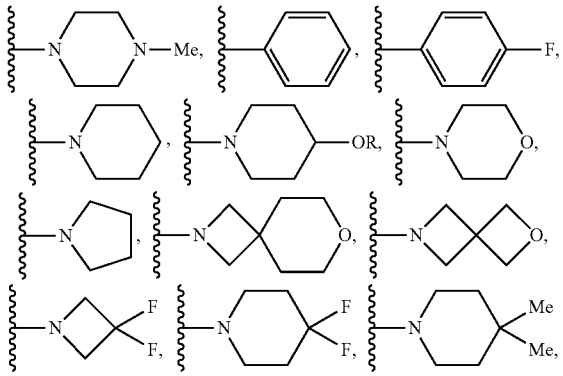

fluoro, bromo, methyl, —OR or —CF₃.

(4ss) R^{X1} is

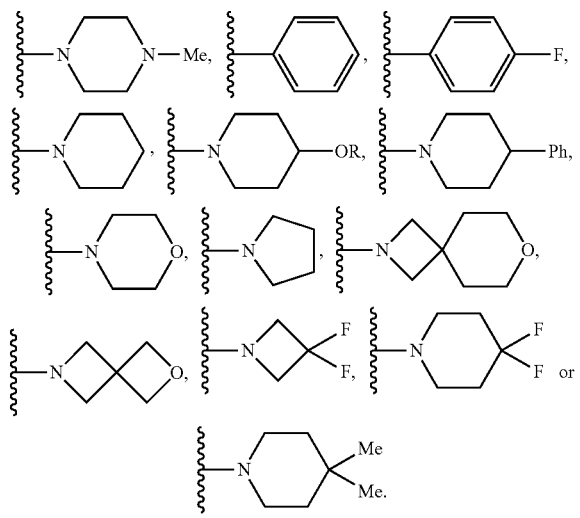

(4tt) R^{X1} is

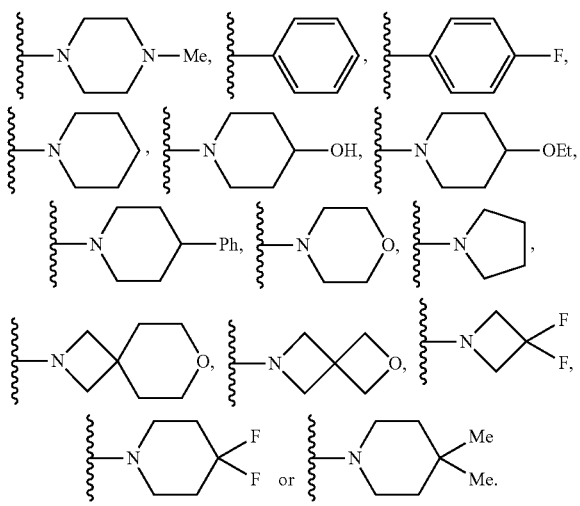

fluoro, bromo, methyl, —OMe or —CF$_3$.

(4uu) R^{X1} is

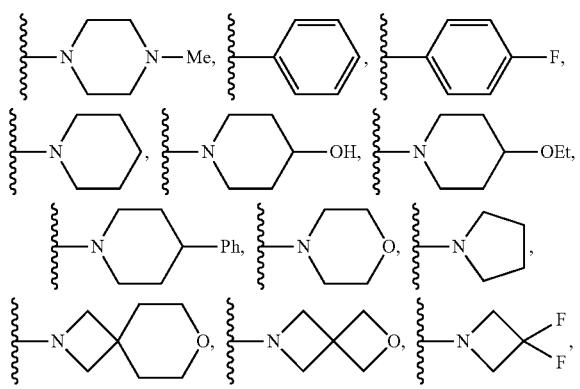

-continued

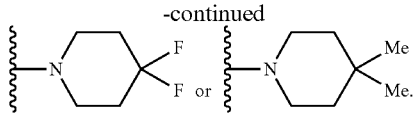

(4vv) R^{X1} is halogen, cyano, $C_1$-$C_6$alkyl, $C_1$-$C_6$haloalkyl, —$C_1$-$C_6$alkoxy, —$C_1$-$C_6$haloalkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR, —N(R)C(O)OR, —N(R)C(O)NR$_2$, —N(R)S(O)$_2$R, —OP(O)(OR)$_2$ or —CH$_2$—OP(O)(OR).

(4ww) R^{X1} is halogen, cyano, $C_1$-$C_6$alkyl, $C_1$-$C_6$haloalkyl, —$C_1$-$C_6$alkoxy, —$C_1$-$C_6$haloalkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$ or —N(R)S(O)$_2$R.

(4xx) R^{X1} is halogen, $C_1$-$C_6$alkyl, $C_1$-$C_6$haloalkyl, —$C_1$-$C_6$alkoxy, —$C_1$-$C_6$haloalkoxy, oxo, —OR, —C(O)R, —C(O)OR, —C(O)NR$_2$, —S(O)$_2$NR$_2$, —S(O)$_2$R, —OC(O)R, —N(R)C(O)R, —N(R)C(O)R, —OC(O)OR, —OC(O)NR$_2$, —N(R)C(O)OR, —N(R)C(O)NR$_2$ or —N(R)S(O)$_2$R (4yy) R^{X1} is halogen, $C_1$-$C_6$alkyl, $C_1$-$C_6$haloalkyl, —$C_1$-$C_6$alkoxy, —$C_1$-$C_6$haloalkoxy, oxo, —OR, —C(O)R, —C(O)OR, —C(O)NR$_2$, —OC(O)R, —N(R)C(O)R, —N(R)C(O)OR, —N(R)C(O)NR$_2$ or —N(R)S(O)$_2$R.

(4zz) R^{X1} is halogen, $C_1$-$C_6$alkyl, $C_1$-$C_6$haloalkyl, —$C_1$-$C_6$alkoxy, —$C_1$-$C_6$haloalkoxy, oxo, —OR, —C(O)R, —C(O)OR, —C(O)NR$_2$, —N(R)C(O)R, —N(R)C(O)OR, —N(R)C(O)NR$_2$ or —N(R)S(O)$_2$R, (4aaa) R^{X1} is halogen, $C_1$-$C_6$alkyl, $C_1$-$C_6$haloalkyl, —$C_1$-$C_6$haloalkoxy, oxo, —OR, —C(O)R, —C(O)OR or —C(O)NR$_2$.

(4bbb) R^{X1} is halogen, $C_1$-$C_6$alkyl, $C_1$-$C_6$haloalkyl, —$C_1$-$C_6$haloalkoxy, oxo or —OR.

(4ccc) R^{X1} is halogen, $C_1$-$C_6$alkyl, $C_1$-$C_6$haloalkyl, oxo or —OR (4ddd) R^{X1} is halogen, $C_1$-$C_6$alkyl, oxo or —OR (4eee) R^{X1} is halogen, $C_1$-$C_6$alkyl or oxo.

(4fff) R^{X1} is halogen or $C_1$-$C_6$alkyl.

(4ggg) R^{X1} is halogen.

(4hhh) R^{X1} is bromo or fluoro.

(4iii) R^{X1} is bromo.

(4jjj) R^{X1} is fluoro.

(4kkk) R^{X1} is any of groups (4a)-(4bb) and (4pp)-(4qq), wherein —R^{X2} is independently halogen, cyano, nitro, oxo, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$alkyl, $C_1$-$C_6$haloalkyl or Ar (4lll) R^{X1} is any of groups (4a)-(4bb) and (4pp)-(4qq), wherein —R^{X2} is independently halogen, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, $C_1$-$C_6$alkyl, $C_1$-$C_6$haloalkyl or Ar.

(4mmm) R^{X1} is any of groups (4a)-(4bb) and (4pp)-(4qq), wherein —R^{X2} is independently halogen, —OR, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, $C_1$-$C_6$alkyl, $C_1$-$C_6$haloalkyl or Ar.

(4nnn) $R^{X1}$ is any of groups (4a)-(4bb) and (4pp)-(4qq), wherein —$R^{X2}$ is independently halogen, —OR, —$C_1$-$C_6$alkyl, $C_1$-$C_6$haloalkyl or Ar.
(4ooo) $R^{X1}$ is any of groups (4a)-(4bb) and (4pp)-(4qq), wherein —$R^{X2}$ is independently halogen, —OR, —$C_1$-$C_6$alkyl or Ar.
(4ppp) $R^{X1}$ is any of groups (4a)-(4bb) and (4pp)-(4qq), wherein —$R^{X2}$ is independently fluoro, —OR, methyl or phenyl.
(4qqq) $R^{X1}$ is any of groups (4a)-(4bb) and (4pp)-(4qq), wherein —$R^{X2}$ is independently fluoro, —OH, —OMe, methyl or phenyl.
(4rrr) $R^{X1}$ is any of groups (4a)-(4bb) and (4pp)-(4qq), wherein —$R^{X2}$ is independently halogen, —OR or $C_1$-$C_6$alkyl.
(4sss) $R^{X1}$ is any of groups (4a)-(4bb) and (4pp)-(4qq), wherein —$R^{X2}$ is independently fluoro, —OR or methyl.
(4ttt) $R^{X1}$ is any of groups (4a)-(4bb) and (4pp)-(4qq), wherein —$R^{X2}$ is independently fluoro, —OH, —OMe or methyl.

Particular embodiments of this aspect of the invention comprise compounds of any one of the formulae (II), (IIa)-(III), (III), and (IIIa)-(IIIn), each as defined in each of the following rows (or a pharmaceutically acceptable salt, prodrug, or N-oxide thereof, or a solvate or hydrate thereof), wherein each entry is a group number as defined above (e.g., (2aa) refers to Z is methyl, and a dash "-" indicates that the variable is as defined in embodiment $I_1$ or defined according to any one of the applicable variable definitions (1a)-(3h) [e.g., when Z is a dash, it can be either as defined in any of embodiments $II_1$-$II_{10}$, $III_1$-$III_4$ or any one of definitions (2a)-(2tt)]):

| | (II)/(III) | Z | $R^1$ | $R^{X1}$ |
|---|---|---|---|---|
| (2)-1 | (IIa) | (1a) | (2a) | (4a) |
| (2)-2 | (IIa) | (1c) | (2b) | (4h) |
| (2)-3 | (IIa) | (1d) | (2x) | (4s) |
| (2)-4 | (IIa) | (1h) | (2aa) | (4kk) |
| (2)-5 | (IIa) | (1i) | (2bb) | (4pp) |
| (2)-6 | (IIa) | (1j) | (2cc) | (4uu) |
| (2)-7 | (IIa) | (1k) | (2dd) | (4vv) |
| (2)-8 | (IIa) | (1l) | (2kk) | (4bbb) |
| (2)-9 | (IIa) | (1m) | (2ll) | (4kkk) |
| (2)-10 | (IIa) | (1n) | (2mm) | (4ooo) |
| (2)-11 | (IIa) | (1o) | (2rr) | (4ttt) |
| (2)-12 | (IIa) | (1p) | (2ss) | (4bbb) |
| (2)-13 | (IIa) | (1x) | (2tt) | (4kkk) |
| (2)-14 | (IIa) | (1ee) | (2a) | (4s) |
| (2)-15 | (IIa) | (1jj) | (2b) | (4s) |
| (2)-16 | (IIa) | (1kk) | (2x) | (4a) |
| (2)-17 | (IIa) | (1nn) | (2rr) | (4vv) |
| (2)-18 | (IIa) | (1rr) | (2ss) | (4bbb) |
| (2)-19 | (IIa) | (1eee) | (2tt) | (4kkk) |
| (2)-20 | (IIa) | (1ggg) | (2b) | (4h) |
| (2)-21 | (IIa) | (1hhh) | (2x) | (4s) |
| (2)-22 | (IIa) | (1www) | (2rr) | (4a) |
| (2)-23 | (IIa) | (1aaaa) | (2rr) | (4a) |
| (2)-24 | (IIa) | (1bbbb) | (2ss) | (4h) |
| (2)-25 | (IIa) | (1j) | (2cc) | (4s) |
| (2)-26 | (IIa) | (1k) | (2aa) | (4kkk) |
| (2)-27 | (IIa) | (1x) | (2bb) | (4vv) |
| (2)-28 | (IIa) | (1ee) | (2ss) | (4bbb) |
| (2)-29 | (IIa) | (1d) | (2x) | (4kkk) |
| (2)-30 | (IIa) | (1h) | (2aa) | (4a) |
| (2)-31 | (IIa) | (1i) | (2bb) | (4bbb) |
| (2)-32 | (IIa) | (1l) | (2bb) | (4kkk) |
| (2)-33 | (IIa) | (1m) | (2cc) | (4a) |
| (2)-34 | (IIa) | (1n) | (2dd) | (4vv) |
| (2)-35 | (IIa) | (1o) | (2kk) | (4bbb) |
| (2)-36 | (IIa) | (1p) | (2rr) | (4kkk) |
| (2)-37 | (IIa) | (1x) | (2ss) | (4a) |
| (2)-38 | (IIa) | (1ee) | (2mm) | (4bbb) |
| (2)-39 | (IIa) | (1jj) | (2rr) | (4kkk) |
| (2)-40 | (IIa) | (1kk) | (2a) | (4s) |
| (2)-41 | (IIa) | (1nn) | (2b) | (4bbb) |
| (2)-42 | (IIa) | (1ggg) | (2x) | (4kkk) |
| (2)-43 | (IIc) | (1a) | (2a) | (4a) |
| (2)-44 | (IIc) | (1c) | (2b) | (4h) |
| (2)-45 | (IIc) | (1d) | (2x) | (4s) |
| (2)-46 | (IIc) | (1h) | (2aa) | (4kk) |
| (2)-47 | (IIc) | (1i) | (2bb) | (4pp) |
| (2)-48 | (IIc) | (1j) | (2cc) | (4uu) |
| (2)-49 | (IIc) | (1k) | (2dd) | (4vv) |
| (2)-50 | (IIc) | (1l) | (2kk) | (4bbb) |
| (2)-51 | (IIc) | (1m) | (2ll) | (4kkk) |
| (2)-52 | (IIc) | (1n) | (2mm) | (4ooo) |
| (2)-53 | (IIc) | (1o) | (2rr) | (4ttt) |
| (2)-54 | (IIc) | (1p) | (2ss) | (4bbb) |
| (2)-55 | (IIc) | (1x) | (2tt) | (4kkk) |
| (2)-56 | (IIc) | (1ee) | (2a) | (4s) |
| (2)-57 | (IIc) | (1jj) | (2b) | (4s) |
| (2)-58 | (IIc) | (1kk) | (2x) | (4a) |
| (2)-59 | (IIc) | (1nn) | (2rr) | (4vv) |
| (2)-60 | (IIc) | (1rr) | (2ss) | (4bbb) |
| (2)-61 | (IIc) | (1eee) | (2tt) | (4kkk) |
| (2)-62 | (IIc) | (1ggg) | (2b) | (4h) |
| (2)-63 | (IIc) | (1hhh) | (2x) | (4s) |
| (2)-64 | (IIc) | (1www) | (2rr) | (4a) |
| (2)-65 | (IIc) | (1aaaa) | (2rr) | (4a) |
| (2)-66 | (IIc) | (1bbbb) | (2ss) | (4h) |
| (2)-67 | (IIc) | (1j) | (2cc) | (4s) |
| (2)-68 | (IIc) | (1k) | (2aa) | (4kkk) |
| (2)-69 | (IIc) | (1x) | (2bb) | (4vv) |
| (2)-70 | (IIc) | (1ee) | (2ss) | (4bbb) |
| (2)-71 | (IIc) | (1d) | (2x) | (4kkk) |
| (2)-72 | (IIc) | (1h) | (2aa) | (4a) |
| (2)-73 | (IIc) | (1i) | (2bb) | (4bbb) |
| (2)-74 | (IIc) | (1l) | (2bb) | (4kkk) |
| (2)-75 | (IIc) | (1m) | (2cc) | (4a) |
| (2)-76 | (IIc) | (1n) | (2dd) | (4vv) |
| (2)-77 | (IIc) | (1o) | (2kk) | (4bbb) |
| (2)-78 | (IIc) | (1p) | (2rr) | (4kkk) |
| (2)-79 | (IIc) | (1x) | (2ss) | (4a) |
| (2)-80 | (IIc) | (1ee) | (2mm) | (4bbb) |
| (2)-81 | (IIc) | (1jj) | (2rr) | (4kkk) |
| (2)-82 | (IIc) | (1kk) | (2a) | (4s) |
| (2)-83 | (IIc) | (1nn) | (2b) | (4bbb) |
| (2)-84 | (IIc) | (1ggg) | (2x) | (4kkk) |
| (2)-85 | (IId) | (1a) | (2a) | (4a) |
| (2)-86 | (IId) | (1c) | (2b) | (4h) |
| (2)-87 | (IId) | (1d) | (2x) | (4s) |
| (2)-88 | (IId) | (1h) | (2aa) | (4kk) |
| (2)-89 | (IId) | (1i) | (2bb) | (4pp) |
| (2)-90 | (IId) | (1j) | (2cc) | (4uu) |
| (2)-91 | (IId) | (1k) | (2dd) | (4vv) |
| (2)-92 | (IId) | (1l) | (2kk) | (4bbb) |
| (2)-93 | (IId) | (1m) | (2ll) | (4kkk) |
| (2)-94 | (IId) | (1n) | (2mm) | (4ooo) |
| (2)-95 | (IId) | (1o) | (2rr) | (4ttt) |
| (2)-96 | (IId) | (1p) | (2ss) | (4bbb) |
| (2)-97 | (IId) | (1x) | (2tt) | (4kkk) |
| (2)-98 | (IId) | (1ee) | (2a) | (4s) |
| (2)-99 | (IId) | (1jj) | (2b) | (4s) |
| (2)-100 | (IId) | (1kk) | (2x) | (4a) |
| (2)-101 | (IId) | (1nn) | (2rr) | (4vv) |
| (2)-102 | (IId) | (1rr) | (2ss) | (4bbb) |
| (2)-103 | (IId) | (1eee) | (2tt) | (4kkk) |
| (2)-104 | (IId) | (1ggg) | (2b) | (4h) |
| (2)-105 | (IId) | (1hhh) | (2x) | (4s) |
| (2)-106 | (IId) | (1www) | (2rr) | (4a) |
| (2)-107 | (IId) | (1aaaa) | (2rr) | (4a) |
| (2)-108 | (IId) | (1bbbb) | (2ss) | (4h) |
| (2)-109 | (IId) | (1j) | (2cc) | (4s) |
| (2)-110 | (IId) | (1k) | (2aa) | (4kkk) |
| (2)-111 | (IId) | (1x) | (2bb) | (4vv) |
| (2)-112 | (IId) | (1ee) | (2ss) | (4bbb) |
| (2)-113 | (IId) | (1d) | (2x) | (4kkk) |

| | (II)/(III) | Z | R¹ | R^X1 |
|---|---|---|---|---|
| (2)-114 | (IId) | (1h) | (2aa) | (4a) |
| (2)-115 | (IId) | (1i) | (2bb) | (4bbb) |
| (2)-116 | (IId) | (1l) | (2bb) | (4kkk) |
| (2)-117 | (IId) | (1m) | (2cc) | (4a) |
| (2)-118 | (IId) | (1n) | (2dd) | (4vv) |
| (2)-119 | (IId) | (1o) | (2kk) | (4bbb) |
| (2)-120 | (IId) | (1p) | (2rr) | (4kkk) |
| (2)-121 | (IId) | (1x) | (2ss) | (4a) |
| (2)-122 | (IId) | (1ee) | (2mm) | (4bbb) |
| (2)-123 | (IId) | (1jj) | (2rr) | (4kkk) |
| (2)-124 | (IId) | (1kk) | (2a) | (4s) |
| (2)-125 | (IId) | (1nn) | (2b) | (4bbb) |
| (2)-126 | (IId) | (1ggg) | (2x) | (4kkk) |
| (2)-127 | (IIg) | (1a) | (2a) | (4a) |
| (2)-128 | (IIg) | (1c) | (2b) | (4h) |
| (2)-129 | (IIg) | (1d) | (2x) | (4s) |
| (2)-130 | (IIg) | (1h) | (2aa) | (4kk) |
| (2)-131 | (IIg) | (1i) | (2bb) | (4pp) |
| (2)-132 | (IIg) | (1j) | (2cc) | (4uu) |
| (2)-133 | (IIg) | (1k) | (2dd) | (4vv) |
| (2)-134 | (IIg) | (1l) | (2kk) | (4bbb) |
| (2)-135 | (IIg) | (1m) | (2ll) | (4kkk) |
| (2)-136 | (IIg) | (1n) | (2mm) | (4ooo) |
| (2)-137 | (IIg) | (1o) | (2rr) | (4ttt) |
| (2)-138 | (IIg) | (1p) | (2ss) | (4bbb) |
| (2)-139 | (IIg) | (1x) | (2tt) | (4kkk) |
| (2)-140 | (IIg) | (1ee) | (2a) | (4s) |
| (2)-141 | (IIg) | (1jj) | (2b) | (4s) |
| (2)-142 | (IIg) | (1kk) | (2x) | (4a) |
| (2)-143 | (IIg) | (1nn) | (2rr) | (4vv) |
| (2)-144 | (IIg) | (1rr) | (2ss) | (4bbb) |
| (2)-145 | (IIg) | (1eee) | (2tt) | (4kkk) |
| (2)-146 | (IIg) | (1ggg) | (2b) | (4h) |
| (2)-147 | (IIg) | (1hhh) | (2x) | (4s) |
| (2)-148 | (IIg) | (1www) | (2rr) | (4a) |
| (2)-149 | (IIg) | (1aaaa) | (2rr) | (4a) |
| (2)-150 | (IIg) | (1bbbb) | (2ss) | (4h) |
| (2)-151 | (IIg) | (1j) | (2cc) | (4s) |
| (2)-152 | (IIg) | (1k) | (2aa) | (4kkk) |
| (2)-153 | (IIg) | (1x) | (2bb) | (4vv) |
| (2)-154 | (IIg) | (1ee) | (2ss) | (4bbb) |
| (2)-155 | (IIg) | (1d) | (2x) | (4kkk) |
| (2)-156 | (IIg) | (1h) | (2aa) | (4a) |
| (2)-157 | (IIg) | (1i) | (2bb) | (4bbb) |
| (2)-158 | (IIg) | (1l) | (2bb) | (4kkk) |
| (2)-159 | (IIg) | (1m) | (2cc) | (4a) |
| (2)-160 | (IIg) | (1n) | (2dd) | (4vv) |
| (2)-161 | (IIg) | (1o) | (2kk) | (4bbb) |
| (2)-162 | (IIg) | (1p) | (2rr) | (4kkk) |
| (2)-163 | (IIg) | (1x) | (2ss) | (4a) |
| (2)-164 | (IIg) | (1ee) | (2mm) | (4bbb) |
| (2)-165 | (IIg) | (1jj) | (2rr) | (4kkk) |
| (2)-166 | (IIg) | (1kk) | (2a) | (4s) |
| (2)-167 | (IIg) | (1nn) | (2b) | (4bbb) |
| (2)-168 | (IIg) | (1ggg) | (2x) | (4kkk) |
| (2)-169 | (IIh) | (1a) | (2a) | X |
| (2)-170 | (IIh) | (1c) | (2b) | X |
| (2)-171 | (IIh) | (1d) | (2x) | X |
| (2)-172 | (IIh) | (1h) | (2aa) | X |
| (2)-173 | (IIh) | (1i) | (2bb) | X |
| (2)-174 | (IIh) | (1j) | (2cc) | X |
| (2)-175 | (IIh) | (1k) | (2dd) | X |
| (2)-176 | (IIh) | (1l) | (2kk) | X |
| (2)-177 | (IIh) | (1m) | (2ll) | X |
| (2)-178 | (IIh) | (1n) | (2mm) | X |
| (2)-179 | (IIh) | (1o) | (2rr) | X |
| (2)-180 | (IIh) | (1p) | (2ss) | X |
| (2)-181 | (IIh) | (1x) | (2tt) | X |
| (2)-182 | (IIh) | (1ee) | (2a) | X |
| (2)-183 | (IIh) | (1jj) | (2b) | X |
| (2)-184 | (IIh) | (1kk) | (2x) | X |
| (2)-185 | (IIh) | (1nn) | (2rr) | X |
| (2)-186 | (IIh) | (1rr) | (2ss) | X |
| (2)-187 | (IIh) | (1eee) | (2tt) | X |
| (2)-188 | (IIh) | (1ggg) | (2b) | X |
| (2)-189 | (IIh) | (1hhh) | (2x) | X |
| (2)-190 | (IIh) | (1www) | (2rr) | X |
| (2)-191 | (IIh) | (1aaaa) | (2rr) | X |
| (2)-192 | (IIh) | (1bbbb) | (2ss) | X |
| (2)-193 | (IIh) | (1j) | (2cc) | X |
| (2)-194 | (IIh) | (1k) | (2aa) | X |
| (2)-195 | (IIh) | (1x) | (2bb) | X |
| (2)-196 | (IIh) | (1ee) | (2ss) | X |
| (2)-197 | (IIh) | (1d) | (2x) | X |
| (2)-198 | (IIh) | (1h) | (2aa) | X |
| (2)-199 | (IIh) | (1i) | (2bb) | X |
| (2)-200 | (IIh) | (1l) | (2bb) | X |
| (2)-201 | (IIh) | (1m) | (2cc) | X |
| (2)-202 | (IIh) | (1n) | (2dd) | X |
| (2)-203 | (IIh) | (1o) | (2kk) | X |
| (2)-204 | (IIh) | (1p) | (2rr) | X |
| (2)-205 | (IIh) | (1x) | (2ss) | X |
| (2)-206 | (IIh) | (1ee) | (2mm) | X |
| (2)-207 | (IIh) | (1jj) | (2rr) | X |
| (2)-208 | (IIh) | (1kk) | (2a) | X |
| (2)-209 | (IIh) | (1nn) | (2b) | X |
| (2)-210 | (IIh) | (1ggg) | (2x) | X |
| (2)-211 | (IIi) | (1a) | (2a) | X |
| (2)-212 | (IIi) | (1c) | (2b) | X |
| (2)-213 | (IIi) | (1d) | (2x) | X |
| (2)-214 | (IIi) | (1h) | (2aa) | X |
| (2)-215 | (IIi) | (1i) | (2bb) | X |
| (2)-216 | (IIi) | (1j) | (2cc) | X |
| (2)-217 | (IIi) | (1k) | (2dd) | X |
| (2)-218 | (IIi) | (1l) | (2kk) | X |
| (2)-219 | (IIi) | (1m) | (2ll) | X |
| (2)-220 | (IIi) | (1n) | (2mm) | X |
| (2)-221 | (IIi) | (1o) | (2rr) | X |
| (2)-222 | (IIi) | (1p) | (2ss) | X |
| (2)-223 | (IIi) | (1x) | (2tt) | X |
| (2)-224 | (IIi) | (1ee) | (2a) | X |
| (2)-225 | (IIi) | (1jj) | (2b) | X |
| (2)-226 | (IIi) | (1kk) | (2x) | X |
| (2)-227 | (IIi) | (1nn) | (2rr) | X |
| (2)-228 | (IIi) | (1rr) | (2ss) | X |
| (2)-229 | (IIi) | (1eee) | (2tt) | X |
| (2)-230 | (IIi) | (1ggg) | (2b) | X |
| (2)-231 | (IIi) | (1hhh) | (2x) | X |
| (2)-232 | (IIi) | (1www) | (2rr) | X |
| (2)-233 | (IIi) | (1aaaa) | (2rr) | X |
| (2)-234 | (IIi) | (1bbbb) | (2ss) | X |
| (2)-235 | (IIi) | (1j) | (2cc) | X |
| (2)-236 | (IIi) | (1k) | (2aa) | X |
| (2)-237 | (IIi) | (1x) | (2bb) | X |
| (2)-238 | (IIi) | (1ee) | (2ss) | X |
| (2)-239 | (IIi) | (1d) | (2x) | X |
| (2)-240 | (IIi) | (1h) | (2aa) | X |
| (2)-241 | (IIi) | (1i) | (2bb) | X |
| (2)-242 | (IIi) | (1l) | (2bb) | X |
| (2)-243 | (IIi) | (1m) | (2cc) | X |
| (2)-244 | (IIi) | (1n) | (2dd) | X |
| (2)-245 | (IIi) | (1o) | (2kk) | X |
| (2)-246 | (IIi) | (1p) | (2rr) | X |
| (2)-247 | (IIi) | (1x) | (2ss) | X |
| (2)-248 | (IIi) | (1ee) | (2mm) | X |
| (2)-249 | (IIi) | (1jj) | (2rr) | X |
| (2)-250 | (IIi) | (1kk) | (2a) | X |
| (2)-251 | (IIi) | (1nn) | (2b) | X |
| (2)-252 | (IIi) | (1ggg) | (2x) | X |
| (2)-253 | (III) | (1a) | (2a) | X |
| (2)-254 | (III) | (1c) | (2b) | X |
| (2)-255 | (III) | (1d) | (2x) | X |
| (2)-256 | (III) | (1h) | (2aa) | X |
| (2)-257 | (III) | (1i) | (2bb) | X |
| (2)-258 | (III) | (1j) | (2cc) | X |
| (2)-259 | (III) | (1k) | (2dd) | X |
| (2)-260 | (III) | (1l) | (2kk) | X |
| (2)-261 | (III) | (1m) | (2ll) | X |
| (2)-262 | (III) | (1n) | (2mm) | X |
| (2)-263 | (III) | (1o) | (2rr) | X |
| (2)-264 | (III) | (1p) | (2ss) | X |
| (2)-265 | (III) | (1x) | (2tt) | X |
| (2)-266 | (III) | (1ee) | (2a) | X |
| (2)-267 | (III) | (1jj) | (2b) | X |

|  | (II)/(III) | Z | R¹ | R^X1 |
|---|---|---|---|---|
| (2)-268 | (III) | (1kk) | (2x) | X |
| (2)-269 | (III) | (1nn) | (2rr) | X |
| (2)-270 | (III) | (1rr) | (2ss) | X |
| (2)-271 | (III) | (1eee) | (2tt) | X |
| (2)-272 | (III) | (1ggg) | (2b) | X |
| (2)-273 | (III) | (1hhh) | (2x) | X |
| (2)-274 | (III) | (1www) | (2rr) | X |
| (2)-275 | (III) | (1aaaa) | (2rr) | X |
| (2)-276 | (III) | (1bbbb) | (2ss) | X |
| (2)-277 | (III) | (1j) | (2cc) | X |
| (2)-278 | (III) | (1k) | (2aa) | X |
| (2)-279 | (III) | (1x) | (2bb) | X |
| (2)-280 | (III) | (1ee) | (2ss) | X |
| (2)-281 | (III) | (1d) | (2x) | X |
| (2)-282 | (III) | (1h) | (2aa) | X |
| (2)-283 | (III) | (1i) | (2bb) | X |
| (2)-284 | (III) | (1l) | (2bb) | X |
| (2)-285 | (III) | (1m) | (2cc) | X |
| (2)-286 | (III) | (1n) | (2dd) | X |
| (2)-287 | (III) | (1o) | (2kk) | X |
| (2)-288 | (III) | (1p) | (2rr) | X |
| (2)-289 | (III) | (1x) | (2ss) | X |
| (2)-290 | (III) | (1ee) | (2mm) | X |
| (2)-291 | (III) | (1jj) | (2rr) | X |
| (2)-292 | (III) | (1kk) | (2a) | X |
| (2)-293 | (III) | (1nn) | (2b) | X |
| (2)-294 | (III) | (1ggg) | (2x) | X |
| (2)-295 | (IIIc) | (1a) | (2a) | (4a) |
| (2)-296 | (IIIc) | (1c) | (2b) | (4h) |
| (2)-297 | (IIIc) | (1d) | (2x) | (4s) |
| (2)-298 | (IIIc) | (1h) | (2aa) | (4kk) |
| (2)-299 | (IIIc) | (1i) | (2bb) | (4pp) |
| (2)-300 | (IIIc) | (1j) | (2cc) | (4uu) |
| (2)-301 | (IIIc) | (1k) | (2dd) | (4vv) |
| (2)-302 | (IIIc) | (1l) | (2kk) | (4bbb) |
| (2)-303 | (IIIc) | (1m) | (2ll) | (4kkk) |
| (2)-304 | (IIIc) | (1n) | (2mm) | (4ooo) |
| (2)-305 | (IIIc) | (1o) | (2rr) | (4ttt) |
| (2)-306 | (IIIc) | (1p) | (2ss) | (4bbb) |
| (2)-307 | (IIIc) | (1x) | (2tt) | (4kkk) |
| (2)-308 | (IIIc) | (1ee) | (2a) | (4s) |
| (2)-309 | (IIIc) | (1jj) | (2b) | (4s) |
| (2)-310 | (IIIc) | (1kk) | (2x) | (4a) |
| (2)-311 | (IIIc) | (1nn) | (2rr) | (4vv) |
| (2)-312 | (IIIc) | (1rr) | (2ss) | (4bbb) |
| (2)-313 | (IIIc) | (1eee) | (2tt) | (4kkk) |
| (2)-314 | (IIIc) | (1ggg) | (2b) | (4h) |
| (2)-315 | (IIIc) | (1hhh) | (2x) | (4s) |
| (2)-316 | (IIIc) | (1www) | (2rr) | (4a) |
| (2)-317 | (IIIc) | (1aaaa) | (2rr) | (4a) |
| (2)-318 | (IIIc) | (1bbbb) | (2ss) | (4h) |
| (2)-319 | (IIIc) | (1j) | (2cc) | (4s) |
| (2)-320 | (IIIc) | (1k) | (2aa) | (4kkk) |
| (2)-321 | (IIIc) | (1x) | (2bb) | (4vv) |
| (2)-322 | (IIIc) | (1ee) | (2ss) | (4bbb) |
| (2)-323 | (IIIc) | (1d) | (2x) | (4kkk) |
| (2)-324 | (IIIc) | (1h) | (2aa) | (4a) |
| (2)-325 | (IIIc) | (1i) | (2bb) | (4bbb) |
| (2)-326 | (IIIc) | (1l) | (2bb) | (4kkk) |
| (2)-327 | (IIIc) | (1m) | (2cc) | (4a) |
| (2)-328 | (IIIc) | (1n) | (2dd) | (4vv) |
| (2)-329 | (IIIc) | (1o) | (2kk) | (4bbb) |
| (2)-330 | (IIIc) | (1p) | (2rr) | (4kkk) |
| (2)-331 | (IIIc) | (1x) | (2ss) | (4a) |
| (2)-332 | (IIIc) | (1ee) | (2mm) | (4bbb) |
| (2)-333 | (IIIc) | (1jj) | (2rr) | (4kkk) |
| (2)-334 | (IIIc) | (1kk) | (2a) | (4s) |
| (2)-335 | (IIIc) | (1nn) | (2b) | (4bbb) |
| (2)-336 | (IIIc) | (1ggg) | (2x) | (4kkk) |
| (2)-337 | (IIId) | (1a) | (2a) | (4a) |
| (2)-338 | (IIId) | (1c) | (2b) | (4h) |
| (2)-339 | (IIId) | (1d) | (2x) | (4s) |
| (2)-340 | (IIId) | (1h) | (2aa) | (4kk) |
| (2)-341 | (IIId) | (1i) | (2bb) | (4pp) |
| (2)-342 | (IIId) | (1j) | (2cc) | (4uu) |
| (2)-343 | (IIId) | (1k) | (2dd) | (4vv) |
| (2)-344 | (IIId) | (1l) | (2kk) | (4bbb) |
| (2)-345 | (IIId) | (1m) | (2ll) | (4kkk) |
| (2)-346 | (IIId) | (1n) | (2mm) | (4ooo) |
| (2)-347 | (IIId) | (1o) | (2rr) | (4ttt) |
| (2)-348 | (IIId) | (1p) | (2ss) | (4bbb) |
| (2)-349 | (IIId) | (1x) | (2tt) | (4kkk) |
| (2)-350 | (IIId) | (1ee) | (2a) | (4s) |
| (2)-351 | (IIId) | (1jj) | (2b) | (4s) |
| (2)-352 | (IIId) | (1kk) | (2x) | (4a) |
| (2)-353 | (IIId) | (1nn) | (2rr) | (4vv) |
| (2)-354 | (IIId) | (1rr) | (2ss) | (4bbb) |
| (2)-355 | (IIId) | (1eee) | (2tt) | (4kkk) |
| (2)-356 | (IIId) | (1ggg) | (2b) | (4h) |
| (2)-357 | (IIId) | (1hhh) | (2x) | (4s) |
| (2)-358 | (IIId) | (1www) | (2rr) | (4a) |
| (2)-359 | (IIId) | (1aaaa) | (2rr) | (4a) |
| (2)-360 | (IIId) | (1bbbb) | (2ss) | (4h) |
| (2)-361 | (IIId) | (1j) | (2cc) | (4s) |
| (2)-362 | (IIId) | (1k) | (2aa) | (4kkk) |
| (2)-363 | (IIId) | (1x) | (2bb) | (4vv) |
| (2)-364 | (IIId) | (1ee) | (2ss) | (4bbb) |
| (2)-365 | (IIId) | (1d) | (2x) | (4kkk) |
| (2)-366 | (IIId) | (1h) | (2aa) | (4a) |
| (2)-367 | (IIId) | (1i) | (2bb) | (4bbb) |
| (2)-368 | (IIId) | (1l) | (2bb) | (4kkk) |
| (2)-369 | (IIId) | (1m) | (2cc) | (4a) |
| (2)-370 | (IIId) | (1n) | (2dd) | (4vv) |
| (2)-371 | (IIId) | (1o) | (2kk) | (4bbb) |
| (2)-372 | (IIId) | (1p) | (2rr) | (4kkk) |
| (2)-373 | (IIId) | (1x) | (2ss) | (4a) |
| (2)-374 | (IIId) | (1ee) | (2mm) | (4bbb) |
| (2)-375 | (IIId) | (1jj) | (2rr) | (4kkk) |
| (2)-376 | (IIId) | (1kk) | (2a) | (4s) |
| (2)-377 | (IIId) | (1nn) | (2b) | (4bbb) |
| (2)-378 | (IIId) | (1ggg) | (2x) | (4kkk) |

In some embodiments, the compound of any of formulae (I), (Ia)-(Io), (II), (IIa)-(III), (III), and (IIIa)-(IIIn) is one of the following compounds (or a pharmaceutically acceptable salt, prodrug, or N-oxide thereof, or a solvate or hydrate thereof): 2, 3, 4, 5, 6, 7, 9, 10, 11, 12, 13, 16, 18, 21, 22, 23, 25, 26, 27, 28, 30, 35, 36, 37, 38, 39, 40, 42, 43, 44, 46, 49.

In some embodiments, the compound of any of formulae (I), (Ia)-(Io), (II), (IIa)-(III), (III), and (IIIa)-(IIIn) is one of the following compounds (or a pharmaceutically acceptable salt, prodrug, or N-oxide thereof, or a solvate or hydrate thereof): 2, 4, 5, 6, 7, 9, 10, 13, 16, 18, 23, 26, 28, 30, 35, 36, 37, 38, 39, 40, 42, 43, 46, 49.

In some embodiments, the compound of any of formulae (I), (Ia)-(Io), (II), (IIa)-(III), (III), and (IIIa)-(IIIn) is one of the following compounds (or a pharmaceutically acceptable salt, prodrug, or N-oxide thereof, or a solvate or hydrate thereof): 4, 5, 6, 10, 26, 28, 30, 35, 36, 38, 39.

In some embodiments, the compound of any of formulae (I), (Ia)-(Io), (II), (IIa)-(III), (III), and (IIIa)-(IIIn) is one of the following compounds (or a pharmaceutically acceptable salt, prodrug, or N-oxide thereof, or a solvate or hydrate thereof): 4, 5, 6, 10, 35, 39.

In another aspect, the present invention comprises pharmaceutical compositions comprising a compound according to any one of the preceding aspects of the invention or any embodiment thereof, together with a pharmaceutically acceptable excipient, diluent, or carrier.

In another aspect, the invention comprises the use of a compound described by any one of the preceding aspects of the invention or any embodiment thereof, for the preparation of a medicament for the treatment of medical diseases or conditions that benefit from the inhibition of cytokine signaling. Medical conditions contemplated in this aspect include all diseases and conditions described herein.

The compounds of formulae (I), (Ia)-(Io), (II), (IIa)-(III), (III), and (IIIa)-(IIIn) described above are useful as tyrosine kinase inhibitors. Tyrosine kinases are characterized by a conserved sequence within the kinase domain and adhesion molecule-like extracellular domains. Tyrosine kinases regulate a number of biological processes, including cell proliferation/survival, cell adhesion and migration, blood clot stabilization, and regulation of inflammatory cytokine release. Genetic or experimental alteration of tyrosine kinase function, specifically of the TAM (Tyro 3, Axl and Mer) receptor family, can contribute to a number of disease states, including coagulopathy, autoimmune disease, retinitis pigmentosa, and cancer. Thus, tyrosine kinases, specifically the TAM (Tyro 3, Axl and Mer) receptor family play a role in oncogenic mechanisms as family members are overexpressed in a spectrum of human cancers and have prognostic significance in some. In one aspect the present compounds are selective for one or more tyrosine kinase. For example, exemplary compounds inhibit on of more of the TAM (Tyro 3, Axl and Mer) receptor family. In certain examples, the present compounds inhibit Mer from about 5-fold less potently to about equipotently with Axl. In other examples, the present compounds inhibit Mer selectively over Axl.

In particular, the present compounds can be use to treat disorders, such as pulmonary hypertension, chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, atherosclerosis, peritoneal and sub-dermal adhesion, kidney fibrosis, lung fibrosis, including idiopathic pulmonary fibrosis, and liver fibrosis, hepatitis B, hepatitis C, alcohol-induced hepatitis, cancer, haemochromatosis, primary biliary cirrhosis, restenosis, retroperitoneal fibrosis, mesenteric fibrosis, endometriosis, keloids, cancer, abnormal bone function, inflammatory disorders, scarring and photoaging of the skin.

Particular proliferative diseases that can be treated with the present compounds include those selected from a benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer, especially colon carcinoma or colorectal adenoma or a tumor of the neck and head, an epidermal hyperproliferation, melanoma, psoriasis, prostate hyperplasia, a neoplasia, a neoplasia of epithelial character, leukemias and lymphomas, a mammary carcinoma or a leukemia. Other diseases include Cowden syndrome, Lhermitte-Dudos disease and Bannayan-Zonana syndrome, or diseases in which the PI3K/PKB pathway is aberrantly activated.

The compounds described herein also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, $^{18}F$ etc. Thus, the disclosed compounds may be enriched in one or more of these isotopes relative to the natural abundance of such isotope. As is known to those of skill in the art, such isotopically enriched compounds are useful for a variety of purposes. For example, substitution with heavier isotopes such as deuterium ($^2H$) may afford certain therapeutic advantages that result from greater metabolic stability. Substitution with positron emitting isotopes, such as 18F can be useful in Positron Emission Tomography (PET) studies. By way of example, deuterium ($^2H$) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

In another aspect, the invention comprises combination therapies for the treatment of cancer, including both pre-malignant and malignant neoplasms. In this aspect, the invention comprises a method of treating cancer comprising administering to a subject a compound disclosed herein in conjunction with a therapeutic treatment of cancer. In some embodiments of the invention, the compounds disclosed herein are used in combination of standard of care antiproliferative treatments of cancer. The amount of a compound disclosed herein for use in the combination therapy is an amount sufficient to inhibit one or more of the TAM (Tyro 3, Axl and Mer) receptor family. Treatment with the present compounds thus blocks the ability of cancer stem cells to recapitulate a tumor destroyed by treatment with standard of care. Efficacy of treatment can be determined by any art recognized method generally employed for the particular cancer being treated and includes, for example, retardation, inhibition, or regression of tumor growth.

Reference to "combination therapy" and treatment with a compound disclosed herein "in conjunction with" another therapeutic treatment means that the compound and other therapeutic treatment can be administered simultaneously or sequentially such that the resultant treatment is more efficacious than either treatment alone.

One embodiment of treating cancer in a subject comprises administering to a subject in need thereof an amount described above of a compound disclosed herein in combination with the administration of a therapeutically effective amount of one or more chemotherapeutic agents, wherein the one or more chemotherapeutic agents is selected from the group consisting of antimetabolites, alkylating agents, coordination compounds, platinum complexes, DNA cross-linking compounds, inhibitors of transcription enzymes, tyrosine kinase inhibitors, protein kinase inhibitors, topoisomerase inhibitors, DNA minor-groove binding compounds, vinca alkyloids, taxanes, antitumor antibiotics, hormones, aromatase inhibitors, enzymes, growth factor receptors antibodies, cytokines, cell surface markers antibodies, HDAC inhibitors, HSP 90 inhibitors, BCL-2 inhibitors, B-raf inhibitors, MEK inhibitors, mTOR inhibitors, proteasome inhibitors and monoclonal antibodies.

Among the BCL-2 inhibitors useful in the invention is ABT-199.

Another embodiment of methods for treating a subject comprises administering to the subject an amount (as described above) of a compound disclosed herein in combination with the administration of a therapeutically effective amount of one or more chemotherapeutic agents, the one or more chemotherapeutic agents being independently selected from the group consisting of mechlorothamine, cyclophosphamide, ifosfamide, melphalan, chlorambucil, ethyleneimines, methylmelamines, procarbazine, dacarbazine, temozolomide, busulfan, carmustine, lomustine, methotrexate, fluorouracil, capecitabine, cytarabine, gemcitabine, cytosine arabinoside, mecaptopurine, fludarabine, cladribine, thioguanine, azathioprine, vinblastine, vincristine, paclitaxel, docetaxel, colchicine, actinomycin D, daunorubicin, bleomycin, L-asparaginase, cisplatin, carboplatin, oxaliplatin, prednisone, dexamethasone, amino glutethimide, formestane, anastrozole, hydroxyprogesterone caproate, medroxyprogesterone, tamoxifen, amsacrine, mitoxantrone, topotecan, irinotecan, camptothecin, afatinib, axitinib, bosutinib, bortezomib, carfilzomib, cabozantinib, cediranib, crizotinib, dasatinib, dabrafenib, evorolimus, ibrutinib, LDK378, LGX818, MEK162, regorafenib, ruxolitinib, selumetinib, sorafenib, trametinib, vemurafenib, erlotinib, gefitinib, imatinib, lapatinib, lestaurtinib, nilotinib, palbociclib, pazopanib, pomatinib, semaxanib, sirolimus, sunitinib, temsirolimus, vatalanib, vandetanib, anti Her2 antibodies, interferon-α, interferon-γ, interleukin 2, GM CSF, anti CTLA 4 antibodies, rituximab, anti CD33 antibodies, MGCD0103, vorinostat, 17-AAG, thalidomide, lenalidomide, rapamycin, CCI-779, doxorubicine, gemcitabine, melphalan, NPI052, gemtuzumab, alemtuzumab, cetuximab, ibritumomab tiuxaetan, tositumomab, iodine-131 tositumomab, trastuzumab, ado-trastuzumab emtansine, obinutuzumab, bevacizumab, rituximab, and anti-TRAIL death receptor antibodies.

In particular, the presently disclosed compounds are useful in combination with immunooncology agents, such as checkpoint inhibitors. Examples of such agents include anti-CTLA 4 agents, anti-PD1 and anti PD-L1 agents. Among the CTLA 4 antibodies that can be used in the present invention is ipilimumab, marketed as YERVOY® by Bristol-Myers Squibb.

Other checkpoint pathway inhibitors include PD-1 inhibitors, such as nivolumab and lambrolizumab, and PD-L1 inhibitors, such as pembrolizumab, atezolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed TAM receptor family inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

The following table displays exemplary cancers treatable in the combination therapies of the invention and the therapeutic drug and/or other treatment for use with the compounds disclosed herein:

| Cancer | Drug or Treatment |
|---|---|
| Glioma | lomustine, temozolide and/or radiation |
| hepatocellular carcinoma | sorafenib, regorafenib |
| myelodysplastic syndromes | decitabine or azacytidine |
| pancreatic cancer | Gemcitabine |
| ovarian cancer, such as epithelial ovarian carcinoma | carboplatin, cisplatin, doxorubicin, gemcitabine, paclitaxel |
| breast cancer | Trastuzumab |
| basal and squamous skin carcinomas | 5-fluorouracil, imiquimod, photodynamic therapy (e.g. with 5-aminolevulinic acid), |
| head and neck carcinoma | bleomycin, cisplatin, cetuximab, docetaxel, fluorouracil, methotrexate |
| triple negative breast cancer | Paclitaxel |
| Prostate | abiraterone, enzalutamide |

In another aspect, the invention comprises a method of determining and measuring the ability of the compounds disclosed herein to inhibit TAM (Tyro 3, Axl and Mer) receptor family, in order to identify cancers and, more specifically, tumors. In one embodiment, neoplasms susceptible to such combination therapy can be identified by testing for TAM (Tyro 3, Axl and Mer) receptor family activity using techniques known to those skilled in the art. Optionally in this embodiment, where the tested compound is found to inhibit on or more of the TAM (Tyro 3, Axl and Mer) receptor family in the tested neoplasm, the compound is subsequently used in a combination therapy for treatment of the neoplasm, as described herein.

Definitions

The names of the chemical structures disclosed herein are generated from the structures by ChemDraw Profession version 16.

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as $(A)_a$-B—, wherein a is 0 or 1. In such instances, when a is 0 the moiety is B— and when a is 1 the moiety is A-B—.

As used herein, the term "alkyl" includes alkyl, alkenyl and alkynyl groups of a designed number of carbon atoms, such as 1 to 6 carbons (i.e., inclusive of 1 and 6), 1 to 6 carbons, 1 to 3 carbons, or 1, 2, 3, 4, 5 or 6. The term "$C_m$-$C_n$alkyl" means an alkyl group having from m to n carbon atoms (i.e., inclusive of m and n). The term "$C_m$-$C_n$alkyl" means an alkyl group having from m to n carbon atoms. For example, "$C_1$-$C_6$alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$alkyl"), the group is simply a single covalent bond if it is a divalent radical or is a hydrogen atom if it is a monovalent radical. For example, the moiety "—($C_0$-$C_6$alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 6 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" or "Ar" refers to an aromatic ring or an aromatic ring system of 6-16 members having at least one carbocyclic aromatic ring (e.g., phenyl) optionally fused to one or more aromatic or non-aromatic rings. "Aryl" includes (a) single aromatic rings and (b) fused ring systems having 6-16 annular atoms in which at least one ring is a carbocyclic aromatic ring. A multicyclic fused ring system is designated as "aryl" if it is attached to the compound of formula (I) (or one of formulae (Ia)-(Io), (II), (IIa)-(III), (III), and (IIIa)-(IIIn)) via an aromatic ring of the multicyclic fused ring system. The one or more aromatic or non-aromatic rings may be, for example, aryl (Ar), heteroaryl (Het), cycloalkyl (Cak) or heterocycloalkyl (Hca) rings as described herein. Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. In certain examples, aryl groups include those having a first carbocyclic aromatic ring fused to a second aromatic or non-aromatic ring, for example, 2,3-dihydrobenzofuranyl. The aryl groups herein are unsubstituted or, when specified as "optionally substituted", can unless stated otherwise be substituted in one or more substitutable positions with various groups, as described below.

The term "heteroaryl" or "Het" refers to an aromatic ring or an aromatic ring system containing 5-15 members and at least one heteroatom selected from nitrogen, oxygen and sulfur in an aromatic ring, optionally fused to one or more aromatic or non-aromatic rings. Heteroaryl groups will have 1-4 O, S, or N atoms, provided no O or S is adjacent to another O or S. Most commonly, the heteroaryl groups will have 1, 2, 3, or 4 heteroatoms. "Heteroaryl" includes (a) single heteroaryl rings and (b) fused ring systems having 5-16 annular atoms in which at least one ring is heteroaryl and the ring system is bonded to the compound of formula (I) (or one of formulae (Ia)-(Io), (II), (IIa)-(IIf), (III), and (IIIa)-(IIIn)) via a heteroaryl ring of the fused ring system. The one or more aromatic or non-aromatic ring may be, for example, aryl (Ar), heteroaryl (Het), cycloalkyl (Cak) and heterocycloalkyl (Hca) rings as described herein. Multicyclic fused ring systems are designated "heteroaryl" if the ring system is bonded to the compound of formula (I) (or one of formulae (Ia)-(Io), (II), (IIa)-(IIf), (III), and (IIIa)-(IIIn)) via a heteroaryl ring of the fused ring system. For example, an 7,8-dihydro-6H-pyrano[3,2-d]pyrimidinyl group bonded to the compound of formula (I) (or one of formulae (Ia)-(Io), (II), (IIa)-(IIf), (III), and (IIIa)-(IIIn)) through the pyrimidinyl ring

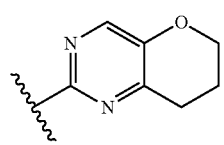 [SMILES: *c1ncc2c(n1)CCCO2]

is categorized as heteroaryl (Het). When the multicyclic heteroaryl ring system is fused through a heteroatom, it can be categorized as if the heteroatom were in the ring bonded to the compound of formula (I) (or one of formulae (Ia)-(Io), (II), (IIa)-(III), (III), and (IIIa)-(IIIn)). For example, an indolizinyl group

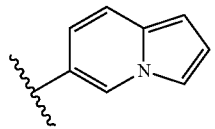 [SMILES: *c1ccc2cccn2c1]

is categorized as a 6-membered heteroaryl fused with a C₅cycloalkenyl ring. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4] oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" or "Hca" refers to a non-aromatic ring or a non-aromatic ring system containing 3-15 members and at least one heteroatom that is preferably selected from nitrogen, oxygen and sulfur, wherein said heteroatom is in a non-aromatic ring, and optionally including one or more other aromatic or non-aromatic rings, which form fused, spiro or bridged ring systems. The heterocycloalkyl may have 1-4 O, S, or N atoms, provided no O or S is adjacent to another O or S. The heterocycloalkyl may have 1, 2, 3 or 4 heteroatoms. The heterocycloalkyl may be saturated (i.e., a heterocycloalkyl) or partially unsaturated (i.e., a heterocycloalkenyl). "Heterocycloalkyl" includes (a) single heterocycloalkyl rings and (b) fused ring systems having 3-15 annular atoms in which at least one ring is heterocycloalkyl and the ring system is bonded to the compound of formula (I) (or one of formulae (Ia)-(Io), (II), (IIa)-(III), (III), and (IIIa)-(IIIn)) via heterocycloalkyl ring of the fused ring system. The one or more aromatic or non-aromatic ring may be, for example, aryl (Ar), heteroaryl (Het), cycloalkyl (Cak) and heterocycloalkyl (Hca) rings as described herein, including bridged, fused and spiro ring systems, wherein each ring includes three to eight annular atoms, or the ring system includes 3-15 members. Multicyclic fused ring systems are designated "heterocycloalkyl" if the ring system is bonded to the compound of formula (I) (or one of formulae (Ia)-(Io), (II), (IIa)-(III), (III), and (IIIa)-(IIIn)) through an atom in a heterocycloalkyl ring. For example, a 7,8-dihydro-6H-pyrano[3,2-d]pyrimidinyl group bonded to the compound of formula (I) (or one of formulae (Ia)-(Io), (II), (IIa)-(III), (II), and (IIIa)-(IIIn)) through the tetrahydro-2H-pyranyl ring

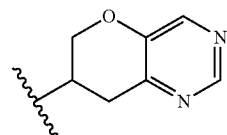 [SMILES: *C1COc2cncnc2C1]

is categorized as heterocycloalkyl (Hca). When a multicyclic heterocycloalkyl ring system is fused through a heteroatom, it can be categorized as if the heteroatom were in the ring bonded to the compound of formula (I) (or one of formulae (Ia)-(Io), (II), (IIa)-(III), (III), and (IIIa)-(IIIn)). For example, 6,7,8,9-tetrahydro-4H-quinolizin-4-on-yl:

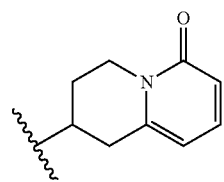 [SMILES: *C1CCn2c(cccc2=O)C1]

is categorized as a 6-membered heterocyclyl ring fused with a C₆cycloalkenyl ring substituted with an oxo group. In certain embodiments, the heterocycloalkyl groups have from 3 to 8 members in a single ring. In other embodiments, heterocycloalkyl groups have 5 or 6 members in a single ring. In some embodiments, the heterocycloalkyl groups have 3, 4, 5, 6, 7 or 8 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butyrolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" or "Cak" refers to a non-aromatic carbocyclic ring or non-aromatic carbocyclic ring system containing 3-15 members, which may be saturated (i.e., a cycloalkyl) or partially unsaturated (i.e., a cycloalkenyl), and optionally including one or more other aromatic and non-aromatic rings, which form fused, spiro or bridged ring systems. "Cycloalkyl" includes (a) single cycloalkyl rings and (b) fused, spiro or bridged ring systems having 3-15 annular atoms in which at least one ring is cycloalkyl and the ring system is bonded to the compound of formula (I) (or one of formulae (Ia)-(Io), (II), (IIa)-(III), (III), and (IIIa)-(IIIn)) via a cycloalkyl ring of the fused, spiro or bridged ring system. The one or more aromatic or non-aromatic ring may be, for example, aryl (Ar), heteroaryl (Het), cycloalkyl (Cak) and heterocycloalkyl (Hca) rings as described herein, including bridged, fused and spiro systems, wherein each ring includes three to eight annular atoms, or the ring system includes 3-15 members. Multicyclic ring systems are designated cycloalkyl if the ring system is bonded to the compound of formula (I) (or one of formulae (Ia)-(Io), (II), (IIa)-(III), (III), and (IIIa)-(IIIn)) through an atom in a cycloalkyl ring. For example, a 5,6,7,8-tetrahydroquinazolinyl group bonded to the compound of formula (I) (or one of formulae (Ia)-(Io), (II), (IIa)-(III), (III), and (IIIa)-(IIIn)) through the cycloalkenyl ring

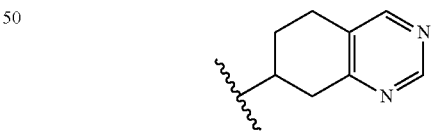

is categorized as cycloalkyl (Hca). Certain examples of cycloalkyl groups present in the disclosed compounds have from 3 to 8 members in a single ring, such as having 5 or 6 members in a single ring. In some embodiments, the cycloalkyl groups have 3, 4, 5, 6, 7 or 8 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "ring system" encompasses monocycles, as well as fused, spiro and/or bridged polycycles.

The term "fused" as used herein refers to a cyclic moiety formed by two adjacent atoms and two available substitutable postions on those atoms. Each of the rings in the fused system is independently aromatic or non-aromatic. For example, a moiety such as

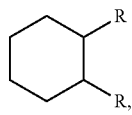

wherein two R, wherein two R groups attached to the adjacent atoms form a fused-Cak group, which includes compounds such as

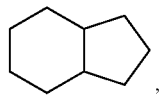

where the fused-cyclopentyl group is formed from the two R groups attached to the parent cyclohexyl ring by two single bonds. Similarly, a fused-Hca group can be formed, including such compounds as

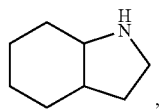

where the fused pyrrolidinyl ring is formed from the two R groups attached to the parent cyclohexyl ring by two single bonds.

The term "spiro" as used herein refers to a cyclic moiety formed by an atom and two available substitutable postions on that same atom. For example, a moiety such as

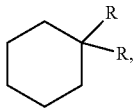

wherein two R groups attached to the same atom form a spiro-Cak group, which includes compounds such as

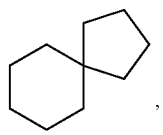

where the spiro-cyclopentyl group is formed from the two R groups attached to the parent cyclohexyl ring by two single bonds. Similarly, a spiro-Hca group can be formed, including such compounds

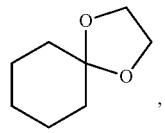

here the spiro-1,3-dioxolanyl ring is formed from the two R groups attached to the parent cyclohexyl ring by two single bonds.

The term "bridged" as used herein refers to a cyclic moiety formed by two non-adjacent atoms and two available substitutable postions on those atoms. For example, a moiety such as

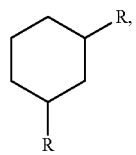

wherein two R groups attached to the adjacent atoms form a fused-Cak group, which includes compounds such as

where the bridged portion is formed from the two R groups attached to the parent cyclohexyl ring by two single bonds. Similarly, a bridged-Hca group can be formed, including such compounds as

where the bridged portion is formed from the two R groups attached to the parent cyclohexyl ring by two single bonds.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo (e.g., fluoro, chloro, bromo, and iodo), cyano, —($C_1$-$C_4$ fluoroalkyl), —O—($C_1$-$C_4$ fluoroalkyl), —C(O)—($C_0$-$C_4$alkyl), —C(O)O—($C_0$-$C_4$alkyl), —C(O)N($C_0$-$C_4$alkyl)($C_0$-$C_4$alkyl), —S(O)$_2$O—($C_0$-$C_4$alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below, unless specified otherwise.

Substituent groups for substituting for hydrogens on saturated carbon atoms in the specified group or radical are, unless otherwise specified, —R, halo, —O$^-$M$^+$, =O, —OR$^{70}$, —SR$^{70}$, —S$^-$M$^+$, =S, —NR$^{80}$R$^{80}$, =NR$^{70}$, =N—OR$^{70}$, trihalomethyl, —CF$_3$, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$. Each R$^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{71}$, —SR$^{71}$, —S$^-$M$^+$, =S, —NR$^{81}$R$^{81}$, =NR$^{71}$, =N—OR$^{71}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{71}$, —OSO$_2$R$^{71}$, —OSO$_2$O$^-$M$^+$, —OS$_2$OR$^{71}$, —P(O)(O$^-$)$_2$(M$^+$)$_2$, —P(O)(OR$^{71}$)O$^-$M$^+$, —P(O)(OR$^{71}$)$_2$, —C(O)R$^{71}$, —C(S)R$^{71}$, —C(NR$^{71}$)R$^{71}$, —C(O)O$^-$M$^+$, —C(O)OR$^{71}$, —C(S)OR$^{71}$, —C(O)NR$^{81}$R$^{81}$, —C(NR$^{71}$)NR$^{81}$R$^{81}$, —OC(O)R$^{71}$, —OC(S)R$^{71}$, —OC(O)O$^-$M$^+$, —OC(O)OR$^{71}$, —OC(S)OR$^{71}$, —NR$^{71}$C(O)R$^{71}$, —NR$^{71}$C(S)R$^{71}$, —NR$^{71}$CO$_2^-$M$^+$, —NR$^{71}$CO$_2$R$^{71}$, —NR$^{71}$C(S)OR$^{71}$, —NR$^{71}$C(O)NR$^{81}$R$^{81}$, —NR$^{71}$C(NR$^{71}$)R$^{71}$ and —NR$^{71}$C(NR$^{71}$)NR$^{81}$R$^{81}$. Each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$alkyl substitution; and each M$^+$ is a counter ion with a net single positive charge. Each R$^{71}$ is independently hydrogen or R$^{61}$, in which R$^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{72}$, —SR$^{72}$, —S$^-$M$^+$, =S, —NR$^{82}$R$^{82}$, =NR$^{72}$, =N—OR$^{72}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{72}$, —OSO$_2$R$^{72}$, —OSO$_2$O$^-$M$^+$, —OSO$_2$OR$^{72}$, —P(O)(O$^-$)$_2$(M$^+$)$_2$, —P(O)(OR$^{72}$)O$^-$M$^+$, —P(O)(OR$^{72}$)$_2$, —C(O)R$^{72}$, —C(S)R$^{72}$, —C(NR$^{72}$)R$^{72}$, —C(O)O$^-$M$^+$, —C(O)OR$^{72}$, —C(S)OR$^{72}$, —C(O)NR$^{82}$R$^{82}$, —C(NR$^{72}$)NR$^{82}$R$^{82}$, —OC(O)R$^{72}$, —OC(S)R$^{72}$, —OC(O)O$^-$M$^+$, —OC(O)OR$^{72}$, —OC(S)OR$^{72}$, —NR$^{72}$C(O)R$^{72}$, —NR$^{72}$C(S)R$^{72}$, —NR$^{72}$CO$_2^-$M$^+$, —NR$^{72}$CO$_2$R$^{72}$, —NR$_2$C(S)OR$^{72}$, —NR$^{72}$C(O)NR$^{82}$R$^{82}$, —NR$^{72}$C(NR$^{72}$)R$^{72}$ and —NR$^{72}$C(NR$^{72}$)NR$^{82}$R$^{82}$; and each R$^{81}$ is independently R$^{71}$ or alternatively, two R$^{81}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution. Each R$^{72}$ is independently hydrogen, (C$_1$-C$_6$alkyl) or (C$_1$-C$_6$fluoroalkyl); each R$^{82}$ is independently R$^{72}$ or alternatively, two R$^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or C$_1$-C$_3$alkyl substitution. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

Substituent groups for hydrogens on nitrogen atoms in "substituted" heteroalkyl and heterocycloalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

In certain embodiments, substituent groups on "substituted" alkyl, cycloalkyl, heterocycloalkyl, aryl and heteroaryl groups are -halo, —OH, —O—(C$_1$-C$_6$alkyl), —O—(C$_1$-C$_4$haloalkyl), —N(C$_0$-C$_4$ alkyl)(C$_0$-C$_4$alkyl), —SH, —S(O)$_{0-2}$—(C$_1$-C$_4$alkyl), —(C$_1$-C$_4$alkyl), —(C$_1$-C$_4$haloalkyl), —C(O)—(C$_0$-C$_4$alkyl), —C(O)N(C$_0$-C$_4$alkyl)(C$_0$-C$_4$alkyl), —N(C$_0$-C$_4$alkyl)C(O)(C$_0$-C$_6$alkyl)(C$_0$-C$_4$alkyl), —C(O)O—(C$_0$-C$_4$alkyl), —OC(O)—(C$_0$-C$_4$alkyl), S(O)$_2$—O(C$_0$-C$_4$alkyl), and —NO$_2$, in which no alkyl is further substituted.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxoglutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that undergoes a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}$F. Similarly, compounds may be enriched in the heavy isotopes of hydrogen: deuterium and tritium; and similarly can be enriched in a radioactive isotope of carbon, such as $^{13}$C. Such isotopic variant compounds undergo different metabolic pathways and can be useful, for example, in studying the ubiquitination pathway and its role in disease.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" an enzyme with a compound includes the administration of a compound described herein to an individual or patient, such as a human, as well as, for example, introducing a compound into a sample containing a cellular or purified preparation containing the enzyme.

As used herein, the terms "individual," "patient," or "subject" are used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed or otherwise susceptible to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; or (3) ameliorating the disease (including a symptom thereof); for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, condition, or disorder (or a symptom thereof), such as, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease or symptom thereof: or (ii) eliciting the referenced biological effect (e.g., modulation or inhibition of one or more of the TAM (Tyro 3, Axl and Mer) receptor family).

Manifestation of amelioration of a disease condition by inhibiting one or more of the TAM (Tyro 3, Axl and Mer) receptor family may require the concomitant or sequential administration of additional therapeutic agents, such as antineoplastic agents in the case of cancer, or antiretroviral agents in the case of viral diseases. For example, administration of inhibitors of one or more of the TAM (Tyro 3, Axl and Mer) receptor family for the treatment of cancer does not always produce a direct antitumor effect when used as a single agent. However, when combined with chemotherapeutic drugs (antineoplastic) the antitumor effect observed is higher than the sum of effects of each agent alone.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical Formulations and Dosage Forms

The compounds of structural formulae (I)-(IV) can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to structural formulae (I)-(IV).

In the pharmaceutical compositions disclosed herein, one or more compounds of structural formulae (I)-(IV) may be present in association with one or more pharmaceutically acceptable carriers, diluents or excipients, and, if desired, other active ingredients. The pharmaceutical compositions containing compounds of structural formulae (I)-(IV) may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In some embodiments, the pharmaceutically acceptable carrier, diluent, or excipient is not water. In other embodiments, the water comprises less than 50% of the composition. In some embodiments, compositions comprising less than 50% water have at least 1%, 2%, 3%, 4% or 5% water. In other embodiments, the water content is present in the composition in a trace amount.

In some embodiments, the pharmaceutically acceptable carrier, diluent, or excipient is not alcohol. In other embodiments, the alcohol comprises less than 50% of the composition. In some embodiments, compositions comprising less than 50% alcohol have at least 1%, 2%, 3%, 4% or 5% alcohol. In other embodiments, the alcohol content is present in the composition in a trace amount.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(IV) can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(IV) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

EXAMPLES

General Synthetic Methodologies

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/1, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formula (I) can be prepared according to Schemes 1-3, or analogous synthetic schemes.

One of skill in the art can adapt the reaction sequences of Schemes 1-3 to fit the desired target molecule. Of course, in certain situations one of skill in the art will use different reagents to affect one or more of the individual steps or to use protected versions of certain of the substituents. Additionally, one skilled in the art would recognize that compounds of structural formulae (I)-(IV) can be synthesized using different routes altogether.

Compounds suitable for use in the presently disclosed pharmaceutical compositions include compounds described herein. These compounds can be made according to the general schemes described above, for example using a procedure similar to that described below in the Examples.

The following examples are intended to further illustrate certain embodiments and are not intended to limit the scope of the presently disclosed compounds.

EXAMPLES

Example 1: Synthesis of 5-((6-Methoxy-7-(3-morpholinopropoxy)quinolin-4-yl)oxy)pyridin-2-amine (5')

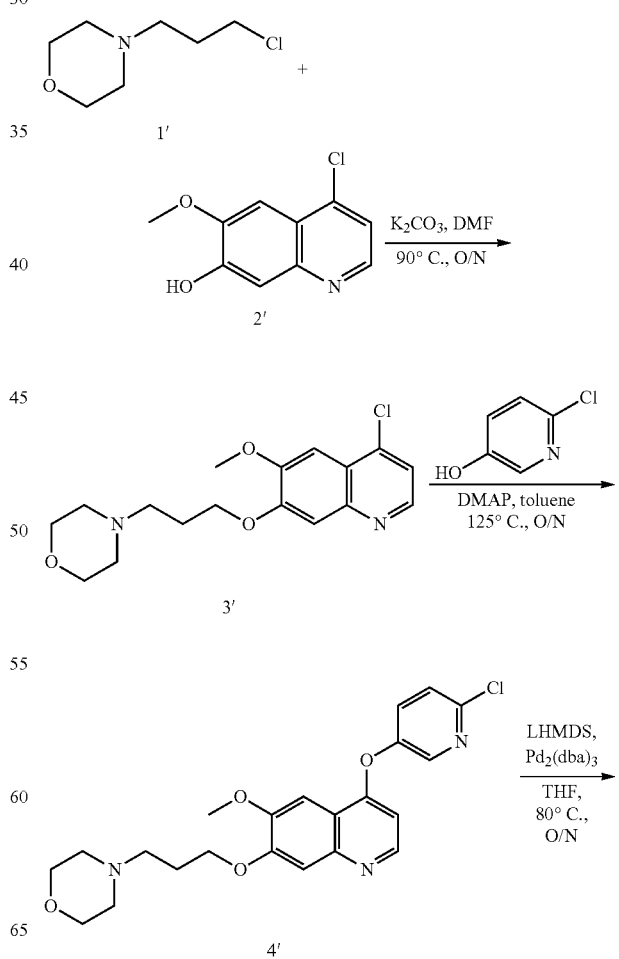

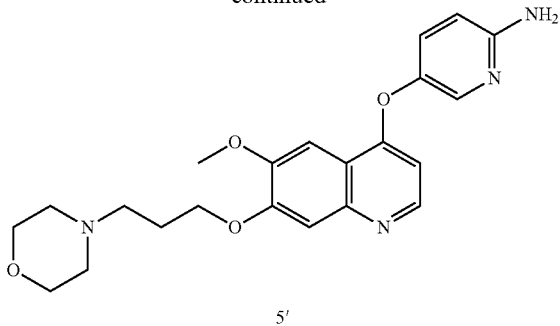

5'

Step 1-1: Synthesis of 4-(3-((4-Chloro-6-methoxy-quinolin-7-yl)oxy)propyl)-morpholine (3'

A solution of 4-chloro-6-methoxyquinolin-7-ol (7.6 g, 36.3 mmol), 4-(3-chloro-propyl)morpholine (6.3 mL, 6.7 g, 40.9 mmol), potassium carbonate (15.0 g, 108.5 mmol) in DMF was allowed to stir at 90° C. for 22 h. LC/MS traces indicated the alkylation reaction is complete and hence, the mixture was cooled down to room temperature, diluted with water (240 mL) and extracted with EtOAc (5×75 mL). The combined organic layer was then washed with water (1×100 mL), brine (1×100 mL), dried (MgSO$_4$), filtered and concentrated under reduced pressure to give a brown residue. Trituration with ethyl ether provided 10.2 g (83%) of 4-(3-((4-chloro-6-methoxyquinolin-7-yl)oxy)propyl)morpholine (3') as a tan solid. $^1$H NMR (DMSO-d$_6$, 300 MHz) δ 8.60 (d, J=4.9 Hz, 1H), 7.55 (d, J=4.8 Hz, 1H), 7.45 (s, 1H), 7.38 (s, 1H), 4.21 (t, J=6.4 Hz, 2H), 3.97 (s, 3H), 3.58 (t, J=4.7 Hz, 4H), 2.46 (t, J=7.2 Hz, 2H), 2.38 (t, J=4.6 Hz, 4H), 1.97 (p, J=6.7 Hz, 2H). MS m/e: 337 (M+H)$^+$.

Step 2: Synthesis of 4-(3-((4-((6-Chloropyridin-3-yl)oxy)-6-methoxyquinolin-7-yl)oxy)propyl)morpholine (4')

A solution of 4-(3-((4-chloro-6-methoxyquinolin-7-yl)oxy)propyl)morpholine (10.0 g, 29.7 mmol), 6-chloropyridin-3-ol (5 g, 38.6 mmol) and DMAP (4.35 g, 35.6 mmol) in toluene (50 mL) was allowed to stir at 125° C. for 24 h. LC/MS traces indicated starting material was still present and hence heating was continued for another 24 h. The reaction mixture was cooled down to room temperature, diluted with DCM (400 mL) and water (400 mL) and the layers were separated. The resulting aqueous layer was extracted with DCM (5×100 mL) add the resulting combined organic layer was dried (MgSO$_4$), filtered and concentrated under reduced pressure to give 9.8 g (77%) of 4-(3-((4-((6-chloropyridin-3-yl)oxy)-6-methoxyquinolin-7-yl)oxy)propyl)-morpholine (4) as an off-white solid. $^1$H NMR (DMSO-d$_6$, 300 MHz) δ 8.51 (d, J=5.3 Hz, 1H), 8.47 (d, J=2.9 Hz, 1H), 7.86 (dd, J=8.8, 2.9 Hz, 1H), 7.66 (d, J=8.5 Hz, 1H), 7.49 (s, 1H), 7.42 (s, 1H), 6.64 (d, J=5.3 Hz, 1H), 4.20 (t, J=6.4 Hz, 2H), 3.93 (s, 3H), 3.59 (dd, J=4.7, 4.4 Hz, 4H), 2.47 (t, J=7.3 Hz, 2H), 2.39 (t, J=4.4 Hz, 4H), 1.98 (p, J=6.7 Hz, 2H). MS m/e: 430 (M+H)$^+$.

Step 3: Synthesis of 5-((6-Methoxy-7-(3-morpholinopropoxy)quinolin-4-yl)oxy)pyridin-2-amine (5')

To a solution of 4-(3-((4-((6-chloropyridin-3-yl)oxy)-6-methoxyquinolin-7-yl)oxy)propyl)morpholine (4') (10.3 g, 0.2 mmol), Pd$_2$(dba)$_3$ (1.1 g, 1.2 mmol), SPHOS (1.0 g, 2.4 mmol) in anhydrous THF (120 mL), a solution of LHMDS (1.06M, 34 mL, 36 mmol) was added. The resulting reaction mixture was allowed to stir under N$_2$ atmosphere at 80° C. overnight. LC/MS traces show product only, reaction mixture cooled down to room temperature and a solution of 2N HCl (36 mL) was added. The resulting aqueous reaction mixture was allowed to stir at room temperature for 2.5 h, and a solution of 0.5 NaOH (350 mL) followed by a solution of saturated NaHCO$_3$ (200 mL) were added. The resulting basic reaction mixture was extracted with DCM (5×200 mL), dried (MgSO$_4$), filtered and concentrated to give a brown solid. Column chromatography (solid loading; chromatographed on a 120 g Redisep silica gel column, eluting with 5% MeOH/DCM for 10 min, 10% MeOH/DCM) provided 7.4 g (75%) of 5-((6-methoxy-7-(3-morpholinopropoxy)quinolin-4-yl)oxy)pyridin-2-amine (5') as a tan solid upon trituration with ethyl ether. $^1$H NMR (DMSO-d$_6$, 300 MHz) δ 8.44 (d, J=5.3 Hz, 1H), 7.89 (d, J=2.9 Hz, 1H), 7.51 (s, 1H), 7.37 (s, 1H), 7.36 (dd, J=8.8, 2.9 Hz, 1H), 6.56 (d, J=9.4 Hz, 1H), 6.41 (d, J=5.3 Hz, 1H), 6.04 (s, 2H), 4.19 (t, J=6.4 Hz, 2H), 3.94 (s, 3H), 3.59 (t, J=4.7 Hz, 4H), 2.47 (t, J=7.3 Hz, 2H), 2.39 (t, J=4.7 Hz, 4H), 1.97 (p, J=6.7 Hz, 2H). MS m/e: 411 (M+H)$^+$.

Example 2: Synthesis of 8-Phenyl-3,4-dihydro-2H-1,4-ethano-1,5-naphthyridine-6-carboxylic acid (13')

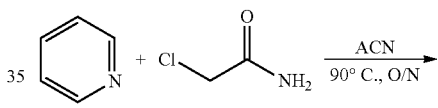

Synthesis of 1-(2-Amino-2-oxoethyl)pyridinium Chloride (6')

A solution of 2-chloroacetamide (50.0 g, 524 mmol) and pyridine (41.5 g, 524 mmol) in 100 mL of acetonitrile was allowed to stir at 90° C. for 10 h. The suspension was cooled to room temperature, resulting solid filtered and washed with hexanes to provide 79.1 g (87%) of 1-(2-amino-2-oxoethyl)pyridinium chloride (6') as a colorless solid.

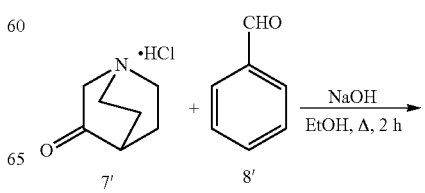

89

-continued

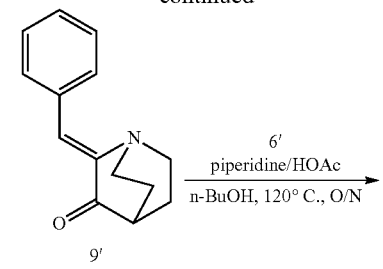

9'

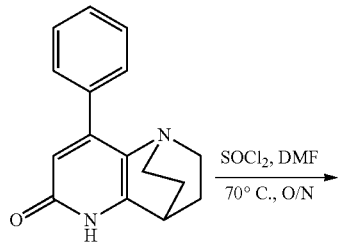

10'

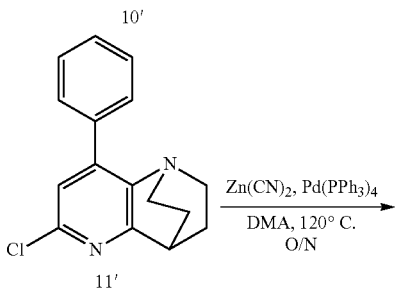

11'

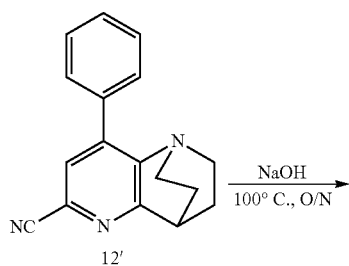

12'

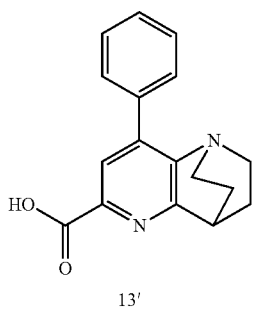

13'

Step 1: Synthesis of
(Z)-2-Benzylidenequinuclidin-3-one (9')

A solution of 3-quinuclidinone hydrochloride (7', 50 g, 309 mmol), benzaldehyde (8', 31.3 mL, 32.7 g, 167 5 mmol) and six pellets of sodium hydroxide in 150 mL of ethanol was allowed to reflux for 2 h. The reaction mixture was then allowed to cool down to room temperature and the resulting yellow precipitate was filtered, triturated with ethanol, filtered and dried to give 57.2 g (87%) of (Z)-2-benzylidene-quinuclidin-3-one (9') as a yellow solid. MS nm/e: 214 (M+H)+.

90

Step 2: Synthesis of 8-Phenyl-3,4-dihydro-2H-1,4-ethano-1,5-naphthyridin-6(5H)-one (10')

A solution of 2-benzylidenequinuclidin-3-one (9', 3.0 g, 14.1 mmol) and 1-(2-amino-2-oxoethyl)pyridinium chloride (6', 7.3 g, 42.3 mmol) in butan-1-ol (100 mL) containing piperidine (5 mL) and HOAc (3 mL) was allowed to stir at 120° C. for 18 h. After cooling to ambient temperature, the reaction mixture was concentrated in vacuo and the resulting residue was partitioned between 5% MeOH/CHCl$_3$ and water, layers separated and the aqueous layer was extracted with 5% MeOH/CHCl$_3$ (2×150 mL). The organic phase was concentrated to give a solid residue, which was recrystallized from MeOH to give 2.9 g (82%) of 8-phenyl-3,4-dihydro-2H-1,4-ethano-1,5-naphthyridin-6(5H)-one (10') as a white solid. MS m/e: 253 (M+H)+.

Step 3: Synthesis of 6-Chloro-8-phenyl-3,4-dihydro-2H-1,4-ethano-1,5-naphthyridine (11')

A solution of 8-phenyl-3,4-dihydro-2H-1,4-ethano-1,5-naphthyridin-6(5H)-one (10') (1.0 g, 4.0 mmol), thionyl chloride (10 mL, 16.3 g, 137 mmol) and DMF (0.25 mL, 0.24 g, 3.2 mmol) was allowed to stir at 70° C. overnight. The reaction mixture was then concentrated in vacuo and the resulting residue was added dropwise to an ice-cold saturated NaHCO$_3$ solution. The aqueous mixture was then extracted with EtOAc (3×50 mL) and the combined organic layer was dried (MgSO$_4$), filtered and concentrated to give a yellow residue. Column chromatography purification (10% to 20%/EtOAc/hexanes) provided 0.54 g (50%) of 6-chloro-8-phenyl-3,4-dihydro-2H-1,4-ethano-1,5-naphthyridine (11') as a white solid. $^1$H NMR (CDCl$_3$, 300 MHz) S 7.61-7.54 (m, 2H), 7.48-7.39 (m, 3H), 7.29 (s, 1H), 3.33 (tt, J=3.5, 2.5 Hz, 1H), 3.24-3.08 (m, 2H), 2.62 (dddd, J=13.3, 10.5, 5.1, 2.5 Hz, 2H), 1.97 (dddd, J=12.2, 9.5, 4.9, 2.5 Hz, 2H), 1.79-1.62 (m, 2H). MS m/e: 271 (M+H)$^+$.

Step 4: Synthesis of 8-Phenyl-3,4-dihydro-2H-1,4-ethano-1,5-naphthyridine-6-carbonitrile (12')

A solution of 6-chloro-8-phenyl-3,4-dihydro-2H-1,4-ethano-1,5-naphthyridine (11', 0.54 g, 2.0 mmol), zinc cyanide (0.28 g, 2.4 mmol) and Pd(PPh$_3$)$_4$ (0.23 g, 0.2 mmol) in DMA (10 mL) was evacuated and back filled with N$_2$ (3×), placed under N$_2$ atmosphere and allowed to stir at 120° C. overnight. Additional equivalents of reagents were added until starting chloride was consumed. The reaction mixture was then concentrated in vacuo and the resulting residue was purified by column chromatography eluting with DCM and 50% EtOAc/DCM to provide 0.32 g (62%) of 8-phenyl-3,4-dihydro-2H-1,4-ethano-1,5-naphthyridine-6-carbonitrile (12') as a white solid upon trituration with ethyl ether. $^1$H NMR (CDCl$_3$, 300 MHz) δ 7.70 (s, 1H), 7.62-7.55 (m, 2H), 7.51-7.45 (m, 3H), 3.41 (tt, J=3.4, 2.5 Hz, 1H), 3.21 (ddd, J=13.9, 9.8, 4.9 Hz, 2H), 2.72-2.59 (m, 2H), 2.03 (dddd, J=12.3, 9.7, 5.0, 2.5 Hz, 2H), 1.80-1.65 (m, 2H). MS m/e: 262 (M+H)$^+$.

Step 5: Synthesis of 8-Phenyl-3,4-dihydro-2H-1,4-ethano-1,5-naphthyridine-6-carboxylic Acid (13')

A solution of 8-phenyl-3,4-dihydro-2H-1,4-ethano-1,5-naphthyridine-6-carbonitrile (12', 0.54 g, 2.0 mmol) in a 1:1 mixture of EtOH and NaOH solution (1N) was allowed to stir at 100° C. overnight. The resulting reaction mixture was concentrated to give 8-phenyl-3,4-dihydro-2H-1,4-ethano-1,5-naphthyridine-6-carboxylic acid (13') as a white solid. MS m/e: 281 (M+H)+.

Example 2a: Synthesis of 4-Phenyl-7,8-dihydro-6H-5,8-ethanopyrido[3,2-d]pyrimidine-2-carboxylic Acid (13b')

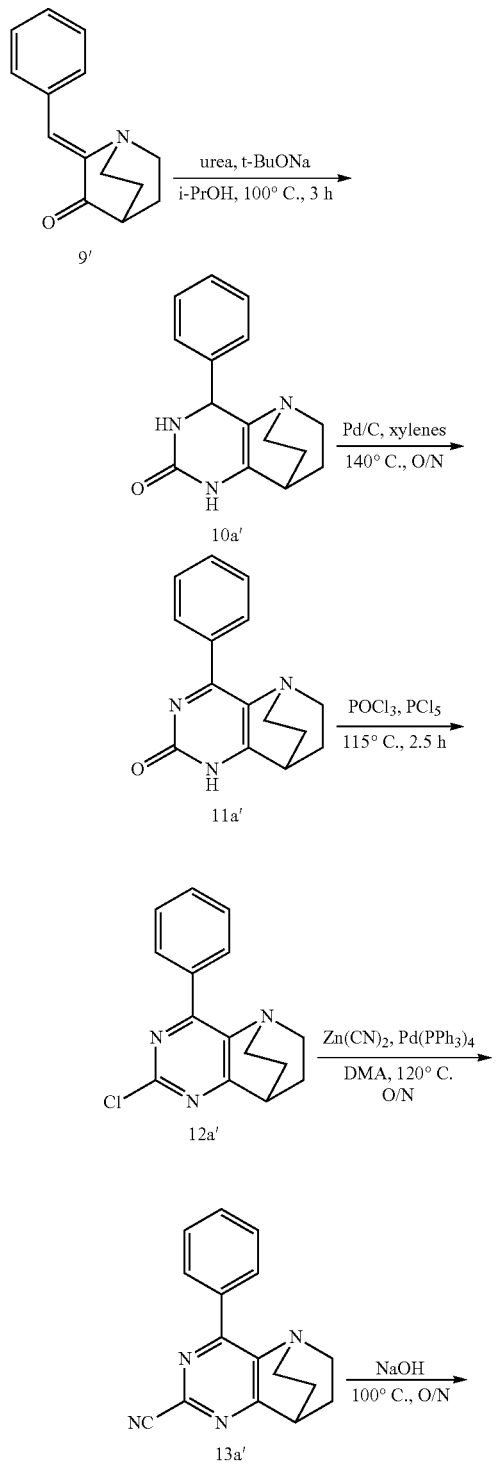

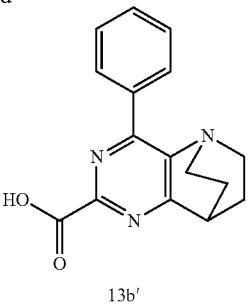

Step 1: Synthesis of 4-Phenyl-4,6,7,8-tetrahydro-1H-5,8-ethanopyrido[3,2-d]pyrimidin-2(3H)-one (10a')

To a solution of 2-benzylidenequinuclidin-3-one (9', 57.2 g, 268 mmol) and urea (38.6 g, 643 mmol) in i-PrOH (500 mL), sodium t-butoxide (60.1 g, 535.6 mmol) was added and the resulting reaction mixture was allowed to stir at 100° C. for 3 h. After cooling to ambient temperature, the reaction mixture was poured into a flask containing water (1.5 L) and the resulting aqueous solution was extracted with 5% MeOH/DCM (3×100 mL), combined organic layers, dried (MgSO4), filtered and concentrated to provide a white solid upon trituration with ethyl ether. Residue from the mother liquor was chromatographed on silica gel eluting with DCM and 2% MeOH/DCM to provide another two batches of white solid upon trituration with i-PrOH. Combined three batches to obtain 34.9 g (51%) of 4-phenyl-4,6,7,8-tetrahydro-1H-5,8-ethanopyrido[3,2-d]pyrimidin-2(3H)-one (10a'). $^1$H NMR (DMSO-$d_6$, 300 MHz) δ 8.33 (s, 1H), 7.45-7.20 (m, 5H), 6.95 (s, 1H), 4.82 (d, J=2.1 Hz, 1H), 2.76 (ddd, J=13.0, 9.1, 5.2 Hz, 1H), 2.64-2.51 (m, 2H), 1.92-1.19 (m, 6H). MS m/e: 256 (M+H)+.

Step 2: Synthesis of 4-Phenyl-7,8-dihydro-1H-5,8-ethanopyrido[3,2-d]pyrimidin-2(6H)-one (11a')

A solution of 4-phenyl-4,6,7,8-tetrahydro-1H-5,8-ethanopyrido[3,2-d]pyrimidin-2(3H)-one (10a', 10 g, 39.2 mmol) and Pd/C (10%) (3.0 g, 2.8 mmol) in xylenes (150 mL) was allowed to stir at 140° C. overnight. The reaction mixture was then filtered through celite, washed the celite plug with 5% MeOH/DCM and concentrated. Trituration with ethyl ether provided a quantitative yield of 4-phenyl-7,8-dihydro-1H-5,8-ethanopyrido[3,2-d]pyrimidin-2(6H)-one (11a') as an off-white solid. $^1$H NMR (DMSO-$d_6$, 300 MHz) δ 11.73 (br s, 1H), 7.89 (br s, 2H), 7.56-7.40 (m, 3H), 3.04 (ddd, J=13.7, 9.7, 4.8 Hz, 2H), 2.94 (br s, 1H), 2.60 (td, J=11.0, 4.9 Hz, 2H), 2.07-1.81 (m, 2H), 1.72-1.89 (m, 2H). MS m/e: 254 (M+H)+.

Step 3: Synthesis of 2-Chloro-4-phenyl-7,8-dihydro-6H-5,8-ethanopyrido[3,2-d]pyrimidine (12a')

A solution of 4-phenyl-7,8-dihydro-6H-5,8-ethanopyrido[3,2-d]pyrimidin-2(6H)-one (11a', 2.53 g, 10.0 mmol), phosphorous oxychloride (25 mL, 41.1 g, 268 mmol) and phosphorous pentachloride (12.9 g, 61.9 mmol) was allowed to stir at 115° C. for 2.5 h. The reaction mixture was then cooled down to room temperature, concentrated in vacuo, and diluted with DCM (50 mL) and ice-cold Na2CO3 saturated solution (50 mL). The layers were separated and the aqueous phase was extracted with 5% MeOH/DCM solution (3×50 mL), combined organic layer washed with saturated Na$_2$CO$_3$ solution (1×50 mL), dried (MgSO$_4$), filtered and concentrated to give a tan solid. Trituration with ethyl ether provided 2.2 g (80%) of 2-chloro-4-phenyl-7,8-dihydro-6H-5,8-ethanopyrido[3,2-d]pyrimidine (12a') as an off-white solid. $^1$H NMR (DMSO-d$_6$, 300 MHz) δ 8.40-8.12 (m, 2H), 7.67-7.37 (m, 3H), 3.33-3.03 (m, 3H), 2.64 (td, J, =10.8, 4.7 Hz, 2H), 2.04 (tdd, J=9.6, 4.7, 2.5 Hz, 2H), 1.65 (tq, J=10.4, 4.4, 3.6 Hz, 2H). MS m/e: 272 (M+H)$^+$.

Step 4: Synthesis of 4-Phenyl-7,8-dihydro-6H-5,8-ethanopyrido[3,2-d]pyrimidine-2-carbonitrile (13a')

A solution of 2-chloro-4-phenyl-7,8-dihydro-6H-5,8-ethanopyrido[3,2-d]pyrimidine (12a', 1.0 g, 3.7 mmol), zinc cyanide (0.52 g, 4.4 mmol) and Pd(PPh$_3$)$_4$ (0.43 g, 0.37 mmol) in DMA (12 mL) was evacuated and back filled with N$_2$ (3×), placed under N$_2$ atmosphere and allowed to stir at 120° C. overnight. An additional one equivalent of reagents was added and heating was repeated overnight as most of the starting chloride was consumed. The reaction mixture was then concentrated in vacuo and the resulting residue was purified by column chromatography eluting with DCM and 50% EtOAc/DCM to provide 0.57 g (59%) of 4-phenyl-7,8-dihydro-6H-5,8-ethanopyrido[3,2-d]pyrimidine-2-carbonitrile (13a') as a white solid upon trituration with ethyl ether. $^1$H NMR (CDCl$_3$, 300 MHz) δ 8.43 (d, J=2.1 Hz, 1H), 8.42-8.40 (m, 1H), 7.51-7.46 (m, 3H), 3.36 (p, J=2.9 Hz, 1H), 3.27 (ddd, J=14.1, 9.7, 4.9 Hz, 2H), 2.75-2.65 (m, 2H), 2.09 (dddd, J=12.3, 9.7, 5.0, 2.5 Hz, 2H), 1.74 (dddd, J=13.4, 10.5, 7.5, 3.5 Hz, 2H). MS m/e: 263 (M+H)$^-$.

Step 5: Synthesis of 4-Phenyl-7,8-dihydro-6H-5,8-ethanopyrido[3,2-d]pyrimidine-2-carboxylic Acid (13b')

A solution of 4-phenyl-7,8-dihydro-6H-5,8-ethanopyrido[3,2-d]pyrimidine-2-carbonitrile (13a', 0.54 g, 2.0 mmol) in a 1:1 mixture of EtOH and NaOH solution (1N) was allowed to stir at 100° C. for 3 h. The resulting reaction mixture was concentrated, water (10 mL) was added and the basic aqueous solution was acidified to pH by adding concentrated HCl dropwise. The resulting white solid was filtered and air dried to give 0.42 g (68%) of 4-phenyl-7,8-dihydro-6H-5,8-ethanopyrido[3,2-d]pyrimidine-2-carboxylic acid (13b') as a white solid. $^1$H NMR (DMSO-d$_6$, 400 MHz) δ 13.43 (s, 1H), 8.34-8.28 (m, 2H), 7.57-7.50 (m, 3H), 3.28 (t, J=3.0 Hz, 1H), 3.22 (ddd, J=13.8, 9.7, 4.7 Hz, 2H), 2.67-2.60 (m, 2H), 2.12-2.01 (m, 2H), 1.65 (dd, J=13.7, 8.8 Hz, 2H). MS m/e: 282 (M+H)$^+$.

Example 3: Synthesis of 4-Phenylpicolinic Acid (16')

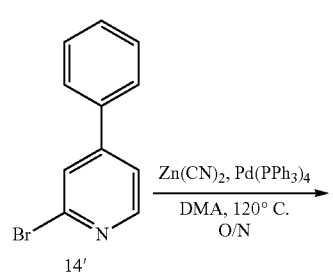

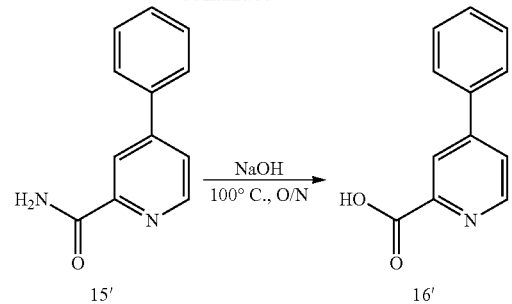

Step 1: Synthesis of 4-Phenylpicolinamide (15'

A solution of 2-bromo-4-phenylpyridine (14', 0.5 g, 2.1 mmol), zinc cyanide (0.3 g, 2.6 mmol) and Pd(PPh$_3$)$_4$ (0.25 g, 0.22 mmol) in DMA (5 mL) was evacuated and back filled with nitrogen (3×), placed under N$_2$ atmosphere and allowed to stir at 120° C. overnight. A mixture of 2-cyano-4-phenylpyridine and 4-phenylpicolinamide (15') was obtained (0.48 g) and therefore it was decided to convert the mixture to the acid and isolate the acid. MS m/e: 199 (M+H)$^+$.

Step 2: Synthesis of 4-Phenylpicolinic Acid (16')

A solution of 2-cyano-4-phenylpyridine and 4-phenylpicolinamide (15', 0.48 g, 2.4 mmol) in a 1:1 mixture of EtOH and NaOH solution (1N) was allowed to stir at 100° C. overnight. The resulting reaction mixture was concentrated and water (10 mL) was added and the resulting precipitate was filtered and disposed of. The aqueous layer was concentrated to give 0.33 g (69%) of 4-phenylpicolinic acid (16') as a white solid. $^1$H NMR (CD$_3$OD, 300 MHz) δ 8.58 (d, J=5.3 Hz, 1H), 8.34 (br s, 1H), 7.84-7.74 (m, 2H), 7.72 (br s, 1H), 7.58-7.42 (m, 3H). MS m/e: 200 (M+H)$^+$.

Example 4A: Synthesis of 4-Phenylpyrimidine-2-carboxylic Acid (19')

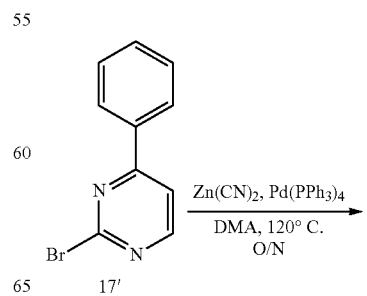

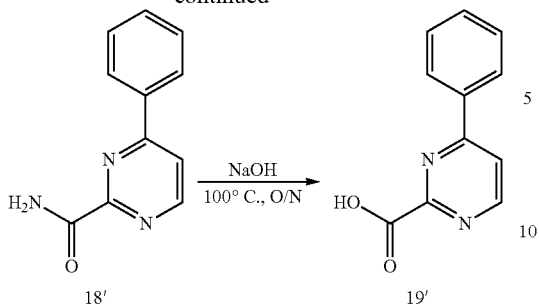

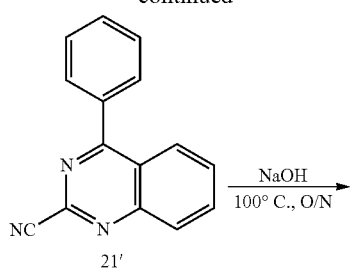

Step 1: Synthesis of 4-Phenylpyrimidine-2-carboxamide (18'

A solution of 2-bromo-4-phenylpyrimidine (17', 0.5 g, 2.1 mmol), zinc cyanide (0.3 g, 2.6 mmol) and Pd(PPh$_3$)$_4$ (0.25 g, 0.22 mmol) in DMA (5 mL) was evacuated and back filled with nitrogen (3×), placed under N$_2$ atmosphere and allowed to stir at 120° C. overnight. A mixture of 2-cyano-4-phenylpyrimidine and 4-phenylpyrimidine-2-carboxamide (18') was obtained (0.42 g) and therefore it was decided to convert the mixture to the acid and isolate the acid. MS m/e: 200 (M+H)$^+$.

Step 2: Synthesis of 4-Phenylpyrimidine-2-carboxylic Acid (19')

A solution of 2-cyano-4-phenylpyrimidine and 4-phenylpyrimidine-2-carboxamide (18', 0.42 g, 2.4 mmol) in a 1:1 mixture of EtOH and NaOH solution (1N) was allowed to stir at 100° C. for 3 h. The resulting reaction mixture was concentrated, water (20 mL) was added and the basic aqueous solution was acidified to pH 6 with concentrated HCl to give 200 mg (47%) of 4-phenylpyrimidine-2-carboxylic acid (19') as a yellow solid. $^1$H NMR (CD$_3$OD, 400 MHz) δ 8.81 (br s, 1H), 8.38 (d, J=6.7 Hz, 2H), 8.21 (br s, 1H), 7.68-7.22 (m, 3H). MS m/e: 201 (M+H)$^+$.

Example 4B: Synthesis of 4-Phenylquinazoline-2-carboxylic Acid (22')

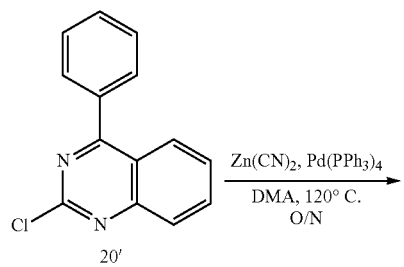

Step 1: Synthesis of 4-Phenylquinazoline-2-carbonitrile (21'

A solution of 2-chloro-4-phenylquinazoline (20', 1.0 g, 4.2 mmol), zinc cyanide (0.6 g, 5.1 mmol) and Pd(PPh$_3$)$_4$ (0.48 g, 0.42 mmol) in DMA (10 mL) was evacuated and back filled with nitrogen (3×), placed under N$_2$ atmosphere and allowed to stir at 120° C. overnight. LC/MS traces indicated the desired product was the major component and therefore the reaction mixture was concentrated and chromatographed on silica gel eluting with DCM. The appropriate fractions were combined to give 0.65 g (68%) of 4-phenylquinazoline-2-carbonitrile (21') as a white solid upon trituration with hexanes/ethyl ether. $^1$H NMR (CDCl$_3$, 400 MHz) δ 8.23 (dd, J=8.8, 1.0 Hz, 1H), 8.19 (dd, J=7.8, 0.8 Hz, 1H), 8.03 (ddd, J=8.4, 6.9, 1.4 Hz, 1H), 7.82-7.76 (m, 3H), 7.64-7.57 (m, 3H). MS m/e: 614 (M+H)$^+$. MS m/e: 232 (M+H)$^+$.

Step 2: Synthesis of 4-Phenylquinazoline-2-carboxylic Acid (22')

A solution of 4-phenylquinazoline-2-carbonitrile (21', 0.65 g, 2.8 mmol) in a 2:1 mixture of EtOH and NaOH solution (1N) was allowed to stir at 100° C. for 2 h. The resulting reaction mixture was concentrated, water (20 mL) was added and the basic aqueous solution was acidified to pH 2 with concentrated HCl to give a mixture of 2-hydroxy-, 2-carboxy- and 2-ethoxy-4-phenylquinazoline. Column chromatography (eluting with DCM and 5% MeOH/DCM) provided 195 mg (28%) of 4-phenylquinazoline-2-carboxylic Acid (22') as a white solid. $^1$H NMR (CD$_3$OD, 400 MHz) δ 8.34 (d, J=8.2 Hz, 1H), 8.26 (d, J=7.8 Hz, 1H), 8.06 (t, J=7.4 Hz, 1H), 7.84-7.76 (m, 3H), 7.64-7.58 (m, 3H). MS m/e: 251 (M+H)$^+$.

Example 5: Synthesis of N-(5-(((6-Methoxy-7-(3-morpholinopropoxy)quinolin-4-yl)oxy)pyridin-2-yl)-4-(4-methylpiperazin-1-yl)picolinamide (1)

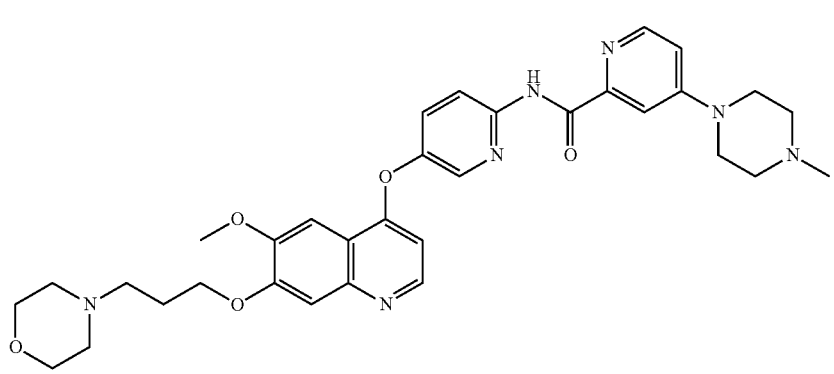

To a solution of 5-((6-methoxy-7-(3-morpholinopropoxy)quinolin-4-yl)oxy)pyridin-2-amine (5') (100 mg, 0.24 mmol), 4-(4-methylpiperazin-1-yl)picolinic acid (65 mg, 7.1 mmol) in DMF (2 mL), DIEA (130 μL, 96 mg, 0.75 mmol) and HATU (150 mg, 0.39 mmol) were added. The reaction mixture was then allowed to stir at room temperature overnight, concentrated under reduced pressure and the resulting residue was purified by column chromatography eluting with 5% and 10% MeOH/DCM to provide 74 mg of N-(5-((6-methoxy-7-(3-morpholinopropoxy)quinolin-4-yl)oxy)pyridin-2-yl)-4-(4-methylpiperazin-1-yl)picolinamide (1) as a white solid: $^1$H NMR (DMSO-$d_6$, 400 MHz) δ 10.62 (s, 1H), 8.50 (d, J=5.1 Hz, 1H), 8.42 (s, 1H), 8.41 (d, J=11.7 Hz, 1H), 8.34 (d, J=5.9 Hz, 1H), 7.91 (dd, J=9.0, 3.1 Hz, 1H), 7.64 (d, J=2.6 Hz, 1H), 7.54 (s, 1H), 7.42 (s, 1H), 7.13 (dd, J=6.0, 2.7 Hz, 1H), 6.57 (d, J=5.2 Hz, 1H), 4.22 (t, J=6.4 Hz, 2H), 3.95 (s, 3H), 3.63 (br s, 4H), 3.58-3.46 (m, 4H), 2.67-2.54 (m, 6H), 2.44-2.30 (m, 4H), 2.03 (m, 2H). MS m/e: 614 (M+H)$^+$.

Example 6: Synthesis of N-(5-(((6-Methoxy-7-(3-morpholinopropoxy)quinolin-4-yl)oxy)-pyridin-2-yl)-8-phenyl-3,4-dihydro-2H-1,4-ethano-1,5-naphthyridine-6-carboxamide (2)

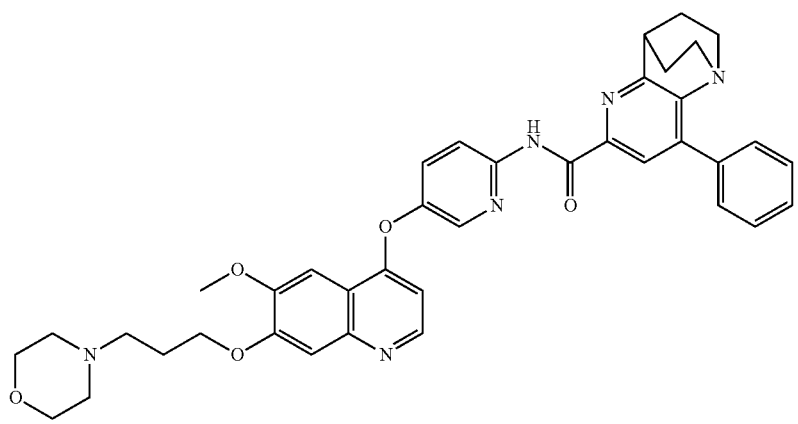

To a solution of 5-(((6-methoxy-7-(3-morpholinopropoxy) quinolin-4-yl)oxy)pyridin-2-amine (5', 100 mg, 0.24 mmol), 8-phenyl-3,4-dihydro-2H-1,4-ethano-1,5-naphthyridine-6-carboxylic acid (13', 80 mg, 0.28 mmol) in DMF (2 mL), DIEA (260 µL, 190 mg, 1.5 mmol) and HATU (280 mg, 0.74 mmol) were added. The reaction mixture was then allowed to stir at room temperature overnight, but a significant amount of the starting material 2-aminopyridine 5 was detected. Additional equivalents of reagents were added and the reaction mixture was allowed to stir at 40° C. until most of the starting 2-aminopyridine 5' was consumed. The reaction mixture was then diluted with water (20 ml) and extracted with DCM (3×10 mL) and the combined organic layer was dried (MgSO$_4$) and concentrated to give a brown residue. Column chromatography purification eluting with DCM and 10% MeOH/DCM provided N-(5-(((6-methoxy-7-(3-morpholinopropoxy)quinolin-4-yl)oxy)pyridin-2-yl)-8-phenyl-3,4-dihydro-2H-1,4-ethano-1,5-naphthyridine-6-carboxamide (2) as a white solid, wt. 77 mg (47%). $^1$H NMR (CDCl$_3$, 300 MHz) δ 10.75 (s, 1H), 8.58 (dd, J=9.0, 0.7 Hz, 1H), 8.51 (d, J=5.3 Hz, 1H), 8.33 (s, 1H), 8.32 (d, J=3.5 Hz, 1H), 7.72-7.66 (m, 2H), 7.62 (dd, J=9.0, 2.9 Hz, 1H), 7.54 (s, 1H), 7.52-7.41 (m, 4H), 6.48 (d, J=5.3 Hz, 1H), 4.28 (t, J=6.7 Hz, 2H), 4.03 (s, 3H), 3.72 (t, J=4.7 Hz, 4H), 3.45 (t, J=2.8 Hz, 1H), 3.24 (ddd, J=13.9, 9.6, 4.7 Hz, 2H), 2.77-2.46 (m, 6H), 2.20-1.98 (m, 4H), 1.82-1.60 (m, 4H). MS m % e: 673 (M+H)$^+$.

Example 7: Synthesis of N-(5-(((6-Methoxy-7-(3-morpholinopropoxy)quinolin-4-yl)oxy)-pyridin-2-yl)-4-phenylpicolinamide (3)

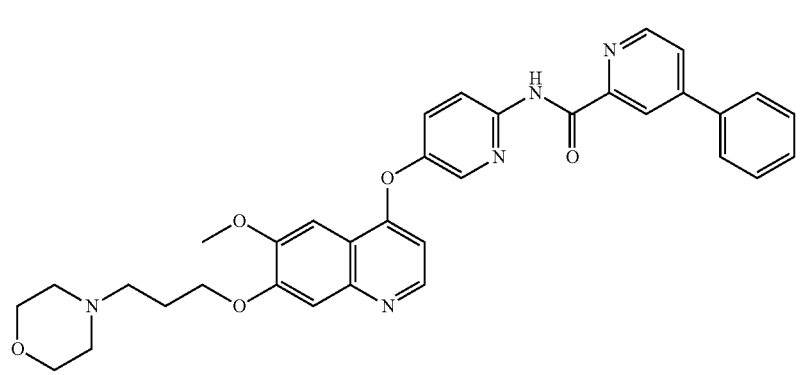

To a solution of 5-(((6-methoxy-7-(3-morpholinopropoxy) quinolin-4-yl)oxy)pyridin-2-amine (5', 50 mg, 0.12 mmol), 4-phenylpicolinic acid (16', 45 mg, 0.23 mmol) in DMF (1 mL), DIEA (100 µL, 74 mg, 0.57 mmol) and HATU (140 mg, 0.37 mmol) were added. The reaction mixture was then allowed to stir at room temperature overnight, but a significant amount of the starting material 2-aminopyridine 5' was detected. Additional equivalents of reagents were added and the reaction mixture was allowed to stir at room temperature until most of the starting 2-aminopyridine 5' was consumed. The reaction mixture was then diluted with water (20 ml) and extracted with DCM (3×10 mL) and the combined organic layer was dried (MgSO$_4$) and concentrated to give a brown residue. Reverse phase chromatography provided 17 mg (24%) of N-(5-(((6-methoxy-7-(3-morpholinopropoxy)quinolin-4-yl)oxy)pyridin-2-yl)-4-phenylpicolinamide (3) as a white solid. $^1$H NMR (CD$_3$OD, 300 MHz) δ 8.77 (dd, J=5.1, 0.8 Hz, 1H), 8.72 (d, J=6.7 Hz, 1H), 8.64 (d, J=9.1 Hz, 1H), 8.52 (dd, J=1.9, 0.8 Hz, 1H), 8.49 (d, J=2.6

Hz, 1H), 8.00-7.92 (m, 2H), 7.88 (s, 1H), 7.83 (dq, J=7.1, 1.5 Hz, 2H), 7.61-7.47 (m, 4H), 7.05 (d, J=6.7 Hz, 1H), 4.47 (t, J=5.6 Hz, 2H), 4.16-4.06 (m, 2H), 4.11 (s, 3H), 3.88 (t, J=12.5 Hz, 2H), 3.67 (d, J=12.2 Hz, 2H), 3.49 (t, J=7.3 Hz, 2H), 3.28-3.16 (m, 2H), 2.48 (p, J=6.2 Hz, 2H). MS m/e: 592 (M+H)$^+$.

Example 8: Synthesis of N-(5-((6-Methoxy-7-(3-morpholinopropoxy)quinolin-4-yl)oxy)-pyridin-2-yl)-4-phenylpyrimidine-2-carboxamide (4)

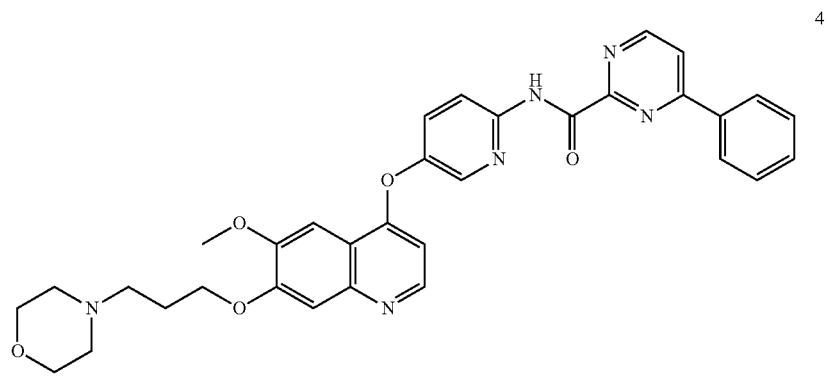 [SMILES: COc1cc2c(Oc3ccc(NC(=O)c4nccc(-c5ccccc5)n4)nc3)ccnc2cc1OCCCN1CCOCC1]

4

To a solution of 5-((6-methoxy-7-(3-morpholinopropoxy) quinolin-4-yl)oxy)pyridin-2-amine (5', 50 mg, 0.12 mmol), 4-phenylpyrimidine-2-carboxylic acid (19', 35 mg, 0.17 mmol) in DMF (1 mL), DIEA (100 µL, 74 mg, 0.57 mmol) and HATU (140 mg, 0.37 mmol) were added. The reaction mixture was then allowed to stir at room temperature overnight, but a significant amount of the starting material 2-aminopyridine 5' was detected. Additional equivalents of reagents were added and the reaction mixture was allowed to stir at room temperature until most of the starting 2-aminopyridine 5' was consumed. The reaction mixture was then diluted with water (20 ml) and extracted with DCM (3×10 mL) and the combined organic layer was dried (MgSO$_4$) and concentrated to give a brown residue. Reverse phase chromatography provided 26 mg (36%) of N-(5-((6-methoxy-7-(3-morpholinopropoxy)quinolin-4-yl)oxy)pyridin-2-yl)-4-phenylpyrimidine-2-carboxamide (4) as a white solid. $^1$H NMR (CD$_3$OD, 300 MHz) δ 9.03 (d, J=5.4 Hz, 1H), 8.72 (d, J=6.7 Hz, 1H), 8.67 (dd, J=9.1, 0.7 Hz, 1H), 8.52 (dd, J=2.9, 0.7 Hz, 1H), 8.40-8.30 (m, 2H), 8.20 (d, J=5.4 Hz, 1H), 7.99 (dd, J=9.1, 2.9 Hz, 1H), 7.86 (s, 1H), 7.66-7.52 (m, 4H), 7.06 (d, J=6.7 Hz, 1H), 4.43 (t, J=5.5 Hz, 2H), 4.19-4.03 (br s, 2H), 4.09 (s, 3H), 3.93-3.75 (m, 2H), 3.67 (d, J=12.5 Hz, 2H), 3.49 (t, J=7.4 Hz, 2H), 3.28-3.13 (m, 2H), 2.45 (p, J=6.4 Hz, 2H). MS m/e: 593 (M+H)$^+$.

Example 9: Synthesis of N-(5-(((6-Methoxy-7-(3-morpholinopropoxy)quinolin-4-yl)oxy)pyridin-2-yl)-4-phenylquinazoline-2-carboxamide (5)

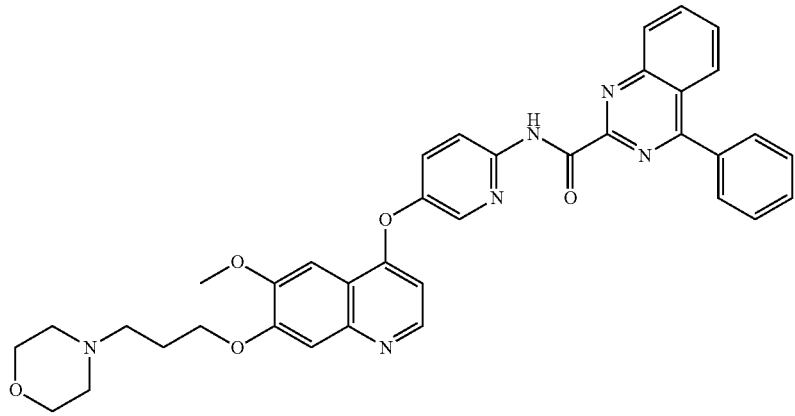

To a solution of 5-((6-methoxy-7-(3-morpholinopropoxy)quinolin-4-yl)oxy)pyridin-2-amine (5', 50 mg, 0.12 mmol), 4-phenylquinazoline-2-carboxylic acid (22', 50 mg, 0.2 mmol) in DMF (1 mL), DIEA (100 μL, 74 mg, 0.57 mmol) and HATU (140 mg, 0.37 mmol) were added. The reaction mixture was then allowed to stir at room temperature overnight. The reaction mixture was then diluted with water (30 ml) and extracted with DCM (3×10 mL) and the combined organic layer was dried (MgSO$_4$) and concentrated to give a brown residue. Reverse phase chromatography provided 45 mg (57%) of N-(5-((6-methoxy-7-(3-morpholinopropoxy)-quinolin-4-yl)oxy)pyridin-2-yl)-4-phenylquinazoline-2-carboxamide (5) as a white solid. $^1$H NMR (CD$_3$OD, 300 MHz) δ 8.73 (dd, J=9.1, 0.6 Hz, 1H), 8.69 (d, J=6.4 Hz, 1H), 8.50 (dd, J=2.9, 0.6 Hz, 1H), 8.36 (dd, J=8.2, 0.9 Hz, 1H), 8.31 (dd, J=8.5, 0.6 Hz, 1H), 8.17 (ddd, J=8.4, 6.9, 1.4 Hz, 1H), 8.00-7.87 (m, 5H), 7.71-7.65 (m, 3H), 7.50 (s, 1H), 7.01 (d, J=6.4 Hz, 1H), 4.43 (t, J=5.5 Hz, 2H), 4.19-4.03 (m, 2H), 4.10 (s, 3H), 3.91-3.73 (m, 2H), 3.71-3.55 (m, 2H), 3.49 (t, J=7.5 Hz, 2H), 3.27-3.15 (m, 2H), 2.47 (p, J=6.3 Hz, 2H). MS m/e: 643 (M+H)$^+$.

Example 10: Synthesis of 4-(4-Hydroxypiperidin-1-yl)-N-(5-((6-methoxy-7-(3-morpholino-propoxy)quinolin-4-yl)oxy)pyridin-2-yl)picolinamide (11)

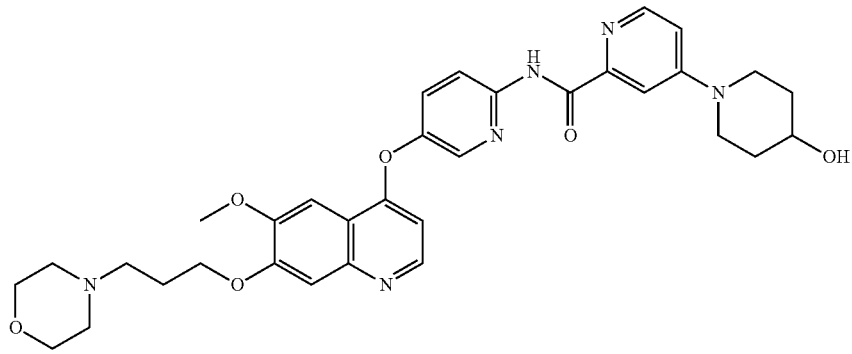

To a solution of 5-(((6-methoxy-7-(3-morpholinopropoxy) quinolin-4-yl)oxy)pyridin-2-amine (5', 50 mg, 0.12 mmol), 4-(4-hydroxypiperidin-1-yl)picolinic acid (50 mg, 0.2 mmol) in DMF (2 mL), DIEA (110 µL, 82 mg, 0.63 mmol) and HATU (140 mg, 0.37 mmol) were added. The reaction mixture was then allowed to stir at room temperature overnight. The reaction mixture was then diluted with water (30 ml) and extracted with 10% MeOH/DCM solution (5×10 mL) and the combined organic layer was dried (MgSO$_4$) and concentrated to give a brown residue. Column chromatography, eluting with DCM and 10% MeOH/DCM provided 25 mg (33%) of 4-(4-hydroxypiperidin-1-yl)-N-(5-((6-methoxy-7-(3-morpholinopropoxy)quinolin-4-yl)oxy)pyridin-2-yl)picolinamide (8) as a white solid. $^1$H NMR (CD$_3$OD, 400 MHz) δ 8.72 (d, J=6.7 Hz, 1H), 8.54-8.50 (m, 2H), 8.23, 8.17 (2 d, J=7.1 Hz, 1H), 8.06, 8.02 (2d, J=2.7 Hz, 1H), 7.96 (dd, J=9.0, 3.1 Hz, 1H), 7.88 (s, 1H), 7.61 (s, 1H), 7.31, 7.27 (2dd, J=7.4, 2.7 Hz, 1H), 7.02 (d, J=7.1 Hz, 1H), 4.45 (t, J=5.5 Hz, 2H), 4.19-3.99 (m, 5H), 4.10 (s, 3H), 3.93-3.78 (m, 3H), 3.72-3.61 (m, 4H), 3.49 (t, J=7.4 Hz, 2H), 3.28-3.15 (m, 2H), 2.46 (p, J=6.3 Hz, 2H), 2.10-1.96 (m, 2H), 1.75-1.05 (m, 2H). MS m/e: 615 (M+H)$^+$.

Example 11: Synthesis of N-(5-(((6-Methoxy-7-(3-morpholinopropoxy)quinolin-4-yl)oxy)pyridin-2-yl)-4-oxo-3,4-dihydroquinazoline-2-carboxamide (12)

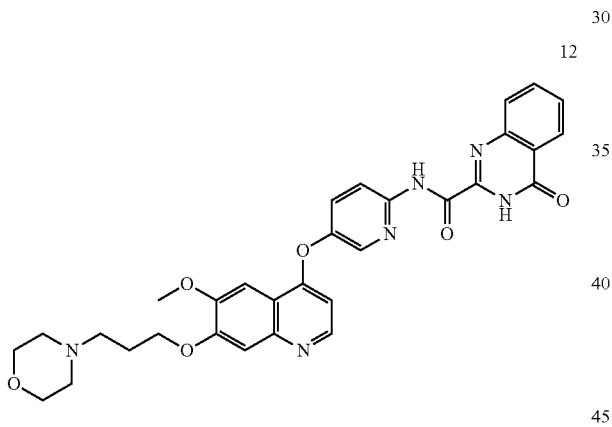

To a solution of 5-(((6-methoxy-7-(3-morpholinopropoxy) quinolin-4-yl)oxy)pyridin-2-amine (5', 25 mg, 0.06 mmol), 4-chloroquinazoline-2-carboxylic acid (16 mg, 0.08 mmol) in DMF (1 mL), DIEA (35 µL, 26 mg, 0.2 mmol) and HATU (70 mg, 0.18 mmol) were added. The reaction mixture was then allowed to stir at room temperature overnight. The reaction mixture was then diluted with water (30 ml) and extracted with DCM (3×10 mL) and the combined organic layer was dried (MgSO$_4$) and concentrated to give a brown residue. Reverse phase chromatography provided 9.0 mg (25%) of N-(5-(((6-methoxy-7-(3-morpholinopropoxy)quinolin-4-yl)oxy)pyridin-2-yl)-4-oxo-3,4-dihydroquinazoline-2-carboxamide (9) as a white solid. $^1$H NMR (CD$_3$OD, 400 MHz) δ 8.73 (d, J=6.7 Hz, 1H), 8.57 (d, J=9.4 Hz, 1H), 8.53 (d, J=3.1 Hz, 1H), 8.31 (d, J=7.8 Hz, 1H), 7.98 (dd, J=9.0, 2.7 Hz, 1H), 7.96-7.91 (m, 2H), 7.87 (s, 1H), 7.68 (ddd, J=8.2, 5.9, 2.4 Hz, 1H), 7.58 (s, 1H), 7.05 (d, J=6.7 Hz, 1H), 4.45 (t, J=5.3 Hz, 2H), 4.17-4.07 (m, 2H), 4.11 (s, 3H), 3.90-3.78 (m, 2H), 3.68 (d, J=10.2 Hz, 2H), 3.50 (t, J=7.4 Hz, 2H), 3.28-3.18 (m, 2H), 2.47 (p, J=6.4 Hz, 2H). MS m/e: 583 (M+H)$^+$.

Example 12: Synthesis of N-(5-((6-Methoxy-7-(3-morpholinopropoxy)quinolin-4-yl)oxy)pyridin-2-yl)-6-phenylpicolinamide (10)

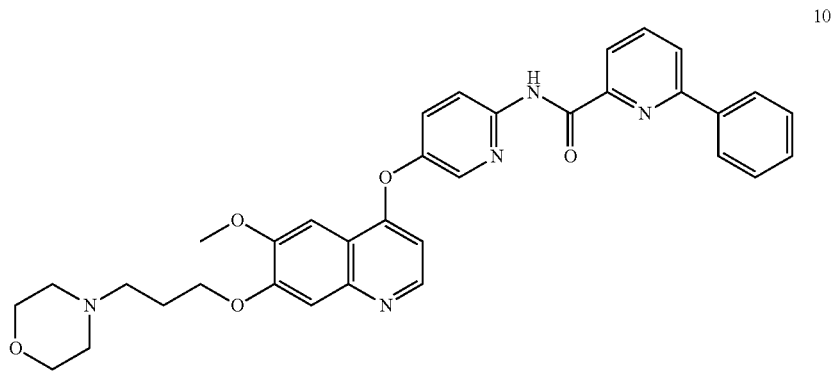 [SMILES: COc1cc2c(Oc3ccc(NC(=O)c4cccc(-c5ccccc5)n4)nc3)ccnc2cc1OCCCN1CCOCC1]

To a solution of 5-((6-methoxy-7-(3-morpholinopropoxy)quinolin-4-yl)oxy)pyridin-2-amine (5', 100 mg, 0.24 mmol), 6-phenylpicolinic acid (75 mg, 0.38 mmol) in DMF (2 mL), DIEA (130 µL, 96 mg, 0.75 mmol) and HATU (280 mg, 0.74 mmol) were added. The reaction mixture was then allowed to stir at room temperature overnight, diluted with water (30 ml) and extracted with DCM (3×10 mL) and the combined organic layer was dried (MgSO₄) and concentrated to give a brown residue. Reverse phase chromatography provided 65 mg (45%) of N-(5-((6-methoxy-7-(3-morpholinopropoxy)quinolin-4-yl)oxy)pyridin-2-yl)-6-phenylpicolinamide (10) as a white solid. $^1$H NMR (CD$_3$OD, 400 MHz) δ8.70 (d, J=3.9 Hz, 1H), 8.68 (d, J=6.3 Hz, 1H), 8.49 (d, J=2.7 Hz, 1H), 8.27-8.22 (m, 2H), 8.20 (s, 1H), 8.17 (dd, J=16.6, 9.2 Hz, 2H), 7.97 (dd, J=9.2, 2.9 Hz, 1H), 7.89 (s, 1H), 7.60-7.50 (m, 4H), 7.02 (d, J=6.3 Hz, 1H), 4.44 (t, J=5.5 Hz, 2H), 4.20-4.08 (br s, 2H), 4.12 (s, 3H), 3.88-3.74 (br s, 2H), 3.72-3.60 (br s, 2H), 3.50 (t, J=7.2 Hz, 2H), 3.27-3.17 (m, 2H), 2.46 (p, J=6.4 Hz, 2H). MS m/e: 592 (M+H)⁺.

Scheme 1

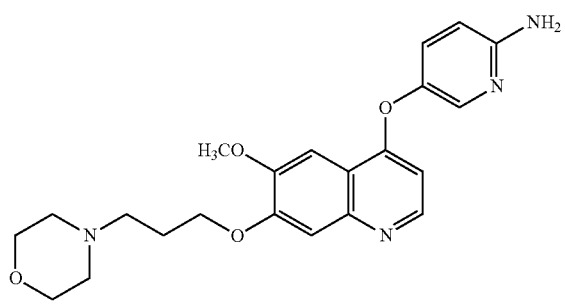

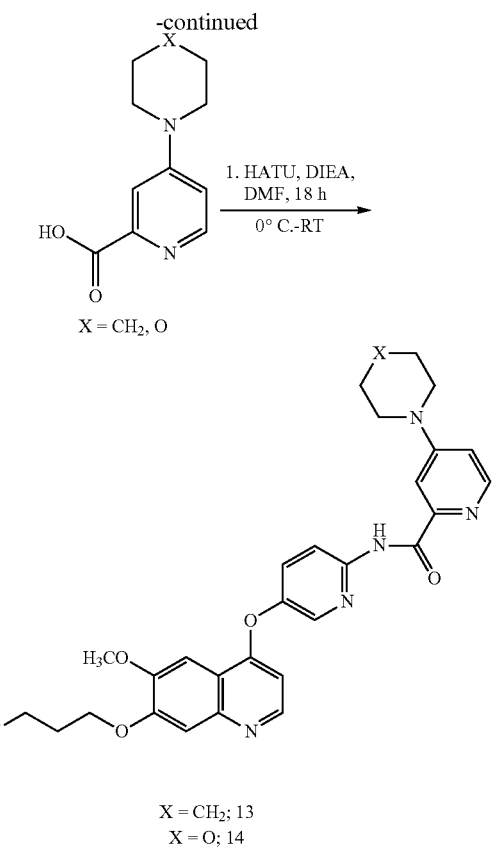

Synthesis of N-(5-((6-methoxy-7-(3-morpholinopropoxy)quinolin-4-yl)oxy)pyridin-2-yl)-4-(piperidin-1-yl)picolinamide (13)

5-((6-methoxy-7-(3-morpholinopropoxy)quinolin-4-yl)oxy)pyridin-2-amine (0.100 g, 1.0 eq, 0.24 mmol) and 4-(piperidin-1-yl)picolinic acid (0.095 g, 1.6 eq, 0.39 mmol) were taken in 15 mL of anhydrous DMF in a 50 mL RB flask. Above solution was cooled to 0° C. while stirring under nitrogen atmosphere. HATU (0.28 g, 3.0 eq, 0.73 mmol) was added to the reaction mixture followed by the addition of DIEA (0.16 g, 5.0 eq, 1.22 mmol) at 0° C. Reaction mixture was allowed to warm to room temperature and the progress of the reaction was monitored by LCMS. After 18 hours, the reaction mixture was diluted with 50 mL of CH$_2$Cl$_2$ and washed with saturated aqueous NaHCO$_2$ solution (2×50 mL). Organic layers were separated, extracted with brine (2×50 mL) and dried over Na$_2$SO$_4$. Dried organic layer was concentrated under reduced pressure and the crude was purified by flash chromatography to give the required product in 64% yield. $^1$H NMR (300 MHz, DMSO-d$_6$) δ 10.63 (s, 1H), 8.50 (d, J=5.3 Hz, 1H), 8.43 (s, 1H), 8.41 (d, J=5.0 Hz, 1H), 8.27 (d, J=6.0 Hz, 1H), 7.91 (dd, J=9.0, 2.9 Hz, 1H), 7.58 (d, J=2.7 Hz, 1H), 7.55 (s, 1H), 7.42 (s, 1H), 7.07 (dd, J=6.1, 2.8 Hz, 1H), 6.57 (d, J=5.2 Hz, 1H), 4.22 (t, J=6.3 Hz, 2H), 3.95 (s, 3H), 3.62 (m, 4H), 3.49 (d, J=5.9 Hz, 4H), 3.29 (s, 2H), 3.21-3.07 (m, 2H), 2.03 (s, 3H), 1.61 (s, 3H), 1.31-1.20 (m, 4H). MS m/e: 599 (M+H)$^+$.

Synthesis of N-(5-((6-methoxy-7-(3-morpholinopropoxy)quinolin-4-yl)oxy)pyridin-2-yl)-4-morpholinopicolinamide (14)

Compound 14 was prepared using same procedure that was used for Compound 13 using 4-morpholinopicolinic acid in the place of 4-(piperidin-1-yl)picolinic acid. Crude mixture was purified by flash chromatography to give the required product in 72% yield.
$^1$H NMR (300 MHz, DMSO-d$_6$) δ 10.62 (s, 1H), 8.49 (d, J=5.2 Hz, 1H), 8.45-8.41 (s, 1H), 8.40 (d, J=0.7 Hz, 1H), 8.35 (d, J=5.9 Hz, 1H), 7.91 (dd, J=8.9, 3.0 Hz, 1H), 7.63 (d, J=2.6 Hz, 1H), 7.54 (s, 1H), 7.41 (s, 1H), 7.12 (dd, J=6.0, 2.7 Hz, 1H), 6.57 (d, J=5.2 Hz, 1H), 4.21 (t, J=6.4 Hz, 2H), 3.95 (s, 3H), 3.75 (t, J=4.9 Hz, 4H), 3.64-3.54 (m, 4H), 3.42 (t, J=5.0 Hz, 4H), 3.29 (s, 4H), 2.45-2.40 (m, 2H), 2.06-1.91 (m, 2H). MS m/e: 601 (M+H)$^+$.

Synthesis of Compounds 15-22 is described in Scheme-2 & Scheme-3. A representative experimental procedure for the synthesis of Compound 15 was described and Compounds 16-22 were synthesized following same procedure by using respective amines.

Synthesis of 4-chloro-N-(5-((6-methoxy-7-(3-morpholinopropoxy)quinolin-4-yl)oxy)pyridin-2-yl)picolinamide (3″)

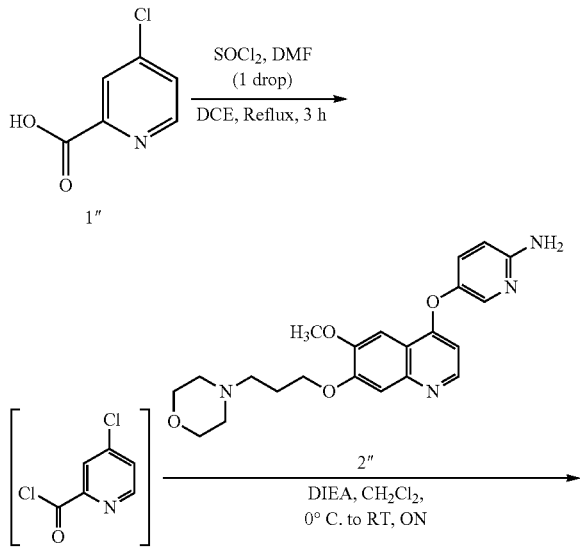

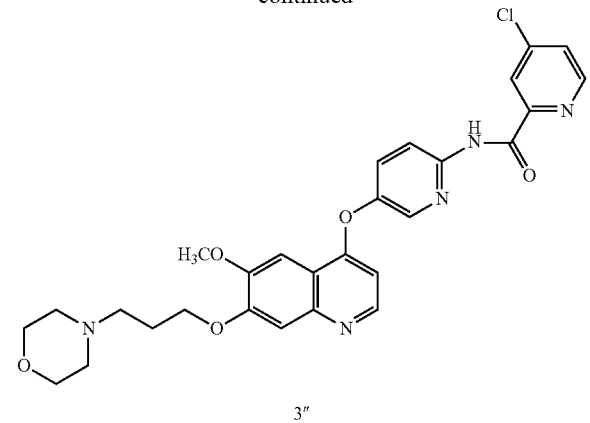

4-Chloropicolinic acid (0.46 g, 1.2 eq, 2.92 mmol) was taken in 10 mL of 1,2-dichoroethane. Thionylchloride (3.47 g, 10 eq, 29.2 mmol) was added to the above solution. A drop of anhydrous DMF was added to the above reaction mixture and the resulting heterogeneous solution was refluxed for 3 hours under N$_2$ atmosphere. After 3 hours, reaction mixture was turned clear and assumed the reaction was completed. The reaction mixture was cooled to room temperature and concentrated to dryness under pressure. Additional 10 mL of 1,2-dichloroethane was added to the flask and concentrated again the resulting reaction mixture to remove excess of thionylchloride. The resulting 4-chloropicolinoyl chloride was dissolved in 20 mL of anhydrous methylene chloride and the solution was cooled to 0° C. in ice-salt bath. 5-((6-methoxy-7-(3-morpholinopropoxy)quinolin-4-yl)oxy)pyridin-2-amine (1.0 g, 1.0 eq, 2.44 mmol) was added to the reaction mixture, followed by the addition of diisopropyl ethyl amine (0.38 g, 1.2 eq, 2.93 mmol). The reaction mixture was allowed to warm to room temperature and stirred for over night. LC/MS analysis indicated completion of the reaction. Crude mixture was diluted with 50 mL of methylene chloride and partitioned with saturate aqueous NaHCO$_3$ solution (50 mL). Organic layers were separated and worked-up with water (1×50 mL) and brine (2×50 mL). Combined organic layers were dried over Na$_2$SO$_4$ and concentrated to dryness. The crude reaction mixture was purified by column chromatography using CH$_2$Cl$_2$/MeOH (100/0 to 90/10 gradient) to get the required product in 63% yield (0.83 g). $^1$H NMR (300 MHz, DMSO-d$_6$) δ 10.54 (s, 1H), 8.76 (dd, J=5.3, 0.6 Hz, 1H), 8.50 (d, J=5.2 Hz, 1H), 8.45 (dd, J=2.9, 0.7 Hz, 1H), 8.39 (dd, J=9.0, 0.7 Hz, 1H), 8.23 (dd, J=2.1, 0.6 Hz, 1H), 7.94 (d, J=2.9 Hz, 1H), 7.93-7.88 (m, 18H), 7.54 (s, 1H), 7.41 (s, 1H), 6.57 (d, J=5.2 Hz, 1H), 4.21 (t, J=6.4 Hz, 2H), 3.94 (s, 3H), 3.65-3.53 (m, 5H), 2.40 (s, 5H), 1.98 (p, J=6.7 Hz, 2H). MS m/e: 551 (M+H)$^+$.

Representative procedure for the synthesis of Compound 15-22:

Scheme 3

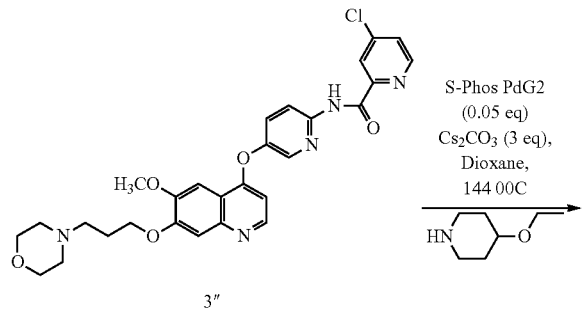

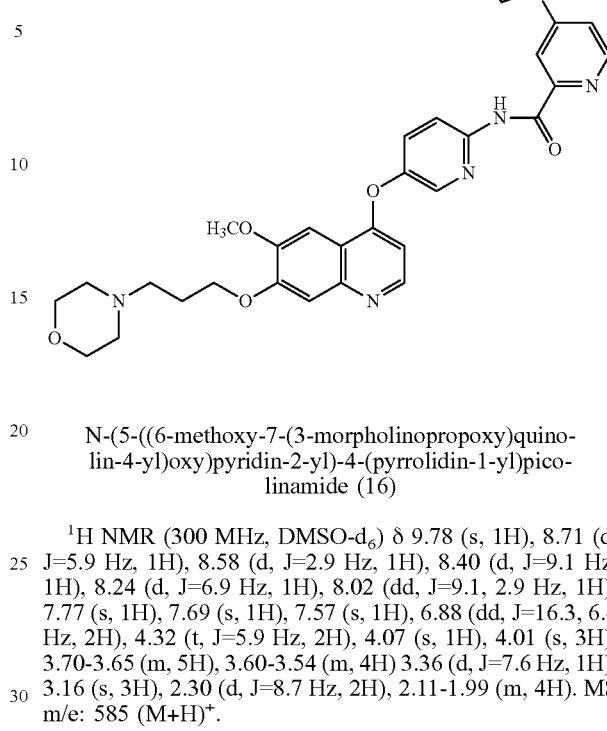

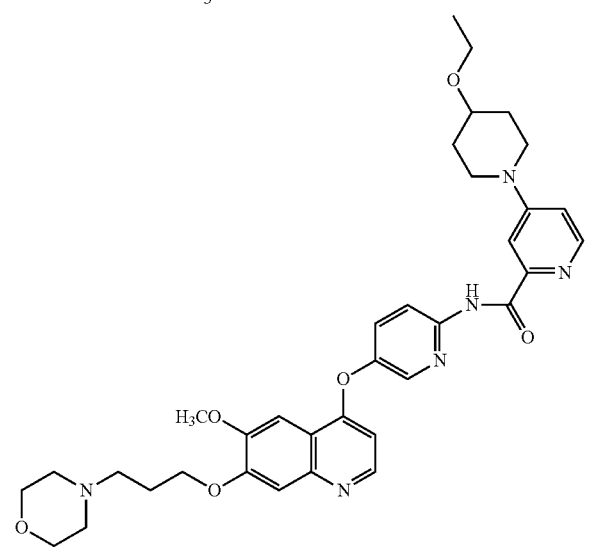

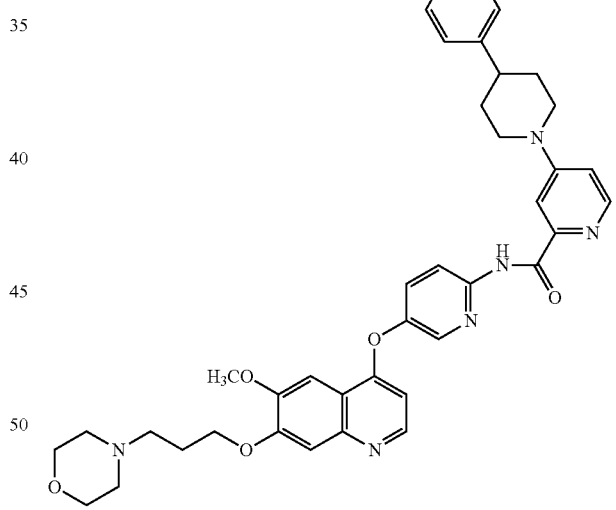

4-(4-ethoxypiperidin-1-yl)-N-(5-(((6-methoxy-7-(3-morpholinopropoxy)quinolin-4-yl)oxy)pyridin-2-yl) picolinamide (15)

4-chloro-N-(5-(((6-methoxy-7-(3-morpholinopropoxy) quinolin-4-yl)oxy)pyridin-2-yl)picolinamide (0.050 g, 1.0eq, 0.091 mmol), S-Phos PdG2 (0.05 eq), Cs2CO3 (3 eq) and 4-ethoxypiperidine (1.8 eq) were taken in a screw cap vial. Anhydrous 1,4-dioxane (3 mL) was added to the vial and the solution was bubbled with argon for few minutes. Reaction vial was closed tightly and heated at 144° C. for 5 hours. LC/MS analysis indicated completion of the reaction. Volatiles were removed under pressure and the crude mixture was purified by reverse phase column chromatography to give the required product in 45% yield. $^1$H NMR (300 MHz, DMSO-d$_6$) δ 10.07 (s, 1H), 8.71 (d, J=5.9 Hz, 1H), 8.56 (d, J=2.9 Hz, 1H), 8.41 (d, J=9.0 Hz, 1H), 8.29-8.22 (m, 1H), 8.05-7.97 (m, 1H), 7.94 (s, 1H), 7.69 (d, J=0.8 Hz, 1H), 7.57 (s, 1H), 7.24 (d, J=6.8 Hz, 1H), 6.84 (d, J=5.9 Hz, 1H), 4.31 (t, J=5.8 Hz, 2H), 4.03-3.98 (m, 3H), 3.92 (s, 1H), 3.80-3.75 (m, 6H), 3.68-3.60 (m, 4H), 3.55-3.43 (m, 1H), 3.36 (d, J=7.5 Hz, 1H), 3.16-3.10 (m, 5H), 2.30 (d, J=8.2 Hz, 2H), 1.95 (s, 2H), 1.56 (d, J=10.3 Hz, 2H), 1.19-1.07 (m, 2H). MS m/e: 643 (M+H)$^+$.

N-(5-(((6-methoxy-7-(3-morpholinopropoxy)quinolin-4-yl)oxy)pyridin-2-yl)-4-(pyrrolidin-1-yl)picolinamide (16)

$^1$H NMR (300 MHz, DMSO-d$_6$) δ 9.78 (s, 1H), 8.71 (d, J=5.9 Hz, 1H), 8.58 (d, J=2.9 Hz, 1H), 8.40 (d, J=9.1 Hz, 1H), 8.24 (d, J=6.9 Hz, 1H), 8.02 (dd, J=9.1, 2.9 Hz, 1H), 7.77 (s, 1H), 7.69 (s, 1H), 7.57 (s, 1H), 6.88 (dd, J=16.3, 6.4 Hz, 2H), 4.32 (t, J=5.9 Hz, 2H), 4.07 (s, 1H), 4.01 (s, 3H), 3.70-3.65 (m, 5H), 3.60-3.54 (m, 4H) 3.36 (d, J=7.6 Hz, 1H), 3.16 (s, 3H), 2.30 (d, J=8.7 Hz, 2H), 2.11-1.99 (m, 4H). MS m/e: 585 (M+H)$^+$.

N-(5-(((6-methoxy-7-(3-morpholinopropoxy)quinolin-4-yl)oxy)pyridin-2-yl)-4-(4-phenylpiperidin-1-yl) picolinamide (17)

$^1$H NMR (300 MHz, DMSO-d$_6$) δ 9.80 (s, 1H), 8.72 (d, J=5.9 Hz, 1H), 8.59-8.54 (m, 1H), 8.42 (d, J=9.1 Hz, 1H), 8.27 (d, J=6.9 Hz, 1H), 8.07-7.97 (m, 1H), 7.70 (s, 1H), 7.57 (s, 1H), 7.38-7.17 (m, 8H), 6.85 (d, J=5.9 Hz, 1H), 4.44 (d, J=13.3 Hz, 3H), 4.32 (t, J=5.9 Hz, 3H), 4.07 (s, 1H), 4.04-3.97 (m, 4H), 3.55 (s, 1H), 3.39-3.22 (m, 4H), 3.16 (s, 1H), 2.98 (s, 1H), 2.29 (t, J=7.2 Hz, 3H), 1.99 (d, J=12.8 Hz, 3H), 1.74 (t, J=12.2 Hz, 2H). MS m/e: 675 (M+H)$^+$.

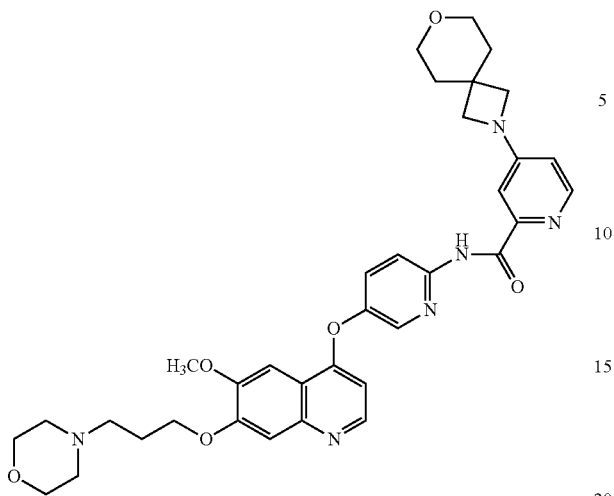

N-(5-(((6-methoxy-7-(3-morpholinopropoxy)quinolin-4-yl)oxy)pyridin-2-yl)-4-(7-oxa-2-azaspiro[3.5]nonan-2-yl)picolinamide (18)

$^1$H NMR (300 MHz, DMSO-d$_6$) δ 10.06 (s, 1H), 8.77 (d, J=6.1 Hz, 1H), 8.59 (d, J=2.9 Hz, 1H), 8.41 (d, J=9.0 Hz, 1H), 8.24 (d, J=6.5 Hz, 1H), 8.04 (dd, J=9.1, 2.9 Hz, 1H), 7.73 (s, 1H), 7.65 (s, 1H), 7.58 (s, 1H), 6.92 (d, J=6.1 Hz, 1H), 6.76-6.67 (m, 1H), 4.33 (t, J=5.8 Hz, 2H), 4.01 (d, J=6.3 Hz, 9H), 3.69 (s, 2H), 3.57 (q, J=3.8, 2.7 Hz, 5H), 3.35 (t, J=7.7 Hz, 2H), 3.16 (s, 3H), 2.30 (t, J=7.4 Hz, 2H), 1.81 (t, J=5.1 Hz, 4H). MS m/e: 641 (M+H)$^+$.

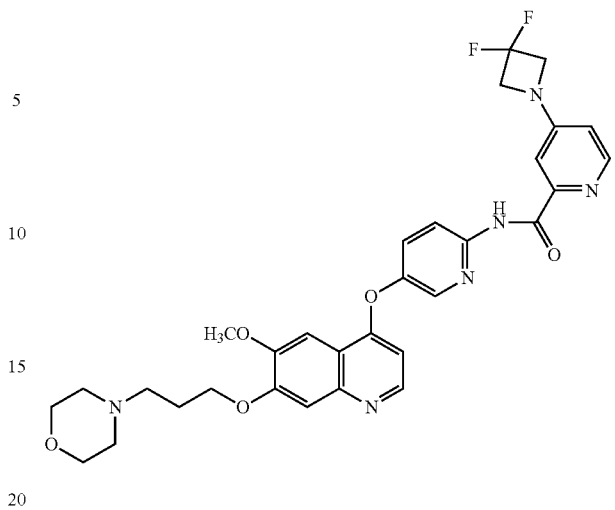

4-(3,3-difluoroazetidin-1-yl)-N-(5-((6-methoxy-7-(3-morpholinopropoxy)quinolin-4-yl)oxy)pyridin-2-yl)picolinamide (20)

$^1$H NMR (300 MHz, DMSO-d$_6$) δ 9.80 (s, 1H), 8.79-8.64 (m, 1H), 8.51 (d, J=2.9 Hz, 1H), 8.45 (d, J=9.1 Hz, 1H), 8.39 (d, J=5.7 Hz, 1H), 8.00 (dd, J=9.0, 3.0 Hz, 1H), 7.70 (s, 1H), 7.57 (s, 1H), 7.39 (d, J=2.5 Hz, 1H), 6.90-6.75 (m, 2H), 4.59 (t, J=12.3 Hz, 3H), 4.32 (t, J=5.8 Hz, 2H), 4.04-3.99 (m, 3H), 3.90-3.85 (m, 3H) 3.82-3.46 (m, 3H), 3.36 (d, J=8.3 Hz, 2H), 3.14 (d, J=11.6 Hz, 3H), 2.29 (s, 2H). MS m/e: 607 (M+H)$^+$.

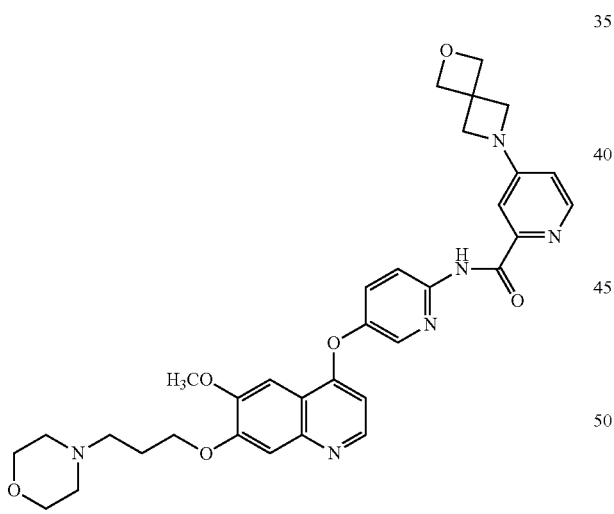

N-(5-(((6-methoxy-7-(3-morpholinopropoxy)quinolin-4-yl)oxy)pyridin-2-yl)-4-(2-oxa-6-azaspiro[3.3]heptan-6-yl)picolinamide (19)

$^1$H NMR (300 MHz, DMSO-d$_6$) δ 9.93 (s, 1H), 8.75 (d, J=5.7 Hz, 1H), 8.58 (dt, J=2.9, 0.9 Hz, 1H), 8.39 (dd, J=9.2, 0.8 Hz, 1H), 8.20 (d, J=6.5 Hz, 1H), 8.03 (dd, J=9.1, 3.0 Hz, 1H), 7.72 (d, J=1.0 Hz, 1H), 7.60 (d, J=7.3 Hz, 2H), 6.89 (d, J=6.2 Hz, 1H), 6.73 (dd, J=6.8, 2.4 Hz, 1H), 4.32 (t, J=5.8 Hz, 2H), 4.05-3.93 (m, 8H), 3.68 (s, 2H), 3.56 (d, J=9.7 Hz, 5H), 3.35 (t, J=7.7 Hz, 2H), 3.15 (s, 3H), 2.29 (d, J=8.6 Hz, 3H). MS m/e: 613 (M+H)$^+$.

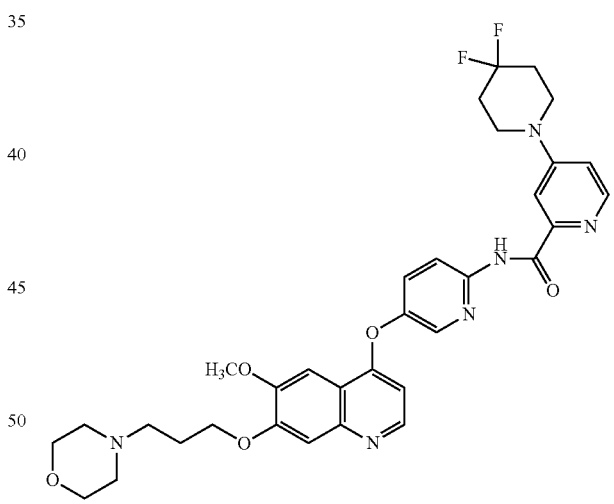

4-(4,4-difluoropiperidin-1-yl)-N-(5-((6-methoxy-7-(3-morpholinopropoxy)quinolin-4-yl)oxy)pyridin-2-yl)picolinamide (21)

$^1$H NMR (300 MHz, DMSO-d$_6$) δ 9.76 (s, 1H), 8.70 (d, J=5.8 Hz, 1H), 8.53 (d, J=2.9 Hz, 1H), 8.44 (d, J=9.0 Hz, 1H), 8.35 (d, J=6.4 Hz, 1H), 8.00 (dd, J=9.1, 2.9 Hz, 1H), 7.86 (s, 1H), 7.69 (s, 1H), 7.56 (s, 1H), 7.28 (d, J=6.3 Hz, 1H), 6.84 (d, J=5.9 Hz, 1H), 4.31 (t, J=5.9 Hz, 2H), 4.01 (s, 3H), 3.90-3.81 (m, 3H), 3.75-3.63 (m, 3H), 3.46-3.35 (m, 4H), 3.15 (s, 4H), 2.36-2.22 (m, 2H), 2.12 (s, 4H). MS m/e: 635 (M+H)$^+$.

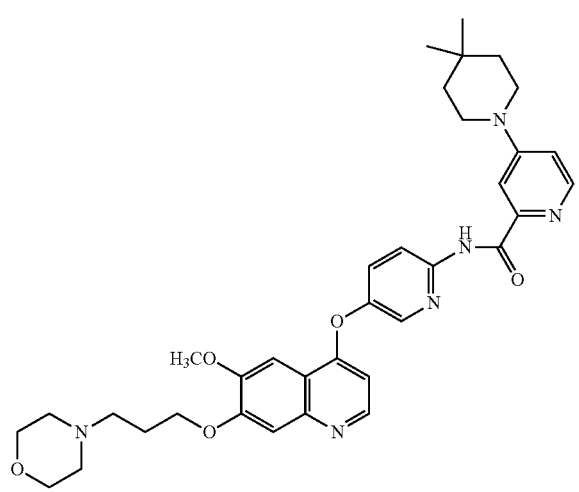 [SMILES: COc1cc2c(Oc3ccc(NC(=O)c4cc(N5CCC(C)(C)CC5)ccn4)nc3)ccnc2cc1OCCCN1CCOCC1]

4-(4,4-dimethylpiperidin-1-yl)-N-(5-((6-methoxy-7-(3-morpholinopropoxy)quinolin-4-yl)oxy)pyridin-2-yl)picolinamide (22)

$^1$H NMR (300 MHz, DMSO-d) δ 9.90 (s, 1H), 8.71 (d, J=5.9 Hz, 1H), 8.56 (d, J=2.9 Hz, 1H), 8.40 (d, J=9.0 Hz, 1H), 8.24 (d, J=6.8 Hz, 1H), 8.01 (dd, J=9.0, 2.9 Hz, 1H), 7.93 (s, 1H), 7.69 (s, 1H), 7.59 (s, 1H), 7.22 (d, J=6.3 Hz, 1H), 6.84 (d, J=5.9 Hz, 1H), 4.31 (t, J=5.9 Hz, 2H), 4.01 (s, 3H), 3.82-3.3.73 (m, 3H), 3.69 (s, 7H), 3.54 (s, 2H), 3.35 (t, J=7.7 Hz, 2H), 2.29 (t, J=7.3 Hz, 2H), 1.47 (t, J=5.7 Hz, 4H), 1.02 (s, 6H). MS m/e: 627 (M+H)$^+$.

Synthesis of 23 to 30 was described in Scheme-4. Similar experimental procedures were used for the synthesis as described in Scheme-2 & Scheme-3.

Scheme 4

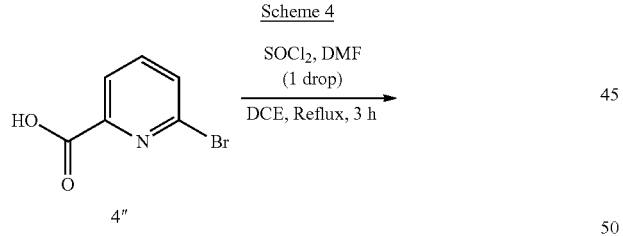

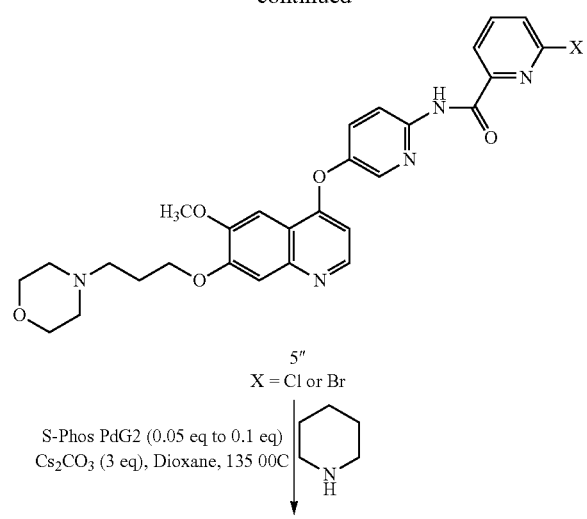

Representative procedure for the synthesis of 23-30:

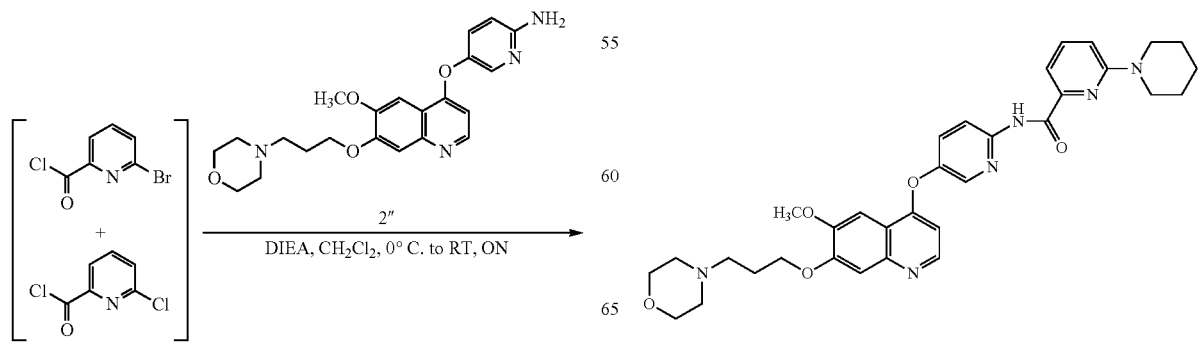

N-(5-((6-methoxy-7-(3-morpholinopropoxy)quinolin-4-yl)oxy)pyridin-2-yl)-6-(piperidin-1-yl)picolinamide (23)

¹H NMR (300 MHz, DMSO-d₆) δ 10.47 (s, 1H), 8.77 (d, J=6.0 Hz, 1H), 8.53 (d, J=2.9 Hz, 1H), 8.51-8.44 (m, 1H), 8.00 (dd, J=9.0, 3.0 Hz, 1H), 7.80-7.69 (m, 2H), 7.62 (s, 1H), 7.44 (d, J=7.3 Hz, 1H), 7.19 (d, J=8.7 Hz, 1H), 6.92 (d, =6.2 Hz, 1H), 4.32 (d, J=6.6 Hz, 3H), 4.03 (s, 3H), 3.65 (d, J=6.1 Hz, 4H), 3.53 (s, 1H), 3.35 (s, 4H), 3.15 (s, 4H), 2.30 (s, 4H), 1.64 (s, 4H). MS m/e: 599 (M+H)⁺.

N-(5-((6-methoxy-7-(3-morpholinopropoxy)quinolin-4-yl)oxy)pyridin-2-yl)-6-morpholinopicolinamide (25)

¹H NMR (300 MHz, DMSO-d₆) δ 10.46 (d, J=5.9 Hz, 1H), 8.53-8.42 (m, 2H), 7.97 (dd, J=9.0, 3.0 Hz, 1H), 7.88-7.80 (m, 1H), 7.72-7.68 (m, 1H), 7.57 (s, 1H), 7.53 (d, J=7.2 Hz, 1H), 7.21 (d, J=8.6 Hz, 1H), 6.82 (d, J=6.2 Hz, 1H), 4.31 (t, J=5.8 Hz, 3H), 4.01 (s, 4H), 3.78 (t, J=4.9 Hz, 4H), 3.59 (t, J=4.9 Hz, 4H), 3.40-3.28 (m, 4H), 3.15 (s, 4H), 2.29 (s, 2H). MS m/e: 601 (M+H)⁺.

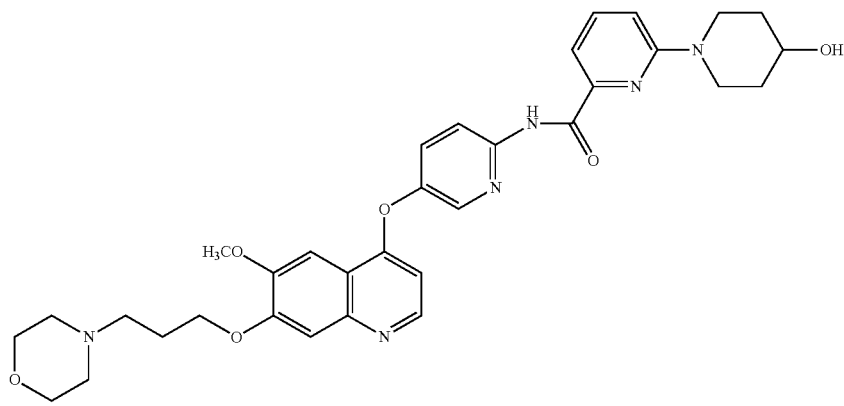 [SMILES: COc1cc2c(Oc3ccc(NC(=O)c4cccc(N5CCC(O)CC5)n4)nc3)ccnc2cc1OCCCN1CCOCC1]

6-(4-hydroxypiperidin-1-yl)-N-(5-((6-methoxy-7-(3-morpholinopropoxy)quinolin-4-yl)oxy)pyridin-2-yl)picolinamide (24)

¹H NMR (300 MHz, DMSO-d₆) δ 10.45 (s, 1H), 8.78-8.71 (m, 1H), 8.55-8.50 (m, 1H), 8.47 (dt, J=9.0, 1.1 Hz, 1H), 8.04-7.94 (m, 1H), 7.83-7.68 (m, 2H), 7.62 (d, J=1.3 Hz, 1H), 7.45 (d, J=7.3 Hz, 1H), 7.21 (d, J=8.7 Hz, 1H), 6.89 (d, J=6.0 Hz, 1H), 4.32 (t, J=5.7 Hz, 2H), 4.15-3.96 (m, 6H), 3.81-3.62 (m, 2H), 3.53 (s, 1H), 3.35 (t, J=7.6 Hz, 2H), 3.22 (dd, J=26.0, 14.6 Hz, 6H), 2.29 (d, J=8.0 Hz, 4H), 1.86 (d, J=12.7 Hz, 2H), 1.44 (d, J=11.1 Hz, 2H). MS m/e: 615 (M+H)⁺.

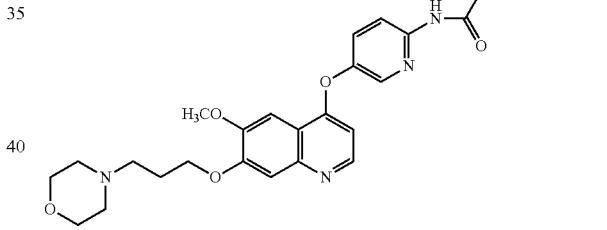

N-(5-((6-methoxy-7-(3-morpholinopropoxy)quinolin-4-yl)oxy)pyridin-2-yl)-6-(pyrrolidin-1-yl)picolinamide (26)

¹H NMR (300 MHz, DMSO-d₆) δ 10.61 (s, 1H), 8.79 (d, J=6.2 Hz, 1H), 8.56-8.45 (m, 2H), 8.02 (dd, J=8.8, 3.1 Hz, 1H), 7.76 (pd, J=4.0, 3.5, 1.3 Hz, 2H), 7.65 (s, 1H), 7.46-7.36 (m, 1H), 6.97 (t, J=4.5 Hz, 1H), 6.85-6.77 (m, 1H), 4.32 (d, J=6.1 Hz, 4H), 4.08-3.99 (m, 4H), 3.69 (s, 1H), 3.52 (s, 4H), 3.35 (d, J=6.8 Hz, 4H), 3.15 (s, 4H), 2.32 (d, J=8.1 Hz, 2H), 2.02 (d, J=6.1 Hz, 2H). MS m/e: 585 (M+H)⁺.

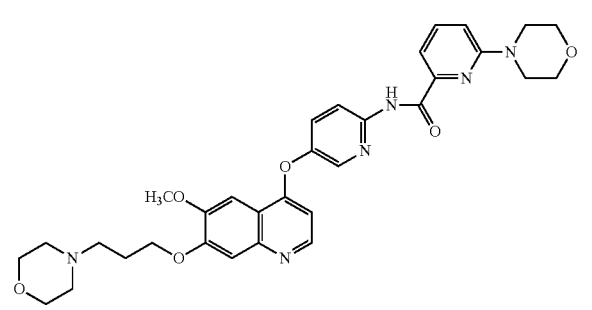 [SMILES: COc1cc2c(Oc3ccc(NC(=O)c4cccc(N5CCOCC5)n4)nc3)ccnc2cc1OCCCN1CCOCC1]

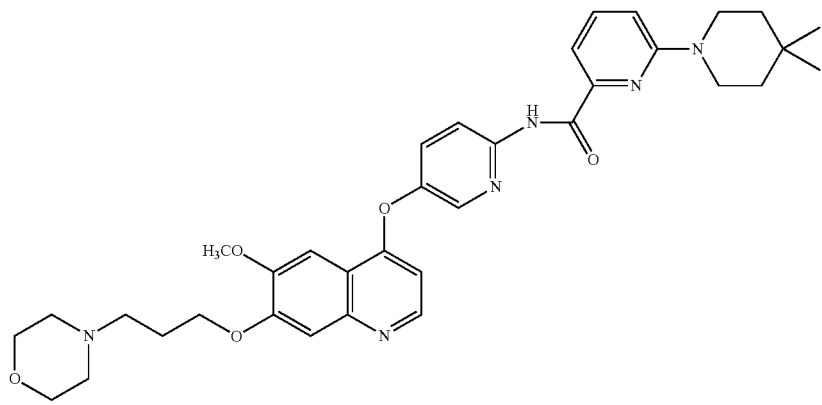 [SMILES: COc1cc2c(Oc3ccc(NC(=O)c4cccc(N5CCC(C)(C)CC5)n4)nc3)ccnc2cc1OCCCN1CCOCC1]

6-(4,4-dimethylpiperidin-1-yl)-N-(5-((6-methoxy-7-(3-morpholinopropoxy)quinolin-4-yl)oxy)pyridin-2-yl)picolinamide (27)

$^1$H NMR (300 MHz, DMSO-d$_6$) δ 10.46 (s, 1H), 8.71 (d, J=6.1 Hz, 1H), 8.56-8.41 (m, 2H), 8.03-7.91 (m, 1H), 7.78 (dd, J=9.0, 7.4 Hz, 1H), 7.71 (d, J=1.8 Hz, 1H), 7.57 (d, J=1.4 Hz, 1H), 7.49-7.40 (m, 1H), 7.20 (d, J=8.5 Hz, 1H), 6.85 (d, =6.2 Hz, 1H), 4.32 (s, 3H), 4.02 (s, 5H), 3.64 (s, 4H), 3.55 (d, J=11.4 Hz, 1H), 3.35 (s, 2H), 3.16 (s, 3H), 2.29 (s, 3H), 1.45 (s, 4H), 1.01 (d, J=2.0 Hz, 6H). MS m/e: 627 (M+H)$^+$.

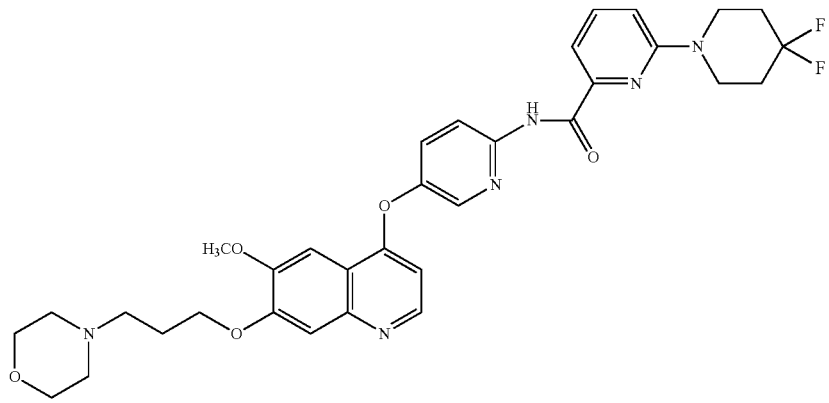 [SMILES: COc1cc2c(Oc3ccc(NC(=O)c4cccc(N5CCC(F)(F)CC5)n4)nc3)ccnc2cc1OCCCN1CCOCC1]

6-(4,4-difluoropiperidin-1-yl)-N-(5-((6-methoxy-7-(3-morpholinopropoxy)quinolin-4-yl)oxy)pyridin-2-yl)picolinamide (28)

$^1$H NMR (300 MHz, DMSO-d$_6$) δ 10.44 (d, J=1.1 Hz, 1H), 8.70 (d, J=6.1 Hz, 1H), 8.55-8.41 (m, 2H), 7.97 (dd, J=9.2, 3.1 Hz, 1H), 7.90-7.78 (m, 1H), 7.71 (d, J=2.4 Hz, 1H), 7.60-7.49 (m, 2H), 7.31 (d, J=8.9 Hz, 1H), 6.89-6.78 (m, 1H), 4.30 (d, J=7.1 Hz, 3H), 4.01 (d, J=2.6 Hz, 4H), 3.83 (d, J=5.9 Hz, 4H), 3.70 (d, J=12.8 Hz, 2H), 3.55 (d, J=12.3 Hz, 2H), 3.35 (s, 2H), 3.15 (s, 4H), 2.29 (s, 2H), 2.09 (s, 2H). MS m/e: 635 (M+H)+.

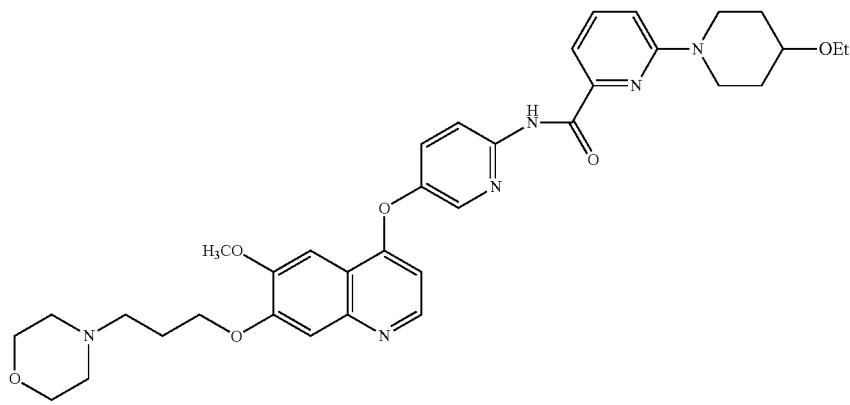 [SMILES: CCOC1CCN(c2cccc(C(=O)Nc3ccc(Oc4ccnc5cc(OCCCN6CCOCC6)c(OC)cc45)cn3)n2)CC1]

6-(4-ethoxypiperidin-1-yl)-N-(5-(((6-methoxy-7-(3-morpholinopropoxy)quinolin-4-yl)oxy)pyridin-2-yl)picolinamide (29)

$^1$H NMR (300 MHz, DMSO-d$_6$) δ 10.42 (s, 1H), 8.62 (d, J=5.7 Hz, 1H), 8.51-8.41 (m, 2H), 7.95 (s, 1H), 7.79 (s, 1H), 7.65 (d, J=2.9 Hz, 1H), 7.49 (d, J=13.4 Hz, 2H), 7.26-7.16 (m, 1H), 6.72 (s, 1H), 4.30 (d, J=5.9 Hz, 3H), 3.99 (s, 4H), 3.89-3.78 (m, 4H), 3.75-3.63 (m, 3H) 3.50-3.41 (m, 4H) 3.15 (s, 3H), 2.28 (s, 3H), 1.97 (d, J=9.3 Hz, 2H), 1.50 (s, 2H), 1.23-1.05 (m, 3H). MS m/e: 643 (M+H)$^+$.

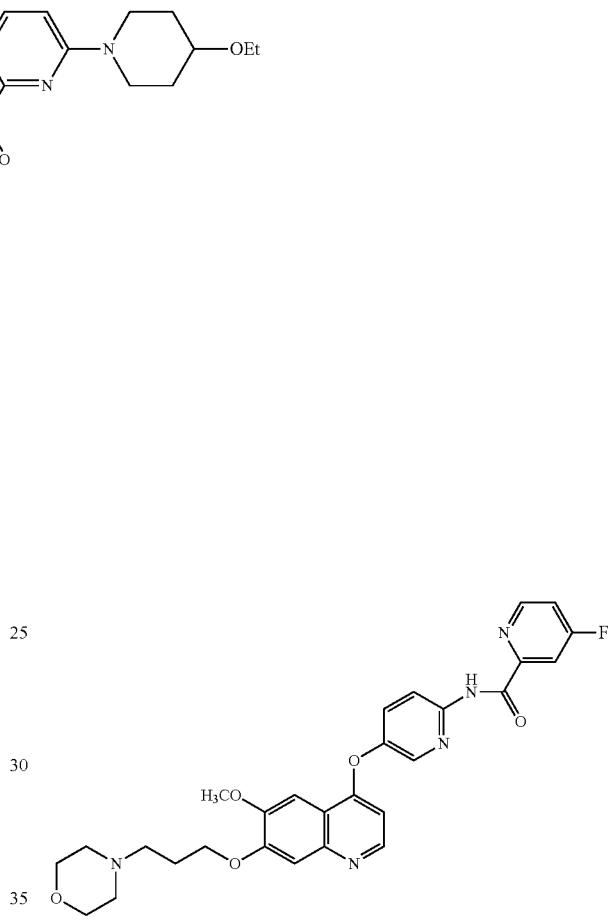

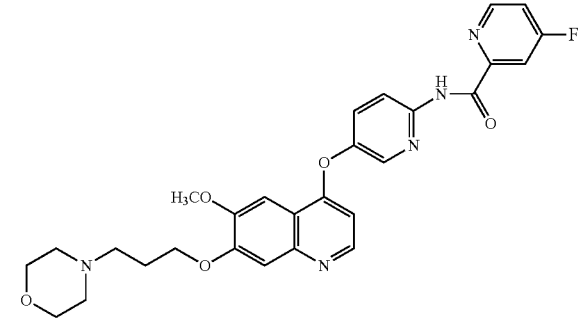 [SMILES: COc1cc2c(Oc3ccc(NC(=O)c4cc(F)ccn4)nc3)ccnc2cc1OCCCN1CCOCC1]

6-(3,3-difluoroazetidin-1-yl)-N-(5-(((6-methoxy-7-(3-morpholinopropoxy)quinolin-4-yl)oxy)pyridin-2-yl)picolinamide (30)

$^1$H NMR (300 MHz, DMSO-d$_6$) δ 10.46 (s, 1H), 8.65 (s, 1H), 8.54-8.41 (m, 2H), 8.01-7.85 (m, 2H), 7.70-7.58 (m, 2H), 7.52 (s, 1H), 6.91 (d, J=8.4 Hz, 1H), 6.77 (s, 1H), 4.57 (t, J=12.6 Hz, 4H), 4.30 (s, 3H), 4.00 (s, 5H), 3.18-3.02 (s, 6H), 2.28 (d, J=6.4 Hz, 2H), 1.23 (s, 1H). MS m/e: 607 (M+H)$^+$.

4-Fluoro-N-(5-(((6-methoxy-7-(3-morpholinopropoxy)quinolin-4-yl)oxy)pyridin-2-yl)picolinamide (31); MS m/e: 534 (M+H).

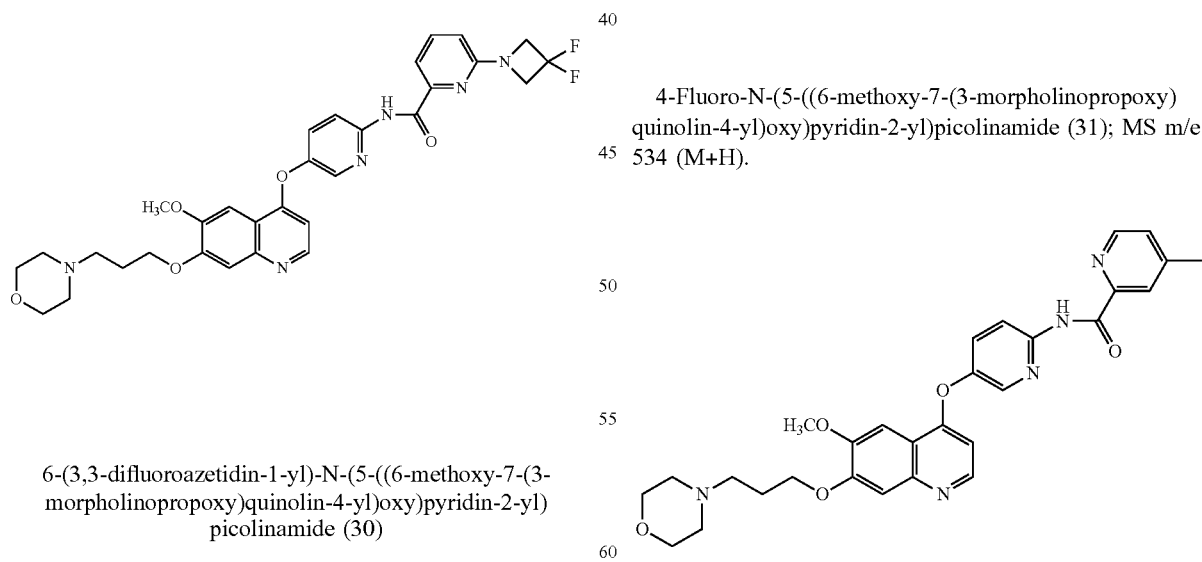

N-(5-(((6-Methoxy-7-(3-morpholinopropoxy)quinolin-4-yl)oxy)pyridin-2-yl)-4-methylpicolinamide (32): MS m/e: 530 (M+H)$^+$.

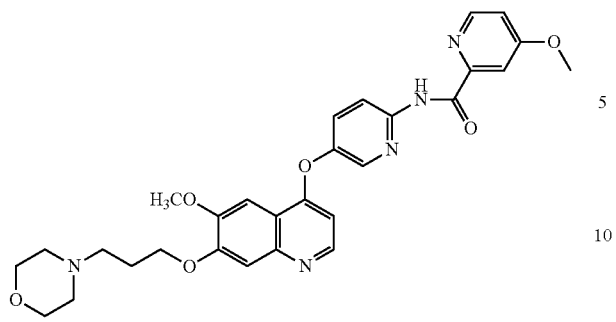
4-Methoxy-N-(5-(((6-methoxy-7-(3-morpholinopropoxy)quinolin-4-yl)oxy)pyridin-2-yl)picolinamide (33): MS m/e: 546 (M+H)+.
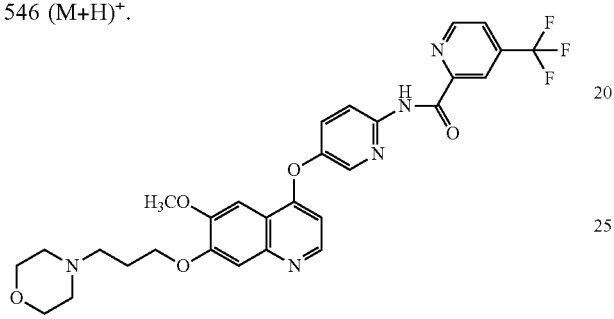
N-(5-(((6-Methoxy-7-(3-morpholinopropoxy)quinolin-4-yl)oxy)pyridin-2-yl)-4-(trifluoromethyl)picolinamide (34): MS m/e: 584 (M+H)+.
Representative synthesis of N-(5-(quinolin-4-yloxy)pyridin-2-yl)thiazole-2-carboxamide and N-(5-(quinolin-4-yloxy)pyridin-2-yl)thiazole-4-carboxamide
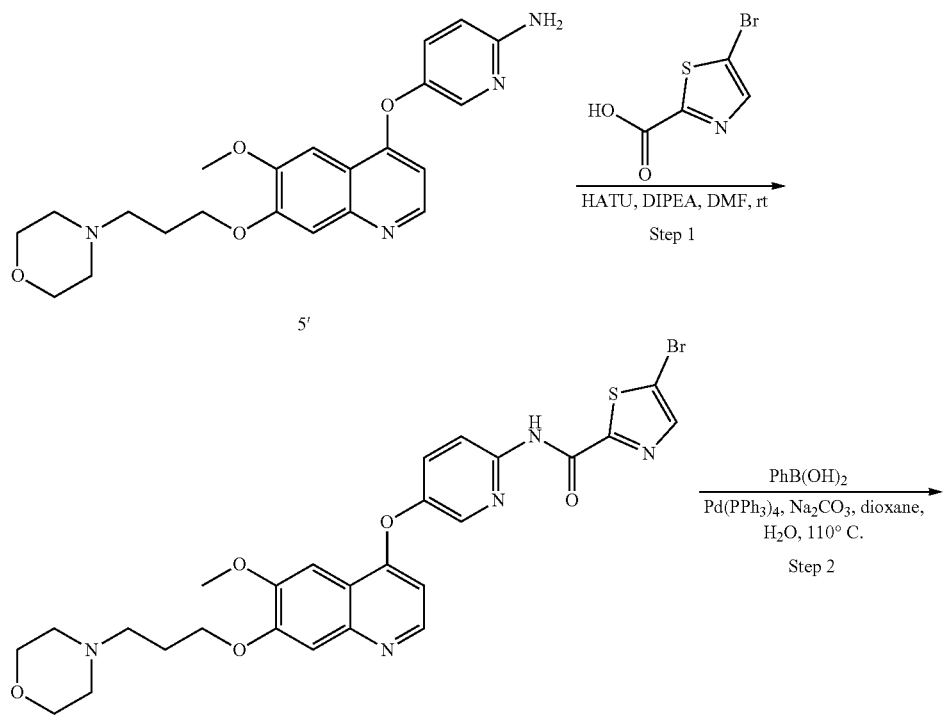

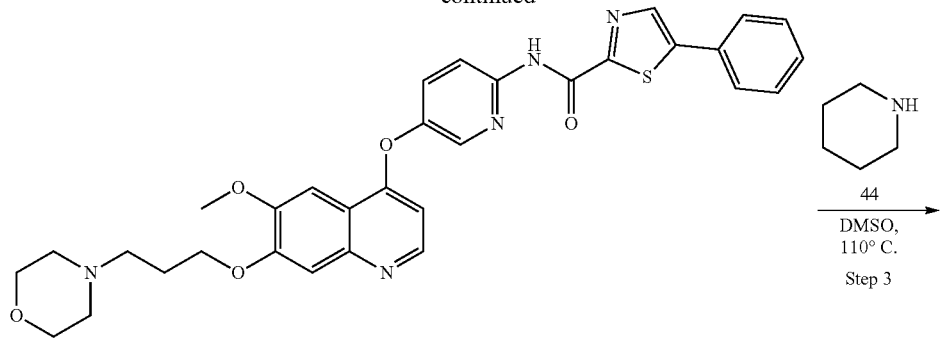

Step 1.

A mixture of 5-(((6-methoxy-7-(3-morpholinopropoxy)quinolin-4-yl)oxy)pyridin-2-amine (0.1 g, 0.24 mmol), 5-bromothiazole-2-carboxylic acid (0.06 g, 0.29 mmol), HATU (0.14 g, 0.36 mmol), and N,N-diisopropylethylamine (0.12 ml, 0.7 mmol) in DMF (2 mL) was stirred at room temperature for 16 h. The reaction mixture was then concentrated under reduced pressure to give a residue, which was purified by chromatography (100% ethyl acetate to dichloromethane/MeOH=10/0.5) to provide 5-bromo-N-(5-((6-methoxy-7-(3-morpholinopropoxy)quinolin-4-yl)oxy)pyridin-2-yl)thiazole-2-carboxamide as a brown solid (0.1 g, 70%).

Step 2.

A mixture of 5-bromo-N-(5-((6-methoxy-7-(3-morpholinopropoxy)quinolin-4-yl)oxy)pyridin-2-yl)thiazole-2-carboxamide (0.06 g, 0.1 mmol), phenylboronic acid (0.05 g, 0.4 mmol), tetrakis(triphenylphosphine)palladium(0) (0.012 g, 0.01 mmol), and $Na_2CO_3$ (0.09 g, 0.8 mmol) in dioxane (1.6 mL) and water (0.2 mL) was stirred at 110° C. for 18 h. The mixture was then concentrated under reduced pressure to give a residue, which was purified by chromatography (100% ethyl acetate to dichloromethane/MeOH=10/0.5) to provide N-(5-((6-methoxy-7-(3-morpholinopropoxy)quinolin-4-yl)oxy)pyridin-2-yl)-5-phenylthiazole-2-carboxamide as a pale white solid (0.03 g, 33%).

Step 3.

A solution of 5-bromo-N-(5-((6-methoxy-7-(3-morpholinopropoxy)quinolin-4-yl)oxy)pyridin-2-yl)thiazole-2-carboxamide (0.06 g, 0.1 mmol) and piperidine (0.2 mL, 2.0 mmol) in DMSO (0.5 mL) was stirred at 110° C. for 18 h. The mixture was then concentrated under reduced pressure to give a residue, which was purified by chromatography (100% ethyl acetate to dichloromethane/MeOH=10/1) to provide N-(5-(((6-methoxy-7-(3-morpholinopropoxy)quinolin-4-yl)oxy)pyridin-2-yl)-5-(piperidin-1-yl)thiazole-2-carboxamide as a pale white solid (0.02 g, 45%).

2-bromo-N-(5-((6-methoxy-7-(3-morpholinopropoxy)quinolin-4-yl)oxy)pyridin-2-yl)thiazole-4-carboxamide (40) $^1$H NMR (DMSO-$d_6$, 300 MHz) 10.1 (s, 1H), 8.59 (s, 1H), 8.48 (d, J=5.4 Hz, 1H), 8.42 (d, J=3.0 Hz, 1H), 8.29 (d, J=9.0 Hz, 1H), 7.87 (dd, J=9.0, 2.7 Hz, 1H), 7.52 (s, 1H), 7.39 (s, 1H), 6.55 (d, J=5.4 Hz, 1H), 4.19 (m, 2H), 3.93 (s, 3H), 3.57 (m, 4H), 2.46 (m, 2H), 2.38 (m, 4H), 1.96 (m, 2H) ppm; MS m/e: 602 (M+H)$^+$.

2-(4-hydroxypiperidin-1-yl)-N-(5-((6-methoxy-7-(3-morpholinopropoxy)quinolin-4-yl)oxy)pyridin-2-yl)thiazole-4-carboxamide (41) $^1$H NMR (DMSO-$d_6$, 300 MHz) 9.82 (s, 1H), 8.47 (d, J=5.4 Hz, 1H), 8.38 (m, 1H), 8.32 (d, J=9.0 Hz, 1H), 7.86 (dd, J=9.0, 2.7 Hz, 1H), 7.69 (s, 1H), 7.52 (s, 1H), 7.39 (s, 1H), 6.53 (d, J=5.4 Hz, 1H), 4.81 (d, J=3.9 Hz, 1H), 4.16 (m, 2H), 3.93 (s, 3H), 3.78 (m, 3H), 3.57 (m, 4H), 3.25 (m, 4H), 2.37 (m, 4H), 1.97 (m, 2H), 1.83 (m, 2H), 1.47 (m, 2H) ppm; MS m %  e: 621.2 (M+H)$^+$.

N-(5-((6-methoxy-7-(3-morpholinopropoxy)quinolin-4-yl)oxy)pyridin-2-yl)-2-phenylthiazole-4-carboxamide (42) MS m/e: 598.2 (M+H)$^+$.

2-(4-fluorophenyl)-N-(5-((6-methoxy-7-(3-morpholinopropoxy)quinolin-4-yl)oxy)pyridin-2-yl)thiazole-4-carboxamide (43) $^1$H NMR (DMSO-$d_6$, 300 MHz) 10.4 (s, 1H), 8.67 (d, J=6.0 Hz, 1H), 8.62 (s, 1H), 8.50 (m, 1H), 8.41 (d, J=8.7 Hz, 1H), 8.21 (m, 2H), 7.96 (dd, J=9.0, 2.7 Hz, 1H), 7.67 (s, 1H), 7.56 (s, 1H), 7.40 (m, 2H), 6.81 (d, J=5.7 Hz, 1H), 4.30 (m, 2H), 3.99 (m, 5H), 3.66 (m, 2H), 3.53 (m, 2H), 3.33 (m, 2H), 3.14 (m, 2H), 2.27 (m, 2H) ppm; MS m/e: 616.2 (M+H)$^+$.

5-bromo-N-(5-((6-methoxy-7-(3-morpholinopropoxy)quinolin-4-yl)oxy)pyridin-2-yl)thiazole-2-carboxamide (44) MS m/e: 602 (M+H)$^+$.

N-(5-(((6-methoxy-7-(3-morpholinopropoxy)quinolin-4-yl)oxy)pyridin-2-yl)-2-(piperidin-1-yl)thiazole-4-carboxamide (46) $^1$H NMR (DMSO-d$_6$, 300 MHz) 9.89 (s, 1H), 8.81 (d, J=6.3 Hz, 1H), 8.49 (m, 1H), 8.38 (d, J=9.0 Hz, 1H), 7.99 (dd, J=9.0, 3.0 Hz, 1H), 7.76 (s, 1H), 7.70 (s, 1H), 7.66 (s, 1H), 6.99 (d, J=6.3 Hz, 1H), 4.32 (m, 2H), 4.02 (m, 6H), 3.67 (m, 2H), 3.50 (m, 6H), 3.34 (m, 3H), 3.13 (m, 3H), 2.29 (m, 2H), 1.62 (s, 6H) ppm; MS m/e: 605.2 (M+H)$^+$.

N-(5-(((6-methoxy-7-(3-morpholinopropoxy)quinolin-4-yl)oxy)pyridin-2-yl)-5-(piperidin-1-yl)thiazole-2-carboxamide (47) $^1$H NMR (DMSO-d$_6$, 300 MHz) 9.92 (s, 1H), 8.70 (d, J=5.7 Hz, 1H), 8.46 (m, 1H), 8.28 (d, J=8.7 Hz, 1H), 7.90 (dd, J=9.0, 2.4 Hz, 1H), 7.69 (s, 1H), 7.55 (s, 1H), 7.25 (m, 1H), 6.84 (d, J=6.3 Hz, 1H), 4.29 (m, 2H), 3.99 (m, 6H), 3.65 (m, 2H), 3.60 (m, 6H), 3.32 (m, 3H), 3.13 (m, 3H), 2.27 (m, 2H), 1.62 (m, 6H) ppm; MS m/e: 605.2 (M+H)

N-(5-(((6-methoxy-7-(3-morpholinopropoxy)quinolin-4-yl)oxy)pyridin-2-yl)-5-phenylthiazole-2-carboxamide (48) $^1$H NMR (DMSO-d$_6$, 300 MHz) 10.4 (s, 1H), 8.54 (s, 1H), 8.49 (d, J=5.1 Hz, 1H), 8.46 (m, 1H), 8.25 (d, J=9.3 Hz, 1H), 7.89 (dd, J=9.0, 3.0 Hz, 1H), 7.82 (m, 2H), 7.49 (m, 4H), 7.40 (s, 1H), 6.56 (d, J=5.1 Hz, 1H), 4.19 (m, 2H), 3.93 (s, 3H), 3.57 (m, 4H), 2.46 (m, 2H), 2.38 (m, 4H), 1.97 (m, 2H) ppm; MS m/e: 598.2 (M+H)$^+$.

Representative synthesis of 4-phenyl-N-(5-(quinolin-4-yloxy)pyridin-2-yl)-7,8-dihydro-6H-5,8-ethanopyrido[3,2-d]pyrimidine-2-carboxamide

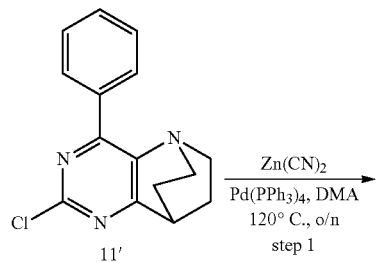

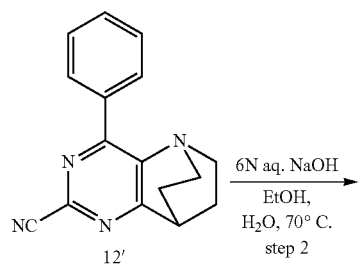

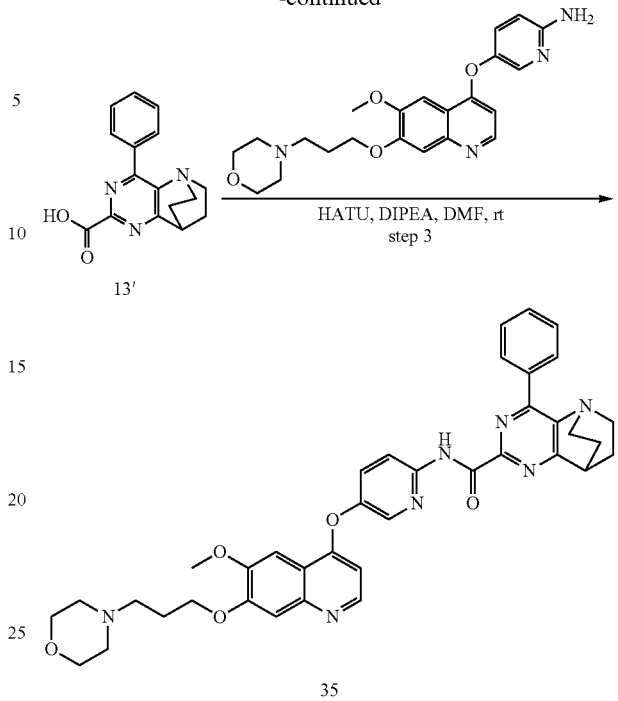

Step 1.

A mixture of 2-chloro-4-phenyl-7,8-dihydro-6H-5,8-ethanopyrido[3,2-d]pyrimidine (0.25 g, 0.92 mmol), zinc cyanide (0.06 g, 0.51 mmol), and tetrakis(triphenylphosphine)palladium(0) (0.32 g, 0.28 mmol) in anhydrous DMA (30 mL) was stirred at 120° C. for 18 h. The reaction mixture was then concentrated under reduced pressure to give a residue, which was purified by chromatography (hexanes/ethyl acetate=4/1) to provide 4-phenyl-7,8-dihydro-6H-5,8-ethanopyrido[3,2-d]pyrimidine-2-carbonitrile as a brown solid (0.21 g, 87%). $^1$H NMR (CDCl$_3$, 300 MHz) 8.42 (m, 2H), 7.50 (m, 3H), 3.36 (m, 3H), 2.74 (m, 2H), 2.14 (m, 2H), 1.75 (m, 2H) ppm; MS m/e: 263.2 (M+H)$^+$.

Step 2.

To a solution of 4-phenyl-7,8-dihydro-6H-5,8-ethanopyrido[3,2-d]pyrimidine-2-carbonitrile (0.21 g, 0.8 mmol) in ethanol (10 mL) was added a 6M aqueous solution of sodium hydroxide (3 mL, 18 mmol). The resulting mixture was stirred at 70° C. for 3 h and then cooled to room temperature. The reaction mixture was concentrated under reduced pressure, and the residue was diluted with water (5 mL). The resulting solution was acidified to pH 2 with 2N aqueous HCl and extracted ethyl acetate (3×10 mL). The combined organic phases were dried over sodium sulfate and filtered. The filtrate was concentrated under reduced pressure to provide 4-phenyl-7,8-dihydro-6H-5,8-ethanopyrido[3,2-d]pyrimidine-2-carboxylic acid as a white solid (0.15 g, 67/). $^1$H NMR (CDC$_3$, 300 MHz) 8.36 (m, 2H), 7.55 (m, 3H), 3.55 (m, 1H), 3.33 (m, 2H), 2.74 (m, 2H), 2.14 (m, 2H), 1.78 (m, 2H) ppm; MS m/e: 282.2 (M+H)-.

Step 3.

A mixture of 5-((6-methoxy-7-(3-morpholinopropoxy)quinolin-4-yl)oxy)pyridin-2-amine (0.04 g, 0.1 mmol), 4-phenyl-7,8-dihydro-6H-5,8-ethanopyrido[3,2-d]pyrimidine-2-carboxylic acid (0.04 g, 0.14 mmol), HATU (0.05 g, 0.13 mmol), and N,N-diisopropylethylamine (0.05 ml, 0.3 mmol) in DMF (1 mL) was stirred at room temperature for 16 h. The reaction mixture was then concentrated under reduced pressure to give a residue, which was purified by chromatography (100% ethyl acetate to dichloromethane/ MeOH=10/1) to provide N-(5-((6-methoxy-7-(3-morpholinopropoxy)quinolin-4-yl)oxy)pyridin-2-yl)-4-phenyl-7,8-dihydro-6H-5,8-ethanopyrido[3,2-d]pyrimidine-2-carboxamide as a brown solid (0.04 g, 60%).

N-(5-((6-methoxy-7-(3-morpholinopropoxy)quinolin-4-yl)oxy)pyridin-2-yl)-4-phenyl-7,8-dihydro-6H-5,8-ethanopyrido[3,2-d]pyrimidine-2-carboxamide (35) $^1$H NMR (DMSO-$d_6$, 300 MHz) 10.8 (s, 1H), 8.49 (d, J=5.1 Hz, 1H), 8.44 (m, 1H), 8.40 (m, 3H), 7.91 (dd, J=9.3, 2.7 Hz, 1H), 7.57 (m, 4H), 7.40 (s, 1H), 6.56 (d, J=5.1 Hz, 1H), 4.19 (m, 2H), 3.93 (s, 3H), 3.58 (m, 4H), 3.37 (m, 1H), 3.26 (m, 4H), 2.67 (m, 2H), 2.39 (m, 4H), 2.09 (m, 2H), 1.97 (m, 2H), 1.68 (m, 2H) ppm; MS m/e: 674.3 (M+H)$^+$.

Representative synthesis of 4-phenyl-N-(5-(quinolin-4-yloxy)pyridin-2-yl)-7,8-dihydro-6H-5,8-ethanopyrido[3,2-d]pyrimidine-2-carboxamide

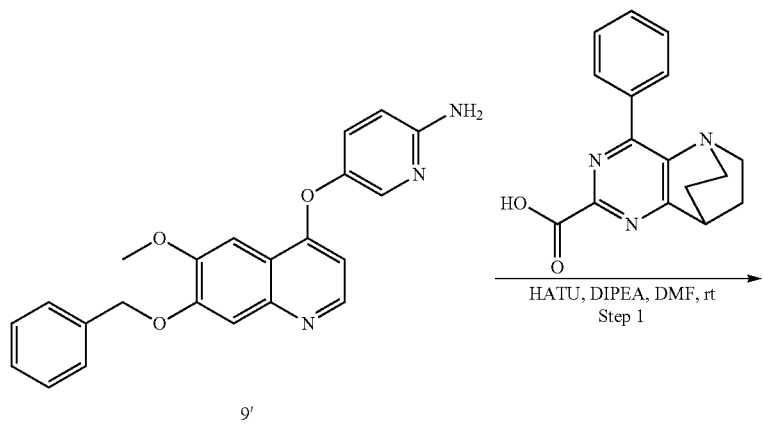

9'

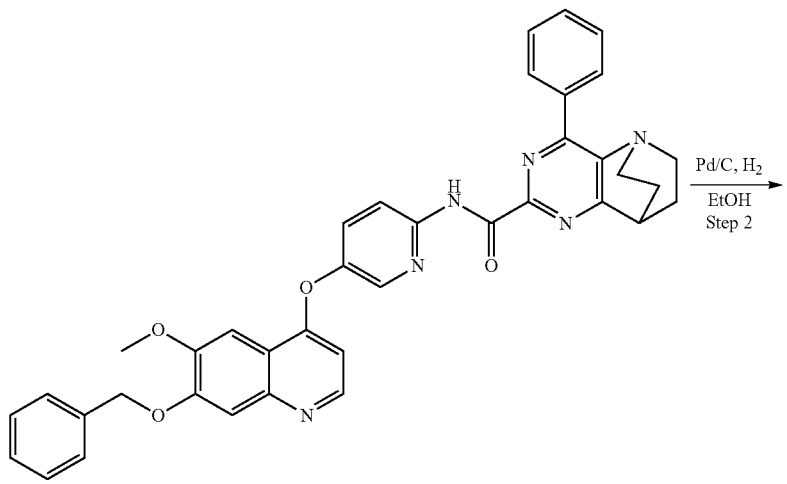

37

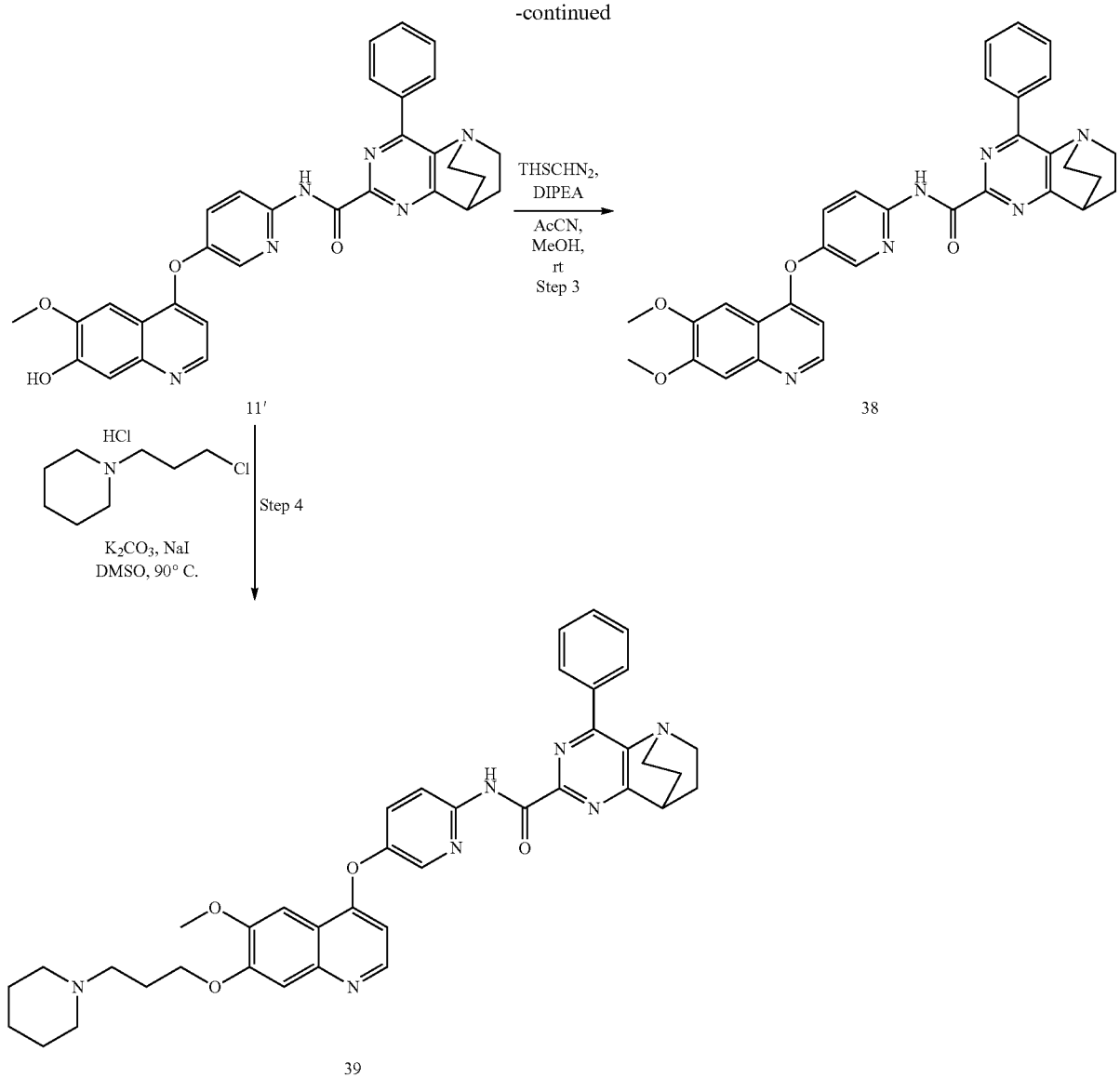

Step 1.

A mixture of 5-((7-(benzyloxy)-6-methoxyquinolin-4-yl)oxy)pyridin-2-amine (0.13 g, 0.35 mmol), 4-phenyl-7,8-dihydro-6H-5,8-ethanopyrido[3,2-d]pyrimidine-2-carboxylic acid (0.13 g, 0.46 mmol), HATU (0.20 g, 0.53 mmol), and N,N-diisopropylethylamine (0.19 ml, 1.1 mmol) in DMF (2 mL) was stirred at room temperature for 16 h. The reaction mixture was then concentrated under reduced pressure to give a residue, which was purified by chromatography (100% ethyl acetate to dichloromethane/MeOH=10/0.5) to provide N-(5-((7-(benzyloxy)-6-methoxyquinolin-4-yl)oxy)pyridin-2-yl)-4-phenyl-7,8-dihydro-6H-5,8-ethanopyrido[3,2-d]pyrimidine-2-carboxamide as a pale white solid (0.13 g, 60%).

Step 2.

A mixture of N-(5-((7-(benzyloxy)-6-methoxyquinolin-4-yl)oxy)pyridin-2-yl)-4-phenyl-7,8-dihydro-6H-5,8-ethanopyrido[3,2-d]pyrimidine-2-carboxamide (0.13 g, 0.20 mmol) and 10% palladium on carbon (0.02 g, ~50% water) in ethanol (10 mL) was shaken under hydrogen (1 atm) at room temperature for 2 h. After this time the reaction mixture was filtered through diatomaceous earth and the filtrate was concentrated under reduced pressure to give a residue, which was purified by chromatography (dichloromethane/MeOH=10/2) to provide N-(5-((7-hydroxy-6-methoxyquinolin-4-yl)oxy)pyridin-2-yl)-4-phenyl-7,8-dihydro-6H-5,8-ethanopyrido[3,2-d]pyrimidine-2-carboxamide as a off-white solid (0.08 g, 68%).

Step 3.

To a mixture of N-(5-((7-hydroxy-6-methoxyquinolin-4-yl)oxy)pyridin-2-yl)-4-phenyl-7,8-dihydro-6H-5,8-ethanopyrido[3,2-d]pyrimidine-2-carboxamide (0.01 g, 0.02 mmol) and N,N-diisopropylethylamine (0.01 ml) in acetonitrile (0.18 ml) and methanol (0.02 ml) was added a 2M solution of trimethylsilyldiazomethane in hexane (0.02 mL, 0.04 mmol). The resulting mixture was stirred at room temperature for 16 h. The reaction mixture was then concentrated under reduced pressure to give a residue, which was purified by chromatography (dichloromethane/MeOH=10/1) to provide N-(5-((6,7-dimethoxyquinolin-4- yl)oxy)pyridin-2-yl)-4-phenyl-7,8-dihydro-6H-5,8-ethanopyrido[3,2-d]pyrimidine-2-carboxamide as a off-white solid (0.008 g, 80%).

Step 4.

A mixture of N-(5-((7-hydroxy-6-methoxyquinolin-4-yl)oxy)pyridin-2-yl)-4-phenyl-7,8-dihydro-6H-5,8-ethanopyrido[3,2-d]pyrimidine-2-carboxamide (0.015 g, 0.027 mmol), 1-(3-chloropropyl)piperidine hydrochloride (0.007 g, 0.032 mmol), $K_2CO_3$ (0.011 g, 0.08 mmol), and NaI (0.001 g) in DMSO (0.5 ml) was stirred at 90° C. for 18 h. The reaction mixture was then concentrated under reduced pressure to give a residue, which was purified by chromatography (dichloromethane/MeOH=10/1.5) to provide N-(5-((6-methoxy-7-(3-(piperidin-1-yl)propoxy)quinolin-4-yl)oxy)pyridin-2-yl)-4-phenyl-7,8-dihydro-6H-5,8-ethanopyrido[3,2-d]pyrimidine-2-carboxamide as a off-white solid (0.01 g, 55%).

N-(5-((7-(benzyloxy)-6-methoxyquinolin-4-yl)oxy)pyridin-2-yl)-4-phenyl-7,8-dihydro-6H-5,8-ethanopyrido[3,2-d]pyrimidine-2-carboxamide (37) $^1$H NMR (DMSO-d$_6$, 300 MHz) 10.8 (s, 1H), 8.48 (d, J=5.1 Hz, 1H), 8.45 (m, 1H), 8.39 (m, 3H), 7.92 (dd, J=9.0, 2.7 Hz, 1H), 7.52 (m, 6H), 7.38 (m, 3H), 6.57 (d, J=5.4 Hz, 1H), 5.30 (s, 2H), 3.95 (s, 3H), 3.38 (m, 1H), 3.25 (m, 2H), 2.65 (m, 2H), 2.09 (m, 2H), 1.68 (m, 2H) ppm; MS m/e: 637.6 (M+H)$^+$.

N-(5-((6,7-dimethoxyquinolin-4-yl)oxy)pyridin-2-yl)-4-phenyl-7,8-dihydro-6H-5,8-ethanopyrido[3,2-d]pyrimidine-2-carboxamide (38) $^1$H NMR (DMSO-d$_6$, 300 MHz) 10.9 (s, 1H), 8.73 (d, J=5.7 Hz, 1H), 8.54 (m, 1H), 8.48 (d, J=9.0 Hz, 1H), 8.38 (m, 2H), 8.02 (dd, J=9.0, 3.0 Hz, 1H), 7.70 (s, 1H), 7.57 (m, 3H), 6.90 (d, J=6.0 Hz, 1H), 4.00 (m, 6H), 3.38 (m, 1H), 3.25 (m, 2H), 2.68 (m, 2H), 2.10 (m, 2H), 1.68 (m, 2H) ppm; MS m/e: 561.7 (M+H)$^+$.

N-(5-((6-methoxy-7-(3-(piperidin-1-yl)propoxy)quinolin-4-yl)oxy)pyridin-2-yl)-4-phenyl-7,8-dihydro-6H-5,8-ethanopyrido[3,2-d]pyrimidine-2-carboxamide (39) $^1$H NMR (DMSO-d$_6$, 300 MHz) 10.9 (s, 1H), 8.76 (d, J=6.3 Hz, 1H), 8.54 (m, 1H), 8.48 (d, J=9.0 Hz, 18H), 8.38 (m, 2H), 8.02 (dd, J=9.0, 3.0 Hz, 18H), 7.73 (s, 18H), 7.58 (m, 4H), 6.94 (d, J=6.0 Hz, 1H), 4.31 (m, 2H), 4.01 (s, 3H), 3.52 (m, 2H), 3.37 (m, 1H), 3.26 (m, 4H), 2.91 (m, 2H), 2.65 (m, 2H), 2.27 (m, 2H), 2.11 (m, 2H), 1.84 (m, 2H), 1.66 (m, 6H) ppm; MS m/e: 672.3 (M+H)$^+$.

Synthesis of N-(3-fluoro-4-((6-methoxy-7-(3-morpholinopropoxy)quinolin-4-yl)oxy)phenyl)-4-phenyl-7,8-dihydro-6H-5,8-ethanopyrido[3,2-d]pyrimidine-2-carboxamide

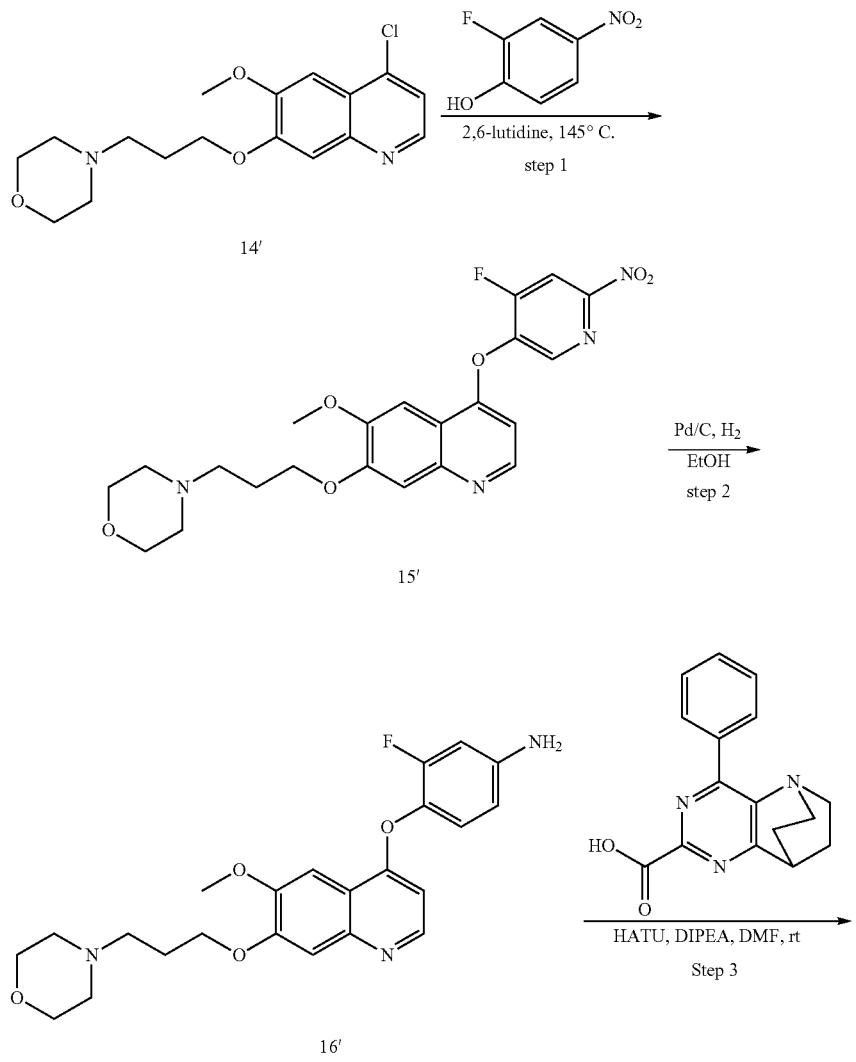

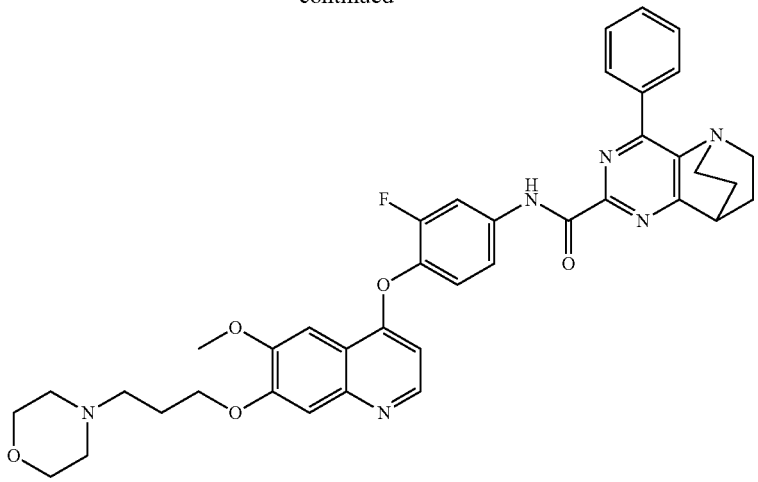

36

Step 1.

A mixture of 4-(3-((4-chloro-6-methoxyquinolin-7-yl)oxy)propyl)morpholine (0.9 g, 2.68 mmol) and 2-fluoro-4-nitrophenol (0.53 g, 3.35 mol) in 2,6-lutidine (10 mL) was stirred at 145° C. for 2 h. The reaction mixture was then cooled to room temperature and concentrated under reduced pressure. The residue was partitioned between water and ethyl acetate. The organic layer was separated and dried over sodium sulfate. The drying agent was filtered off, and the filtrate concentrated under reduced pressure to give a residue, which was purified by chromatography (100% ethyl acetate) to provide 4-(3-((4-(2-fluoro-4-nitrophenoxy)-6-methoxyquinolin-7-yl)oxy)propyl)morpholine as a off-white solid (0.82 g, 67%). $^1$H NMR (DMSO-d$_6$, 300 MHz) 8.55 (d, J=5.1 Hz, 1H), 8.44 (dd, J=10.4, 2.7 Hz, 1H), 8.18 (m, 1H), 7.60 (m, 1H), 7.43 (s, 2H), 7.52 (s, 1H), 6.76 (d, J=5.4 Hz, 1H), 4.20 (m, 2H), 3.91 (s, 3H), 3.57 (m, 4H), 2.46 (m, 2H), 2.38 (m, 4H), 1.96 (m, 2H) ppm; MS m/e: 458.2 (M+H)$^+$.

Step 2.

A mixture of 4-(3-((4-(2-fluoro-4-nitrophenoxy)-6-methoxyquinolin-7-yl)oxy)propyl)morpholine (0.4 g, 0.87 mmol) and 10% palladium on carbon (0.04 g, ~50% water) in ethanol (20 mL) was shaken under hydrogen (40 psi) at room temperature for 1 h. After this time the reaction mixture was filtered through diatomaceous earth and the filtrate was concentrated under reduced pressure to give a residue, which was purified by chromatography (dichloromethane/MeOH=10/1) to provide 3-fluoro-4-((6-methoxy-7-(3-morpholinopropoxy)quinolin-4-yl)oxy)aniline as a off-white solid (0.18 g, 47%).

$^1$H NMR (DMSO-d$_6$, 300 MHz) 8.43 (d, J=5.4 Hz, 1H), 7.48 (s, 1H), 7.35 (s, 1H), 7.05 (m, 1H), 6.52 (m, 1H), 6.44 (m, 1H), 6.36 (m, 1H), 5.46 (s, 2H), 4.17 (m, 2H), 3.92 (s, 3H), 3.57 (m, 4H), 2.47 (m, 2H), 2.37 (m, 4H), 1.96 (m, 2H) ppm; MS m/e: 428.2 (M+H)$^+$.

Step 3.

A mixture of 3-fluoro-4-((6-methoxy-7-(3-morpholinopropoxy)quinolin-4-yl)oxy)aniline (0.04 g, 0.10 mmol), 4-phenyl-7,8-dihydro-6H-5,8-ethanopyrido[3,2-d]pyrimidine-2-carboxylic acid (0.04 g, 0.13 mmol), HATU (0.06 g, 0.15 mmol), and N,N-diisopropylethylamine (0.05 ml, 0.3 mmol) in DMF (1 mL) was stirred at room temperature for 16 h. The reaction mixture was then concentrated under reduced pressure to give a residue, which was purified by chromatography (100% ethyl acetate to dichloromethane/MeOH=10/0.5) to provide N-(3-fluoro-4-((6-methoxy-7-(3-morpholinopropoxy)quinolin-4-yl)oxy)phenyl)-4-phenyl-7,8-dihydro-6H-5,8-ethanopyrido[3,2-d]pyrimidine-2-carboxamide as a white solid (0.05 g, 76%).

N-(3-fluoro-4-((6-methoxy-7-(3-morpholinopropoxy)quinolin-4-yl)oxy)phenyl)-4-phenyl-7,8-dihydro-6H-5,8-ethanopyrido[3,2-d]pyrimidine-2-carboxamide (36) $^1$H NMR (DMSO-d$_6$, 300 MHz) 10.9 (s, 1H), 8.48 (m, 1H), 8.42 (m, 2H), 8.19 (m, 1H), 8.11 (m, 1H), 7.84 (m, 1H), 7.54 (m, 4H), 7.40 (s, 1H), 6.48 (d, J=5.1 Hz, 1H), 4.19 (m, 2H), 3.95 (s, 3H), 3.58 (m, 4H), 3.37 (m, 1H), 3.25 (m, 2H), 2.66 (m, 2H), 2.38 (m, 4H), 2.11 (m, 2H), 1.97 (m, 2H), 1.68 (m, 2H) ppm; MS m/e: 691.3 (M+H)$^+$.

Synthesis of N-(5-(((6,7-dimethoxyquinazolin-4-yl)oxy)pyridin-2-yl)-4-phenyl-7,8-dihydro-6H-5,8-ethanopyrido[3,2-d]pyrimidine-2-carboxamide (49)

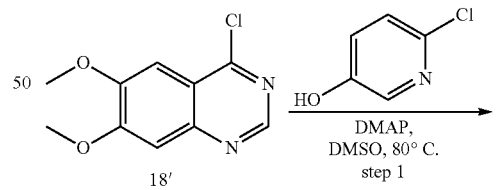

18'

DMAP,
DMSO, 80° C.
step 1

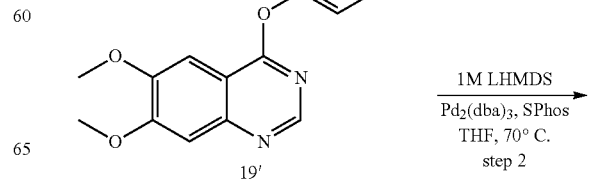

19'

1M LHMDS
Pd$_2$(dba)$_3$, SPhos
THF, 70° C.
step 2

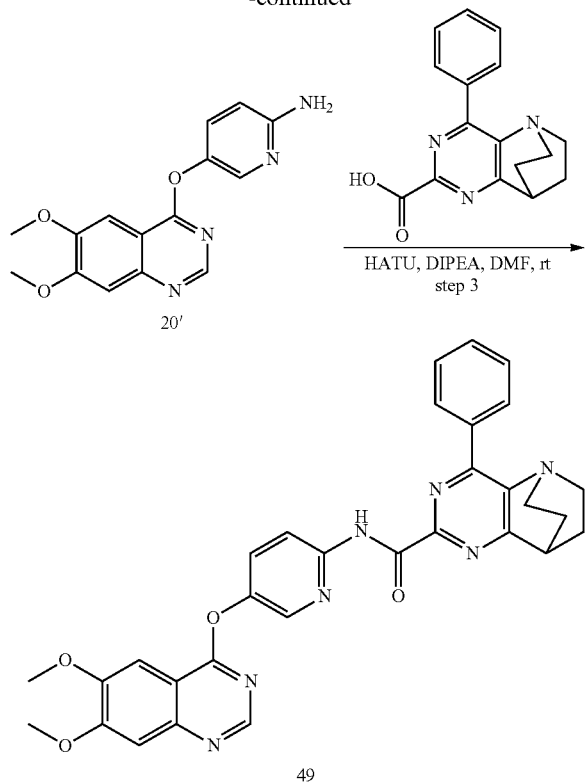

Step 1.

A mixture of 4-chloro-6,7-dimethoxyquinazoline (0.63 g, 2.80 mmol), 6-chloropyridin-3-ol (0.37 g, 2.84 mol), and DMAP (0.35 g, 2.84 mmol) in DMSO (3 mL) was stirred at 80° C. for 3 h. The reaction mixture was then cooled to room temperature and partitioned between water and ethyl acetate. The organic layer was separated and dried over sodium sulfate. The drying agent was filtered off, and the filtrate concentrated under reduced pressure to give a residue, which was purified by chromatography (ethyl acetate/hexanes=6/4) to provide 4-((6-chloropyridin-3-yl)oxy)-6,7-dimethoxyquinazoline as a white solid (0.8 g, 90%). $^1$H NMR (DMSO-$d_6$, 300 MHz) 8.57 (s, 1H), 8.50 (d, J=3.0 Hz, 1H), 7.95 (dd, J=8.7, 3.0 Hz, 1H), 7.67 (d, J=8.7 Hz, 1H), 7.57 (s, 1H), 7.40 (s, 1H), 3.98 (s, 3H), 3.97 (s, 3H) ppm; MS m/e: 318.1 (M+H)$^+$.

Step 2.

To a mixture of 4-((6-chloropyridin-3-yl)oxy)-6,7-dimethoxyquinazoline (0.4 g, 1.26 mmol), tris(dibenzylideneacetone) dipalladium (0) chloroform complex (0.06 g, 0.06 mmol), 2-dicyclohexylphosphino-2',6'-dimethoxybiphenyl (0.07 g, 0.17 mmol) in THF (6 mL) was added a 1M solution of LHMDS in THF (2 mL, 2 mmol). The resulting mixture was stirred at 70° C. for 16 h. The reaction mixture was then cooled to room temperature, poured into ice water, and extracted with ethyl acetate. The organic layer was washed with water, dried over anhydrous sodium sulfate, and concentrated under reduced pressure. The resulting residue was stirred in acetonitrile (12 mL) and 2N hydrochloric acid (4 mL). The mixture was stirred at room temperature for 30 minutes. The precipitate formed was filtered and dried in vacuo to provide 5-((6,7-dimethoxyquinazolin-4-yl)oxy)pyridin-2-amine as a off-white solid (0.25 g, 66%). $^1$H NMR (DMSO-$d_6$, 300 MHz) 8.61 (s, 1H), 8.20 (d, J=3.0 Hz, 1H), 8.12 (bs, 2H), 8.07 (dd, J=9.9, 3.0 Hz, 1H), 7.53 (s, 1H), 7.41 (s, 1H), 7.08 (d, J=9.9 Hz, 1H), 3.98 (s, 3H), 3.96 (s, 3H) ppm; MS m/e: 299.2 (M+H)$^+$.

Step 3.

A mixture of 5-((6,7-dimethoxyquinazolin-4-yl)oxy)pyridin-2-amine (0.02 g, 0.067 mmol), 4-phenyl-7,8-dihydro-6H-5,8-ethanopyrido[3,2-d]pyrimidine-2-carboxylic acid (0.024 g, 0.087 mmol), HATU (0.04 g, 0.10 mmol), and N,N-diisopropylethylamine (0.035 ml, 0.2 mmol) in DMF (0.5 mL) was stirred at room temperature for 16 h. The reaction mixture was then concentrated under reduced pressure to give a residue, which was purified by chromatography (100% ethyl acetate to dichloromethane/MeOH=10/0.5) to provide N-(5-((6,7-dimethoxyquinazolin-4-yl)oxy)pyridin-2-yl)-4-phenyl-7,8-dihydro-6H-5,8-ethanopyrido[3,2-d]pyrimidine-2-carboxamide as a pale white solid (0.027 g, 71%). $^1$H NMR (DMSO-$d_6$, 300 MHz) 10.8 (s, 1H), 8.58 (s, 1H), 8.46 (m, 1H), 8.39 (m, 3H), 7.97 (m, 1H), 7.58 (m, 4H), 7.41 (s, 1H), 3.99 (s, 3H), 3.98 (s, 3H), 3.38 (m, 1H), 3.25 (m, 2H), 2.68 (m, 2H), 2.10 (m, 2H), 1.68 (m, 2H) ppm; MS m/e: 562.5 (M+H)$^+$.

Example 13: PAKT HTRF-HUVEC Assay

Materials

Dimethyl Sulfoxide (DMSO) (Sigma-Aldrich, D2650)

Corning™ Costar™ 96-Well White Clear-Bottom Plates (Fisher Scientific, 07-200-587)

ProxiPlate-384 Plus, White 384-shallow well Microplate (Perkin Elmer, 6008280)

Phospho Akt (Ser473) Assay kit-10,000 tests (Cisbio US, 64AKSPEH)

HUVEC cells (Lonza, CC-2519)

EGM-2 BulletKit (Lonza, CC-3162)

EBM-2 Basal Medium (Lonza, CC-3156)

Biotin-SP-conjugated Anti-mouse IgG (Jackson Immunoresearch Labs, 115-065-003)

Anti-human MerTK antibody (Clone 125518) (R&D Systems, MAB8912)

Equipment

SpectraMax Paradigm Multi-Mode Microplate Reader (Molecular Devices)

Method

Seed HUVECs (10K cells/well) in EBM-2 complete media (EBM-2 basal medium plus EGM-2 BulletKit supplements) overnight at 37° C., 5% $CO_2$ in Costar 96-well white clear-bottom plates. Remove culture media and starve cells for 3-4 hours in 50 μL/well EBM-2 basal medium. Perform serial dilution of compounds in DMSO from 2.5 mM in 4-fold dilutions, and then dilute 1:125 in EBM-2 basal media. Mix 50 μL/well 2× compounds with 50 μL/well HUVECs in duplicate in Costar 96-well white clear-bottom plates. Incubate plates for 1 hour at 37° C., 5% $CO_2$. Cross-link anti-human MerTK antibody to Biotin-SP-conjugated anti-mouse IgG antibody (1:1) to give final concentrations of 5 μg/mL of anti-human MerTK-XL. Stimulate HUVECs with 25 μL/well 5× anti-human MerTK-XL to give final concentrations of 1 ug/mL for 10 minutes at 37° C., 5% $CO_2$. Completely remove media and lyse HUVECs with 40 uL:WELL per well of Cisbio HTRF 1× lysis buffer. Performed pAkt(Ser473) HTRF assay in ProxiPlate-384 Plus, white 384-shallow well microplate according to the vendor protocol and read plates with a SpectralMax Paradigm plate reader. Enter the HTRF values into Athena (Rigel) for curve fitting, $EC_{50}$ calculation, and database storage.

Representative results for inhibition of MerTK (μM)) is shown in Table 1:

| No. | Phospho-AKT HTRF, HUVEC, Axl ABX-L, 8 pt | Phospho-AKT HTRF, HUVEC, Mer-XL, 8 pt |
|---|---|---|
| 1 | 0.4029 | 0.4206 |
| 2 | 0.0408 | 0.047 |
| 3 | 0.1619 | 0.0987 |
| 4 | 0.005 | 0.0039 |
| 5 | 0.0014 | 0.0022 |
| 6 | 0.0033 | 0.0025 |
| 7 | 0.0182 | 0.01 |
| 8 | 0.228 | 0.0909 |
| 9 | 0.0717 | 0.0427 |
| 10 | 0.0129 | 0.0049 |
| 11 | 0.197 | 0.086 |
| 12 | 0.0994 | 0.0721 |
| 13 | 0.0538 | 0.0202 |
| 14 | 0.8049 | 0.4295 |
| 15 | 0.2573 | 0.2041 |
| 16 | 0.0432 | 0.0279 |
| 17 | 1.369 | 1.637 |
| 18 | 0.1141 | 0.098 |
| 19 | 0.5679 | 0.505 |
| 20 | 0.1628 | 0.2086 |
| 21 | 0.0628 | 0.0806 |
| 22 | 0.1867 | 0.096 |
| 23 | 0.0668 | 0.013 |
| 24 | 0.7418 | 0.6538 |
| 25 | 0.1123 | 0.0143 |
| 26 | 0.032 | 0.007 |
| 27 | 0.0849 | 0.1022 |
| 28 | 0.0387 | 0.0061 |
| 29 | 0.6514 | 0.6897 |
| 30 | 0.1101 | 0.0094 |
| 31 | 0.7389 | 0.3108 |
| 32 | 0.4617 | 0.1625 |
| 33 | 0.1878 | 0.1608 |
| 34 | 0.3268 | 0.1835 |
| 35 | 0.003 | 0.005 |
| 36 | 0.0058 | 0.0095 |
| 37 | 0.0384 | 0.0636 |
| 38 | 0.0131 | 0.0077 |
| 39 | 0.0067 | 0.0046 |
| 40 | 0.1473 | 0.0272 |
| 41 | 2.125 | 0.6403 |
| 42 | 0.05 | 0.0472 |
| 43 | 0.0552 | 0.0449 |
| 44 | 0.1015 | 0.0799 |
| 45 | 0.6491 | 0.4594 |
| 46 | 0.0209 | 0.0128 |
| 47 | 0.1301 | 0.1193 |
| 48 | 0.3439 | 0.2384 |
| 49 | 0.0268 | 0.0154 |

What is claimed is:

1. A compound having the structure formula (I):

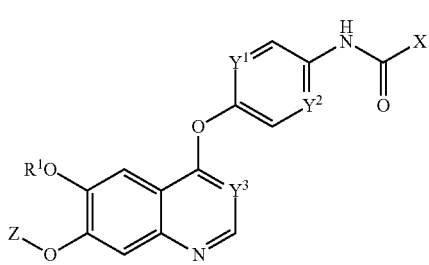

or a pharmaceutically acceptable salt, prodrug, or N-oxide thereof, or a solvate or hydrate thereof, wherein X is selected from

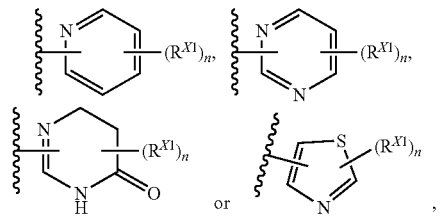

wherein n is 0, 1, 2, 3 or 4;

each —$R^{X1}$ is independently halogen, cyano, $C_1$-$C_6$alkyl, $C_1$-$C_6$haloalkyl, —$C_1$-$C_6$alkoxy, —$C_1$-$C_6$haloalkoxy, oxo, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), Cak($C_0$-$C_6$alkyl), Ar($C_0$-$C_6$alkyl) or Hca($C_0$-$C_6$alkyl), wherein Cak, Ar and Hca are optionally substituted with one or two —$R^{X2}$ groups, wherein each —$R^{X2}$ is independently halogen, cyano, nitro, oxo, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$alkyl, $C_1$-$C_6$haloalkyl or Ar;

$Y^1$ is CH or CF;

$Y^2$ is N;

$Y^3$ is CH;

Z is $C_1$-$C_6$alkyl, Ar($C_0$-$C_6$alkyl) or Hca($C_0$-$C_6$alkyl), each optionally substituted by 1, 2 or 3 —$R^{Z1}$ groups;

wherein each —$R^{Z1}$ is independently halogen, cyano, $C_1$-$C_6$alkyl, Cak, $C_1$-$C_6$haloalkyl, —$C_1$-$C_6$alkoxy, oxo, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR);

each R is independently hydrogen or $C_1$-$C_6$alkyl; and $R^1$ is hydrogen or $C_1$-$C_6$alkyl;

wherein

Hca is a 3-15 membered ring or ring system comprising at least one ring and 1, 2, 3, or 4 O, S, or N atoms, provided no O or S is adjacent to another O or S;

Het is a 5-15 membered aromatic ring or ring system comprising at least one ring and 1, 2, 3, or 4 O, S, or N atoms, provided no O or S is adjacent to another O or S;

Cak is a 3-8 membered non-aromatic carbocyclic ring or ring system, which may be saturated or partially unsaturated; and Ar is a 6-16 membered aromatic ring or ring system having at least one carbocyclic aromatic ring optionally fused one or more aromatic or non-aromatic rings.

2. The compound according to claim 1, wherein n is 1, 2, 3 or 4
wherein
each —R$^{X1}$ is independently halogen, C$_1$-C$_6$alkyl, C$_1$-C$_6$haloalkyl, oxo, —OR, Ar(C$_0$-C$_6$alkyl) or Hca(C$_0$-C$_6$alkyl), wherein Ar and Hca are optionally substituted with one or two —R$^{X2}$ groups, or when —R$^{X1}$ is Hca(C$_0$-C$_6$alkyl), two —R$^{X2}$ groups taken together, when attached to the same carbon atom, form an Hca, or two —R$^{X1}$ groups taken together, when attached to adjacent atoms, form a Ar or Hca, wherein the Hca comprises a 3-8 membered ring optionally substituted with one or two —R$^{X2}$ groups,
wherein each —R$^{X2}$ is independently halogen, —OR, C$_1$-C$_6$alkyl, C$_1$-C$_6$haloalkyl or Ar; and
Z is unsubstituted C$_1$-C$_6$alkyl, Ar(C$_0$-C$_6$alkyl) or Hca(C$_0$-C$_6$alkyl).

3. The compound according to claim 1, wherein X is

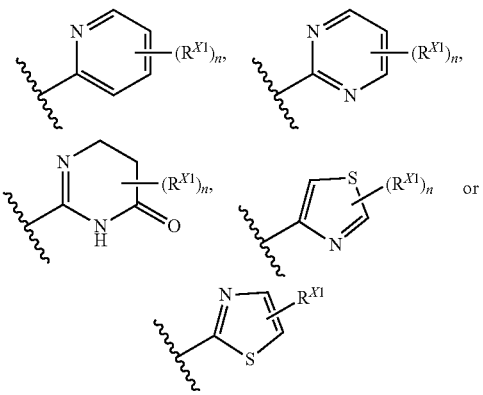

wherein n is 0, 1, 2, 3 or 4.

4. The compound according to claim 1, wherein X is

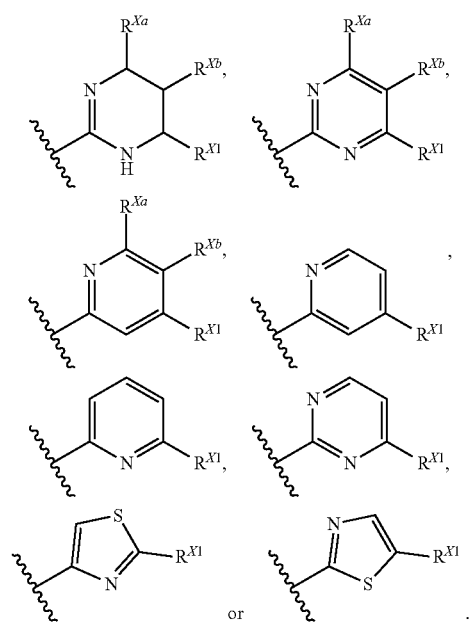

5. The compound according to claim 1, wherein X is

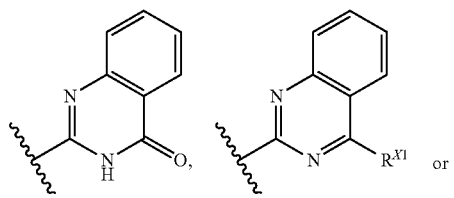

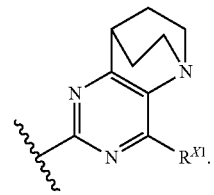

6. The compound according to claim 1, wherein X is

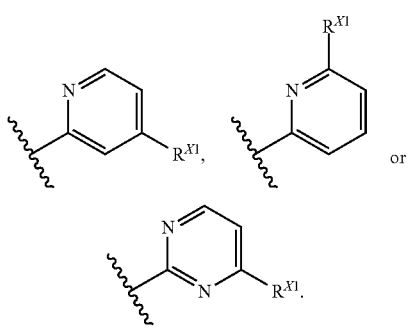

7. The compound according to claim 1, having the structure of formula (IIa):

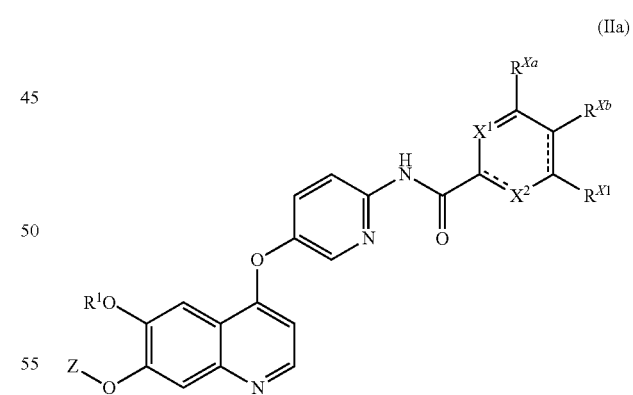

(IIa)

or a pharmaceutically acceptable salt, prodrug or N-oxide thereof, or solvate or hydrate thereof,
X$^1$ is =N—, =C(H)—;
X$^2$ is =C(H)—, =N—, —N(H)—; and
R$^{Xa}$ and R$^{Xb}$ are each hydrogen, or R$^{Xa}$ and R$^{Xb}$ combine with the atoms to which they are attached to form an Ar or Hca.

8. The compound according to claim 1, having the structure of formula (IIc):

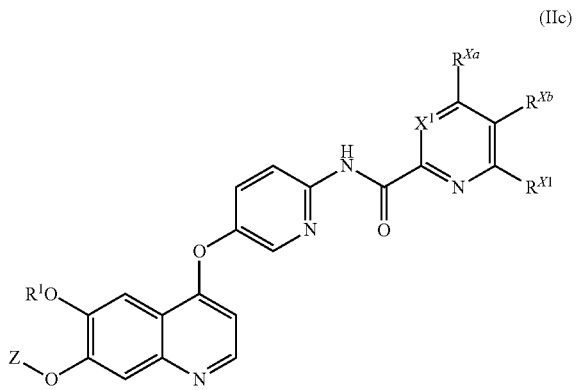

(IIc)

or a pharmaceutically acceptable salt, prodrug or N-oxide thereof, or solvate or hydrate thereof, $X^1$ is —N═, —C(H)═; and $R^{Xa}$ and $R^{Xb}$ are each hydrogen, or $R^{Xa}$ and $R^{Xb}$ combine with the atoms to which they are attached to form an Ar or Hca.

9. The compound according to claim 1, having the structure of formula (IIIa):

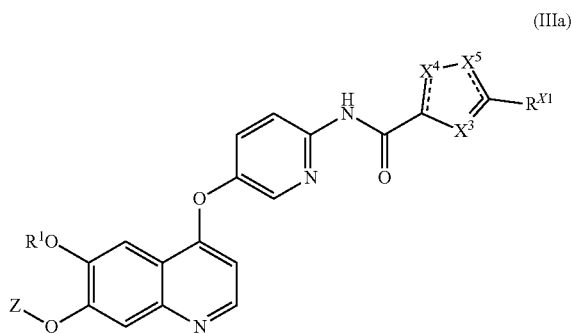

(IIIa)

or a pharmaceutically acceptable salt, prodrug or N-oxide thereof, or solvate or hydrate thereof, $X^3$ is —N═ or —S—;

$X^4$ is ═N—, ═C(H)—; and $X^5$ is —S—, ═C(H)-.

10. The compound according to claim 9, having the structure of formula (IIIe):

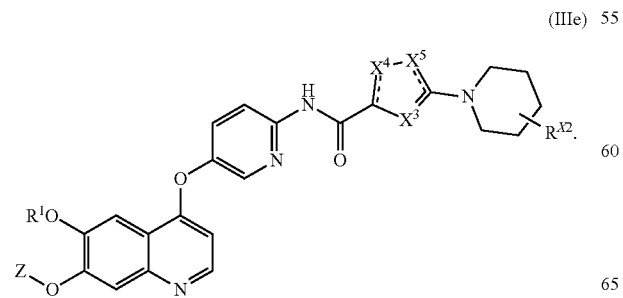

(IIIe)

11. The compound according to claim 1, wherein each —$R^{X1}$ is independently halogen, $C_1$-$C_6$alkyl, $C_1$-$C_6$haloalkyl, oxo, —OR, Ar($C_0$-$C_6$alkyl) or Hca ($C_0$-$C_6$alkyl), wherein Ar and Hca are optionally substituted with one or two —$R^{X2}$ groups.

12. The compound according to claim 1, wherein —$R^{X1}$ is Hca($C_0$-$C_6$alkyl).

13. The compound according to claim 1, wherein each —$R^{X2}$ is independently halogen, —OR, $C_1$-$C_6$alkyl or $C_1$-$C_6$haloalkyl.

14. The compound according to claim 1, wherein each —$R^{X2}$ is independently halogen or —OR.

15. The compound according to claim 1, wherein $R^1$ is $C_1$-$C_6$alkyl.

16. A compound that is:
N-(5-((6-Methoxy-7-(3-morpholinopropoxy)quinolin-4-yl)oxy)pyridin-2-yl)-4-(4-methylpiperazin-1-yl)picolinamide;
N-(5-((6-Methoxy-7-(3-morpholinopropoxy)quinolin-4-yl)oxy)pyridin-2-yl)-8-phenyl-3,4-dihydro-2H-1,4-ethano-1,5-naphthyridine-6-carboxamide;
N-(5-((6-Methoxy-7-(3-morpholinopropoxy)quinolin-4-yl)oxy)pyridin-2-yl)-4-phenylpicolinamide;
N-(5-((6-Methoxy-7-(3-morpholinopropoxy)quinolin-4-yl)oxy)pyridin-2-yl)-4-phenylpyrimidine-2-carboxamide;
N-(5-((6-Methoxy-7-(3-morpholinopropoxy)quinolin-4-yl)oxy)pyridin-2-yl)-4-phenylquinazoline-2-carboxamide;
N-(5-((6-methoxy-7-(3-morpholinopropoxy)quinolin-4-yl)oxy)pyridin-2-yl)-4-phenyl-7,8-dihydro-6H-5,8-ethanopyrido[3,2-d]pyrimidine-2-carboxamide, hydrochloric acid;
N-(5-((6-Methoxy-7-(3-morpholinopropoxy)quinolin-4-yl)oxy)pyridin-2-yl)-8-phenyl-3,4-dihydro-2H-1,4-ethano-1,5-naphthyridine-6-carboxamide, hydrochloric acid;
4-(4-Hydroxypiperidin-1-yl)-N-(5-((6-methoxy-7-(3-morpholinopropoxy)quinolin-4-yl)oxy)pyridin-2-yl)picolinamide, trifluoroacetic acid;
N-(5-((6-Methoxy-7-(3-morpholinopropoxy)quinolin-4-yl)oxy)pyridin-2-yl)-4-oxo-3,4-dihydroquinazoline-2-carboxamide, trifluoroacetic acid;
N-(5-((6-Methoxy-7-(3-morpholinopropoxy)quinolin-4-yl)oxy)pyridin-2-yl)-6-phenylpicolinamide;
4-(4-Hydroxypiperidin-1-yl)-N-(5-((6-methoxy-7-(3-morpholinopropoxy)quinolin-4-yl)oxy)pyridin-2-yl)picolinamide;
N-(5-((6-Methoxy-7-(3-morpholinopropoxy)quinolin-4-yl)oxy)pyridin-2-yl)-4-oxo-3,4-dihydroquinazoline-2-carboxamide;
N-(5-((6-methoxy-7-(3-morpholinopropoxy)quinolin-4-yl)oxy)pyridin-2-yl)-4-(piperidin-1-yl)picolinamide;
N-(5-((6-methoxy-7-(3-morpholinopropoxy)quinolin-4-yl)oxy)pyridin-2-yl)-4-morpholinopicolinamide;
4-(4-ethoxypiperidin-1-yl)-N-(5-((6-methoxy-7-(3-morpholinopropoxy)quinolin-4-yl)oxy)pyridin-2-yl)picolinamide;
N-(5-((6-methoxy-7-(3-morpholinopropoxy)quinolin-4-yl)oxy)pyridin-2-yl)-4-(pyrrolidin-1-yl)picolinamide;
N-(5-((6-methoxy-7-(3-morpholinopropoxy)quinolin-4-yl)oxy)pyridin-2-yl)-4-(4-phenylpiperidin-1-yl)picolinamide;
N-(5-((6-methoxy-7-(3-morpholinopropoxy)quinolin-4-yl)oxy)pyridin-2-yl)-4-(7-oxa-2-azaspiro[3.5]nonan-2-yl)picolinamide;

N-(5-(((6-methoxy-7-(3-morpholinopropoxy)quinolin-4-yl)oxy)pyridin-2-yl)-4-(2-oxa-6-azaspiro[3.3]heptan-6-yl)picolinamide;
4-(3,3-difluoroazetidin-1-yl)-N-(5-(((6-methoxy-7-(3-morpholinopropoxy)quinolin-4-yl)oxy)pyridin-2-yl)picolinamide;
4-(4,4-difluoropiperidin-1-yl)-N-(5-(((6-methoxy-7-(3-morpholinopropoxy)quinolin-4-yl)oxy)pyridin-2-yl)picolinamide;
4-(4,4-dimethylpiperidin-1-yl)-N-(5-(((6-methoxy-7-(3-morpholinopropoxy)quinolin-4-yl)oxy)pyridin-2-yl)picolinamide;
N-(5-(((6-methoxy-7-(3-morpholinopropoxy)quinolin-4-yl)oxy)pyridin-2-yl)-6-(piperidin-1-yl)picolinamide;
6-(4-hydroxypiperidin-1-yl)-N-(5-(((6-methoxy-7-(3-morpholinopropoxy)quinolin-4-yl)oxy)pyridin-2-yl)picolinamide;
N-(5-(((6-methoxy-7-(3-morpholinopropoxy)quinolin-4-yl)oxy)pyridin-2-yl)-6-morpholinopicolinamide;
N-(5-(((6-methoxy-7-(3-morpholinopropoxy)quinolin-4-yl)oxy)pyridin-2-yl)-6-(pyrrolidin-1-yl)picolinamide;
6-(4,4-dimethylpiperidin-1-yl)-N-(5-(((6-methoxy-7-(3-morpholinopropoxy)quinolin-4-yl)oxy)pyridin-2-yl)picolinamide;
6-(4,4-difluoropiperidin-1-yl)-N-(5-(((6-methoxy-7-(3-morpholinopropoxy)quinolin-4-yl)oxy)pyridin-2-yl)picolinamide;
6-(4-ethoxypiperidin-1-yl)-N-(5-(((6-methoxy-7-(3-morpholinopropoxy)quinolin-4-yl)oxy)pyridin-2-yl)picolinamide;
6-(3,3-difluoroazetidin-1-yl)-N-(5-(((6-methoxy-7-(3-morpholinopropoxy)quinolin-4-yl)oxy)pyridin-2-yl)picolinamide;
4-Fluoro-N-(5-(((6-methoxy-7-(3-morpholinopropoxy)quinolin-4-yl)oxy)pyridin-2-yl)picolinamide;
N-(5-((6-Methoxy-7-(3-morpholinopropoxy)quinolin-4-yl)oxy)pyridin-2-yl)-4-methylpicolinamide;
4-Methoxy-N-(5-(((6-methoxy-7-(3-morpholinopropoxy)quinolin-4-yl)oxy)pyridin-2-yl)picolinamide;
N-(5-(((6-Methoxy-7-(3-morpholinopropoxy)quinolin-4-yl)oxy)pyridin-2-yl)-4-(trifluoromethyl)picolinamide;
N-(5-(((6-methoxy-7-(3-morpholinopropoxy)quinolin-4-yl)oxy)pyridin-2-yl)-4-phenyl-7,8-dihydro-6H-5,8-ethanopyrido[3,2-d]pyrimidine-2-carboxamide;
N-(3-fluoro-4-((6-methoxy-7-(3-morpholinopropoxy)quinolin-4-yl)oxy)phenyl)-4-phenyl-7,8-dihydro-6H-5,8-ethanopyrido[3,2-d]pyrimidine-2-carboxamide;
N-(5-(((7-(benzyloxy)-6-methoxyquinolin-4-yl)oxy)pyridin-2-yl)-4-phenyl-7,8-dihydro-6H-5,8-ethanopyrido[3,2-d]pyrimidine-2-carboxamide;
N-(5-(((6,7-dimethoxyquinolin-4-yl)oxy)pyridin-2-yl)-4-phenyl-7,8-dihydro-6H-5,8-ethanopyrido[3,2-d]pyrimidine-2-carboxamide;
N-(5-(((6-methoxy-7-(3-(piperidin-1-yl)propoxy)quinolin-4-yl)oxy)pyridin-2-yl)-4-phenyl-7,8-dihydro-6H-5,8-ethanopyrido[3,2-d]pyrimidine-2-carboxamide;
2-bromo-N-(5-(((6-methoxy-7-(3-morpholinopropoxy)quinolin-4-yl)oxy)pyridin-2-yl)thiazole-4-carboxamide;
2-(4-hydroxypiperidin-1-yl)-N-(5-(((6-methoxy-7-(3-morpholinopropoxy)quinolin-4-yl)oxy)pyridin-2-yl)thiazole-4-carboxamide;
N-(5-(((6-methoxy-7-(3-morpholinopropoxy)quinolin-4-yl)oxy)pyridin-2-yl)-2-phenylthiazole-4-carboxamide;
2-(4-fluorophenyl)-N-(5-(((6-methoxy-7-(3-morpholinopropoxy)quinolin-4-yl)oxy)pyridin-2-yl)thiazole-4-carboxamide;
5-bromo-N-(5-(((6-methoxy-7-(3-morpholinopropoxy)quinolin-4-yl)oxy)pyridin-2-yl)thiazole-2-carboxamide;
2-(4-hydroxypiperidin-1-yl)-N-(5-(((6-methoxy-7-(3-morpholinopropoxy)quinolin-4-yl)oxy)pyridin-2-yl)thiazole-4-carboxamide, hydrochloric acid;
N-(5-(((6-methoxy-7-(3-morpholinopropoxy)quinolin-4-yl)oxy)pyridin-2-yl)-2-(piperidin-1-yl)thiazole-4-carboxamide;
N-(5-(((6-methoxy-7-(3-morpholinopropoxy)quinolin-4-yl)oxy)pyridin-2-yl)-5-(piperidin-1-yl)thiazole-2-carboxamide;
N-(5-(((6-methoxy-7-(3-morpholinopropoxy)quinolin-4-yl)oxy)pyridin-2-yl)-5-phenylthiazole-2-carboxamide;
N-(5-(((6,7-dimethoxyquinazolin-4-yl)oxy)pyridin-2-yl)-4-phenyl-7,8-dihydro-6H-5,8-ethanopyrido[3,2-d]pyrimidine-2-carboxamide;
N-(5-(((6-Methoxy-7-(3-morpholinopropoxy)quinolin-4-yl)oxy)pyridin-2-yl)-8-phenyl-3,4-dihydro-2H-1,4-ethano-1,5-naphthyridine-6-carboxamide;
N-(5-(((6-Methoxy-7-(3-morpholinopropoxy)quinolin-4-yl)oxy)pyridin-2-yl)-4-phenylpyrimidine-2-carboxamide;
N-(5-(((6-Methoxy-7-(3-morpholinopropoxy)quinolin-4-yl)oxy)pyridin-2-yl)-4-phenylquinazoline-2-carboxamide;
N-(5-(((6-methoxy-7-(3-morpholinopropoxy)quinolin-4-yl)oxy)pyridin-2-yl)-4-phenyl-7,8-dihydro-6H-5,8-ethanopyrido[3,2-d]pyrimidine-2-carboxamide, hydrochloric acid;
N-(5-(((6-Methoxy-7-(3-morpholinopropoxy)quinolin-4-yl)oxy)pyridin-2-yl)-8-phenyl-3,4-dihydro-2H-1,4-ethano-1,5-naphthyridine-6-carboxamide, hydrochloric acid;
N-(5-(((6-Methoxy-7-(3-morpholinopropoxy)quinolin-4-yl)oxy)pyridin-2-yl)-4-oxo-3,4-dihydroquinazoline-2-carboxamide, trifluoroacetic acid;
N-(5-(((6-Methoxy-7-(3-morpholinopropoxy)quinolin-4-yl)oxy)pyridin-2-yl)-6-phenylpicolinamide;
N-(5-(((6-methoxy-7-(3-morpholinopropoxy)quinolin-4-yl)oxy)pyridin-2-yl)-4-(piperidin-1-yl)picolinamide;
N-(5-(((6-methoxy-7-(3-morpholinopropoxy)quinolin-4-yl)oxy)pyridin-2-yl)-4-(pyrrolidin-1-yl)picolinamide;
N-(54(6-methoxy-7-(3-morpholinopropoxy)quinolin-4-yl)oxy)pyridin-2-yl)-4-(7-oxa-2-azaspiro[3.5]nonan-2-yl)picolinamide;
N-(5-(((6-methoxy-7-(3-morpholinopropoxy)quinolin-4-yl)oxy)pyridin-2-yl)-6-(piperidin-1-yl)picolinamide;
N-(5-(((6-methoxy-7-(3-morpholinopropoxy)quinolin-4-yl)oxy)pyridin-2-yl)-6-(pyrrolidin-1-yl)picolinamide;
6-(4,4-difluoropiperidin-1-yl)-N-(5-(((6-methoxy-7-(3-morpholinopropoxy)quinolin-4-yl)oxy)pyridin-2-yl)picolinamide;
6-(3,3-difluoroazetidin-1-yl)-N-(5-(((6-methoxy-7-(3-morpholinopropoxy)quinolin-4-yl)oxy)pyridin-2-yl)picolinamide;
N-(5-(((6-methoxy-7-(3-morpholinopropoxy)quinolin-4-yl)oxy)pyridin-2-yl)-4-phenyl-7,8-dihydro-6H-5,8-ethanopyrido[3,2-d]pyrimidine-2-carboxamide;
N-(3-fluoro-4-((6-methoxy-7-(3-morpholinopropoxy)quinolin-4-yl)oxy)phenyl)-4-phenyl-7,8-dihydro-6H-5,8-ethanopyrido[3,2-d]pyrimidine-2-carboxamide;
N-(5-(((7-(benzyloxy)-6-methoxyquinolin-4-yl)oxy)pyridin-2-yl)-4-phenyl-7,8-dihydro-6H-5,8-ethanopyrido[3,2-d]pyrimidine-2-carboxamide;

N-(5-((6,7-dimethoxyquinolin-4-yl)oxy)pyridin-2-yl)-4-phenyl-7,8-dihydro-6H-5,8-ethanopyrido[3,2-d]pyrimidine-2-carboxamide;

N-(5-((6-methoxy-7-(3-(piperidin-1-yl)propoxy)quinolin-4-yl)oxy)pyridin-2-yl)-4-phenyl-7,8-dihydro-6H-5,8-ethanopyrido[3,2-d]pyrimidine-2-carboxamide;

2-bromo-N-(5-((6-methoxy-7-(3-morpholinopropoxy)quinolin-4-yl)oxy)pyridin-2-yl)thiazole-4-carboxamide;

N-(5-((6-methoxy-7-(3-morpholinopropoxy)quinolin-4-yl)oxy)pyridin-2-yl)-2-phenylthiazole-4-carboxamide;

2-(4-fluorophenyl)-N-(5-((6-methoxy-7-(3-morpholinopropoxy)quinolin-4-yl)oxy)pyridin-2-yl)thiazole-4-carboxamide;

N-(5-((6-methoxy-7-(3-morpholinopropoxy)quinolin-4-yl)oxy)pyridin-2-yl)-2-(piperidin-1-yl)thiazole-4-carboxamide;

N-(5-((6,7-dimethoxyquinazolin-4-yl)oxy)pyridin-2-yl)-4-phenyl-7,8-dihydro-6H-5,8-ethanopyrido[3,2-d]pyrimidine-2-carboxamide;

or a pharmaceutically acceptable salt, prodrug or N-oxide thereof, or solvate or hydrate thereof.

17. A pharmaceutical composition comprising a pharmaceutically acceptable diluent, carrier, or excipient and a compound according to claim 1 or a pharmaceutically acceptable salt, prodrug or N-oxide thereof, or solvate or hydrate thereof.

* * * * *